(12) United States Patent
Mori et al.

(10) Patent No.: US 7,323,541 B2
(45) Date of Patent: Jan. 29, 2008

(54) POLYPEPTIDE DNA THEREOF AND USE OF THE SAME

(75) Inventors: Masaaki Mori, Ibaraki (JP); Kozo Hayashi, Ibaraki (JP); Hiroyuki Miya, Ibaraki (JP); Shuji Sato, Ibaraki (JP); Chieko Kitada, Osaka (JP); Hirokazu Matsumoto, Ibaraki (JP); Toshimi Nagi, Ibaraki (JP); Yukio Shimomura, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 510 days.

(21) Appl. No.: 10/489,537

(22) PCT Filed: Sep. 13, 2002

(86) PCT No.: PCT/JP02/09446

§ 371 (c)(1),
(2), (4) Date: Mar. 12, 2004

(87) PCT Pub. No.: WO03/025179

PCT Pub. Date: Mar. 27, 2003

(65) Prior Publication Data

US 2005/0048605 A1 Mar. 3, 2005

(30) Foreign Application Priority Data

Sep. 14, 2001 (JP) ............................ 2001-279232
Oct. 12, 2001 (JP) ............................ 2001-315148
Apr. 10, 2002 (JP) ............................ 2002-108621
Jun. 10, 2002 (JP) ............................ 2002-169232

(51) Int. Cl.
*A61K 38/04* (2006.01)
(52) U.S. Cl. ............... 530/300; 530/326; 530/350; 514/2; 435/69.1
(58) Field of Classification Search ............... None
See application file for complete search history.

(56) References Cited

U.S. PATENT DOCUMENTS

2002/0166131 A1* 11/2002 Goodearl et al. ............ 800/8
2003/0157558 A1* 8/2003 Matsumoto et al. ......... 435/7.1

FOREIGN PATENT DOCUMENTS

| JP | 2001-245666 | 9/2001 |
| WO | WO 01/18206 A1 | 3/2001 |
| WO | WO-01/18206 A1 | 3/2001 |
| WO | WO 01/48015 A2 | 7/2001 |
| WO | WO 01/48188 A1 | 7/2001 |
| WO | WO 01/48189 A1 | 7/2001 |
| WO | WO 02/31145 A1 | 4/2002 |
| WO | WO 02/42458 A2 | 5/2002 |
| WO | WO-03/007187 A1 | 1/2003 |

OTHER PUBLICATIONS

Bays, H. Obsity Research 12: 1197-1211, 2004.*
Dorlands Medical Dictionary, p. 44.*

* cited by examiner

*Primary Examiner*—Robert Landsman
*Assistant Examiner*—Gyan Chandra
(74) *Attorney, Agent, or Firm*—David G. Conlin; Christine C. O'Day; Edwards Angell Palmer & Dodge LLP

(57) ABSTRACT

The present invention aims at providing a novel polypeptide, a receptor, a DNA thereof, and the like. Specifically, the present invention provides a polypeptide having a binding ability to the protein represented by SEQ ID NO: 1 or SEQ ID NO: 3, or its amide, its ester or its salt, a polynucleotide encoding the polypeptide, an antisense polynucleotide or an antibody to the polypeptide, a screening of agent for prevention and/or treatment of cancer, obesity, etc., which comprises using the above, and the like.

The polypeptide, receptor, polynucleotide, antisense polynucleotide, antibody and the like are useful for an agent of prevention and/or treatment of cancer, obesity and the like. Further, they are useful for a screening of an agent for prevention and/or treatment of cancer, obesity and the like.

9 Claims, 30 Drawing Sheets

Fig. 3

MPANFTEGSFDSSGTGQTLDSSPVACTETVTFTEVVEGKEWGSFYYSFKTEQLITLWLFVFTIVGNSVVLFSTW
RRKKKSRMTFFVTQLAITDSFTGLVNILTDINWRFTGDFTAPDLVCRVVRYLQVVLLYASTYVLVSLSIDRYHAI
VYPMKFLQGEKQARVLIVIAWSLSFLFSIPTLIIFGKRTLSNGEVQCWALWPDDSYWTPYMTIVAFLVYFIPLTI
ISIMYGIVIRTIWIKSKTYETVISNCSDGKLCSSYNRGLISKAKIKAIKYSIIILAFICCWSPYFLFDILDNFN
LLPDTQERFYASVIIQNLPALNSAINPLIYCVFSSSISFPCREQRSQDSRMTFRERTERHEMQILSKPEFI

Fig. 4

MPANFTEGSFDSSGTGQTLDSSPVACTETVTFTEVVEGKEWGSFYYSFKTEQLITLVLFVFTIVGNSVVLFSTW

RRKKKSRMTFFVTQLAITDSFTGLVNILTDIIWRFTGDFTAPDLVCRVVRYLQVVLLYASTYVLVSLSIDRYHAI

VYPLKFLQGEKQARVLIVIAWSLSFLFSIPTLIIFGKRTLSNGEVQCWALWPDDSYWTPYMTIVAFLVYFIPLTI

ISIMYGIVIRTIWIKSKTYETVISNCSDGKLCSSYNRGLISKAKIKAIKYSIIILAFICCWSPYFLFDILDNFN

LLPDTQERFYASVIQNLPALNSAINPLIYCVFSSSISFPCRERRSQDSRMTFRERTERHEMQILSKPEFI

POLYPEPTIDE DNA THEREOF AND USE OF THE SAME

This application is a national stage application claiming priority to international application number PCT/JP02/09446, filed 13 Sep. 2002.

TECHNICAL FIELD

The present invention relates to a novel polypeptide and a polynucleotide encoding the same, a method for screening a medicine using the novel polypeptide, a compound obtained by the screening and the like. Further, it also relates to a novel receptor to which the novel polypeptide is bound, etc. Furthermore, it relates to prophylactic/therapeutic agents for cancer and obesity, etc.

BACKGROUND ART

Regulation of important functions including maintenance of homeostasis in the living body, reproduction, development of individuals, metabolism, growth, is control of the nervous, circulatory, immune, digestive or metabolic system, sensory adaptation, and the like, is done by receiving endogenous factors such as various hormones and neurotransmitters or sensory stimulation like light or odor, via specific receptors present on cell membranes, which are furnished in the living body, and responding accordingly. Many of these receptors for hormones or neurotransmitters, which take part in such functional regulation, are coupled to guanine nucleotide-binding proteins (hereinafter, referred to as G proteins), and are characterized by developing a variety of functions through mediation of intracellular signal transduction via activation of the G proteins. In addition, these receptor proteins possess common seven transmembrane regions. Based on the foregoing, these receptors are thus collectively referred to as G protein-coupled receptors or seven transmembrane receptors. As such, it is known that various hormones or neurotransmitters and their receptor proteins are present and interact with each other to play important roles for regulating the biological functions. However, it often remains unclear if there are any other unknown substances (hormones, neurotansmitters, etc.) and receptors to these substances.

In recent years, accumulated sequence information of human genome DNA or various human tissue-derived cDNAs by random sequencing and rapid progress in gene analysis technology have been accelerating the investigation of human genes. With such advance, it has been clarified that there are many genes supposed to encode proteins with unknown functions. G protein-coupled receptors not only have seven transmembrane domains but many common sequences are present in their nucleic acids or amino acids. Thus, these receptors can be precisely identified to be G protein-coupled receptors in such proteins. On the other hand, these G protein-coupled receptor genes are obtained also by polymerase chain reaction (hereinafter abbreviated as PCR) utilizing such a structural similarity. In these G protein-coupled receptors thus obtained so far, ligands to some receptors that are subtypes having high homology in structure to known receptors may be readily predictable but in most cases, their endogenous ligands are unpredictable so that ligands corresponding to these receptors are hardly found. For this reason, these receptors are termed orphan receptors. It is likely that unidentified endogenous ligands to such orphan receptors would participate in biological phenomena poorly analyzed because the ligands were unknown. When such ligands are associated with important physiological effects or pathologic conditions, it is expected that development of these receptor agonists or antagonists will result in breakthrough new drugs (Stadel, J. et al., TiPS, 18, 430-437, 1997; Marchese, A. et al., TiPS, 20, 370-375, 1999; Civelli, O. et al., Brain Res., 848, 63-65, 1999). Until now, however, there are few examples to actually identify ligands to orphan G protein-coupled receptors.

Recently, some groups attempted to investigate ligands to these orphan receptors and reported isolation/structural determination of ligands, which are novel physiologically active peptides. Independently, Reinsheid et al. and Meunier et al. introduced a cDNA coding for orphan G protein-coupled receptor LC132 or ORL1 into animal cells to express a receptor, isolated a novel peptide from porcine brain or rat brain extract, which was named orphanin FQ or nociceptin, with reference to its response and determined its sequence (Reinsheid, R. K. et al., Science, 270, 792-794, 1995; Meunier, J.-C. et al., Nature, 377, 532-535, 1995). This peptide was reported to be associated with pain. Further research on the receptor in knockout mice reveals that the peptide takes part in memory (Manabe, T. et al., Nature, 394, 577-581, 1998).

Subsequently, novel peptides such as PrRP (prolactin releasing peptide), orexin, apelin, ghrelin, GALP (galanin-like peptide) and metastin were isolated as ligands to orphan G protein-coupled receptors by the similar method (Hinuma, S. et al., Nature, 393, 272-276, 1998; Sakurai, T. et al., Cell, 92, 573-585, 1998; Tatemoto, K. et al., Biohem. Biophys. Res. Commun., 251, 471-476, 1998; Kojima, M. et al., Nature, 402, 656-660, 1999; Ohtaki, T. et al., J. Biol. Chem., 274, 37041-37045, 1999; Ohtaki, T. et al., Nature, 411, 613-617, 2001). So far, among them, it has been reported that orexin relates to feeding and sleeping (Sakurai, T. et al., Cell, 92, 573-585, 1998; Lin, L. et al., Cell, 98, 365-376, 1999; Chemelli, R. M. et al., Cell, 98, 437-451, 1999), and that ghrelin exhibits feeding accentuation activity (Tschop, M. et al., Nature, 407, 908-913, 2000; Nakazato, M. et al., Nature, 409, 194-198, 2001). Further, it has been suggested that metastin has a possibility to suppress metastasis (Ohtaki, T. et al., Nature, 411, 613-617, 2001).

On the other hand, some receptors to physiologically active peptides, which were so far unknown, were clarified according to the similar manner. It was revealed that a receptor to motilin associated with contraction of intestinal tracts was GPR38 (Feighner, S. D. et al., Science, 284, 2184-2188, 1999). Furthermore, SLC-1 (MCHR1) (Chambers, J. et al., Nature, 400, 261-265, 1999; Saito, Y. et al., Nature, 400, 265-269, 1999; Shimomura, Y. et al., Biochem. Biophys. Res. Commun., 261, 622-626, 1999; Lembo, P. M. C. et al., Nature Cell Biol., 1, 267-271, 1999; Bachner, D. et al., FEBS Lett., 457, 522-524, 1999) and SLT (MCHR2) (Mori, M. et al., Biochem. Biophys. Res. Commun., 283, 1013-1018, 2001; Hill, J. et al., J. Biol. Chem., 276, 20125-20129, 2001; Sailer, A. W. et al., Proc. Natl. Acad. Sci. USA, 98, 7564-7569, 2001; An, S. et al., Proc. Natl. Acad. Sci. USA, 98, 7576-7581, 2001) were identified as a receptor to MCH. Also, it was reported that GPR14 (SENR) was a receptor to urotensin II (Ames, R. S. et al., Nature, 401, 282-286, 1999; Mori, M. et al., Biochem. Biophys. Res. Commun., 265, 123-129, 1999; Nothacker, H.-P. et al., Nature Cell Biol., 1, 383-385, 1999, Liu, Q. et al., Biochem. Biophys. Res. Commun., 266, 174-178, 1999) and that FM3 (GPR66) and FM4 were a receptor to neuromedin U (Howard, A. D. et al., Nature, 406, 70-74, 2000; Szekeres, P. G. et al., J. Biol. Chem., 275, 20274-20250, 2000; Fujii, R. et al., J. Biol. Chem., 275, 221068-21074, 2000; Hosoya, M. et al., J. Biol. Chem., 275, 29528-29532, 2000; Raddatz, R. et al., J. Biol. Chem., 275, 39482-39486, 2000; Kojima, M. et al., Biochem. Biophys. Res. Commun., 276, 435-438, 2000). It was shown that MCH took part in obesity since its knockout mouse showed the reduced body weight and lean phenotype (Shimada, M. et al., Nature, 396, 670-674, 1998), and because its receptor was identified, it became possible to explore a receptor antagonist likely to be an anti-obesity agent. It is further reported that urotensin II shows a potent action on the cardiocirculatory system, since it induces heart ischemia by intravenous injection to monkey (Ames, R. S. et al., Nature, 401, 282-286, 1999). Neuromedin U was shown to function as suppression of feeding (Howard, A. D. et al., Nature, 406, 70-74, 2000; Kojima, M. et al., Biochem. Biophys. Res. Commun., 276, 435-438, 2000).

As described above, orphan receptors and ligands thereto often take part in a new physiological activity, and it is expected that their identification will lead to development of new drugs. However, it is known that research on ligands to orphan receptors is accompanied by many difficulties. For example, since it is generally unknown that orphan receptor, which is expressed in the cells, responds to the ligand and thereafter second signal transduction is activated, it is necessary for investigation of various response system. Further, since it is not easily predicted where the tissues having ligand are, various tissue extracts should be prepared. Furthermore, when the ligand is a peptide, since the ligand level necessary for stimulation of the receptor is enough to be extremely low concentration, there is many cases that in vivo level of such a ligand is extremely trace. In addition, since an activity of the peptide is lost due to digestion by protease and recovery of the peptide during purification steps is retarded due to non-specific adsorption, the fact that an amount of the peptide to be needed for determination of the structure is extracted from the living body and isolated is generally very difficult. Due to these issues, the presence of many orphan receptors was unraveled, but due to the foregoing problems, only a very small part of ligands to these receptors were discovered so far.

By finding out a ligand of novel G protein-coupled receptor and directly applying the ligand, or by using a screening system for medicine with the ligand, it is desired to develop a medicine having a quite novel mechanism of action.

DISCLOSURE OF THE INVENTION

As a result of extensive investigations for solving the above-mentioned problems, the present inventors have succeeded in finding out and purifying an endogenous ligand, which can be bound to the human colon-derived orphan G protein-coupled receptor having the amino acid sequence represented by SEQ ID NO: 1 or SEQ ID NO: 3. In addition, a novel receptor, to which the endogenous ligand can bind, was acquired. Based on such findings, the inventors have thus come to accomplish the present invention.

That is, the present invention provides the following features:

(1) A polypeptide, which comprises having an ability to bind to the G protein-coupled receptor protein containing the same or substantially the same amino acid sequence as the amino acid sequence represented by SEQ ID NO: 1 or SEQ ID NO: 3, or a salt thereof, its amide or its ester, or salts thereof;

(2) The polypeptide according to (1), which contains the same or substantially the same amino acid sequence as the amino acid sequence represented by SEQ ID NO: 22, SEQ ID NO: 14 or SEQ ID NO: 31, its amide or its ester, or salts thereof;

(3) The polypeptide according to (2), which contains the same or substantially the same amino acid sequence as the amino acid sequence represented by SEQ ID NO: 20, SEQ ID NO: 21, SEQ ID NO: 22, SEQ ID NO: 23, SEQ ID NO: 49, SEQ ID NO: 12, SEQ ID NO: 13, SEQ ID NO: 14, SEQ ID NO: 36, SEQ ID NO: 29, SEQ ID NO: 30, SEQ ID NO: 31 or SEQ ID NO: 32, its amide or its ester, or salts thereof;

(4) The polypeptide according to (2), which contains the same amino acid sequence as the amino acid sequence represented by SEQ ID NO: 62, its amide or its ester, or salts thereof;

(5) The polypeptide according to (4), which is labeled, its amide or its ester, or salts thereof;

(6) The polypeptide according to (2), which contains the same amino acid sequence as the amino acid sequence represented by SEQ ID NO: 19, SEQ ID NO: 28 or SEQ ID NO: 68, its amide or its ester, or salts thereof;

(7) A polynucleotide, which contains the polynucleotide encoding the polypeptide according to (1);

(8) The polynucleotide according to (7), which contains the base sequence represented by SEQ ID NO: 41, SEQ ID NO: 42, SEQ ID NO: 43, SEQ ID NO: 44, SEQ ID NO: 37, SEQ ID NO: 38, SEQ ID NO: 39, SEQ ID NO: 40, SEQ ID NO: 45, SEQ ID NO: 46, SEQ ID NO: 47, SEQ ID NO: 48 or SEQ ID NO: 50;

(9) The polynucleotide according to (7), which contains the base sequence represented by SEQ ID NO: 18, SEQ ID NO: 27 or SEQ ID NO: 60;

(10) The polynucleotide according to (7) through (9), which is a DNA;

(11) A recombinant vector, which contains the polynucleotide according to (7);

(12) A transformant, which is transformed with the recombinant vector according to (11);

(13) A method for manufacturing the polypeptide according to (1), which comprises culturing the transformant according to (12), and producing and accumulating the polypeptide according to (1), its amide or its ester, or salts thereof;

(14) A medicine, which comprises the polypeptide according to (1), its amide or its ester, or salts thereof;

(15) A medicine, which comprises the polynucleotide according to (7);

(16) A diagnostic product, which comprises the polynucleotide according to (7);

(17) The medicine according to (14) or (15), which is a prophylactic/therapeutic agent for obesity;

(18) The diagnostic product according to (16), which is a diagnostic product for obesity;

(19) An antibody against the polypeptide, its amide or its ester, or salts thereof according to (1);

(20) A medicine, which comprises the antibody according to (19);

(21) A diagnostic product, which comprises the antibody according to (19);

(22) The medicine according to (20), which is a prophylactic/therapeutic agent for cancer;

(23) The medicine according to (20), which is an agent for enhancing ingestion;

(24) The diagnostic product according to (21), which is a diagnostic product for cancer;

(25) A polynucleotide, which has a base sequence complement or substantially complement to that of the polynucleotide according to (7), or a portion thereof;
(26) The polynucleotide according to (25), which is a DNA;
(27) A medicine, which comprises the polynucleotide according to (25);
(28) The medicine according to (27), which is a prophylactic/therapeutic agent for cancer;
(29) The medicine according to (27), which is a feeding enhancer;
(30) A method for screening a compound that enhances or inhibits an activity of the polypeptide, its amide or its ester, or salts thereof according to (1), or its salt, which comprises using the polypeptide according to (1), its amide or its ester, or salts thereof;
(31) The method for screening according to (30), which uses the labeled polypeptide according to (1), its amide or its ester, or salts thereof;
(32) The method for screening according to (30), which uses the polypeptide according to (5), its amide or its ester, or salts thereof;
(33) The method for screening according to (30), which further uses a protein containing the same or substantially the same amino acid sequence as the amino acid sequence represented by SEQ ID NO: 1 or SEQ ID NO: 3, a partial peptide thereof, its amide or its ester, or salts thereof;
(34) The method for screening according to (30), which further uses a protein containing the amino acid sequence represented by SEQ ID NO: 1, SEQ ID NO: 3, SEQ ID NO: 63, SEQ ID NO: 65, SEQ ID NO: 95, SEQ ID NO: 97, SEQ ID NO: 77, SEQ ID NO: 85, SEQ ID NO: 87, SEQ ID NO: 89, SEQ ID NO: 91, SEQ ID NO: 93, SEQ ID NO: 71, SEQ ID NO: 75, SEQ ID NO: 83, SEQ ID NO: 51, SEQ ID NO: 55, SEQ ID NO: 69, SEQ ID NO: 102 or SEQ ID NO: 104, a partial peptide thereof, its amide or its ester, or salts thereof;
(35) The method for screening according to (33), which uses a protein containing the amino acid sequence represented by SEQ ID NO: 3, a partial peptide thereof, its amide or its ester, or salts thereof;
(36) The method for screening according to (30), which uses the labeled polypeptide according to (1), its amide or its ester, or salts thereof, and the protein containing the amino acid sequence represented by SEQ ID NO: 3, a partial peptide thereof, its amide or its ester, or salts thereof;
(37) The method for screening according to (30), which uses the polypeptide according to (5), its amide or its ester, or salts thereof, and the protein containing the amino acid sequence represented by SEQ ID NO: 3, a partial peptide thereof, its amide or its ester, or salts thereof;
(38) The method for screening according to (30), which comprises comparing (i) the case where the polypeptide according to (1), its amide or its ester, or salts thereof is contacted with the protein containing the same or substantially the same amino acid sequence as that represented by SEQ ID NO: 1 or SEQ ID NO: 3, a partial peptide thereof, its amide or its ester, or salts thereof, with (ii) the case where the polypeptide according to (1), its amide or its ester, or salts thereof is contacted with the protein containing the same or substantially the same amino acid sequence as that represented by SEQ ID NO: 1 or SEQ ID NO: 3, a partial peptide thereof, its amide or its ester, or salts thereof and test compound;
(39) The method for screening according to (38), which comprises measuring and comparing an amount of the polypeptide bound to the cell or a cell stimulating activity in (i) the case where the polypeptide according to (1), its amide or its ester, or salts thereof is contacted with the cells containing the protein containing the same or substantially the same amino acid sequence as that represented by SEQ ID NO: 1 or SEQ ID NO: 3, a partial peptide thereof, its amide or its ester, or salts thereof, and (ii) the case where the polypeptide according to (1), its amide or its ester, or salts thereof and test compound are contacted with the cells containing the protein containing the same or substantially the same amino acid sequence as that represented by SEQ ID NO: 1 or SEQ ID NO: 3, a partial peptide thereof, its amide or its ester, or salts thereof;
(40) The method for screening according to (38), which comprises measuring and comparing an amount of the polypeptide bound to the cell or a cell stimulating activity in (i) the case where the polypeptide according to (1), its amide or its ester, or salts thereof is contacted with membrane fraction of the cells containing the protein containing the same or substantially the same amino acid sequence as that represented by SEQ ID NO: 1 or SEQ ID NO: 3, a partial peptide thereof, its amide or its ester, or salts thereof, and (ii) the case where the polypeptide according to (1), its amide or its ester, or salts thereof and test compound are contacted with membrane fraction of the cells containing the protein containing the same or substantially the same amino acid sequence as that represented by SEQ ID NO: 1 or SEQ ID NO: 3, a partial peptide thereof, its amide or its ester, or salts thereof;
(41) The method for screening according to (38), which comprises measuring and comparing an amount of the polypeptide bound to the cell or a cell stimulating activity in (i) the case where the polypeptide according to (1), its amide or its ester, or salts thereof is contacted with the protein, which is expressed in the cell membrane of the transformant according to (12) by culturing the transformant, and (ii) the case where the polypeptide according to (1), its amide or its ester, or salts thereof and test compound are contacted with the protein, which is expressed in the cell membrane of the transformant according to (12) by culturing the transformant;
(42) The method for screening according to (38) through (41), which uses the labeled polypeptide according to (1), its amide or its ester, or salts thereof;
(43) A kit for screening a compound that enhances or inhibits the activity of the polypeptide according to (1), its amide or its ester, or salts thereof, which comprises the polypeptide according to (1), its amide or its ester, or salts thereof;
(44) The kit for screening according to (43), which contains the labeled polypeptide according to (1), its amide or its ester, or salts thereof;
(45) The kit for screening according to (43), which contains the polypeptide according to (5), its amide or its ester, or salts thereof;
(46) The kit for screening according to (43), which further contains the protein containing the same or substantially the same amino acid sequence as that represented by SEQ ID NO: 1 or SEQ ID NO: 3, a partial peptide thereof, its amide or its ester, or salts thereof:
(47) The kit for screening according to (43), which further contains the protein containing the amino acid sequence represented by SEQ ID NO: 1, SEQ ID NO: 3, SEQ ID NO: 63, SEQ ID NO: 65, SEQ ID NO: 95, SEQ ID NO: 97, SEQ ID NO: 77, SEQ ID NO: 85, SEQ ID NO: 87, SEQ ID NO: 89, SEQ ID NO: 91, SEQ ID NO: 93, SEQ ID NO: 71, SEQ ID NO: 75, SEQ ID NO: 83, SEQ ID NO: 51, SEQ ID NO: 55, SEQ ID NO: 69, SEQ ID NO:

102, or SEQ ID NO: 104, a partial peptide thereof, its amide or its ester, or salts thereof;

(48) The kit for screening according to (46), which contains the protein containing the amino acid sequence represented by SEQ ID NO: 3, a partial peptide thereof, its amide or its ester, or salts thereof;

(49) The kit for screening according to (46), which contains the labeled polypeptide according to (1), its amide or its ester, or salts thereof, and the protein containing the amino acid sequence represented by SEQ ID NO: 3, a partial peptide thereof, its amide or its ester, or salts thereof;

(50) The kit for screening according to (46), which contains the polypeptide according to (5), its amide or its ester, or salts thereof, and the protein containing the amino acid sequence represented by SEQ ID NO: 3, a partial peptide thereof, its amide or its ester, or salts thereof;

(51) The kit for screening according to (46), which comprises containing the cells that contain the protein containing the same or substantially the same amino acid sequence as that represented by SEQ ID NO: 1 or SEQ ID NO: 3, a partial peptide thereof, its amide or its ester, or salts thereof;

(52) The kit for screening according to (46), which comprises containing membrane fraction of the cells that contain the protein containing the same or substantially the same amino acid sequence as that represented by SEQ ID NO: 1 or SEQ ID NO: 3, a partial peptide thereof, its amide or its ester, or salts thereof;

(53) The kit for screening according to (46), which comprises containing the protein that is expressed in cell membrane of the transformant according to (12) by culturing the transformant;

(54) A compound that enhances the activity of the polypeptide according to (1), its amide or its ester, or salts thereof, or a salt thereof, which is obtainable by using the screening method according to (30) or the screening kit according to (43);

(55) A compound that inhibits the activity of the polypeptide according to (1), its amide or its ester, or salts thereof, or a salt thereof, which is obtainable by using the screening method according to (30) or the screening kit according to (43);

(56) A medicine, which comprises the compound according to (54) or its salt;

(57) A medicine, which comprises the compound according to (55) or its salt;

(58) The medicine according to (56), which is a prophylactic/therapeutic agent for obesity;

(59) The medicine according to (57), which is a prophylactic/therapeutic agent for cancer;

(60) The medicine according to (57), which is an agent for enhancing ingestion;

(61) A protein, which contains the amino acid sequence represented by SEQ ID NO: 63, SEQ ID NO: 65, SEQ ID NO: 95, SEQ ID NO: 102 or SEQ ID NO: 104, or a salt thereof;

(62) A partial peptide of the protein according to (61), or a salt thereof;

(63) A polynucleotide, which contains a polynucleotide encoding the protein according to (62) or its partial peptide;

(64) The polynucleotide according to (63), which is a DNA;

(65) The polynucleotide according to (64), which contains the base sequence represented by SEQ ID NO: 64, SEQ ID NO: 66, SEQ ID NO: 96, SEQ ID NO: 99, SEQ ID NO: 100, SEQ ID NO: 103 or SEQ ID NO: 105;

(66) A polynucleotide, which contains the base sequence represented by SEQ ID NO: 101;

(67) A protein, which contains the amino acid sequence represented by SEQ ID NO: 85, SEQ ID NO: 87, SEQ ID NO: 89, SEQ ID NO: 91 or SEQ ID NO: 93, or a salt thereof;

(68) A partial peptide of the protein according to (67), or a salt thereof;

(69) A polynucleotide, which contains a polynucleotide encoding the protein according to (67) or a partial peptide thereof;

(70) The polynucleotide according to (69), which is a DNA;

(71) The polynucleotide according to (70), which contains the base sequence represented by SEQ ID NO: 86, SEQ ID NO: 88, SEQ ID NO: 90, SEQ ID NO: 92 or SEQ ID NO: 94;

(72) A protein, which contains the amino acid sequence represented by SEQ ID NO: 75 or SEQ ID NO: 83, or a salt thereof;

(73) A partial peptide of the protein according to (72), or a salt thereof;

(74) A polynucleotide, which contains a polynucleotide encoding the protein according to (72) or a partial peptide thereof;

(75) The polynucleotide according to (74), which is a DNA;

(76) The polynucleotide according to (75), which contains the base sequence represented by SEQ ID NO: 76 or SEQ ID NO: 84;

(77) A recombinant vector, which contains the polynucleotide according to (63), (69) or (74);

(78) A transformant, which is transformed with the recombinant vector according to (70);

(79) A method for manufacturing the protein according to (61), (67) or (71), its partial peptide, or salts thereof, which comprises culturing the transformant according to (78), and producing and accumulating the protein according to (61), (67) or (71), or its partial peptide;

(80) A medicine, which comprises the protein according to (61), (67) or (71), its partial peptide, or salts thereof;

(81) A medicine, which comprises the polynucleotide according to (63), (66), (69) or (74);

(82) A diagnostic product, which comprises the polynucleotide according to (63), (66), (69) or (74);

(83) The medicine according to (80) or (81), which is a prophylactic/therapeutic agent for obesity;

(84) The diagnostic product according to (82), which is a diagnostic product for obesity;

(85) A prophylactic/therapeutic agent for obesity, which comprises the protein containing the same or substantially the same amino acid sequence as that represented by SEQ ID NO: 1 or SEQ ID NO: 3, the protein containing the amino acid sequence represented by SEQ ID NO: 51, SEQ ID NO: 55 or SEQ ID NO: 69, or partial peptides thereof, or salts thereof;

(86) A prophylactic/therapeutic agent for obesity, which comprises a polynucleotide containing the polynucleotide encoding the protein containing the same or substantially the same amino acid sequence as that represented by SEQ ID NO: 1 or SEQ ID NO: 3, the protein containing the amino acid sequence represented by SEQ ID NO: 51, SEQ ID NO: 55 or SEQ ID NO: 69, or partial peptides thereof, or salts thereof;

(87) A diagnostic product for obesity, which comprises a polynucleotide containing the polynucleotide encoding the protein containing the same or substantially the same amino acid sequence as that represented by SEQ ID NO: 1 or SEQ ID NO: 3, the protein containing the amino acid sequence represented by SEQ ID NO: 51, SEQ ID NO: 55 or SEQ ID NO: 69, or partial peptides thereof, or salts thereof;

(88) An antibody against the protein according to (61), (67) or (71), or its partial peptide, or salts thereof;

(89) A medicine, which comprises the antibody according to (88);

(90) A diagnostic product, which comprises the antibody according to (88);

(91) The medicine according to (89), which is a prophylactic/therapeutic agent for cancer;

(92) The medicine according to (89), which is a feeding enhancer;

(93) The diagnostic product according to (90), which is a diagnostic product for cancer;

(94) A prophylactic/therapeutic agent for cancer, which comprises the antibody against the protein containing the same or substantially the same amino acid sequence as that represented by SEQ ID NO: 1 or SEQ ID NO: 3, the protein containing the amino acid sequence represented by SEQ ID NO: 51, SEQ ID NO: 55 or SEQ ID NO: 69, or partial peptides thereof, or salts thereof;

(95) A feeding enhancer, which comprises the antibody against the protein containing the same or substantially the same amino acid sequence as that represented by SEQ ID NO: 1 or SEQ ID NO: 3, the protein containing the amino acid sequence represented by SEQ ID NO: 51, SEQ ID NO: 55 or SEQ ID NO: 69, or partial peptides thereof, or salts thereof;

(96) A diagnostic product for cancer, which comprises the antibody against the protein containing the same or substantially the same amino acid sequence as that represented by SEQ ID NO: 1 or SEQ ID NO: 3, the protein containing the amino acid sequence represented by SEQ ID NO: 51, SEQ ID NO: 55 or SEQ ID NO: 69, or partial peptides thereof, or salts thereof;

(97) A polynucleotide, which has a complement or substantially complement base sequence to that according to (63), (66), (69) or (74), or a portion thereof;

(98) The polynucleotide according to (97), which is a DNA;

(99) A medicine, which comprises the polynucleotide according to (97);

(100) The medicine according to (99), which is a prophylactic/therapeutic agent for cancer;

(101) The medicine according to (99), which is a feeding enhancer;

(102) A prophylactic/therapeutic agent for cancer, which comprises a polynucleotide having a complement or substantially complement base sequence to a polynucleotide containing the polynucleotide encoding the protein containing the same or substantially the same amino acid sequence as that represented by SEQ ID NO: 1 or SEQ ID NO: 3, the protein containing the amino acid sequence represented by SEQ ID NO: 51, SEQ ID NO: 55 or SEQ ID NO: 69, or partial peptides thereof, or salts thereof, or a portion thereof;

(103) A feeding enhancer, which comprises a polynucleotide having a complement or substantially complement base sequence to a polynucleotide containing the polynucleotide encoding the protein containing the same or substantially the same amino acid sequence as that represented by SEQ ID NO: 1 or SEQ ID NO: 3, the protein containing the amino acid sequence represented by SEQ ID NO: 51, SEQ ID NO: 55 or SEQ ID NO: 69, or partial peptides thereof, or salts thereof, or a portion thereof;

(104) A method for screening a compound that enhances or inhibits gene expression of the polypeptide according to (1), or a salt thereof, which comprises containing the polynucleotide according to (7);

(105) A kit for screening a compound that enhances or inhibits gene expression of the polypeptide according to (1), or a salt thereof, which comprises containing the polynucleotide according to (7);

(106) A compound that enhances gene expression of the polypeptide according to (1), or a salt thereof, which is obtainable by using the method for screening according to (104) or the kit for screening according to (105);

(107) A compound that inhibits gene expression of the polypeptide according to (1), or a salt thereof, which is obtainable by using the method for screening according to (104) or the kit for screening according to (105);

(108) A medicine, which comprises the compound according to (106), or a salt thereof;

(109) A medicine, which comprises the compound according to (107), or a salt thereof;

(110) The medicine according to (108), which is a prophylactic/therapeutic agent for obesity;

(111) The medicine according to (109), which is a prophylactic/therapeutic agent for cancer;

(112) The medicine according to (109), which is a feeding enhancer;

(113) A transgenic non-human mammal, which has the exogenous polynucleotide according to (10), or its mutated DNA;

(114) The mammal according to (113), wherein the non-human mammal is a rodent;

(115) The mammal according to (114), wherein the rodent is a mouse or a rat;

(116) A recombinant vector, which contains the exogenous polynucleotide according to (10), or its mutated DNA, and has an ability of expression in the non-human mammals;

(117) A method for screening a compound having an effect on diseases caused by deletion and/or damage of the polynucleotide according to (10), or a salt thereof, which comprises using the mammal according to (113);

(118) A non-human mammalian embryonic stem cell, wherein the polynucleotide according to (10) is inactivated;

(119) The embryonic stem cell according to (118), wherein the polynucleotide is inactivated by introduction of reporter gene;

(120) The embryonic stem cell, wherein the non-human mammal is a rodent;

(121) A DNA expression deficient non-human mammal, wherein the polynucleotide according to (10) is inactivated;

(122) The non-human mammal according to (121), wherein the polynucleotide is inactivated by introduction of reporter gene and the reporter gene can be expressed under control of the promoter for the polynucleotide according to (10);

(123) The non-human mammal according to (121), wherein the non-human mammal is a rodent;

(124) The non-human mammal according to (123), wherein the rodent is a mouse or a rat;

(125) A method for screening a compound that enhances or inhibits the promoter activity for the polynucleotide according to (10), or a salt thereof, which comprises administrating a test compound to the mammal according to (122) and detecting expression of a reporter gene;

(126) A method for screening a prophylactic/therapeutic agent for obesity, which comprises using the mammal according to (121);

(127) A method for screening a compound that enhances or inhibits expression of gene encoding the protein according to (61), (67) or (72), or a salt thereof, which comprises using the polynucleotide according to (63), (69) or (74);

(128) A method for screening a compound that enhances or inhibits expression of gene encoding the protein according to (61), (67) or (72), or a salt thereof, which comprises containing the polynucleotide according to (63), (69) or (74);

(129) A compound that enhances expression of the protein according to (61), (67) or (72), its partial peptide or salts thereof, or a salt thereof, which is obtainable by using the method for screening according to (127) or the kit for screening according to (128);

(130) A compound that inhibits expression of the protein according to (61), (67) or (72), its partial peptide or salts thereof, or a salt thereof, which is obtainable by using the method for screening according to (127) or the kit for screening according to (128);

(131) A medicine, which comprises the compound according to (129), or a salt thereof;

(132) A medicine, which comprises the compound according to (130), or a salt thereof;

(133) The medicine according to (131), which is a prophylactic/therapeutic agent for obesity;

(134) The medicine according to (132), which is a prophylactic/therapeutic agent for cancer;

(135) The medicine according to (132), which is a feeding enhancer;

(136) A transgenic non-human mammal, which has the exogenous polynucleotide according to (64), (70) or (75), or a mutated DNA thereof;

(137) The mammal according to (136), wherein the non-human mammal is a rodent;

(138) The mammal according to (137), wherein the rodent is a mouse or a rat;

(139) A recombinant vector, which contains the exogenous polynucleotide according to (64), (70) or (75), or a mutated DNA thereof and can be expressed in the non-human mammal;

(140) A method for screening a compound having an effect on diseases caused by deletion and damage of the polynucleotide according to (64), (70) or (75), or a salt thereof, which comprises using the mammal according to (136);

(141) A protein containing an amino acid sequence, wherein one amino acid is inserted into the position adjacent to 160 Glu in the amino acid sequence represented by SEQ ID NO: 1, SEQ ID NO: 3, SEQ ID NO: 63, SEQ ID NO: 65, SEQ ID NO: 95, SEQ ID NO: 97, SEQ ID NO: 102, SEQ ID NO: 104, SEQ ID NO: 77, SEQ ID NO: 85, SEQ ID NO: 87, SEQ ID NO: 89 or SEQ ID NO: 75, or a salt thereof;

(142) The protein or its salt according to (141), wherein one amino acid is alanine;

(143) A partial peptide of the protein according to (141), or a salt thereof;

(144) A polynucleotide, which contains the polynucleotide encoding the protein according to (141) or (142), or a partial peptide thereof;

(145) A prophylactic/therapeutic agent for cancer, which comprises the protein according to (141), its partial peptide or salts thereof;

(146) The prophylactic/therapeutic agent according to (145), which comprises the protein consisting of the amino acid sequence represented by SEQ ID NO: 83, SEQ ID NO: 91 or SEQ ID NO: 93, its partial peptide or salts thereof;

(147) A prophylactic/therapeutic agent for cancer, which comprises the polynucleotide according to (144);

(148) A method for prevention and/or treatment of obesity, which comprises administering an effective dose of the compound or its salt according to (54) to mammal;

(149) A method for prevention and/or treatment of cancer, which comprises administering an effective dose of the compound or its salt according to (55) to mammal;

(150) Use of the compound according to (54), or a salt thereof for manufacturing the prophylactic/therapeutic agent for obesity;

(151) Use of the compound according to (55), or a salt thereof for manufacturing the prophylactic/therapeutic agent for cancer;

(152) A prophylactic/therapeutic agent for obesity, which comprises the compound that enhances the activity of the polypeptide according to (1), its amide or its ester, or salts thereof, or its salt;

(153) A prophylactic/therapeutic agent for cancer, a feeding enhancer or an apoptosis inducing agent, which comprises the compound that inhibits the activity of the polypeptide according to (1), its amide or its ester, or salts thereof, or its salt;

(154) An apoptosis inducing agent, which comprises (i) a polynucleotide having a complement or substantially complement base sequence to a polynucleotide containing the polynucleotide encoding the protein containing the same or substantially the same amino acid sequence as that represented by SEQ ID NO: 1 or SEQ ID NO: 3, the protein containing the same or substantially the same amino acid sequence as that represented by SEQ ID NO: 51, SEQ ID NO: 55 or SEQ ID NO: 69, partial peptides or salts thereof, or a portion thereof, (ii) an antibody against the above protein, its partial peptide or salts thereof, (iii) The protein according to (141), its partial peptide or salts thereof, or (iv) the polynucleotide according to (144);

(155) The medicine according to (20), (27), (57), (89) or (99), which is an apoptosis inducing agent.

The present invention further provides the following features:

(I) The polypeptide, its amide or its ester, or salts thereof according to (2), wherein substantially the same amino acid sequence as the amino acid sequence represented by SEQ ID NO: 22, SEQ ID NO: 14 or SEQ ID NO: 31 is an amino acid sequence having homology of at least about 50%, preferably at least about 60%, further preferably at least about 70%, more preferably at least about 80%, furthermore preferably at least about 90%, most preferably at least about 95% to the amino acid sequence represented by SEQ ID NO: 22, SEQ ID NO: 14 or SEQ ID NO: 31;

(II) The polypeptide, its amide or its ester, or salts thereof according to (2), wherein substantially the same amino acid sequence as the amino acid sequence represented by SEQ ID NO: 22, SEQ ID NO: 14 or SEQ ID NO: 31 is (i) an amino acid sequence wherein 1 to 5 (preferably 1 to 3, further preferably 1 to 2, more preferably 1) amino acids are deleted in the amino acid sequence represented by SEQ ID NO: 22, SEQ ID NO: 14 or SEQ ID NO: 31, (ii) an amino acid sequence wherein 1 to 5 (preferably 1 to 3, further preferably 1 to 2, more preferably 1) amino acids are added to the amino acid sequence represented by SEQ ID NO: 22, SEQ ID NO: 14 or SEQ ID NO: 31, (iii) an amino acid sequence wherein 1 to 5 (preferably 1 to 3, further preferably 1 to 2, more preferably 1) amino acids are inserted into the amino acid sequence represented by SEQ ID NO: 22, SEQ ID NO: 14 or SEQ ID NO: 31, (iv) an amino acid sequence wherein 1 to 5 (preferably 1 to 3, further preferably 1 to 2, more preferably 1) amino acids in the amino acid sequence represented by SEQ ID NO: 22, SEQ ID NO: 14 or SEQ ID NO: 31 are substituted with other amino acids, or (v) an amino acid sequence in combination thereof;

(III) A polynucleotide, which hybridizes on the high stringent conditions to the polynucleotide according to (7);

(IV) A polynucleotide, which hybridizes on the high stringent conditions to the polynucleotide according to (63), (69) or (74).

BRIEF DESCRIPTION OF THE DRAWINGS

FIG. 3 shows the amino acid sequence of TGR23-1 (SEQ ID NO: 1) by one letter code.

FIG. 4 shows the amino acid sequence of TGR23-2 (SEQ ID NO: 3) by one letter code.

BEST MODE FOR CARRYING OUT THE INVENTION

Figure 1:
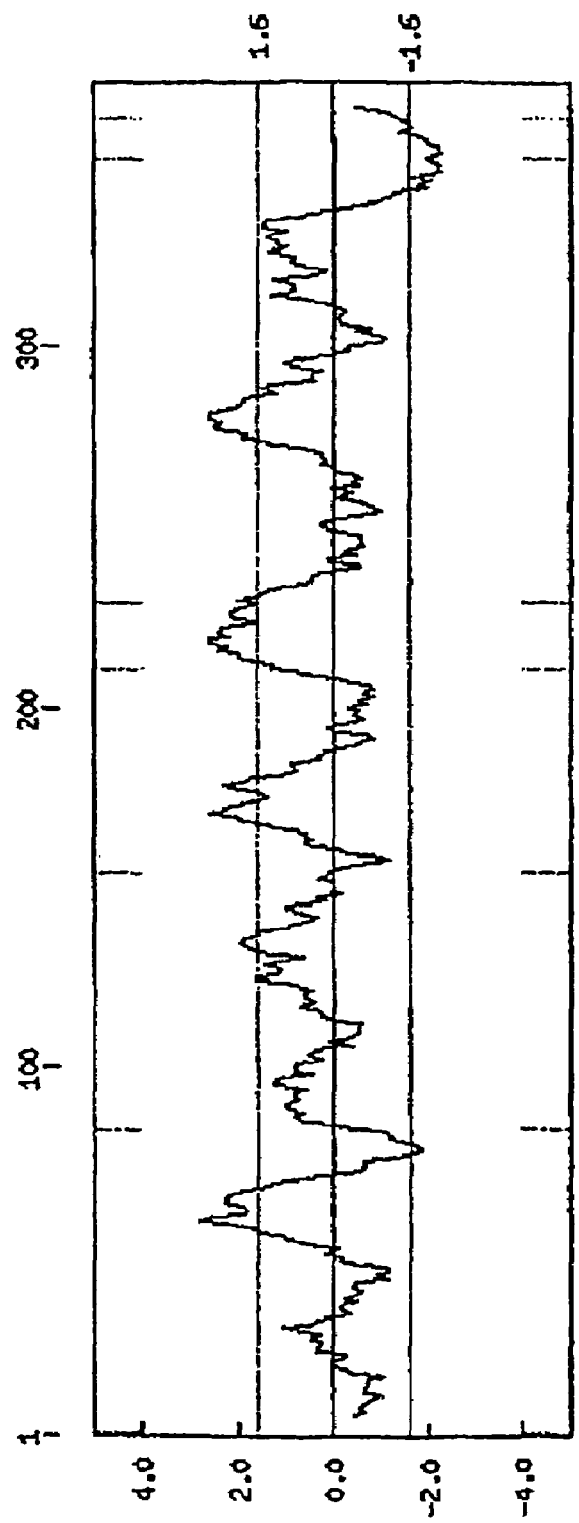
FIG. 1 shows a hydrophobic plot of TGR23-1.

Examples of "A polypeptide having an ability to bind the G protein-coupled receptor protein characterized by containing the same or substantially the same amino acid sequence as that represented by SEQ ID NO: 1 or SEQ ID NO: 3 or its salt, its amide or its ester or salts thereof" of the present invention include a polypeptide, its amide or its ester, or salts thereof, wherein dissociation constant for binding to a polypeptide having an ability to bind the G protein-coupled receptor protein containing the same or substantially the same amino acid sequence as that represented by SEQ ID NO: 1 or SEQ ID NO: 3 or its salt, its amide or its ester or salts thereof, is less than or equal to 1 nM, preferably less than or equal to 200 pM, further preferably less than or equal to 100 pM, especially preferably less than or equal to 80 pM, or most preferably less than or equal to 50 pM.

The polypeptide of the present invention containing the same or substantially the same amino acid sequence as that represented by SEQ ID NO: 22, SEQ ID NO: 14 or SEQ ID NO: 31 (hereinafter, sometimes referred to as the receptor of the present invention) may be any peptide derived from any cell of human or warm-blooded animals (e.g., guinea pig, rat, mouse, fowl, rabbit, swine, sheep, bovine, monkey, etc.) (e.g., retinal cells, splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophages, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or the corresponding precursor cells, stem cells, cancer cells, etc.); or any tissues where such cells are present, such as brain or any of brain regions (e.g., retina, olfactory bulb, amygdaloid nucleus, basal ganglia, hippocampus, thalamus, hypothalamus, cerebral cortex, medulla oblongata, cerebellum), spinal cord, pituitary gland, stomach, pancreas, kidneys, liver, gonads, thyroid gland, gallbladder, bone marrow, adrenal glands, skin, muscle, lung, digestive tracts (e.g., large intestine, small intestine), vascular vessels, heart, thymus, spleen, submandibular gland, peripheral blood, prostate, testicles, ovaries, placenta, uterus, bones, joints, skeletal muscles, etc., or blood cells or cultured cells thereof (e.g., MEL, M1, CTLL-2, HT-2, WEHI-3, HL-60, JOSK-1, K562, ML-1, MOLT-3, MOLT4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01). The peptide may also be a synthetic peptide.

Examples of substantially the same amino acid sequence as that represented by SEQ ID NO: 22 include an amino acid sequence having at least about 50%, preferably at least about 60%, further preferably at least about 70%, furthermore preferably at least about 80%, more preferably at least about 90%, most preferably at least about 95% homology to the amino acid sequence represented by SEQ ID NO: 22.

Substantially the same amino acid sequence as that represented by SEQ ID NO: 22 includes (i) the amino acid sequence shown by SEQ ID NO: 22, wherein 1 to 5 (preferably 1 to 3, further preferably 1 to 2, more preferably one) amino acids are deleted, (ii) the amino acid sequence shown by SEQ ID NO: 22, wherein 1 to 5 (preferably 1 to 3, further preferably 1 to 2, more preferably one) amino acids are added; (iii) the amino acid sequence shown by SEQ ID NO: 22, wherein 1 to 5 (preferably 1 to 3, further preferably 1 to 2, more preferably one) amino acids are inserted; or (iv) the amino acid sequence shown by SEQ ID NO: 22, wherein 1 to 5 (preferably 1 to 3, further preferably 1 to 2, more preferably one) amino acids are substituted to other amino acids; and (v) the amino acid sequence containing a combination of these amino acid sequences.

Example of the polypeptide containing substantially the same amino acid sequence as that represented by SEQ ID NO: 22 is preferred to a polypeptide containing substantially the same amino acid sequence as that represented by SEQ ID NO: 22 and having substantially equivalent activity to that of the polypeptide containing the amino acid sequence represented by SEQ ID NO: 22.

The substantially equivalent activity refers to, for example, activities, which the polypeptide of the present invention possesses, such as preventive/therapeutic activity of diseases later described, binding activity to the receptor, cell stimulating activity on receptor expressing cells (e.g., activities that enhance arachidonic acid release, acetylcholine release, intracellular Ca$^{2+}$ release, intracellular cAMP production, suppression of intracellular cAMP production, intracellular cGMP production, inositolphosphate production, cell membrane potential changes, phosphorylation of intracellular protein, activation of c-fos, reduction of pH, GTPγS binding activity, activation of cAMP-dependent protein kinase, activation of cGMP-dependent protein kinase, activation of phopholipids-dependent protein kinase, or activation of microtubule associated protein phosphorylation enzyme (MAP kinase)), feeding suppression activity, carcinoma growth activity, etc. The term "substantially equivalent" is used to mean that these activities are equivalent in nature (e.g., physiologically or pharmacologically).

Specific examples of substantially the same amino acid sequence as that represented by SEQ ID NO: 22 include the amino acid sequence represented by SEQ ID NO: 20, SEQ ID NO: 21, SEQ ID NO: 23, SEQ ID NO: 49 or SEQ ID NO: 62, and the like.

Examples of substantially the same amino acid sequence as that represented by SEQ ID NO: 14 include an amino acid sequence having at least about 50%, preferably at least about 60%, further preferably at least about 70%, furthermore preferably at least about 80%, more preferably at least about 90%, most preferably at least about 95% homology to the amino acid sequence represented by SEQ ID NO: 14.

Substantially the same amino acid sequence as that represented by SEQ ID NO: 14 is preferred to (i) the amino acid sequence shown by SEQ ID NO: 14, wherein 1 to 5 (preferably 1 to 3, further preferably 1 to 2, more preferably one) amino acids are deleted, (ii) the amino acid sequence shown by SEQ ID NO: 14, wherein 1 to 5 (preferably 1 to 3, further preferably 1 to 2, more preferably one) amino acids are added; (iii) the amino acid sequence shown by SEQ ID NO: 14, wherein 1 to 5 (preferably 1 to 3, further preferably 1 to 2, more preferably one) amino acids are inserted; or (iv) the amino acid sequence shown by SEQ ID NO: 14, wherein 1 to 5 (preferably 1 to 3, further preferably 1 to 2, more preferably one) amino acids are substituted to other amino acids; and (v) the amino acid sequence containing a combination of these amino acid sequences.

Example of the polypeptide containing substantially the same amino acid sequence as that represented by SEQ ID NO: 14 is preferred to a polypeptide containing substantially the same amino acid sequence as that represented by SEQ ID NO: 14 and having substantially equivalent activity to that of the polypeptide containing the amino acid sequence represented by SEQ ID NO: 14.

The substantially equivalent activity refers to, for example, activities, which the polypeptide of the present invention possesses, such as preventive/therapeutic activity of diseases later described, binding activity to the receptor, cell stimulating activity on receptor expressing cells (e.g., activities that enhance arachidonic acid release, acetylcholine release, intracellular $Ca^{2+}$ release, intracellular cAMP production, suppression of intracellular cAMP production, intracellular cGMP production, inositolphosphate production, cell membrane potential changes, phosphorylation of intracellular protein, activation of c-fos, reduction of pH, GTPγS binding activity, activation of cAMP-dependent protein kinase, activation of cGMP-dependent protein kinase, activation of phopholipids-dependent protein kinase, or activation of microtubule associated protein phosphorylation enzyme (MAP kinase)), feeding suppression activity, carcinoma growth activity, etc. The term "substantially equivalent" is used to mean that these activities are equivalent in nature (e.g., physiologically or pharmacologically).

Specific examples of substantially the same amino acid sequence as that represented by SEQ ID NO: 14 include the amino acid sequence represented by SEQ ID NO: 12, SEQ ID NO: 13 or SEQ ID NO: 36, and the like.

Examples of substantially the same amino acid sequence as that represented by SEQ ID NO: 31 include an amino acid sequence having at least about 50%, preferably at least about 60%, further preferably at least about 70%, furthermore preferably at least about 80%, more preferably at least about 90%, most preferably at least about 95% homology to the amino acid sequence represented by SEQ ID NO: 31.

Substantially the same amino acid sequence as that represented by SEQ ID NO: 31 is preferred to (i) the amino acid sequence shown by SEQ ID NO: 31, wherein 1 to 5 (preferably 1 to 3, further preferably 1 to 2, more preferably one) amino acids are deleted, (ii) the amino acid sequence shown by SEQ ID NO: 31, wherein 1 to 5 (preferably 1 to 3, further preferably 1 to 2, more preferably one) amino acids are added; (iii) the amino acid sequence shown by SEQ ID NO: 31, wherein 1 to 5 (preferably 1 to 3, further preferably 1 to 2, more preferably one) amino acids are inserted; or (iv) the amino acid sequence shown by SEQ ID NO: 31, wherein 1 to 5 (preferably 1 to 3, further preferably 1 to 2, more preferably one) amino acids are substituted to other amino acids; and (v) the amino acid sequence containing a combination of these amino acid sequences.

Example of the polypeptide containing substantially the same amino acid sequence as that represented by SEQ ID NO: 31 is preferred to a polypeptide containing substantially the same amino acid sequence as that represented by SEQ ID NO: 31 and having substantially equivalent activity to that of the polypeptide containing the amino acid sequence represented by SEQ ID NO: 31.

The substantially equivalent activity refers to, for example, activities, which the polypeptide of the present invention possesses, such as preventive/therapeutic activity of diseases later described, binding activity to the receptor, cell stimulating activity on receptor expressing cells (e.g., activities that enhance arachidonic acid release, acetylcholine release, intracellular $Ca^{2+}$ release, intracellular cAMP production, suppression of intracellular cAMP production, intracellular cGMP production, inositolphosphate production, cell membrane potential changes, phosphorylation of intracellular protein, activation of c-fos, reduction of pH, GTPγS binding activity, activation of cAMP-dependent protein kinase, activation of cGMP-dependent protein kinase, activation of phopholipids-dependent protein kinase, or activation of microtubule associated protein phosphorylation enzyme (MAP kinase)), feeding suppression activity, carcinoma growth activity, etc. The term "substantially equivalent" is used to mean that these activities are equivalent in nature (e.g., physiologically or pharmacologically).

Specific examples of substantially the same amino acid sequence as that represented by SEQ ID NO: 31 include the amino acid sequence represented by SEQ ID NO: 29, SEQ ID NO: 30 or SEQ ID NO: 32, and the like.

Specific examples of the polypeptide of the present invention include a polypeptide having an ability of binding specific to the receptor of the present invention, such as a polypeptide containing the amino acid sequence represented by SEQ ID NO: 22, a polypeptide containing the amino acid sequence represented by SEQ ID NO: 20, a polypeptide containing the amino acid sequence represented by SEQ ID NO: 21, a polypeptide containing the amino acid sequence represented by SEQ ID NO: 23, a polypeptide containing the amino acid sequence represented by SEQ ID NO: 49, a polypeptide containing the amino acid sequence represented by SEQ ID NO: 62, a polypeptide containing the amino acid sequence represented by SEQ ID NO: 14, a polypeptide containing the amino acid sequence represented by SEQ ID NO: 12, a polypeptide containing the amino acid sequence represented by SEQ ID NO: 13, a polypeptide containing the amino acid sequence represented by SEQ ID NO: 36, a polypeptide containing the amino acid sequence represented by SEQ ID NO: 31, a polypeptide containing the amino acid sequence represented by SEQ ID NO: 29, a polypeptide containing the amino acid sequence represented by SEQ ID NO: 30, a polypeptide containing the amino acid sequence represented by SEQ ID NO: 32.

Further, the polypeptide of the present invention encompasses not only a polypeptide having a binding activity to the receptor of the present invention later described, a cell-stimulating activity to the cells, which express the receptor of the present invention (e.g., activity that enhances arachidonic acid release, acetylcholine release, intracellular $Ca^{2+}$ release, intracellular cAMP production, suppression of intracellular cAMP production, intracellular cGMP production, inositol phosphate production, changes in cell membrane potential, phosphorylation of intracellular proteins, activation of c-fos, pH reduction, GTPγS binding activity, activation of cAMP dependent protein kinase, activation of cGMP dependent protein kinase, activation of phospholipids dependent protein kinase or activation of microtubule binding protein phosphorylase, etc.) and the like, but a precursor polypeptide of the polypeptide having the binding activity or the cell-stimulating activity.

Specific examples of the precursor polypeptide of the polypeptide having the binding activity or the cell-stimulating activity include (i) a polypeptide containing the same or substantially the same amino acid sequence as that represented by SEQ ID NO: 19, (ii) a polypeptide containing the same or substantially the same amino acid sequence as that represented by SEQ ID NO: 28, (iii) a polypeptide containing the same or substantially the same amino acid sequence as that represented by SEQ ID NO: 61.

Specifically, it includes (i) for substantially the same amino acid sequence as that represented by SEQ ID NO: 19, an amino acid sequence having at least about 50%, preferably at least about 60%, further preferably at least about 70%, furthermore preferably at least about 80%, more preferably at least about 90%, and most preferably at least about 95% homology to the amino acid sequence represented by SEQ ID NO: 19, (ii) for substantially the same amino acid sequence as that represented by SEQ ID NO: 28, an amino acid sequence having at least about 50%, preferably at least about 60%, further preferably at least about 70%, furthermore preferably at least about 80%, more preferably at least about 90%, and most preferably at least about 95% homology to the amino acid sequence represented by SEQ ID NO: 28, (iii) for substantially the same amino acid sequence as that represented by SEQ ID NO: 61, an amino acid sequence having at least about 50%, preferably at least about 60%, further preferably at least about 70%, furthermore preferably at least about 80%, more preferably at least about 90%, and most preferably at least about 95% homology to the amino acid sequence represented by SEQ ID NO: 61.

The amino acid sequence which has substantially the same amino acid sequence as that represented by SEQ ID NO: 19 includes (i) amino acid sequences represented by SEQ ID NO: 19, wherein 1 to 15 amino acids (preferably 1 to 10 amino acids, further preferably 1 to 5 amino acids, more preferably 1 to 3 amino acids) are deleted; (ii) amino acid sequences represented by SEQ ID NO: 19, to which 1 to 15 amino acids (preferably 1 to 10 amino acids, further preferably 1 to 5 amino acids, more preferably 1 to 3 amino acids) are added; (iii) amino acid sequences represented by SEQ ID NO: 19, to which 1 to 15 amino acids (preferably 1 to 5 amino acids, further preferably 1 to 5 amino acids, more preferably 1 to 3 amino acids) are inserted; (iv) amino acid sequences represented by SEQ ID NO: 19, in which 1 to 15 amino acids (preferably 1 to 10 amino acids, more preferably approximately 1 to 5 amino acids, and most preferably 1 to 3 amino acids) are substituted by other amino acids; or (v) combination of the amino acid sequences described in the above (i) through (iv).

The amino acid sequence which has substantially the same amino acid sequence as that represented by SEQ ID NO: 28 includes (i) amino acid sequences represented by SEQ ID NO: 28, wherein 1 to 15 amino acids (preferably 1 to 10 amino acids, further preferably 1 to 5 amino acids, more preferably 1 to 3 amino acids) are deleted; (ii) amino acid sequences represented by SEQ ID NO: 28, to which 1 to 15 amino acids (preferably 1 to 10 amino acids, further preferably 1 to 5 amino acids, more preferably 1 to 3 amino acids) are added; (iii) amino acid sequences represented by SEQ ID NO: 28, to which 1 to 15 amino acids (preferably 1 to 5 amino acids, further preferably 1 to 5 amino acids, more preferably 1 to 3 amino acids) are inserted; (iv) amino acid sequences represented by SEQ ID NO: 28, in which 1 to 15 amino acids (preferably 1 to 10 amino acids, more preferably approximately 1 to 5 amino acids, and most preferably 1 to 3 amino acids) are substituted by other amino acids; or (v) combination of the amino acid sequences described in the above (i) through (iv).

The amino acid sequence which has substantially the same amino acid sequence as that represented by SEQ ID NO: 61 includes (i) amino acid sequences represented by SEQ ID NO: 61, wherein 1 to 15 amino acids (preferably 1 to 10 amino acids, further preferably 1 to 5 amino acids, more preferably 1 to 3 amino acids) are deleted; (ii) amino acid sequences represented by SEQ ID NO: 61, to which 1 to 15 amino acids (preferably 1 to 10 amino acids, further preferably 1 to 5 amino acids, more preferably 1 to 3 amino acids) are added; (iii) amino acid sequences represented by SEQ ID NO: 61, to which 1 to 15 amino acids (preferably 1 to 5 amino acids, further preferably 1 to 5 amino acids, more preferably 1 to 3 amino acids) are inserted; (iv) amino acid sequences represented by SEQ ID NO: 61, in which 1 to 15 amino acids (preferably 1 to 10 amino acids, more preferably approximately 1 to 5 amino acids, and most preferably 1 to 3 amino acids) are substituted by other amino acids; or (v) combination of the amino acid sequences described in the above (i) through (iv).

Specific examples of the above-mentioned precursor polypeptide include a polypeptide containing the amino acid sequence represented by SEQ ID NO: 19, a polypeptide containing the amino acid sequence represented by SEQ ID NO: 28, a polypeptide containing the amino acid sequence represented by SEQ ID NO: 61, and the like.

The receptor to the polypeptide of the present invention includes, among a variety of receptors, a receptor having a binding activity to the polypeptide of the present invention, wherein the cell-stimulating activity to the receptor expressing cells (e.g., activity that enhances arachidonic acid release, acetylcholine release, intracellular $Ca^{2+}$ release, intracellular cAMP production, suppression of intracellular cAMP production, intracellular cGMP production, inositol phosphate production, changes in cell membrane potential, phosphorylation of intracellular proteins, activation of c-fos, pH reduction, GTPγS binding activity, activation of cAMP dependent protein kinase, activation of cGMP dependent protein kinase, activation of phospholipids dependent protein kinase or activation of microtubule binding protein phosphorylase, etc.) by the polypeptide of the present invention was observed. These were referred to as the receptor of the present invention.

Specific examples include a G protein-coupled receptor protein containing the same or substantially the same amino acid sequence as that represented by SEQ ID NO: 1 or SEQ ID NO: 3, or a salt thereof (FIGS. 3 and 4). The protein is a novel seven transmembrane receptor protein, wherein the protein has about 32% to 36% homology at the amino acid sequence to vasotocin receptor, methotocin receptor, isotocin receptor or oxytocin receptor. In addition, a G protein-coupled receptor protein containing the amino acid sequence represented by SEQ ID NO: 51 (WO 01/18206), a G protein-coupled receptor protein containing the amino acid sequence represented by SEQ ID NO: 53 (WO 01/48188), a G protein-coupled receptor protein containing the amino acid sequence represented by SEQ ID NO: 55 (WO 01/48015), a G protein-coupled receptor protein containing the amino acid sequence represented by SEQ ID NO: 67 (Tokkai 2001-245666), a G protein-coupled receptor protein containing the amino acid sequence represented by SEQ ID NO: 69 (WO 01/96400) are used as a receptor to the polypeptide of the present invention.

Further, a protein containing the amino acid sequence, which one amino acid (preferably Ala) is inserted just before Glu at the 160th position of the amino acid sequence represented by SEQ ID NO: 1, SEQ ID NO: 3, SEQ ID NO: 63, SEQ ID NO: 65, SEQ ID NO: 95, SEQ ID NO: 97, SEQ ID NO: 102, SEQ ID NO: 104, SEQ ID NO: 77, SEQ ID NO: 85, SEQ ID NO: 87, SEQ ID NO: 89 or SEQ ID NO: 75, or a salt thereof (hereinafter, sometimes referred to as the receptor A of the present invention), and the like are used as a receptor of the present invention.

The receptor of the present invention may be any protein derived from any cell of human or warm-blooded animals (e.g., guinea pig, rat, mouse, fowl, rabbit, swine, sheep, bovine, monkey, etc.) (e.g., retinal cells, splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophages, T cells, B cells, natural killer cells, mast cells, neutrophils, basophils, eosinophils, monocytes, leukocytes), megakaryocytes, synovial cells, chondrocytes, bone cells, osteoblasts, osteoclasts, mammary gland cells, hepatocytes or interstitial cells; or the corresponding precursor cells, stem cells, cancer cells (e.g., breast cancer cell line (GI-101), colon cancer cell lines (CX-1, GI-112, COLO 205, LoVo, COLO 201, SW 403, SNU-C1, HT-29, LS 174T, LS 180, SK-CO1) stomach cancer cell line (KATOIII), lung cancer cell lines (LX-1, GI-117), ovarian cancer cell line (GI-102), prostate cancer cell line (PC3) and the like); or any tissues where such cells are present, such as brain or any of brain regions (e.g., retina, olfactory bulb, amygdaloid nucleus, basal ganglia, hippocampus, thalamus, hypothalamus, cerebral cortex, medulla oblongata, cerebellum), spinal cord, pituitary gland, stomach, pancreas, kidneys, liver, gonads, thyroid gland, gallbladder, bone marrow, adrenal glands, skin, muscle, lung, digestive tracts (e.g., large intestine, small intestine), vascular vessels, heart, thymus, spleen, submandibular gland, peripheral blood, prostate, testicles, ovaries, placenta, uterus, bones, joints, skeletal muscles, etc., or blood cells or cultured cells thereof (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01). The peptide may also be a synthetic protein.

Examples of substantially the same amino acid sequence as that represented by SEQ ID NO: 1 or SEQ ID NO: 3 include an amino acid sequence having at least about 50%, preferably at least about 60%, further preferably at least about 70%, furthermore preferably at least about 80%, more preferably at least about 90%, most preferably at least about 95% homology to the amino acid sequence represented by SEQ ID NO: 1 or SEQ ID NO: 3. Specifically, it includes the amino acid sequence represented by SEQ ID NO: 63, SEQ ID NO: 65, SEQ ID NO: 95, SEQ ID NO: 97, SEQ ID NO: 77, SEQ ID NO: 85, SEQ ID NO: 87, SEQ ID NO: 89, SEQ ID NO: 91, SEQ ID NO: 93, SEQ ID NO: 71, SEQ ID NO: 75 or SEQ ID NO: 83.

Examples of substantially the same amino acid sequence as that represented by SEQ ID NO: 1 or SEQ ID NO: 3 include (1) (i) the amino acid sequence shown by SEQ ID NO: 1 or SEQ ID NO: 3, wherein 1 to 15 (preferably 1 to 10, further preferably 1 to 5, more preferably 1 to 3) amino acids are deleted, (ii) the amino acid sequence shown by SEQ ID NO: 1 or SEQ ID NO: 3, wherein 1 to 15 (preferably 1 to 10, further preferably 1 to 5, more preferably 1 to 3) amino acids are added; (iii) the amino acid sequence shown by SEQ ID NO: 1 or SEQ ID NO: 3, wherein 1 to 15 (preferably 1 to 10, further preferably 1 to 5, more preferably 1 to 3) amino acids are inserted; (iv) the amino acid sequence shown by SEQ ID NO: 1 or SEQ ID NO: 3, wherein 1 to 15 (preferably 1 to 10, further preferably 1 to 5, more preferably 1 to 3) amino acids are substituted to other amino acids; and (v) the amino acid sequence containing a combination of these amino acid sequences, and (2) (i) the amino acid sequence shown by SEQ ID NO: 63 or SEQ ID NO: 65, wherein 1 to 15 (preferably 1 to 10, further preferably 1 to 5, more preferably 1 to 3) amino acids are deleted, (ii) the amino acid sequence shown by SEQ ID NO: 63 or SEQ ID NO: 65, wherein 1 to 15 (preferably 1 to 10, further preferably 1 to 5, more preferably 1 to 3) amino acids are added; (iii) the amino acid sequence shown by SEQ ID NO: 63 or SEQ ID NO: 65, wherein 1 to 15 (preferably 1 to 10, further preferably 1 to 5, more preferably 1 to 3) amino acids are inserted; (iv) the amino acid sequence shown by SEQ ID NO: 63 or SEQ ID NO: 65, wherein 1 to 15 (preferably 1 to 10, further preferably 1 to 5, more preferably 1 to 3) amino acids are substituted to other amino acids; and (v) the amino acid sequence containing a combination of these amino acid sequences.

Example of the protein containing substantially the same amino acid sequence as that represented by SEQ ID NO: 1 or SEQ ID NO: 3 is preferred to a polypeptide containing substantially the same amino acid sequence as that represented by SEQ ID NO: 1 or SEQ ID NO: 3 and having substantially equivalent activity to that of the polypeptide containing the amino acid sequence represented by SEQ ID NO: 1 or SEQ ID NO: 3.

As the substantially equivalent activity, there are, for example, a ligand binding activity, a signal transduction activity, and the like. The term substantially equivalent is used to mean that these activities are equivalent in nature to one another. It is thus preferred that the activity such as a ligand binding activity or a signal transduction activity is equivalent (e.g., approximately 0.01 to 100 times, preferably about 0.5 to 20 times, more preferably about 0.5 to 2 times), but quantitative factors such as the degree of these activities, a molecular weight of protein, etc. may be different from each other. The activities such as a ligand binding activity, a signal transduction activity, etc. may be determined by modifications of publicly known methods.

Specific examples of the receptor protein of the present invention include (i) a protein containing the amino acid sequence represented by SEQ ID NO: 1, (ii) a protein containing the amino acid sequence represented by SEQ ID NO: 3, (iii) a protein containing the amino acid sequence represented by SEQ ID NO: 63, (iv) a protein containing the amino acid sequence represented by SEQ ID NO: 65, (v) a protein containing the amino acid sequence represented by SEQ ID NO: 51, (vi) a protein containing the amino acid sequence represented by SEQ ID NO: 55, (vii) a protein containing the amino acid sequence represented by SEQ ID NO: 69, (viii) a protein containing the amino acid sequence represented by SEQ ID NO: 95, (ix) a protein containing the amino acid sequence represented by SEQ ID NO: 97, (x) a protein containing the amino acid sequence represented by SEQ ID NO: 77, (xi) a protein containing the amino acid sequence represented by SEQ ID NO: 85, (xii) a protein containing the amino acid sequence represented by SEQ ID NO: 87, (xiii) a protein containing the amino acid sequence represented by SEQ ID NO: 89, (xiv) a protein containing the amino acid sequence represented by SEQ ID NO: 91, (xv) a protein containing the amino acid sequence represented by SEQ ID NO: 93, (xvi) a protein containing the amino acid sequence represented by SEQ ID NO: 71, (xvii) a protein containing the amino acid sequence represented by SEQ ID NO: 75, (xviii) a protein containing the amino acid sequence represented by SEQ ID NO: 83, (xix) a protein containing the amino acid sequence represented by SEQ ID NO: 102, and (xx) a protein containing the amino acid sequence represented by SEQ ID NO: 104.

The partial peptides of the receptor of the present invention (hereinafter, sometimes referred to as the partial peptide of the present invention) may be any partial peptides so long as they can be employed for the screening methods for medicines, etc., which will be later described. Preferably, a partial peptide having a binding ability to the polypeptide of the present invention, a partial peptide containing the amino acid sequence corresponding to the extracellular region and the like are used.

Specifically, examples include a partial peptide containing one or at least two partial amino acid sequences selected from the partial amino acid sequence represented by the sequence from the 50th (Thr) to the 335th (Ser) in the amino acid sequence represented by SEQ ID NO: 1 or SEQ ID NO: 3.

The polypeptides, the receptor and the partial peptide of the present invention are represented in accordance with the conventional way of describing peptides, that is, the N-terminus (amino terminus) at the left hand and the C-terminus (carboxyl terminus) at the right hand. In the polypeptides, the receptor and the partial peptide of the present invention, the C-terminus may be in the form of a carboxyl group (—COOH), a carboxylate (—COO$^-$), an amide (—CONH$_2$) or an ester (—COOR).

Herein, examples of the ester group represented by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; and the like. In addition, pivaloyloxymethyl or the like, which is used widely as an ester for oral administration, may also be used.

Where the polypeptides, the receptor and the partial peptide of the present invention contain a carboxyl group (or a carboxylate) at a position other than the C-terminus, it may be amidated or esterified and such an amide or ester is also included within the peptide/protein of the invention. The ester group in this case may be the same ester group as that described with respect to the above C-terminal group, etc.

Furthermore, examples of the polypeptides, the receptor and the partial peptide of the present invention include variants of the polypeptides, the receptor and the partial peptide of the present invention described above, wherein the amino group of amino acid residue (e.g., methionine residue) at the N-terminus is protected with a protecting group (e.g., a $C_{1-6}$ acyl group such as a $C_{1-6}$ alkanoyl group, e.g., formyl group, acetyl group, etc.), those wherein the N-terminal region is cleaved in vivo and the glutamyl group thus formed is pyroglutaminated, those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), conjugated proteins such as glycoproteins having sugar chains; and the like.

As the salts of the polypeptides, the receptor and the partial peptide of the present invention, a salt with physiologically acceptable acid (e.g., inorganic acid, organic acid) or base (e.g., alkali metal salt) is used, particularly preferred is physiologically acceptable acid addition salt. Examples of such salts are salts with, for example, inorganic acids (e.g., hydrochloric acid, phosphoric acid, hydrobromic acid or sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid or benzenesulfonic acid), and the like.

The polypeptides, the receptor and the partial peptide of the present invention may be labeled by the publicly known methods. Specific examples include isotope labeling, fluorescence labeling (e.g., fluorescence labeling with fluorescein), biotinylation or enzyme labeling.

The polypeptides, the receptor and the partial peptide of the present invention may be manufactured by publicly known methods used to purify polypeptides from the human or mammal cells or tissues described above, or may also be manufactured by culturing transformants containing DNAs encoding polypeptide later described. Alternatively, the polypeptides, the receptor and the partial peptide of the present invention may also be manufactured by the peptide synthesis methods later described or by its modification.

Where the polypeptides, the receptor and the partial peptide of the present invention are manufactured from human or mammalian tissues or cells, the human or mammalian tissues or cells are homogenized, then the polypeptides, the receptor and the partial peptide are extracted with an acid, etc., isolated and purified from the extract obtained by a combination of chromatography techniques such as reversed phase chromatography, ion exchange chromatography, and the like.

To synthesize the polypeptides, the receptor and the partial peptide of the present invention (including amides or salts thereof), commercially available resins that are normally used for the polypeptide synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective polypeptide according to various condensation methods publicly known. At the end of the reaction, the polypeptide is excised from the resin and at the same time, the protecting groups are removed. Then, intramolecular disulfide bond-forming reaction is performed in a highly diluted solution to obtain the objective polypeptide, receptor, partial peptide or amides thereof.

For condensation of the protected amino acids described above, a variety of activation reagents available for the polypeptide synthesis may be used, and carbodiimides are particularly preferably employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents used to activate the protected amino acids or condense with the resin may be chosen from solvents that are known to be usable for polypeptide condensation reactions. For example, there may be employed acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxan, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, by acetylation of unreacted amino acids with acetic anhydride or acetylimidazole, it is made possible to have no effect on the following steps.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group and ethoxycarbonyl group. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting amino acids include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)]. As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia, etc.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the polypeptide, the receptor or the partial peptide of the present invention, for example, the α-carboxyl group of the carboxy terminal amino acid is first protected by amidation; the peptide (polypeptide) chain is then extended to amino group for a desired length. Thereafter, a polypeptide in which only the protecting group of the N-terminal α-amino group has been eliminated from the peptide chain and a polypeptide in which only the protecting group of the C-terminal carboxyl group has been eliminated are manufactured. The two polypeptides are condensed in a mixture of the solvents described above. The details of the condensation reaction are the same as described above. After the protected polypeptide obtained by the condensation is purified, all the protecting groups are eliminated by the method described above to give the desired crude polypeptide. This crude polypeptide is purified by various known purification means. Lyophilization of the major fraction gives the amide of the desired polypeptide, receptor or partial peptide.

To prepare the esterified polypeptide, receptor or partial peptide of the present invention, for example, the α-carboxyl group of the carboxy terminal amino acid is condensed with a desired alcohol to prepare the amino acid ester, which is followed by procedure similar to the preparation of the amidated polypeptide, receptor or partial peptide above to give the desired esterified polypeptide, receptor or partial peptide.

The polypeptide, the receptor or the partial peptide of the invention can be manufactured by publicly known methods for peptide synthesis. Also, the partial peptides of the receptor can be manufactured by cleaving the receptor with an appropriate peptidase. For the methods of peptide synthesis, for example, either solid phase synthesis or liquid phase synthesis may be used. That is, the partial peptide or amino acids that can constitute the polypeptide, the receptor or the partial peptide of the present invention can be condensed with the remaining part of the partial peptide. Where the product contains protecting groups, these protecting groups are removed to give the desired peptide. Publicly known methods for condensation and elimination of the protecting groups are described in (i) to (v) below:

(i) M. Bodanszky & M. A. Ondetti: Peptide Synthesis, Interscience Publishers, New York (1966);
(ii) Schroeder & Luebke: The Peptide, Academic Press, New York (1965);
(iii) Nobuo Izumiya, et al.: *Peptide Gosei-no-Kiso to Jikken* (Basics and experiments of peptide synthesis), published by Maruzen Co. (1975);
(iv) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977); and
(v) Haruaki Yajima ed.: *Zoku Jyakuhin no Kaihatsu* (A sequel to Development of Pharmaceuticals), Vol. 14, Peptide Synthesis, published by Hirokawa Shoten.

After completion of the reaction, the polypeptide, the receptor of the invention or the partial peptide thereof can be purified and isolated by a combination of conventional purification methods such as solvent extraction, distillation, column chromatography, liquid chromatography and recrystallization. When the polypeptide, receptor or partial peptide obtained by the above methods is in a free form, the polypeptide, receptor or partial peptide can be converted into an appropriate salt by a publicly known method or modified thereof; when the polypeptide, receptor or partial peptide is obtained in a salt form, it can be converted into a free form by a publicly known method or modified thereof.

The polynucleotide encoding the polypeptide, the receptor or the partial peptide of the invention may be any polynucleotide, so long as it contains the base sequence encoding the polypeptide, the receptor or the partial peptide of the invention described above (DNA or RNA, preferably DNA). Such a polynucleotide may be DNA encoding the polypeptide, the receptor or the partial peptide of the present invention, or RNA such as mRNA. It may be either double-stranded or single-stranded. In the case of double strands, double-stranded DNA, double-stranded RNA or DNA:RNA hybrid may be included. In the case of single strand, it may be either sense strand (i.e., coding strand) or antisense strand (i.e., non-coding strand). Such a DNA may be any one of genomic DNA, genomic DNA library, cDNA derived from the cells or tissues described above, cDNA library derived from the cells or tissues described above and synthetic DNA.

The vector to be used for the library may be any of bacteriophage, plasmid, cosmid, phagemid, and the like. In addition, the DNA can directly be amplified by RT-PCR with total RNA or mRNA fraction prepared from the cells or tissues described above.

The polynucleotide encoding the polypeptide of the present invention may be any one of (i) a polynucleotide containing the base sequence represented by SEQ ID NO: 41, SEQ ID NO: 42, SEQ ID NO: 43, SEQ ID NO: 44, SEQ ID NO: 37, SEQ ID NO: 38, SEQ ID NO: 39, SEQ ID NO: 40, SEQ ID NO: 45, SEQ ID NO: 46, SEQ ID NO: 47, SEQ ID NO: 48 or SEQ ID NO: 50, (ii) a polynucleotide having a base sequence, which hybridizes under high stringent conditions to the base sequence represented by SEQ ID NO: 41, SEQ ID NO: 42, SEQ ID NO: 43, SEQ ID NO: 44, SEQ ID NO: 37, SEQ ID NO: 38, SEQ ID NO: 39, SEQ ID NO: 40, SEQ ID NO: 45, SEQ ID NO: 46, SEQ ID NO: 47, SEQ ID NO: 48 or SEQ ID NO: 50, and encoding a polypeptide having substantially equivalent activity to that of the polypeptide of the present invention, (iii) a polynucleotide containing the base sequence represented by SEQ ID NO: 18, SEQ ID NO: 27 or SEQ ID NO: 60, or (iv) a polynucleotide having a base sequence, which hybridizes under high stringent conditions to the base sequence represented by SEQ ID NO: 18, SEQ ID NO: 27 or SEQ ID NO: 60.

Examples of the polynucleotide that is hybridizable under high stringent conditions to the base sequence represented by SEQ ID NO: 41, SEQ ID NO: 42, SEQ ID NO: 43, SEQ ID NO: 44, SEQ ID NO: 37, SEQ ID NO: 38, SEQ ID NO: 39, SEQ ID NO: 40, SEQ ID NO: 45, SEQ ID NO: 46, SEQ ID NO: 47, SEQ ID NO: 48 or SEQ ID NO: 50 include a polynucleotide containing the base sequence having at least about 70% homology, preferably at least about 80% homology, further preferably at least about 90% and more preferably at least about 95% homology, to the base sequence represented by SEQ ID NO: 41, SEQ ID NO: 42, SEQ ID NO: 43, SEQ ID NO: 44, SEQ ID NO: 37, SEQ ID NO: 38, SEQ ID NO: 39, SEQ ID NO: 40, SEQ ID NO: 45, SEQ ID NO: 46, SEQ ID NO: 47, SEQ ID NO: 48 or SEQ ID NO: 50.

Examples of the polynucleotide that is hybridizable under high stringent conditions to the base sequence represented by SEQ ID NO: 18, SEQ ID NO: 27 or SEQ ID NO: 60 include a polynucleotide containing the base sequence having at least about 70% homology, preferably at least about 80% homology, further preferably at least about 90% and more preferably at least about 95% homology, to the base sequence represented by SEQ ID NO: 18, SEQ ID NO: 27 or SEQ ID NO: 60.

The hybridization can be carried out by publicly known methods or by a modification thereof, for example, according to the method described in Molecular Cloning, 2nd. (J. Sambrook et al., Cold Spring Harbor Lab. Press, 1989), etc. When a commercially available library is used, hybridization may be carried out according to the instructions of the attached manufacturer's protocol. More preferably, the hybridization can be carried out under high stringent conditions.

The high stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration at about 19 mM at a temperature of about 65° C. are most preferred.

Specifically, (i) the polynucleotide encoding the polypeptide containing the amino acid sequence represented by SEQ ID NO: 20 includes a polynucleotide containing the base sequence represented by SEQ ID NO: 41; (ii) the polynucleotide encoding the polypeptide containing the amino acid sequence represented by SEQ ID NO: 21 includes a polynucleotide containing the base sequence represented by SEQ ID NO: 42; (iii) the polynucleotide encoding the polypeptide containing the amino acid sequence represented by SEQ ID NO: 22 includes a polynucleotide containing the base sequence represented by SEQ ID NO: 43; (iv) the polynucleotide encoding the polypeptide containing the amino acid sequence represented by SEQ ID NO: 23 includes a polynucleotide containing the base sequence represented by SEQ ID NO: 44; (v) the polynucleotide encoding the polypeptide containing the amino acid sequence represented by SEQ ID NO: 49 includes a polynucleotide containing the base sequence represented by SEQ ID NO: 50; (vi) the polynucleotide encoding the polypeptide containing the amino acid sequence represented by SEQ ID NO: 12 includes a polynucleotide containing the base sequence represented by SEQ ID NO: 37; (vii) the polynucleotide encoding the polypeptide containing the amino acid sequence represented by SEQ ID NO: 13 includes a polynucleotide containing the base sequence represented by SEQ ID NO: 38; (viii) the polynucleotide encoding the polypeptide containing the amino acid sequence represented by SEQ ID NO: 14 includes a polynucleotide containing the base sequence represented by SEQ ID NO: 39; (ix) the polynucleotide encoding the polypeptide containing the amino acid sequence represented by SEQ ID NO: 36 includes a polynucleotide containing the base sequence represented by SEQ ID NO: 40; (x) the polynucleotide encoding the polypeptide containing the amino acid sequence represented by SEQ ID NO: 29 includes a polynucleotide containing the base sequence represented by SEQ ID NO: 45; (xi) the polynucleotide encoding the polypeptide containing the amino acid sequence represented by SEQ ID NO: 30 includes a polynucleotide containing the base sequence represented by SEQ ID NO: 46; (xii) the polynucleotide encoding the polypeptide containing the amino acid sequence represented by SEQ ID NO: 31 includes a polynucleotide containing the base sequence represented by SEQ ID NO: 47; (xiii) the polynucleotide encoding the polypeptide containing the amino acid sequence represented by SEQ ID NO: 32 includes a polynucleotide containing the base sequence represented by SEQ ID NO: 48; (xiv) the polynucleotide encoding the polypeptide containing the amino acid sequence represented by SEQ ID NO: 19 includes a polynucleotide containing the base sequence represented by SEQ ID NO: 18; (xv) the polynucleotide encoding the polypeptide containing the amino acid sequence represented by SEQ ID NO: 28 includes a polynucleotide containing the base sequence represented by SEQ ID NO: 27; and (xvi) the polynucleotide encoding the polypeptide containing the amino acid sequence represented by SEQ ID NO: 61 includes a polynucleotide containing the base sequence represented by SEQ ID NO: 60.

The polynucleotide encoding the receptor of the present invention includes, for example, a polynucleotide containing the base sequence represented by SEQ ID NO: 2 or SEQ ID NO: 4, or a polynucleotide having a base sequence, which hybridizes under high stringent conditions to the base sequence represented by SEQ ID NO: 2 or SEQ ID NO: 4, and encoding a polypeptide having substantially equivalent activity to that of the receptor of the present invention.

Examples of the polynucleotide that is hybridizable under high stringent conditions to the base sequence represented by SEQ ID NO: 2 or SEQ ID NO: 4 include a polynucleotide containing the base sequence having at least about 70% homology, preferably at least about 80% homology, further preferably at least about 90% and more preferably at least about 95% homology, to the base sequence represented by SEQ ID NO: 2 or SEQ ID NO: 4. Specifically, it includes a polynucleotide containing the base sequence represented by the polynucleotide containing the base sequence represented by SEQ ID NO: 64, SEQ ID NO: 66, SEQ ID NO: 96, SEQ ID NO: 98, SEQ ID NO: 99, SEQ ID NO: 100, SEQ ID NO: 101, SEQ ID NO: 52, SEQ ID NO: 54, SEQ ID NO: 56, SEQ ID NO: 68, SEQ ID NO: 70, SEQ ID NO: 78, SEQ ID NO: 86, SEQ ID NO: 88, SEQ ID NO: 90, SEQ ID NO: 92, SEQ ID NO: 94, SEQ ID NO: 72, SEQ ID NO: 76, SEQ ID NO: 84, SEQ ID NO: 103, or SEQ ID NO: 105.

The hybridization can be carried out by publicly known methods or by a modification thereof, for example, according to the method described in Molecular Cloning, 2nd. (J. Sambrook et al., Cold Spring Harbor Lab. Press, 1989), etc. When a commercially available library is used, hybridization may be carried out according to the instructions of the attached manufacturer's protocol. More preferably, the hybridization can be carried out under high stringent conditions.

The high stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration at about 19 mM at a temperature of about 65° C. are most preferred.

Specifically, (i) the polynucleotide encoding the protein containing the amino acid sequence represented by SEQ ID NO: 1 includes a polynucleotide containing the base sequence represented by SEQ ID NO: 41, a polynucleotide containing the base sequence represented by SEQ ID NO: 54 or a polynucleotide containing the base sequence represented by SEQ ID NO: 68; (ii) the polynucleotide encoding the protein containing the amino acid sequence represented by SEQ ID NO: 3 includes a polynucleotide containing the base sequence represented by SEQ ID NO: 4 or a polynucleotide containing the base sequence represented by SEQ ID NO: 101; (iii) the polynucleotide encoding the protein containing the amino acid sequence represented by SEQ ID NO: 63 includes a polynucleotide containing the base sequence represented by SEQ ID NO: 64; (iv) the polynucleotide encoding the protein containing the amino acid sequence represented by SEQ ID NO: 65 includes a polynucleotide containing the base sequence represented by SEQ ID NO: 66; (v) the polynucleotide encoding the protein containing the amino acid sequence represented by SEQ ID NO: 95 includes a polynucleotide containing the base sequence represented by SEQ ID NO: 96, a polynucleotide containing the base sequence represented by SEQ ID NO: 99 or a polynucleotide containing the base sequence represented by SEQ ID NO: 100; (vi) the polynucleotide encoding the protein containing the amino acid sequence represented by SEQ ID NO: 97 includes a polynucleotide containing the base sequence represented by SEQ ID NO: 98; (vii) the polynucleotide encoding the protein containing the amino acid sequence represented by SEQ ID NO: 51 includes a polynucleotide containing the base sequence represented by SEQ ID NO: 52; (viii) the polynucleotide encoding the protein containing the amino acid sequence represented by SEQ ID NO: 55 includes a polynucleotide containing the base sequence represented by SEQ ID NO: 56; (ix) the polynucleotide encoding the protein containing the amino acid sequence represented by SEQ ID NO: 69 includes a polynucleotide containing the base sequence represented by SEQ ID NO: 70; (x) the polynucleotide encoding the protein containing the amino acid sequence represented by SEQ ID NO: 77 includes a polynucleotide containing the base sequence represented by SEQ ID NO: 78; (xi) the polynucleotide encoding the protein containing the amino acid sequence represented by SEQ ID NO: 85 includes a polynucleotide containing the base sequence represented by SEQ ID NO: 86; (xii) the polynucleotide encoding the protein containing the amino acid sequence represented by SEQ ID NO: 87 includes a polynucleotide containing the base sequence represented by SEQ ID NO: 88; (xiii) the polynucleotide encoding the protein containing the amino acid sequence represented by SEQ ID NO: 89 includes a polynucleotide containing the base sequence represented by SEQ ID NO: 90; (xiv) the polynucleotide encoding the protein containing the amino acid sequence represented by SEQ ID NO: 91 includes a polynucleotide containing the base sequence represented by SEQ ID NO: 92; (xv) the polynucleotide encoding the protein containing the amino acid sequence represented by SEQ ID NO: 93 includes a polynucleotide containing the base sequence represented by SEQ ID NO: 94; (xvi) the polynucleotide encoding the protein containing the amino acid sequence represented by SEQ ID NO: 71 includes a polynucleotide containing the base sequence represented by SEQ ID NO: 72; (xvii) the polynucleotide encoding the protein containing the amino acid sequence represented by SEQ ID NO: 75 includes a polynucleotide containing the base sequence represented by SEQ ID NO: 76; (xviii) the polynucleotide encoding the protein containing the amino acid sequence represented by SEQ ID NO: 83 includes a polynucleotide containing the base sequence represented by SEQ ID NO: 84; (xix) the polynucleotide encoding the protein containing the amino acid sequence represented by SEQ ID NO: 102 includes a polynucleotide containing the base sequence represented by SEQ ID NO: 103; and (xx) the polynucleotide encoding the protein containing the amino acid sequence represented by SEQ ID NO: 104 includes a polynucleotide containing the base sequence represented by SEQ ID NO: 105.

The polynucleotide encoding the partial peptide of the present invention includes, for example, a polynucleotide containing the base sequence represented by SEQ ID NO: 2 or SEQ ID NO: 4, or a polynucleotide having a base sequence, which hybridizes under high stringent conditions to the base sequence represented by SEQ ID NO: 2 or SEQ ID NO: 4, and encoding a polypeptide having substantially equivalent activity to that of the receptor of the present invention.

The polynucleotide hybridizable to the base sequence represented by SEQ ID NO: 2 or SEQ ID NO: 4 is equivalent to the above description.

As hybridization method and high stringent conditions, the same as the above description are used.

Specifically, examples of a polynucleotide encoding the partial peptide of the present invention include a polynucleotide containing a polynucleotide having the base sequence encoding the partial peptide containing one or at least two partial amino acid sequences selected from the partial amino acid sequence represented by the sequence from the 50th (Thr) to the 335th (Ser) in the amino acid sequence represented by SEQ ID NO: 1 or SEQ ID NO: 3, or a polynucleotide containing a polynucleotide having the base sequence, which hybridizes under high stringent conditions to the above.

The polynucleotide encoding the polypeptides, the receptor and the partial peptide of the present invention may be labeled by the publicly known methods. Specific examples include isotope labeling, fluorescence labeling (e.g., fluorescence labeling with fluorescein), biotinylation or enzyme labeling.

For cloning of the DNA that completely encodes the polypeptide, the receptor or the partial peptide of the present invention (hereinafter, in the description on the cloning and expression of DNA encoding these polypeptides, these polypeptides are sometimes merely referred to as the polypeptide of the present invention), the DNA may be either amplified by PCR using synthetic DNA primers containing a part of the base sequence of the polypeptide of the present invention, or the DNA inserted into an appropriate vector can be selected by hybridization with a labeled DNA fragment or synthetic DNA that encodes a part or the entire region of the polypeptide of the present invention. The hybridization can be carried out, for example, according to the method described in Molecular Cloning, 2nd. (J. Sambrook et al., Cold Spring Harbor Lab. Press, 1989). Where commercially available library is used, the hybridization may also be performed in accordance with the protocol described in the attached instructions.

Substitution of the DNA base sequence can be effected by PCR or publicly known methods such as the ODA-LA PCR method, the Gapped duplex method or the Kunkel method, or modifications thereof, by using publicly known kits available as Mutan™-super Express Km (TaKaRa Shuzo Co., Ltd.) or Mutan™-K (TaKaRa Shuzo Co., Ltd.), etc.

The cloned DNA encoding the polypeptide can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector for the polypeptide of the present invention can be manufactured, for example, by (a) excising the desired DNA fragment from the DNA encoding the polypeptide of the present invention, (b) and then ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, HIV-LTR promoter, CMV promoter, HSV-TK promoter, etc.

Among them, CMV (cytomegalovirus) promoter, SRα promoter or the like is preferably used. Where the host is bacteria of the genus *Escherichia*, preferred examples of the promoter include trp promoter, lac promoter, recA promoter, λP$_L$ promoter, lpp promoter, T7 promoter, etc. In the case of using bacteria of the genus *Bacillus* as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin promoter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), neomycin resistant gene (hereinafter sometimes abbreviated as Neo$^r$, G418 resistance), etc. In particular, when dhfr gene is used as the selection marker using dhfr gene defective Chinese hamster cells, the objective gene may also be selected on thymidine free media.

If necessary, a signal sequence that matches with a host is added to the N-terminal side of the protein of the invention. Examples of the signal sequence that can be used are PhoA signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector containing the DNA encoding the polypeptide of the present invention thus constructed, transformants can be manufactured.

Examples of the host, which may be employed, are bacteria belonging to the genus *Escherichia*, bacteria belonging to the genus *Bacillus*, yeast, insect cells, insects, animal cells, and the like.

Specific examples of the bacteria belonging to the genus *Escherichia* include *Escherichia coli* K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus *Bacillus* include *Bacillus subtilis* MI114 [Gene, 24, 255 (1983)], 207-21 [Journal of Biochemistry, 95, 87 (1984)], etc.

Examples of yeast include *Saccharomyces cereviseae* AH22, AH22R⁻, NA87-11 A, DKD-5D, 20B-12, *Schizosaccharomyces pombe* NCYC1913, NCYC2036, *Pichia pastoris*, etc.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from *Estigmena acrea*, etc.; and for the virus BmNPV, *Bombyx mori* N cell (BmN cell), etc. is used. Examples of the Sf cell which can be used are Sf9 cell (ATCC CRL1711) and Sf21 cell (both cells are described in Vaughn, J. L. et al., In vivo, 13, 213-217 (1977).

As the insect, for example, a larva of *Bombyx mori* can be used (Maeda et al., Nature, 315, 592 (1985)).

Examples of animal cells include monkey cell COS-7, Vero, Chinese hamster cell CHO (hereinafter referred to as CHO cell), dhfr gene deficient Chinese hamster cell CHO (hereinafter simply referred to as CHO(dhfr⁻) cell), mouse L cell, mouse AtT-20, mouse myeloma cell, rat GH 3, human FL cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55(1988), etc.

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263-267 (1995), published by Shujunsha, or Virology, 52, 456 (1973).

Thus, the transformant transformed with the expression vector containing the DNA encoding the polypeptide can be obtained.

Where the host is bacteria belonging to the genus *Escherichia* or the genus *Bacillus*, the transformant can be appropriately cultured in a liquid medium which contains materials required for growth of the transformant such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast extracts, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium containing glucose and Casamino acids [Miller, Journal of Experiments in Molecular Genetics, 431-433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at approximately 15 to 43° C. for about 3 hours to about 24 hours. If necessary, the culture may further be aerated or agitated.

Where the bacteria belonging to the genus *Bacillus* are used as the host, the transformant is cultivated generally at approximately 30 to 40° C. for about 6 hours to about 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium containing 0.5% Casamino acids [Bitter, G. A. et al., Proc. Natl. Acad. Sci. U.S.A., 81, 5330 (1984)]. Preferably, pH of the medium is adjusted to about 5 to about 8. In general, the transformant is cultivated at about 20° C. to about 35° C. for about 24 hours to about 72 hours. If necessary, the culture can be aerated or agitated.

Where insect cells or insects are used as the host, the transformant is cultivated in, for example, Grace's Insect Medium (Grace, T. C. C., Nature, 195,788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture may be aerated or agitated.

Where animal cells are employed as the host, the transformant is cultivated in, for example, MEM medium containing about 5% to about 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 hours to about 60 hours and, if necessary, the culture may be aerated or agitated.

As described above, the polypeptide of the present invention can be produced in the cell or cell membrane, or outside the cell, of the transformant.

The polypeptide of the present invention can be separated and purified from the culture described above, e.g., by the following procedures.

When the polypeptide of the present invention is extracted from the culture or cells, after cultivation, the transformants or cells are collected by a publicly known method and suspended in an appropriate buffer. The transformants or cells are then disrupted by publicly known methods such as ultrasonication, a treatment with lysozyme and/or freeze-thaw cycling, followed by centrifugation, filtration, etc. Thus, the crude extract of the polypeptide can be obtained. The buffer used for the procedures may contain a protein denaturant such as urea or guanidine hydrochloride, or a surfactant such as Triton X-100™, etc. When the polypeptide is secreted in the culture broth, after completion of the cultivation, the supernatant can be separated from the transformants or cells and collected by publicly known methods.

The polypeptide contained in the supernatant or the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the polypeptide thus obtained is in a free form, it can be converted into the salt by publicly known methods or modifications thereof. On the other hand, when the polypeptide is obtained in the form of a salt, it can be converted into the free form or in the form of a different salt by publicly known methods or modifications thereof.

The polypeptide produced by the recombinant can be treated, prior to or after the purification, with an appropriate protein modifying enzyme so that the polypeptide can be appropriately modified to partially remove a polypeptide. Examples of the protein-modifying enzyme include trypsin, chymotrypsin, arginyl endopeptidase, protein kinase, glycosidase and the like.

Antibodies against the polypeptide of the present invention or the receptor of the present invention (hereinafter, sometimes merely referred to as the antibody of the present invention) may be any of polyclonal and monoclonal antibodies, so long as they can recognize the antibody against the polypeptide or the receptor of the present invention (including a partial peptide thereof, its amide or its ester, or salts thereof). Examples of the antibody against the receptor of the present invention include an antibody that inactivates signal transduction of the receptor, an antibody that activates signal transduction of the receptor, and the like.

The antibody against the polypeptide or the receptor of the present invention can be manufactured according to publicly known methods for producing antibodies or antisera, using the polypeptide or the receptor of the present invention as antigens.

[Preparation of Monoclonal Antibody]

(a) Preparation of Monoclonal Antibody-producing Cells

The polypeptide or the receptor of the present invention is administered to warm-blooded animals either solely or together with carriers or diluents to the site where the antibody can be produced by the administration. In order to potentiate the antibody productivity upon the administration, complete Freund's adjuvants or incomplete Freund's adjuvants may be administered. The administration is usually carried out once every 2 to 6 weeks approximately 2 to 10 times in total. Examples of the applicable warm-blooded animals are monkeys, rabbits, dogs, guinea pigs, mice, rats, sheep, goats and fowl with the use of mice and rats being preferred.

In the preparation of monoclonal antibody-producing cells, a warm-blooded animal such as mouse, immunized with an antigen is selected, then spleen or lymph nodes are collected after 2 to 5 days from the final immunization and antibody-producing cells contained therein are fused with myeloma cells, which is homogeneous or heterogeneous to the immunized animals, to give monoclonal antibody-producing hybridomas. Measurement of the antibody titer in antisera may be carried out, for example, by reacting a labeled form of the polypeptide described later with the antiserum followed by assaying the binding activity of the labeling agent bound to the antibody. The fusion operation may be carried out, for example, using the method known by Koehler and Milstein [Nature, 256, 495 (1975)]. Examples of the fusion promoter are polyethylene glycol (PEG), Sendai virus, etc., among which PEG is preferably employed.

Examples of the myeloma cells are myeloma cells of the warm-blooded animals such as NS-1, P3U1, SP2/0, AP-1. In particular, P3U1 is preferably employed. A preferred ratio of the count of the antibody-producing cells (spleen cells) used to the count of myeloma cells is within a range of approximately 1:1 to 20:1. When PEG (preferably, PEG 1000 to PEG 6000) is added in a concentration of approximately 10 to 80% followed by culturing at about 20 to 40° C., preferably at about 30 to 37° C. for about 1 to 10 minutes, efficient cell fusion can be carried out.

Various methods can be used for screening of a monoclonal antibody-producing hybridoma. Examples of such methods include a method which comprises adding the hybridoma supernatant to a solid phase (e.g., a microplate) adsorbed with the polypeptide (protein) as an antigen directly or together with a carrier, adding an anti-immunoglobulin antibody (where mouse cells are used for the cell fusion, anti-mouse immunoglobulin antibody is used) labeled with a radioactive substance or an enzyme, or protein A and detecting the monoclonal antibody bound to the solid phase; a method which comprises adding the hybridoma culture supernatant to a solid phase adsorbed with an anti-immunoglobulin antibody or protein A, adding the polypeptide labeled with a radioactive substance or an enzyme and detecting the monoclonal antibody bound to the solid phase; and the like.

The monoclonal antibody can be selected in accordance with publicly known methods or modifications thereof. In general, the selection can be effected in a medium for animal cells supplemented with HAT (hypoxanthine, aminopterin and thymidine). Any selection and growth media can be employed as far as the hybridoma can grow there. For example, RPMI 1640 medium containing 1 to 20%, preferably 10 to 20% fetal bovine serum, GIT medium (Wako Pure Chemical Industries, Ltd.) containing 1 to 10% fetal bovine serum, a serum free medium for cultivation of a hybridoma (SFM-101, Nissui Seiyaku Co., Ltd.), etc. can be used for the selection and growth medium. The cultivation is carried out generally at 20 to 40° C., preferably at about 37° C. The time for cultivation is normally for 5 days to 3 weeks, preferably 1 to 2 weeks. The cultivation is carried out generally in 5% $CO_2$. The antibody titer of the hybridoma culture supernatant can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or the specific purification method which comprises collecting an antibody alone with an activated adsorbent such as an antigen-binding solid phase, protein A or protein G and dissociating the binding to obtain the antibody].

[Preparation of Polyclonal Antibody]

The polyclonal antibody of the present invention can be manufactured by publicly known methods or modifications thereof. For example, a complex of immunogen (antigen such as the polypeptide of the present invention) and a carrier protein is prepared, and a mammal is immunized with the immunogen per se or the complex in a manner similar to the method described above for the manufacture of monoclonal antibodies. The product containing the antibody against the polypeptide of the present invention is collected from the immunized animal followed by separation and purification of the antibody.

In the complex of an immunogen and a carrier protein used to immunize a mammal, the type of carrier protein and the mixing ratio of a carrier to hapten may be any type and in any ratio, as long as the antibody is efficiently produced to the hapten immunized by crosslinking to the carrier. For example, bovine serum albumin, bovine thyroglobulins, keyhole limpet hemocyanin, etc. is coupled to hapten in a carrier-to-hapten weight ratio of approximately 0.1 to 20, preferably about 1 to about 5.

A variety of condensing agents can be used for the coupling of a carrier to hapten. Glutaraldehyde, carbodiimide, maleimide-activated ester, activated ester reagents containing thiol group or dithiopyridyl group, etc. are used for the coupling.

The condensation product is administered to warm-blooded animals either solely or together with carriers or diluents to the site in which the antibody can be produce by the administration. In order to potentiate the antibody productivity upon the administration, complete Freund's adjuvant or incomplete Freund's adjuvant may be administered. The administration is usually made once approximately in every 2 to 6 weeks and about 3 to about 10 times in total.

The polyclonal antibody can be collected from the blood, ascites, etc., preferably from the blood of mammals immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as applied to the separation and purification of monoclonal antibodies described hereinabove.

Example of a polynucleotide (e.g., DNA) having a base sequence complement or substantially complement to the polynucleotide (e.g., DNA) encoding the polypeptide, the receptor or the partial peptide of the present invention, or a portion thereof may be any one of the polynucleotide (antisense polynucleotide) so long as a polynucleotide has a base sequence complement or substantially complement to the polynucleotide of the present invention, or a portion thereof, and exhibits a suppressing action against expression of the polypeptide of the present invention.

Specifically, it includes an antisense DNA having a base sequence complement or substantially complement to the DNA encoding the polypeptide, the receptor or the partial peptide of the present invention (hereinafter, sometimes this DNA is referred to as the DNA of the present invention), or a portion thereof (hereinafter, sometimes this DNA is referred to as the antisense DNA of the present invention). It may be any one of the antisense DNA so long as the antisense DNA has a base sequence complement or substantially complement to the DNA of the present invention, or a portion thereof, and exhibits a suppressing action against expression of the DNA of the present invention.

The base sequence substantially complement to the DNA of the present invention is a base sequence, which, for example, has at least about 70%, preferably at least about 80%, more preferably at least about 90%, and most preferably at least about 95% homology to the whole or partial base sequence of the base sequence complement to the DNA of the present invention (i.e., complement strand of the DNA of the present invention). In particular, the antisense DNA is preferred, wherein the antisense DNA has at least about 70%, preferably at least about 80%, more preferably at least about 90% and most preferably at least about 95% homology to complement strand of the base sequence encoding the N-terminus of the polypeptide of the present invention (e.g., the base sequence around the initiation codon) among the whole base sequence of complement strand of the DNA of the present invention. The antisense DNA can be manufactured using a publicly known DNA synthesizer.

Specifically, it includes the antisense polynucleotide having the base sequence complement or substantially complement to the base sequence of the DNA having the base sequence represented by SEQ ID NO: 2, SEQ ID NO: 4, SEQ ID NO: 18, SEQ ID NO: 27, SEQ ID NOs: 37-48, SEQ ID NO: 50, SEQ ID NO: 52, SEQ ID NOs: 54-56, SEQ ID NO: 60, SEQ ID NO: 64, SEQ ID NO: 66, SEQ ID NO: 68, SEQ ID NO: 70, SEQ ID NO: 72, SEQ ID NO: 76, SEQ ID NO: 78, SEQ ID NO: 84, SEQ ID NO: 86, SEQ ID NOs: 88-90, SEQ ID NO: 92, SEQ ID NO: 94, SEQ ID NO: 96, SEQ ID NOs: 98-101, SEQ ID NO: 103 or SEQ ID NO: 105, or a portion thereof, preferably the antisense polynucleotide having the base sequence complement to the base sequence of the DNA having the base sequence represented by SEQ ID NO: 2, SEQ ID NO: 4, SEQ ID NO: 18, SEQ ID NO: 27, SEQ ID NOs: 37-48, SEQ ID NO: 50, SEQ ID NO: 52, SEQ ID NOs: 54-56, SEQ ID NO: 60, SEQ ID NO: 64, SEQ ID NO: 66, SEQ ID NO: 68, SEQ ID NO: 70, SEQ ID NO: 72, SEQ ID NO: 76, SEQ ID NO: 78, SEQ ID NO: 84, SEQ ID NO: 86, SEQ ID NOs: 88-90, SEQ ID NO: 92, SEQ ID NO: 94, SEQ ID NO: 96, SEQ ID NOs: 98-101, SEQ ID NO: 103 or SEQ ID NO: 105, or a portion thereof.

Antisense polynucleotide ordinarily consists of 10 to 40, preferably 15 to 30 bases.

To prevent digestion with a hydrolase such as nuclease, the phosphoric acid residue (phosphate) of each nucleotide that constitutes the antisense DNA may be substituted with chemically modified phosphoric acid residues, e.g., phosphorothioate, methylphosphonate, phosphorodithionate. These antisense nucleotides may be synthesized using a publicly known DNA synthesizer, etc.

According to the present invention, antisense polynucleotides (nucleic acids) that can inhibit replication or expression of the gene of the receptor or the polypeptide of the present invention can be designed and synthesized, on the basis of base sequence information of a DNA encoding the cloned or sequenced protein. Such polynucleotides (nucleic acids) can hybridize to RNA of the gene of the receptor or the polypeptide of the present invention and inhibit the synthesis or function of the RNA, or can regulate/control the expression of the gene of the receptor or the polypeptide of the present invention via interaction with RNAs associated with the receptor or the polypeptide of the present invention. Polynucleotides complementary to the specified sequences of RNAs associated with the receptor or the polypeptide of the present invention and polynucleotides that can specifically hybridize to RNAs associated with the receptor or the polypeptide of the present invention are useful for regulating/controlling expression of the gene of the receptor or the polypeptide of the present invention in vivo and in vitro, and are also useful for the treatment or diagnosis of diseases. The 5' end hairpin loop, 5' end 6-base-pair repeats, 5' end untranslated region, polypeptide translation initiation codon, protein coding region, ORF translation initiation codon, 3' untranslated region, 3' end palindrome region, and 3' end hairpin loop of the gene of the receptor or the polypeptide of the present invention may be selected as preferred target regions, though any region may be a target within genes of the receptor or the polypeptide of the present invention.

The relationship between the targeted nucleic acids and the polynucleotides complementary to at least a portion of the target region, specifically the relationship between the target and the polynucleotides hybridizable to the target, is denoted to be in "an antisense". The antisense polynucleotides may be polynucleotides containing 2-deoxy-D-ribose, polynucleotides containing D-ribose, any other type of polynucleotides which are N-glycosides of a purine or pyrimidine base, other polymers containing non-nucleotide backbones (e.g., protein nucleic acids and synthetic sequence-specific nucleic acid polymers that are commercially available), other polymers containing nonstandard linkages (provided that the polymers contain nucleotides with such a configuration that allows base pairing or base stacking, as is found in DNAs or RNAs), etc. They may be a double-stranded DNA, a single-stranded DNA, a double-stranded RNA, a single-stranded RNA and also a DNA:RNA hybrid, and further includes unmodified polynucleotides or unmodified oligonucleotides, those with publicly known types of modifications, for example, those with labels known in the art, those with caps, methylated (oligo)nucleotides, those with substitution of one or more naturally occurring nucleotides with their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (including nucleases, nuclease inhibitors, toxins, antibodies, signal peptides, poly-L-lysine, etc.), saccharides (e.g., monosaccharides, etc.), etc., those with intercalators (e.g., acridine, psoralen, etc.), those containing chelators (e.g., metals, radioactive metals, boron, oxidative metals, etc.), those containing alkylating agents, those with modified linkages (e.g., $\alpha$ anomeric nucleic acids, etc.). Herein, the terms "nucleoside", "nucleotide" and "nucleic acid" are used to refer to moieties that contain not only the purine and pyrimidine bases, but also other heterocyclic bases, which have been modified. Such modifications include methylated purines and pyrimidines, acylated purines and pyrimidines and other heterocyclic rings. Modified nucleotides and modified nucleotides also include modifications on the sugar moiety, for example, wherein one or more hydroxyl groups may optionally be replaced with a halogen, aliphatic groups, or may be converted into the corresponding functional groups such as ethers, amines, or the like.

The antisense polynucleotide (nucleic acid) of the present invention is RNA, DNA or a modified nucleic acid. Specific examples of the modified nucleic acid are, but not limited to, sulfurized and thiophosphate derivatives of nucleic acids and those resistant to degradation of polynucleoside amides or oligonucleoside amides. The antisense nucleic acids of the present invention can be modified preferably based on the following design, that is, by increasing the intracellular stability of the antisense nucleic acid, increasing the cellular permeability of the antisense nucleic acid, increasing the affinity of the nucleic acid to the target sense strand to a higher level, or minimizing the toxicity, if any, of the antisense nucleic acid.

Many such modifications are known in the art, as disclosed in J. Kawakami, et al., Pharm. Tech. Japan, Vol. 8, pp. 247, 1992; Vol. 8, pp. 395, 1992; S. T. Crooke et al. ed., Antisense Research and Applications, CRC Press, 1993; etc.

The antisense polynucleotide of the present invention may contain altered or modified sugars, bases or linkages. The antisense polynucleotide may also be provided in a specialized form such as liposomes, microspheres or may be applied to gene therapy or may be provided in combination with attached moieties. Such attached moieties include polycations such as polylysine that act as charge neutralizers of the phosphate backbone, or hydrophobic moieties such as lipids (e.g., phospholipids, cholesterols, etc.) that potentiate the interaction with cell membranes or increase uptake of the nucleic acid. Preferred examples of the lipids to be attached are cholesterols or derivatives thereof (e.g., cholesteryl chloroformate, cholic acid, etc.). These moieties may be attached at the 3' or 5' ends of the nucleic acid and may be also attached through a base, sugar, or intramolecular nucleoside linkage. Other moieties may be capping groups specifically placed at the 3' or 5' ends of the nucleic acid to prevent degradation by nuclease such as exonuclease, RNase, etc Such capping groups include, but are not limited to, hydroxyl protecting groups known in the art, including glycols such as polyethylene glycol, tetraethylene glycol, and the like.

The inhibitory activity of the antisense nucleic acid can be examined using the transformant of the present invention, the in vitro or in vivo gene expression system of the present invention, or the in vitro and in vivo translation system of proteins. The nucleic acid can be applied to cells by a variety of publicly known methods.

Hereinafter, (i) the polypeptide or the receptor of the present invention, (ii) the polynucleotide encoding the polypeptide or the receptor of the present invention (the polynucleotide of the invention), (iii) the antibody against the polypeptide or the receptor of the present invention (the antibody of the present invention) and (iv) the antisense polynucleotide of the polypeptide or the receptor of the present invention (e.g., the antisense DNA of the present invention) will be specifically described, with reference to their use.

(1) Agents for the Treatment/Prevention of Various Diseases with which the Polypeptide or the Receptor of the Present Invention is Associated The polypeptide of the present invention has a binding activity to the receptor of the present invention and a cell stimulating activity on the receptor expressing cells (e.g., activities that enhance arachidonic acid release, acetylcholine release, intracellular $Ca^{2+}$ release, intracellular cAMP production, suppression of intracellular cAMP production, intracellular cGMP production, inositolphosphate production, cell membrane potential changes, phosphorylation of intracellular protein, activation of c-fos, reduction of pH, GTPγS binding activity, activation of cAMP-dependent protein kinase, activation of cGMP-dependent protein kinase, activation of phopholipids-dependent protein kinase, or activation of microtubule associated protein phosphorylation enzyme (MAP kinase)), and is an endogenous ligand for the receptor of the present invention.

When the receptor of the present invention responds to the polypeptide of the present invention, athrocytosis is suppressed and carcinomas proliferate.

Therefore, where the polypeptide, the receptor or the polynucleotide (e.g., DNA) of the present invention is abnormal or deficient, or where the receptor or the DNA encoding the receptor is abnormal or deficient, there is a high possibility that adiposis (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity) and hyperphagia are suffered. Thus the polypeptide, the receptor or the polynucleotide (e.g., DNA) of the present invention can be used as a low toxic and safe medicine such as a prevention/treatment agent for adiposis, hyperphagia and the like. Further, where the polypeptide, the receptor or the polynucleotide of the present invention is abnormal or deficient, there is a possibility that central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.) and the like develop. Then, the polypeptide, the receptor or the polynucleotide of the present invention can be used as a medicine such as a prevention/treatment agent for these various diseases, preferably a prevention/treatment agent for adiposis.

When a patient has a reduced level of, or deficient of the polypeptide or the receptor of the present invention in his or her body, the polypeptide or the receptor of the present invention can provide its role sufficiently or properly for the patient, (a) by administering the polynucleotide of the present invention to the patient to express the polypeptide or the receptor of the present invention in the body, (b) by inserting the polynucleotide of the present invention into a cell to express the polypeptide or the receptor of the present invention and then transplanting the cell to the patient, or (c) by administering the polypeptide or the receptor of the present invention to the patient, etc.

When the polynucleotide of the present invention is used as the agent for the prevention/treatment described above, the polynucleotide itself is administered to human or other warm-blooded animal; or the polynucleotide is inserted into an appropriate vector such as retrovirus vector, adenovirus vector, adenovirus-associated virus vector, etc. and then administered to human or other warm-blooded animal in a conventional manner. The polynucleotide of the present invention may also be administered as it is; or the polynucleotide may be prepared into a pharmaceutical composition with physiologically acceptable carriers such as adjuvants, etc. to accelerate its uptake and the composition may be administered by gene gun or through a catheter such as a catheter with a hydrogel.

When the peptide of the invention is used as the agent for the prevention/treatment described above, it is advantageous to use the polypeptide or the receptor in a purity of at least 90%, preferably at least 95%, more preferably at least 98% and most preferably at least 99%.

The polypeptide or the receptor of the present invention can be used orally, for example, in the form of tablets which, if necessary, may be sugar coated, capsules, elixirs, microcapsules etc., or parenterally in the form of injectable preparations such as a sterile solution or a suspension, etc. in water or in other pharmaceutically acceptable liquid. These preparations can be manufactured, for example, by mixing the polypeptide or the receptor of the present invention with a physiologically acceptable known carrier, a flavoring agent, an excipient, a vehicle, an antiseptic agent, a stabilizer, a binder, etc. in a unit dosage form required in a generally accepted fashion that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose and saccharin, and a flavoring agent such as peppermint, akamono oil or cherry, etc. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol, etc.), a polyalcohol (e.g., propylene glycol, polyethylene glycol, etc.), a nonionic surfactant (e.g., polysorbate 80™, HCO-50, etc.), or the like. Examples of the oily medium include sesame oil, soybean oil, etc., which may also be used in combination with a dissolution aid such as benzyl benzoate, benzyl alcohol, etc. The oily medium may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The vector in which the polynucleotide of the present invention (e.g., DNA) is inserted may also be prepared into pharmaceutical preparations in a manner similar to the procedures above. Such preparations are generally used parenterally.

Since the thus obtained pharmaceutical preparation is safe and low toxic, the preparation can be administered to human or other warm-blooded animal (e.g., rat, mouse, guinea pig, rabbit, fowl, sheep, swine, bovine, horse, cat, dog, monkey, etc.).

The dose of the polypeptide or the receptor of the present invention varies depending on target disease, subject to be administered, route for administration, etc.; for example, in oral administration of the polypeptide of the present invention for the treatment of adiposis, the dose is normally about 0.1 mg to about 100 mg, preferably about 1.0 to about 50 mg, and more preferably about 1.0 to about 20 mg per day for adult (as 60 kg body weight). In parenteral administration, a single dose varies depending on subject to be administered, target disease, etc. but it is advantageous for the treatment of adiposis to inject the active ingredient into the affected area at a daily dose of about 0.01 to about 30 mg, preferably about 0.1 to about 20 mg, and more preferably about 0.1 to about 10 mg for adult (as 60 kg body weight). For other animal species, the corresponding dose as converted per 60 kg body weight can be administered.

The receptor A of the present invention exhibits a dominant negative effect by co-expression with the receptor of the present invention. Therefore, the receptor A or the polynucleotide encoding the receptor A of the present invention can also be used as a low toxic and safe medicine such as a preventive/therapeutic agent for cancer (e.g., carcinoma of large intestine, colon cancer, rectum cancer, breast cancer, lung cancer, non-small-cell lung cancer, prostate cancer, esophageal cancer, stomach cancer, liver cancer, carcinoma of biliary tract, spleen cancer, renal cancer, bladder carcinoma, uterine cancer, ovarian cancer, carcinoma of uterine cervix, carcinoma of testis, thyroid carcinoma, pancreatic cancer, brain tumor, blood cancer) and apoptosis inducer. Pharmaceutical preparation, methods for administration, amount of administration and the like for the receptor A or the polynucleotide encoding the receptor A of the present invention is based on the above description.

(2) Screening of a Candidate Compound of Medicine for Diseases

The polypeptide of the present invention has a binding activity to the receptor of the present invention and a cell stimulating activity on the receptor expressing cells, and is an endogenous ligand for the receptor of the present invention. When the receptor of the present invention responds to the polypeptide of the present invention, athrocytosis is suppressed and carcinomas proliferate.

Thus, the compound that enhances activities or functions of the polypeptide or the receptor of the present invention, or its salts can be used as a medicine such as a safe and low toxic preventive/therapeutic agent for adiposis (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity) and hyperphagia. Alternatively, it can be used as a medicine such as a safe and low toxic preventive/therapeutic agent for central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid meta-bolic disorders, hyperlipemia, etc.). Among them, a preventive/therapeutic agent for adiposis is preferred.

On the other hand, the compound that inhibits activities or functions of the polypeptide or the receptor of the present invention, or its salts can be used as a low toxic and safe medicine such as a preventive/therapeutic agent for cancer (e.g., carcinoma of large intestine, colon cancer, rectum cancer, breast cancer, lung cancer, non-small-cell lung cancer, prostate cancer, esophageal cancer, stomach cancer, liver cancer, carcinoma of biliary tract, spleen cancer, renal cancer, bladder carcinoma, uterine cancer, ovarian cancer, carcinoma of uterine cervix, carcinoma of testis, thyroid carcinoma, pancreatic cancer, brain tumor, blood cancer), feeding enhancer, a preventive/therapeutic agent for anorexia and apoptosis inducer. Alternatively, it can be used as a medicine such as a safe and low toxic preventive/therapeutic agent for central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.). Among them, a preventive/therapeutic agent for cancer, apoptosis inducer and feeding enhancer are preferred.

By constructing an expression system for the polypeptide of the present invention or the recombinant polypeptide of the present invention or an expression system for the receptor of the present invention or the recombinant receptor of the present invention, and using the receptor binding assay with the expression system, a compound that enhances or inhibits activities of the polypeptide of the present invention, or its salt (e.g., peptides, proteins, non-peptidic compounds, synthetic compounds, fermentation products) can be screened. Such a compound includes a compound having a cell stimulating activity (e.g., activities that enhance arachidonic acid release, acetylcholine release, intracellular $Ca^{2+}$ release, intracellular cAMP production, suppression of intracellular cAMP production, intracellular cGMP production, inositolphosphate production, cell membrane potential changes, phosphorylation of intracellular protein, activation of c-fos, reduction of pH, GTP$\gamma$S binding activity, activation of cAMP-dependent protein kinase, activation of cGMP-dependent protein kinase, activation of phopholipids-dependent protein kinase, or activation of microtubule associated protein phosphorylation enzyme (MAP kinase)) via the receptor of the present invention (agonist), a compound having no cell stimulating activity (antagonist), a compound that potentiates a binding between the polypeptide and the receptor of the present invention, or a compound that reduces a binding between the polypeptide and the receptor of the present invention.

The present invention provides a method for screening a compound that enhances or inhibits activities of the polypeptide of the present invention, or its salt, which comprises using the polypeptide of the present invention.

Specifically, the present invention provides the method for screening a compound that enhances or inhibits activities of the polypeptide of the present invention (a compound that alters the binding property between the polypeptide and the receptor of the present invention) or its salt, which comprises comparing (i) the case wherein the receptor or the partial peptide of the present invention (hereinafter, sometimes merely referred to as the receptor of the present invention) is brought in contact with the polypeptide of the present invention and (ii) the case wherein the polypeptide of the present invention and a test compound are brought in contact with the receptor of the present invention.

According to the screening method of the present invention, the method comprises assaying, for example, the binding amount of the polypeptide of the present invention to the receptor of the present invention, the cell stimulating activity, or the like, (i) when the polypeptide of the present invention is brought in contact with the receptor of the present invention and (ii) when the polypeptide of the present invention and a test compound are brought in contact with the receptor of the present invention, and comparing (i) and (ii).

Specific examples of the screening method of the present invention include:

(a) A method for screening a compound that enhances or inhibits activities of the polypeptide of the present invention (a compound that alters the binding property between the polypeptide and the receptor of the present invention) or its salt, which comprises measuring and comparing a binding amount of the polypeptide of the present invention (preferably the labeled polypeptide of the present invention) to the receptor of the present invention in (i) the case wherein the polypeptide of the present invention (preferably the labeled polypeptide of the present invention) is brought in contact with the receptor of the present invention and (ii) the case wherein the polypeptide of the present invention (preferably the labeled polypeptide of the present invention) and a test compound are brought in contact with the receptor of the present invention; or preferably, (b) A method for screening a compound that enhances or inhibits activities of the polypeptide of the present invention (a compound that alters the binding property between the polypeptide and the receptor of the present invention) or its salt, which comprises measuring and comparing a binding amount of the polypeptide of the present invention (preferably the labeled polypeptide of the present invention) to the cells or the membrane fraction in (i) the case wherein the polypeptide of the present invention (preferably the labeled polypeptide of the present invention) is brought in contact with the cells containing the receptor of the present invention (preferably, the transformant containing a polynucleotide encoding the receptor of the present invention) or membrane fraction of the cells and (ii) the case wherein the polypeptide of the present invention (preferably the labeled polypeptide of the present invention) and a test compound are brought in contact with the cells containing the receptor of the present invention (preferably, the transformant containing a polynucleotide encoding the receptor of the present invention) or membrane fraction of the cells;

(c) A method for screening a compound that enhances or inhibits activities of the polypeptide of the present invention (a compound that alters the binding property between the polypeptide and the receptor of the present invention) or its salt, which comprises measuring and comparing a binding amount of the polypeptide of the present invention (preferably the labeled polypeptide of the present invention) to the receptor of the present invention in (i) the case wherein the polypeptide of the present invention (preferably the labeled polypeptide of the present invention) is brought in contact with the receptor of the present invention, which expressed on the cell membrane by culturing the transformant containing a polynucleotide encoding the receptor of the present invention and (ii) the case wherein the polypeptide of the present invention (preferably the labeled polypeptide of the present invention) and a test compound are brought in contact with the receptor of the present invention, which expressed on the cell membrane by culturing the transformant containing a polynucleotide encoding the receptor of the present invention;

(d) A method for screening a compound that enhances or inhibits activities of the polypeptide of the present invention (a compound that alters the binding property between the polypeptide and the receptor of the present invention) or its salt, which comprises measuring and comparing a cell stimulating activity (e.g., activities that enhance arachidonic acid release, acetylcholine release, intracellular $Ca^{2+}$ release, intracellular cAMP production, suppression of intracellular cAMP production, intracellular cGMP production, inositolphosphate production, cell membrane potential changes, phosphorylation of intracellular protein, activation of c-fos, reduction of pH, GTPγS binding activity, activation of cAMP-dependent protein kinase, activation of cGMP-dependent protein kinase, activation of phopholipids-dependent protein kinase, or activation of microtubule associated protein phosphorylation enzyme (MAP kinase)) via the receptor of the present invention in (i) the case wherein a substance, which activates the receptor of the present invention (e.g., the polypeptide of the present invention) is brought in contact with the cells containing the receptor of the present invention and (ii) the case wherein a substance, which activates the receptor of the present invention and a test compound are brought in contact with the cells containing the receptor of the present invention; and (e) A method for screening a compound that enhances or inhibits activities of the polypeptide of the present invention (a compound that alters the binding property between the polypeptide and the receptor of the present invention) or its salt, which comprises measuring and comparing a cell stimulating activity (e.g., activities that enhance arachidonic acid release, acetylcholine release, intracellular $Ca^{2+}$ release, intracellular cAMP production, suppression of intracellular cAMP production, intracellular cGMP production, inositolphosphate production, cell membrane potential changes, phosphorylation of intracellular protein, activation of c-fos, reduction of pH, GTPγS binding activity, activation of cAMP-dependent protein kinase, activation of cGMP-dependent protein kinase, activation of phopholipids-dependent protein kinase, or activation of microtubule associated protein phosphorylation enzyme (MAP kinase)) mediated by the receptor of the present invention in (i) the case wherein a substance, which activates the receptor of the present invention (e.g., the polypeptide of the present invention) is brought in contact with the receptor of the present invention, which expressed on the cell membrane by culturing the transformant containing a polynucleotide encoding the receptor of the present invention and (ii) the case wherein a substance, which activates the receptor of the present invention and a test compound are brought in contact with the receptor of the present invention, which expressed on the cell membrane by culturing the transformant containing a polynucleotide encoding the receptor of the present invention.

The method for screening of the present invention will be specifically described below.

First, the receptor of the present invention used for the screening methods of the present invention may be any of those recognizing the polypeptide of the present invention, preferred is membrane fraction derived from organs of human or other warm-blooded animals. However, since human-derived organs in particular are obtained only with extreme difficulty, the receptor of the present invention, etc. expressed in large quantities by use of recombinants are suitable.

When cells containing the receptor of the present invention or membrane fractions of these cells are employed in the screening methods of the invention, these cells or membrane fractions may be prepared following the procedures later described.

Where cells containing the receptor of the present invention are employed, the cells may be fixed using glutaraldehyde, formalin, etc. The fixation can be made by publicly known methods.

The cells containing the receptor of the present invention refer to host cells wherein the receptor of the present invention is expressed, and such host cells include *Escherichia coli*, *Bacillus subtilis*, yeast, insect cells, animal cells, etc. described above. Further, host cells, in which the receptor of the present invention is expressed, are prepared in the similar method to the manufacturing method for the transformant transformed with an expression vector containing the polypeptide of the present invention described above.

The cell membrane fraction is used to mean a fraction abundant in cell membrane obtained by cell disruption and subsequent fractionation by publicly known methods. The cell disruption methods include cell squashing using a Potter-Elvehjem homogenizer, disruption using a Waring blender or Polytron (manufactured by Kinematica Inc.), disruption by ultrasonication, disruption by cell spraying through thin nozzles under an increased pressure using a French press, and the like. Cell membrane fractionation is effected mainly by fractionation using a centrifugal force, such as fractional centrifugation, density gradient centrifugation, etc. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the receptor of the present invention expressed and membrane components such as cell-derived phospholipids, membrane proteins, etc.

The amount of the receptor of the present invention in the cells or cell membrane fractions containing the receptor of the present invention is preferably $10^3$ to $10^8$ molecules, more preferably $10^5$ to $10^7$ molecules, per cell. As the amount of expression increases, the ligand binding activity per unit of the membrane fraction (specific activity) increases so that not only the highly sensitive screening system can be constructed but also large quantities of samples can be assayed on the same lot.

For carrying out the screening methods (a) through (c), an appropriate receptor fraction of the present invention and the polypeptide of the present invention, which is labeled, can be used. As the receptor fraction of the present invention, the fraction of naturally occurring receptor of the present invention or the fraction of recombinant receptor of the present invention having equivalent activities to that of the naturally occurring receptor is desirable. Herein, the term "equivalent activities" means an equivalent ligand binding activity or the like. As the labeled polypeptide of the present invention, the labeled polypeptide of the present invention and an analogue compound of the polypeptide of the present invention, which is labeled, are usable.

As labeling agents, there are employed, for example, radioisotopes, enzymes, fluorescent substances, luminescent substances, etc. As the radioisotopes, there are employed, for example, [$^{125}$I], [$^{131}$I], [$^{3}$H], [$^{14}$C], etc. As the enzymes described above, stable enzymes with a high specific activity are preferred; for example, β-galactosidase, β-glucosidase, alkaline phosphatase, peroxidase, malate dehydrogenase and the like are used. Examples of the fluorescent substance used are fluorescamine, fluorescein isothiocyanate and the like. As the luminescent substances, there are employed, for example, luminol, luminol derivatives, luciferin, lucigenin and the like.

For example, the polypeptide of the present invention, which is labeled with radioisotopes, can preferably be used. Among them, the polypeptide of the present invention labeled with [$^{125}$I] is preferred. More preferably, the peptide containing the amino acid sequence represented by SEQ ID NO: 62, which is labeled with [125I] can be used.

Specifically, a receptor preparation is firstly prepared by suspending cells containing the receptor of the present invention or their membrane fractions in a buffer appropriate for screening. Any buffer can be used so long as it does not interfere with ligand-receptor binding, such buffer including a phosphate buffer, a Tris-HCl buffer, etc. having pH of 4 to 10 (desirably pH of 6 to 8). For the purpose of minimizing non-specific binding, a surfactant such as CHAPS, Tween-80™ (manufactured by Kao-Atlas Inc.), digitonin, deoxycholate, etc. may be added to the buffer. Further for the purpose of suppressing degradation of the receptor of the present invention or the polypeptide of the present invention by a protease, a protease inhibitor such as PMSF, leupeptin, E-64 (manufactured by Peptide Institute, Inc.), pepstatin, etc. may also be added. A given quantity (5,000 cpm to 500,000 cpm) of a labeled form of the polypeptide of the present invention is added to 0.01 ml to 10 ml of the receptor solution, and at the same time, $10^{-10}$ to $10^{-7}$ μM of a test compound is allowed to be co-present. To determine the amount of non-specific binding (NSB), a reaction tube containing a large excess of the polypeptide of the present invention in an unlabeled form is also provided. The reaction is carried out at 0° C. to 50° C., preferably about 4° C. to 37° C. for 20 minutes to 24 hours, prefer 30 minutes to 3 hours. After completion of the reaction, the reaction mixture is filtered through glass fiber filter paper, etc. and washed with an appropriate volume of the same buffer. The residual radioactivity in the glass fiber filter paper is then measured by means of a liquid scintillation counter or a γ-counter. When the nonspecific binding (NSB) is subtracted from the count ($B_0$) when any antagonizing compound is absent and the thus obtained count ($B_0$–NSB) is made 100%, a test compound having the specific binding (B–NSB) of, e.g., 50% or less, can be selected as a candidate substance capable of competitive inhibition.

To perform the screening methods (d) and (e) described above, the cell stimulating activity (e.g., activities that enhance arachidonic acid release, acetylcholine release, intracellular $Ca^{2+}$ release, intracellular cAMP production, suppression of intracellular cAMP production, intracellular cGMP production, inositolphosphate production, cell membrane potential changes, phosphorylation of intracellular protein, activation of c-fos, reduction of pH, GTPγS binding activity, activation of cAMP-dependent protein kinase, activation of cGMP-dependent protein kinase, activation of phopholipids-dependent protein kinase, or activation of microtubule associated protein phosphorylation enzyme (MAP kinase)) mediated by the receptor of the present invention may be assayed by publicly known methods, or using assay kits commercially available. Specifically, the cells containing the receptor of the present invention are firstly cultured on a multi-well plate, etc. Prior to screening, the medium is replaced with a fresh medium or with an appropriate non-cytotoxic buffer, and a test compound or the like is added thereto, followed by culturing for a given period of time. Subsequently, the cells are extracted or the supernatant is recovered and the resulting product is quantified by the respective methods. Where it is difficult to detect the production of an indicator substance for the cell stimulating activity (e.g., arachidonic acid, etc.) due to a degrading enzyme contained in the cells, an inhibitor against such a degrading enzyme may be added prior to the assay. For detecting activities such as the cAMP production suppressing activity, the baseline production in the cells is increased by forskolin or the like and the suppressing effect on the increased baseline production can be detected.

To perform the screening through assaying the cell stimulating activity, cells in which an appropriate form of the receptor of the present invention is expressed are preferred. As the cells wherein the receptor of the present invention is expressed, a recombinant type of the aforesaid cell line wherein the receptor of the present invention is expressed, etc. are desirable.

Examples of the test compound include peptides, proteins, non-peptide compounds, synthetic compounds, fermentation products, cell extracts, plant extracts, animal tissue extracts, and the like.

The kit for screening the compound that enhances or inhibits activities of the polypeptide of the present invention (the compound that alters the binding property between the polypeptide and the receptor of the present invention), or its salt, comprises the receptor of the present invention (including a partial peptide of the receptor of the present invention), cells containing the receptor of the present invention or membrane fractions of the cells containing the receptor of the present invention, as well as the polypeptide of the present invention.

Examples of the screening kits of the present invention are as follow.

1. Reagents for Screening (i) Assay Buffer and Wash Buffer

Hanks' balanced salt solution (manufactured by Gibco Co.) supplemented with 0.05% bovine serum albumin (manufactured by Sigma Co.).

The solution is sterilized by filtration through a 0.45 μm filter, and stored at 4° C. or may be prepared at use.

(ii) Receptor Preparation of the Present Invention

CHO cells wherein the receptor of the present invention is expressed are subcultured on a 12-well plate at a density of $5 \times 10^5$ cells/well and cultured at 37° C. under 5% $CO_2$ and 95% air for 2 days.

(iii) The Polypeptide of the Present Invention

A solution of the polypeptide of the present invention labeled with [$^3$H], [$^{125}$I], [$^{14}$C], [35S], etc., dissolved in an appropriate solvent or buffer is stored at 4° C. or −20° C. and upon use, diluted to 1 μM with the assay buffer.

(iv) Polypeptide Standard Solution

The polypeptide of the present invention is dissolved in PBS containing 0.1% bovine serum albumin (manufactured by Sigma Co.) in a volume of 1 mM, and the solution is stored at −20° C.

2. Assay Method (i) The cells wherein the receptor of the present invention is expressed are cultured on a 12-well culture plate. After washing twice with 1 ml of the assay buffer, 490 μl of the assay buffer is added to each well.

(ii) After 5 μl of a solution of test compound in $10^{-3}$ to $10^{-10}$ M is added, 5 μl of a labeled form of the peptide of the invention is added thereto. The reaction is carried out at room temperature for an hour. To examine the non-specific binding, 5 μl of the peptide of the invention of $10^{-3}$ M is previously added in place of the test compound.

(iii) The reaction solution is removed and the wells are washed 3 times with 1 ml of the wash buffer. The labeled polypeptide of the present invention bound to the cells is dissolved in 0.2N NaOH-1% SDS, and mixed with 4 ml of liquid scintillator A (manufactured by Wako Pure Chemical Industries, Ltd.).

(iv) The radioactivity is measured using a liquid scintillation counter (manufactured by Beckman Co.), and the percent maximum binding (PMB) is calculated in accordance with the following equation.

$$PMB = [(B - NSB)/(B_0 - NSB)] \times 100$$

| | |
|---|---|
| PMB | Percent maximum binding |
| B | Value obtained in the presence of a test compound |
| NSB | Non-specific binding |
| $B_0$ | Maximum binding |

The compound or its salt, which is obtainable using the screening methods or the screening kits of the present invention, is a compound that enhances or inhibits activities of the polypeptide of the present invention (a compound that alters the binding of the polypeptide of the present invention to the receptor of the present invention) (a compound that enhances or inhibits the binding), and specifically, is a compound or its salt that has the cell stimulating activity mediated by the receptor of the present invention (a so-called an agonist to the receptor of the present invention); or a compound that does not have the stimulating activity (a so-called an antagonist to the receptor of the present invention). The compounds may be peptides, proteins, non-peptide compounds, synthetic compounds, fermentation products, etc. These compounds may be novel or publicly known compounds.

In order to specifically determine if the compounds are agonists or antagonists to the receptor of the present invention described above, it may be accordance with the following (a) or (b):

(i) The binding assay recited in the screening methods (a)-(c) described above is performed to obtain the compound that alters the binding property between the polypeptide of the present invention and the receptor of the present invention (especially inhibits the binding) followed by assay for the compound to determine if the compound has the cell stimulating activity mediated by the receptor of the present invention as described above. The compound or its salts having the cell stimulating activity are agonists to the receptor of the present invention, whereas the compound or its salts having no such activity are antagonists to the receptor of the present invention;

(ii) (a) A test compound is brought in contact with cells containing the receptor of the present invention to assay the cell stimulating activity mediated by the receptor of the present invention. The compound or its salts having the cell stimulating activity are agonists to the receptor of the present invention;

(b) The cell stimulating activity mediated by the receptor of the present invention is assayed in the case that a compound (e.g., the polypeptide of the present invention or an agonist to the receptor of the present invention, etc.) that activates the receptor of the present invention is brought in contact with the cells containing the receptor of the present invention and in the case that a compound that activates the receptor of the present invention and a test compound are brought in contact with the cells containing the receptor of the present invention, and comparison is made on the cell stimulating activity between both cases. The compound or its salts capable of reducing the cell stimulating activity by the compound that activates the receptor of the present invention are antagonists to the receptor of the present invention.

The agonists to the receptor of the present invention exhibit activities similar to the physiological activities that the polypeptide or the receptor of the present invention has, and are thus useful as a medicine such as a safe and low toxic preventive/therapeutic agent for adiposis (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), hyperphagia and the like, as well as the polypeptide or the receptor of the present invention. Alternatively, it can be used for a medicine such as a safe and low toxic preventive/therapeutic agent for central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.) and the like.

The antagonists to the receptor of the present invention can suppress the physiological activities that the polypeptide or the receptor of the present invention has, and are useful as safe and low toxic medicines such as a preventive/therapeutic agent for cancer (carcinoma of large intestine, colon cancer, rectum cancer, breast cancer, lung cancer, non-small-cell lung cancer, prostate cancer, esophageal cancer, stomach cancer, liver cancer, carcinoma of biliary tract, spleen cancer, renal cancer, bladder carcinoma, uterine cancer, ovarian cancer, carcinoma of uterine cervix, carcinoma of testis, thyroid carcinoma, pancreatic cancer, brain tumor, blood cancer), feeding enhancer, a preventive/therapeutic agent for anorexia, apoptosis inducer and the like. Alternatively, it is useful for a medicine such as a safe and low toxic preventive/therapeutic agent for central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.) and the like. Preferred are preventive/therapeutic agents for cancer, apoptosis inducer, feeding enhancer, etc.

In addition, the present invention provides a method for screening a compound that enhances or inhibits expression of the polypeptide or the receptor of the present invention, or its salt, which comprises using the polynucleotide of the present invention encoding the polypeptide or the receptor of the present invention.

Specifically, by comparing (i) the case when the cells having an ability of producing the polypeptide or the receptor of the present invention is cultured, and (ii) the case when the mixture of the cells having an ability of producing the polypeptide or the receptor of the present invention and a test compound is cultured, a screening of a compound that enhances or inhibits expression of the gene for the polypeptide or the receptor of the present invention, or its salt, is carried out.

In the above screening method, for example, expression level of the gene for the polypeptide or the receptor of the present invention (specifically, a level of the polypeptide of the present invention, a level of the receptor of the present invention, a level of mRNA encoding the polypeptide or the receptor of the present invention, or the like) in the case of both (i) and (ii), is measured and compared.

Examples of the test compound include peptides, proteins, non-peptide compounds, synthetic compounds, fermentation products, cell extracts, plant extracts, animal tissue extracts, and the like. These compounds may be either novel or publicly known.

In order to carry out the above screening methods, cells having an ability of producing the polypeptide or the receptor of the present invention are firstly prepared by suspending in a buffer appropriate for screening. Any buffer can be used so long as it does not inhibit activities of the polypeptide or the receptor of the present invention, such buffer including a phosphate buffer, a borate buffer, etc. having pH of about 4 to 10 (desirably pH of about 6 to 8).

Examples of the cells having an ability of producing the polypeptide or the receptor of the present invention include hosts transformed with a vector containing the DNA encoding the polypeptide or the receptor of the present invention described above (transformant) or the like. For hosts, animal cells such as CHO cells and the like are preferably used. In the screening, a transformant wherein the polypeptide or the receptor of the present invention is expressed on the cell membrane, is preferably used.

Assay for a protein level of the polypeptide or the receptor of the present invention, can be performed by measuring the above polypeptide or the receptor present in the cell extracts with publicly known methods, for example, using the antibody of the present invention in accordance with the methods such as Western analysis, ELISA and the like, or the modification thereof.

The level of expression of the gene for the polypeptide or the receptor of the present invention can be measured by publicly known methods such as methods of Northern blotting, reverse transcription-polymerase chain reaction (RT-PCR,) or real time PCR analysis system (ABI Corp. made, TaqMan polymerase chain reaction) or similar methods.

For example, a test compound enhancing the level of gene expression in a ratio of at least about 20%, preferably at least about 30%, and more preferably at least about 50%, in the case (ii) in comparison with the case of (ii) as described above can be selected as a the compound enhancing the activities of the polypeptide or the receptor of the present invention.

For example, a test compound inhibiting the level of gene expression in a ratio of at least about 20%, preferably at least about 30%, and more preferably at least about 50%, in the case (ii) in comparison with the case of (ii) as described above can be selected as a the compound inhibiting the activities of the polypeptide or the receptor of the present invention.

The compound that enhances expression of the gene for the polypeptide or the receptor of the present invention (increases a level of expression), or its salt, as well as the polypeptide or the receptor of the present invention, can be used as a medicine such as a safe and low toxic preventive/therapeutic agent for adiposis (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), hyperphagia and the like, as well as the polypeptide or the receptor of the present invention. Alternatively, it can be used for a medicine such as a safe and low toxic preventive/therapeutic agent for central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.) and the like. Among them, preferred is a preventive/therapeutic agent for adiposis.

The compound that inhibits expression of the gene for the polypeptide or the receptor of the present invention, or its salt, can suppress the physiological activities that the polypeptide or the receptor of the present invention has, and thus are useful as safe and low toxic medicines such as a preventive/therapeutic agent for cancer (carcinoma of large intestine, colon cancer, rectum cancer, breast cancer, lung cancer, non-small-cell lung cancer, prostate cancer, esophageal cancer, stomach cancer, liver cancer, carcinoma of biliary tract, spleen cancer, renal cancer, bladder carcinoma, uterine cancer, ovarian cancer, carcinoma of uterine cervix, carcinoma of testis, thyroid carcinoma, pancreatic cancer, brain tumor, blood cancer), feeding enhancer, a preventive/therapeutic agent for anorexia, apoptosis inducer and the like. Alternatively, it is useful for a medicine such as a safe and low toxic preventive/therapeutic agent for central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.) and the like. Preferred are preventive/therapeutic agents for cancer, apoptosis inducer, feeding enhancer, etc.

Examples of the compound or its salt, which is obtained using the screening methods or the screening kit of the present invention, include peptides, proteins, non-peptide compounds, synthetic compounds, fermentation products, cell extracts, plant extracts, animal tissue extracts, blood plasma and the like. It also may be a compound that enhances or inhibits activities or functions of the polypeptide or the receptor of the present invention, or a compound that enhances or inhibits expression of the gene for the polypeptide or the receptor of the present invention (increases or decreases a level of expression).

Examples of salts for the compound include the same as the salt for the polypeptide of the present invention.

For the use of the compound, which is obtained by the screening method or the screening kit of the present invention, as the above-described medicines, preparation can be practiced after usual means. For example, forms of tablets, capsules, elixir, microcapsules, sterile solution, suspension, etc. are possible.

Since the pharmaceutical preparation thus obtained is safe and low toxic, it can be administered to human or other warm-blooded animals (e.g., mouse, rat, guinea pig, rabbit, sheep, swine, bovine, horse, fowl, cat, dog, monkey, chimpanzee, etc.).

A dose of the above-mentioned compound or salts thereof varies depending on its action, target disease, subject to be administered, route for administration, etc.; when the compound, which enhances activities or functions of the polypeptide or the receptor of the present invention, is orally administered for the purpose of treatment for adiposis, the compound or its salt is generally administered to an adult (as 60 kg body weight) in a daily dose of about 0.1 to 100 mg, preferably about 1.0 to 50 mg, more preferably about 1.0 to 20 mg. In parenteral administration, a single dose of the compound or its salt varies depending on subject to be administered, target disease, etc. but when the compound, which enhances activities or functions of the polypeptide or the receptor of the present invention, is administered to the adult (as 60 kg body weight) in the form of injectable preparation for the purpose of treating for adiposis, it is advantageous to administer the compound or its salt intravenously in a daily dose of about 0.01 to about 30 mg, preferably about 0.1 to about 20 mg, more preferably about 0.1 to about 10 mg. For other animal species, the corresponding dose as converted per 60 kg weight can be administered.

For example, when the compound, which inhibits activities or functions of the polypeptide or the receptor of the present invention, is orally administered for the purpose of treatment for cancer, the compound or its salt is generally administered to an adult (as 60 kg body weight) in a daily dose of about 0.1 to 100 mg, preferably about 1.0 to 50 mg, more preferably about 1.0 to 20 mg. In parenteral administration, a single dose of the compound or its salt varies depending on subject to be administered, target disease, etc. but when the compound, which inhibits activities or functions of the polypeptide or the receptor of the present invention, is administered to the adult (as 60 kg body weight) in the form of injectable preparation for the purpose of treating for cancer, it is advantageous to administer the compound or its salt intravenously in a daily dose of about 0.01 to about 30 mg, preferably about 0.1 to about 20 mg, more preferably about 0.1 to about 10 mg. For other animal species, the corresponding dose as converted per 60 kg weight can be administered.

For example, when the compound, which enhances expression of the gene for the polypeptide or the receptor of the present invention, is orally administered for the purpose of treatment for adiposis, the compound or its salt is generally administered to an adult (as 60 kg body weight) in a daily dose of about 0.1 to 100 mg, preferably about 1.0 to 50 mg, more preferably about 1.0 to 20 mg. In parenteral administration, a single dose of the compound or its salt varies depending on subject to be administered, target disease, etc. but when the compound, which enhances expression of the gene for the polypeptide or the receptor of the present invention, is administered to the adult (as 60 kg body weight) in the form of injectable preparation for the purpose of treating for adiposis, it is advantageous to administer the compound or its salt intravenously in a daily dose of about 0.01 to about 30 mg, preferably about 0.1 to about 20 mg, more preferably about 0.1 to about 10 mg. For other animal species, the corresponding dose as converted per 60 kg weight can be administered.

For example, when the compound, which inhibits expression of the gene for the polypeptide or the receptor of the present invention, is orally administered for the purpose of treatment for cancer, the compound or its salt is generally administered to an adult (as 60 kg body weight) in a daily dose of about 0.1 to 100 mg, preferably about 1.0 to 50 mg, more preferably about 1.0 to 20 mg. In parenteral administration, a single dose of the compound or its salt varies depending on subject to be administered, target disease, etc. but when the compound, which inhibits expression of the gene for the polypeptide or the receptor of the present invention, is administered to the adult (as 60 kg body weight) in the form of injectable preparation for the purpose of treating for cancer, it is advantageous to administer the compound or its salt intravenously in a daily dose of about 0.01 to about 30 mg, preferably about 0.1 to about 20 mg, more preferably about 0.1 to about 10 mg. For other animal species, the corresponding dose as converted per 60 kg weight can be administered.

(3) Quantification of the Polypeptide or the Receptor of the Present Invention

The antibody of the present invention can specifically recognize the polypeptide or the receptor of the present invention. Therefore, the antibody can be used to quantify the polypeptide or the receptor of the present invention in a test fluid, especially for quantification by the sandwich immunoassay, etc.

That is, the present invention provides, for example, the following methods of quantification:

(i) A method of quantifying the polypeptide or the receptor of the present invention in a test fluid, which comprises competitively reacting the antibody of the present invention with the test fluid and a labeled form of the polypeptide or the receptor of the present invention, and measuring the ratio of the labeled polypeptide or the receptor of the present invention bound to the antibody; and, (ii) A method of quantifying the polypeptide or the receptor of the present invention in a test fluid, which comprises reacting the test fluid with the antibody of the present invention immobilized on a carrier and a labeled form of the antibody of the present invention simultaneously or sequentially, and measuring the activity of the label on the immobilized carrier.

In the quantifying method (ii), it is preferred that one antibody recognizes the N-terminus of the polypeptide or the receptor of the present invention, and another antibody reacts with the C-terminus of the polypeptide or the receptor of the present invention.

Using a monoclonal antibody against the polypeptide or the receptor of the present invention, quantification for the polypeptide or the receptor of the present invention can be performed, and the polypeptide or the receptor of the present invention can further be detected by tissue staining or the like. For these purposes, the antibody molecule itself may be used, or $F(ab')_2$, Fab' or Fab fractions of the antibody molecule may be used as well.

The methods for quantifying the polypeptide of the present invention using the antibody of the present invention are not to be limited particularly. Any method can be used, so long as the amount of antibody, antigen, or antibody-antigen complex in response to the amount of antigen (e.g., the amount of the polypeptide of the present invention) in a test fluid can be detected by chemical or physical means and can be calculated from a standard curve prepared from standard solutions containing known amounts of the antigen. For example, nephrometry, competitive method, immunometric method, and sandwich method are advantageously used, among which the sandwich method described below is particularly preferable in terms of sensitivity and specificity.

As labeling agents for the methods using labeled substances, there are employed, for example, radioisotopes, enzymes, fluorescent substances, luminescent substances, etc. As the radioisotopes, there are employed, for example, $[^{125}I]$, $[^{131}I]$, $[^{3}H]$, $[^{14}C]$, etc. As the enzymes described above, stable enzymes with a high specific activity are preferred; for example, β-galactosidase, β-glucosidase, alkaline phosphatase, peroxidase, malate dehydrogenase and the like are used. Examples of the fluorescent substance used are fluorescamine, fluorescein isothiocyanate and the like. As the luminescent substances, there are employed, for example, luminol, luminol derivatives, luciferin, lucigenin and the like. Furthermore, the biotin-avidin system may also be used for binding an antibody or antigen to the label.

For immobilization of the antigen or antibody, physical adsorption may be used. Chemical binding methods conventionally used for insolubilization or immobilization of polypeptides, enzymes, etc. may be used as well. For the carriers, examples include insoluble polysaccharides such as agarose, dextran, cellulose, etc.; synthetic resin such as polystyrene, polyacrylamide, silicone, etc., or glass, etc.

In the sandwich method, the immobilized monoclonal antibody of the present invention is reacted with a test fluid (primary reaction), then with a labeled form of another monoclonal antibody of the present invention (secondary reaction), and the activity of the labeling agent on the immobilizing carrier is assayed, whereby the amount of the polypeptide or the receptor of the present invention in the test fluid can be quantified. The order of the primary and secondary reactions may be reversed, and the reactions may be performed simultaneously or with some time intervals. The methods of labeling and immobilization can be performed by modifications of those methods described above. In the immunoassay by the sandwich method, the antibody used for immobilized or labeled antibody is not necessarily from one species, but a mixture of two or more species of antibodies may be used to increase the measurement sensitivity.

In the methods of assaying the polypeptide or the receptor of the present invention by the sandwich method, antibodies that bind to different sites of the polypeptide or the receptor of the present invention are preferably used as the monoclonal antibodies of the present invention for the primary and secondary reactions. That is, in the antibodies used for the primary and secondary reactions, for example, when the antibody used in the secondary reaction recognizes the C-terminal region of the peptide of the invention, it is preferable to use the antibody capable of recognizing the region other than the C-terminal region for the primary reaction, e.g., the antibody capable of recognizing the N-terminal region.

The monoclonal antibody of the present invention can be used for the assay systems other than the sandwich method, for example, the competitive method, immunometric method, nephrometry, etc.

In the competitive method, an antigen in a test fluid and a labeled antigen are competitively reacted with an antibody, and the unreacted labeled antigen (F) and the labeled antigen bound to the antibody (B) are separated (B/F separation). The amount of the labeling agent in B or F is measured, and the amount of the antigen in the test fluid is quantified. This reaction method includes a liquid phase method using a soluble antibody as an antibody, polyethylene glycol for B/F separation and a secondary antibody, etc. to the soluble antibody, and an immobilized method either using an immobilized antibody as the primary antibody, or using a soluble antibody as the primary antibody and an immobilized antibody as the secondary antibody.

In the immunometric method, an antigen in a test fluid and an immobilized antigen are competitively reacted with a definite amount of labeled antibody, the immobilized phase is separated from the liquid phase, or an antigen in a test fluid is reacted with an excess amount of labeled antibody, the immobilized antigen is then added to bind the unreacted labeled antibody to the immobilized phase, and the immobilized phase is separated from the liquid phase. Then, the amount of the labeling agent in either phase is measured to quantify the antigen in the test fluid.

In the nephrometry, insoluble precipitates produced after the antigen-antibody reaction in gel or solution, are quantified. Even when the amount of an antigen in a test fluid is small and only a small amount of precipitates is obtained, laser nephrometry using scattering of laser can be advantageously employed.

For applying these immunological assay methods to the quantification methods of the present invention, any particular conditions or procedures are not required. The assay systems for the polypeptide or the receptor of the present invention may be constructed by adding ordinary technical consideration in the art to conventional conditions and procedures in the respective methods. For the details of these general technical means, reference can be made to the following reviews and texts.

For example, reference can be made on Hiroshi Irie, ed. "Radioimmunoassay" (Kodansha, published in 1974), Hiroshi Irie, ed. "Sequel to the Radioimmunoassay" (Kodansha, published in 1979), Eiji Ishikawa, et al. ed. "Enzyme immonoassay" (Igakushoin, published in 1978), Eiji Ishikawa, et al. ed. "Immunoenzyme assay" (2nd ed.) (Igakushoin, published in 1982), Eiji Ishikawa, et al. ed. "Immunoenzyme assay" (3rd ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies))(all published by Academic Press Publishing), etc.

As described above, the polypeptide or the receptor of the present invention can be quantified with high sensitivity, by using the antibody of the present invention.

Furthermore, by quantifying the concentration of the polypeptide or the receptor of the present invention using the antibody of the present invention, when an increased concentration of the polypeptide or the receptor of the present invention is detected, it can be diagnosed that one suffers from, for example, cancer (carcinoma of large intestine, colon cancer, rectum cancer, breast cancer, lung cancer, non-small-cell lung cancer, prostate cancer, esophageal cancer, stomach cancer, liver cancer, carcinoma of biliary tract, spleen cancer, renal cancer, bladder carcinoma, uterine cancer, ovarian cancer, carcinoma of uterine cervix, carcinoma of testis, thyroid carcinoma, pancreatic cancer, brain tumor, blood cancer), anorexia and the like or it is highly likely that one would suffer from these disease in the future. Alternatively, it can be diagnosed that one suffers from central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.) and the like or it is highly likely that one would suffer from these disease in the future.

Also, when a decreased concentration of the polypeptide or the receptor of the present invention is detected, it can be diagnosed that one suffers from, for example, adiposis (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), hyperphagia and the like or it is highly likely that one would suffer from these disease in the future. Alternatively, it can be diagnosed that one suffers from central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.) and the like or it is highly likely that one would suffer from these disease in the future.

Besides, the antibody of the present invention may be used for detecting the polypeptide or the receptor of the present invention, which exists in test samples such as body fluids, tissues, etc. The antibody may also be used for preparation of antibody columns used to purify the polypeptide or the receptor of the present invention, for detection of the polypeptide or the receptor of the present invention in each fraction upon purification, for analysis of the behavior of the polypeptide or the receptor of the present invention in test cells; etc.

(4) Gene Diagnostic Product

By using the polynucleotide (DNA) of the present invention, e.g., as a probe, an abnormality (gene abnormality) of the DNA or mRNA encoding the polypeptide or the receptor of the present invention in human or other warm-blooded animal (e.g., rat, mouse, guinea pig, rabbit, fowl, sheep, swine, bovine, horse, cat, dog, monkey, etc.) can be detected. Therefore, the DNA of the present invention is useful as a gene diagnostic product for damages to the DNA or mRNA, its mutation or decreased expression, or increased expression or overexpression of the DNA or mRNA.

The gene diagnosis described above using the DNA of the present invention can be performed by, for example, publicly known Northern hybridization or PCR-SSCP assay (Genomics, 5, 874-879 (1989); Proceedings of the National Academy of Sciences of the United States of America, 86, 2766-2770 (1989)).

For example, when overexpression of the gene for the polypeptide or the receptor of the present invention is detected, it can be diagnosed that cancer (carcinoma of large intestine, colon cancer, rectum cancer, breast cancer, lung cancer, non-small-cell lung cancer, prostate cancer, esophageal cancer, stomach cancer, liver cancer, carcinoma of biliary tract, spleen cancer, renal cancer, bladder carcinoma, uterine cancer, ovarian cancer, carcinoma of uterine cervix, carcinoma of testis, thyroid carcinoma, pancreatic cancer, brain tumor, blood cancer), anorexia and the like are involved or it is highly likely to suffer in the future from these diseases. Alternatively, it can be diagnosed that central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.) are involved or it is highly likely to suffer in the future from these diseases.

Further, when reduced expression is detected by northern hybridization or DNA microarray, or when DNA mutation is detected by PCR-SS or DNA microarray, it can be diagnosed that adiposis (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), hyperphagia and the like are involved or it is highly likely to suffer in the future from these diseases. Alternatively, it can be diagnosed that central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.) are involved or it is highly likely to suffer in the future from these diseases.

(5) A Medicine Containing the Antisense Polynucleotide

Antisense polynucleotide that binds to the polynucleotide (e.g., DNA) of the present invention complementarily and suppresses expression of the polynucleotide (e.g., DNA) has the functions for inducing apoptosis in cancer cells. Thus it can be used as a low toxic and safe medicine such as the agent for the prevention/treatment of cancer (e.g., carcinoma of large intestine, colon cancer, rectum cancer, breast cancer, lung cancer, non-small-cell lung cancer, prostate cancer, esophageal cancer, stomach cancer, liver cancer, carcinoma of biliary tract, spleen cancer, renal cancer, bladder carcinoma, uterine cancer, ovarian cancer, carcinoma of uterine cervix, carcinoma of testis, thyroid carcinoma, pancreatic cancer, brain tumor, blood cancer), feeding (appetite) enhancer, prophylactic/therapeutic agents for anorexia, apoptosis inducer and the like. Alternatively, it is useful as a safe and low toxic medicine such as the prophylactic/therapeutic agent for central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.). Among them, a prophylactic/therapeutic agent for cancer, apoptosis inducer, feeding enhancer and the like are preferable.

For example, the antisense DNA is administered solely, or the antisense DNA is inserted into an appropriate vector such as retrovirus vector, adenovirus vector, adenovirus-associated virus vector, etc., which is then administered in a conventional manner. The antisense DNA may be administered as it stands, or may be prepared into a dosage form together with a physiologically acceptable carrier to increase its uptake and administered by gene gun or through a catheter such as a catheter with a hydrogel.

In addition, the antisense DNA may also be employed as an oligonucleotide probe for diagnosis to examine the presence of the DNA of the present invention in tissues or cells and the conditions of its expression.

As in the antisense polynucleotide described above, the double-stranded RNA containing a part of RNA encoding the receptor of the present invention, ribozyme containing a part of RNA encoding the polypeptide or the receptor of the present invention, etc. can suppress the expression of the polynucleotide of the present invention and the in vivo functions of the polypeptide, the receptor or the polynucleotide of the present invention. Thus it is useful as a safe and low toxic medicine such as the agent for the prevention/treatment of cancer (e.g., carcinoma of large intestine, colon cancer, rectum cancer, breast cancer, lung cancer, non-small-cell lung cancer, prostate cancer, esophageal cancer, stomach cancer, liver cancer, carcinoma of biliary tract, spleen cancer, renal cancer, bladder carcinoma, uterine cancer, ovarian cancer, carcinoma of uterine cervix, carcinoma of testis, thyroid carcinoma, pancreatic cancer, brain tumor, blood cancer), feeding (appetite) enhancer, prophylactic/therapeutic agents for anorexia, apoptosis inducer and the like. Alternatively, it is useful as a safe and low toxic medicine such as the prophylactic/therapeutic agent for central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.). Among them, a prophylactic/therapeutic agent for cancer, apoptosis inducer, feeding enhancer and the like are preferable.

The double-stranded RNA can be manufactured by designing the same based on the sequence of the polynucleotide of the present invention, by a modification of publicly known methods (e.g., Nature, 411, 494, 2001).

The ribozyme can be manufactured by designing the same based on the sequence of the polynucleotide of the present invention, by a modification of publicly known methods (e.g., TRENDS in Molecular Medicine, 7, 221, 2001). For example, the ribozyme can be manufactured by ligating a publicly known ribozyme to a part of the RNA encoding the polypeptide or the receptor of the present invention. The part of the RNA encoding the polypeptide or the receptor of the present invention includes a contiguous part (RNA fragment) to the cleavage site on the RNA of the present invention, which can be cleaved by a publicly known ribozyme.

Where the double-stranded RNA or ribozyme described above is used as the prophylactic/therapeutic agent described above, the RNA or ribozyme may be prepared into pharmaceutical preparations, as in the antisense polynucleotide, which are provided for administration.

(6) A Medicine Containing the Antibody of the Present Invention

The antibody against the polypeptide of the present invention is useful as a low toxic and safe medicine such as the agent for the prevention/treatment of cancer (e.g., carcinoma of large intestine, colon cancer, rectum cancer, breast cancer, lung cancer, non-small-cell lung cancer, prostate cancer, esophageal cancer, stomach cancer, liver cancer, carcinoma of biliary tract, spleen cancer, renal cancer, bladder carcinoma, uterine cancer, ovarian cancer, carcinoma of uterine cervix, carcinoma of testis, thyroid carcinoma, pancreatic cancer, brain tumor, blood cancer), feeding (appetite) enhancer, prophylactic/therapeutic agents for anorexia, apoptosis inducer and the like. Alternatively, it is useful as a safe and low toxic medicine such as the prophylactic/therapeutic agent for central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.). Among them, a prophylactic/therapeutic agent for cancer, apoptosis inducer, feeding enhancer and the like are preferable.

The antibody of the present invention, which has a function of neutralizing the receptor of the present invention (that inactivates the signal transduction), is useful as a low toxic and safe medicine such as the agent for the prevention/treatment of cancer (e.g., carcinoma of large intestine, colon cancer, rectum cancer, breast cancer, lung cancer, non-small-cell lung cancer, prostate cancer, esophageal cancer, stomach cancer, liver cancer, carcinoma of biliary tract, spleen cancer, renal cancer, bladder carcinoma, uterine cancer, ovarian cancer, carcinoma of uterine cervix, carcinoma of testis, thyroid carcinoma, pancreatic cancer, brain tumor, blood cancer), feeding (appetite) enhancer, prophylactic/therapeutic agents for anorexia, apoptosis inducer and the like. Alternatively, it is useful as a safe and low toxic medicine such as the prophylactic/therapeutic agent for central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.). Among them, a prophylactic/therapeutic agent for cancer, apoptosis inducer, feeding enhancer and the like are preferable.

The antibody of the present invention, which activates the signal transduction of the receptor of the present invention, can be used as a medicine such as a safe and low toxic therapeutic and preventive agent for adiposis (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), hyperphagia and the like. Among them, a prophylactic/therapeutic agent for adiposis is preferred.

The above-mentioned medicine containing the antibody of the present invention can be orally or non-orally administered, directly as a liquid medicine or by formulating into an appropriate pharmaceutical composition, to human and mammals (e.g., rat, rabbit, sheep, swine, bovine, cat, dog and monkey). While the dosage is different depending on the administration object, diseases, disease conditions and administration route, favorable dosage is usually 0.01 to 20 mg, preferably 0.1 to 10 mg, and more preferably 0.1 to 5 mg per kg body weight preferably 1 to 3 times per day by intravenous injection for treatment and prevention of an adult patient with cancer. Approximately the same dosage of oral or non-oral administration is possible. The dosage may be increased depending on the disease conditions, particularly when the condition is severe.

The antibody of the present invention may be administered alone or as an appropriate pharmaceutical composition. The pharmaceutical composition used in the above administration contains a salt of the antibody, and a pharmaceutically acceptable carrier, diluent or excipient. Such composition is provided as a drug suitable for oral or non-oral administration.

Examples of the composition for oral administration include solid or liquid drugs such as tablets (including sugarcoated and film coated pills), pellets, granules, powders, capsules (including soft capsules), syrups, emulsions and dispersions. Such composition is manufactured by the method known in the art, and contains carriers, diluent or excipients conventionally used in formulation. The excipient includes galactose, starch, sucrose and magnesium stearate.

Compositions for non-oral administration are used, for example, for injection agents and suppositories, and the injection agent comprises drugs for hypodermic injection, intradermal injection, intramuscular injection and intravenous feeding. Such injection agents are prepared by the method known in the art, for example by dissolving, dispersing or emulsifying the antibody or a salt thereof in an asceptic aqueous or oily solution usually used for injection. Examples of the aqueous solution available for injection include a physiological saline solution and isotonic solutions containing glucose and other auxiliary agents, and appropriate solubilizing agents such as alcohols (such as ethanol), polyalcohols (such as propyleneglycol or polyethylene glycol) and nonionic surfactants [such as polysorbate 80 or HCO-50 (a polyoxyethylene (50 mol) adduct of hydrated castor oil)] may be used together. Examples of the oily solution available include sesame oil and soy bean oil, and benzyl benzoate or benzyl alcohol may be used together as a solubilizing agent. The injection solution prepared is usually filled in an appropriate ampoule. The suppository used for intrarectum administration can be prepared by mixing the antigen or a salt thereof with a suppository base.

The pharmaceutical composition for oral or non-oral administration is desirably formulated as a drug for a single dosage suitable for administering the active ingredient. Examples of such single dosage formulation include tablets, pills, capsules, injection agents (ampoules) and suppositories, and the dosage is 5 to 500 mg, particularly 5 to 100 mg in the injection agent and 10 to 250 mg in other formulations.

The composition above may contain other active ingredients so long as they do not cause unfavorable interactions with the antibody by blending.

(7) DNA Transgenic Animals

The present invention provides a non-human mammal bearing an exogenous DNA encoding the polypeptide or the receptor of the present invention (hereinafter merely referred to as the exogenous DNA of the present invention) or its variant DNA (sometimes simply referred to as the exogenous variant DNA of the present invention).

That is, the present invention provides:
(1) A non-human mammal bearing the exogenous DNA of the present invention or its variant DNA;
(2) The mammal according to (1), wherein the non-human mammal is a rodent;
(3) The mammal according to (2), wherein the rodent is mouse or rat; and,
(4) A recombinant vector bearing the exogenous DNA of the present invention or its variant DNA and capable of expressing in a mammal.

The non-human mammal bearing the exogenous DNA of the present invention or its variant DNA (hereinafter simply referred to as the DNA transgenic animal of the present invention) can be prepared by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method etc. Also, it is possible to transfect the exogenous DNA of the present invention into a somatic cell, a living organ, a tissue cell, or the like by the DNA transfection methods, and utilize the transformant for cell culture, tissue culture, etc. In addition, these cells may be fused with the above-described germinal cell by a publicly known cell fusion method to create the DNA transgenic animal of the present invention.

Examples of the non-human mammal that can be used include bovine, swine, sheep, goats, rabbits, dogs, cats, guinea pigs, hamsters, mice, rats, and the like. Above all, preferred are rodents, especially mice (e.g., C57BL/6 strain, DBA2 strain, etc. for a pure line and for a cross line, B6C3F$_1$ strain, BDF$_1$ strain B6D2F$_1$ strain, BALB/c strain, ICR strain, etc.) or rats (Wistar, SD, etc.), since they are relatively short in ontogeny and life cycle from a standpoint of creating model animals for human disease.

"Mammals" in a recombinant vector that can be expressed in the mammals include the aforementioned non-human mammals and human, etc.

The exogenous DNA of the present invention refers to the DNA of the present invention that is once isolated/extracted from mammals, not the DNA of the present invention inherently possessed by the non-human mammals.

The variant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean such a DNA that expresses the abnormal polypeptide or the abnormal receptor of the present invention and exemplified by the DNA that expresses a polypeptide to suppress the functions of the normal polypeptide or the normal receptor of the present invention.

The exogenous DNA of the present invention may be any one of those derived from a mammal of the same species as, or a different species from, the mammal as the target animal. In transfecting the DNA of the present invention into the target animal, it is generally advantageous to use the DNA as a DNA construct in which the DNA is ligated downstream a promoter capable of expressing the DNA in the animal cells. For example, in the case of transfecting the human DNA of the present invention, a DNA-introduced mammal that expresses the DNA of the present invention to a high level, can be prepared by microinjecting a DNA construct (e.g., vector, etc.) ligated with the human DNA of the present invention into a fertilized egg of the target non-human mammal, for example mouse, downstream various promoters, which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the polypeptide or the receptor of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include (1) promoters for the DNA derived from viruses (e.g., simian virus, cytomegalovirus, Moloney leukemia virus, JC virus, breast cancer virus, poliovirus, etc.), and (2) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), protein chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin, etc. Among them, cytomegalovirus promoters, human protein elongation factor 1α (EF-1α) promoters, human and chicken β actin promoters etc., wherein the proteins can highly express in the whole body, are preferred.

It is preferred that the vectors described above have a sequence for terminating the transcription of the desired mRNA in the DNA-introduced animal (generally called a terminator); for example, a sequence of each DNA derived from viruses and various mammals. SV40 terminator of the simian virus and the like, are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The normal translational region can be acquired as whole genomic DNA or portion thereof from liver-, kidney-, thyroid cell-, or fibroblast cell-derived DNA of human or other mammals (e.g., rabbits, dogs, cats, guinea pigs, hamsters, rats, mice) and commercially available various genomic DNA library, or from a complement DNA as a raw material, which is prepared by publicly known methods from liver-, kidney-, thyroid cell-, or fibroblast cell-derived RNA. Alternatively, the exogenous abnormal DNA can be prepared by mutating the translational region of the normal receptor protein, which is obtained from the above cells or tissues, to variant translational region using site-directed mutagenesis.

The translational region can be prepared as a DNA construct that can be expressed in the transgenic animal by an ordinary DNA engineering method, wherein the DNA is ligated downstream the abovementioned promoters and if desired, upstream transcription termination site.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA in all of the germinal cells and somatic cells thereof.

The non-human mammal in which the normal exogenous DNA of the present invention has been transfected can be passaged as the DNA-bearing animal under ordinary breeding environment, by confirming the fact that the exogenous DNA is stably retained by mating.

By the transfection of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfection means that the DNA of the present invention is excessively present in all of the germinal cells and somatic cells thereof. The offspring of the animal that inherits the exogenous DNA of the present invention have excessively the DNA of the present invention in all of the germinal cells and somatic cells thereof.

By obtaining a homozygous animal having the transfected DNA in both of homologous chromosomes and mating a male and female of the animal, all offspring can be passaged to retain the DNA.

In a non-human mammal bearing the normal DNA of the present invention, the normal DNA of the present invention has expressed to a high level, and may eventually develop the hyperfunction of the polypeptide or the receptor of the present invention by promoting the functions of endogenous normal DNA. Therefore, the animal can be utilized as a pathologic model animal for such a disease. Specifically, using the normal DNA transgenic animal of the present invention, it is possible to elucidate the mechanism of the hyperfunction of the polypeptide or the receptor of the present invention and the pathological mechanism of the disease associated with the polypeptide or the receptor of the present invention and to determine how to treat the disease.

Furthermore, since a mammal transfected with the exogenous normal DNA of the present invention exhibits an increasing symptom of the polypeptide or the receptor of the present invention librated, the animal is usable for screening of prophylactic/therapeutic agents for the disease associated with the polypeptide or the receptor of the present invention (e.g., adiposis, cancer).

On the other hand, non-human mammal having the exogenous abnormal DNA of the present invention can be passaged under normal breeding conditions as the DNA-bearing animal by confirming the stable retention of the exogenous DNA via crossing. Moreover, the objective exogenous DNA can be utilized as a starting material by inserting the DNA into the plasmid described above. The DNA construct with a promoter can be prepared by conventional DNA engineering techniques. The transfection of the abnormal DNA of the present invention at the fertilized egg cell stage is preserved to be present in all of the germinal and somatic cells of the target mammal. The fact that the abnormal DNA of the present invention is present in the germinal cells of the animal after DNA transfection means that all of the offspring of the animal prepared have the abnormal DNA of the present invention in all of the germinal and somatic cells. Such an offspring, which passaged the exogenous DNA of the present invention, retains the abnormal DNA of the present invention in all the germinal and somatic cells. By obtaining a homozygous animal having the transfected DNA in both of homologous chromosomes and mating a male and female of the animal, all offspring can be passaged to retain the DNA.

Since non-human mammal having the abnormal DNA of the present invention may express the abnormal DNA of the present invention at a high level, the animal may sometimes be the function inactivation type inadaptability to the polypeptide or the receptor of the present invention by inhibiting the function of the endogenous normal DNA and can be utilized as its disease model animal. For example, using the abnormal DNA transgenic animal of the present invention, it is possible to elucidate the mechanism of inadaptability to the polypeptide or the receptor of the present invention and to perform to study a method for treatment of this disease.

More specifically, the transgenic animal of the present invention expressing the abnormal DNA of the present invention to a high level is also expected to serve as an experimental model to elucidate the mechanism of the functional inhibition (dominant negative effect) of normal polypeptide or normal receptor by the abnormal polypeptide or abnormal receptor of the present invention in the function inactive type inadaptability to the polypeptide or the receptor of the present invention.

A mammal bearing the abnormal exogenous DNA of the present invention is also expected to serve for screening a candidate drug for the treatment of the function inactive type inadaptability to the polypeptide or the receptor of the present invention, since the polypeptide or the receptor of the present invention increases in such an animal in its free form.

Other potential applications of two kinds of the transgenic animals described above include:

(1) Use as a cell source for tissue culture;
(2) Elucidation of the relation to a polypeptide or a receptor that is specifically expressed or activated by the polypeptide or the receptor of the present invention, by direct analysis of DNA or RNA in tissues of the DNA transgenic animal of the present invention or by analysis of the polypeptide or the receptor expressed by the DNA in the tissues;
(3) Research in the function of cells derived from tissues that are usually cultured only with difficulty, using cells in tissues bearing the DNA cultured by a standard tissue culture technique;
(4) Screening a medicine that enhances the functions of cells using the cells described in (3) above; and,
(5) Isolation and purification of the variant polypeptide or the variant receptor of the present invention and preparation of an antibody thereto.

Furthermore, clinical conditions of a disease associated wit the polypeptide or the receptor of the present invention (e.g., cancer, adiposis), including the function inactive type inadaptability to the polypeptide or the receptor of the present invention can be determined by using the DNA transgenic animal of the present invention. Also, pathological findings on each organ in a disease model associated with the polypeptide of the invention can be obtained in more detail, leading to the development of a new method for treatment as well as the research and therapy of any secondary diseases associated with the disease.

It is also possible to obtain a free cell, in which the DNA is transfected, by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve to identify cells capable of producing the polypeptide or the receptor of the present invention, and to study in association with apoptosis, differentiation or propagation or on the mechanism of signal transduction in these properties to inspect any abnormality therein. Thus, the DNA transgenic animal of the present invention can provide an effective research material for the polypeptide or the receptor of the invention and for elucidation of the function and effect thereof.

To develop a drug for the treatment of diseases associated with the polypeptide or the receptor of the invention, including the function inactive type inadaptability to the polypeptide or the receptor of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the polypeptide of the present invention, using the DNA transgenic animal of the present invention or a vector capable of expressing the exogenous DNA of the present invention.

(8) Knockout Animal

The present invention provides a non-human mammal embryonic stem cell bearing the DNA of the present invention inactivated and a non-human mammal deficient in expressing the DNA of the present invention.

Thus, the present invention provides:
(1) A non-human mammal embryonic stem cell in which the DNA of the present invention is inactivated;
(2) The embryonic stem cell according to (1), wherein the DNA is inactivated by introducing a reporter gene (e.g., β-galactosidase gene derived from *Escherichia coli*);
(3) The embryonic stem cell according to (1), which is resistant to neomycin;
(4) The embryonic stem cell according to (1), wherein the non-human mammal is a rodent;
(5) The embryonic stem cell according to (4), wherein the rodent is mouse;
(6) A non-human mammal deficient in expressing the DNA of the present invention, wherein the DNA of the present invention is inactivated;
(7) The non-human mammal according to (6), wherein the DNA is inactivated by introducing a reporter gene (e.g., β-galactosidase derived from *Escherichia coli*) therein and the reporter gene is capable of being expressed under control of the promoter for the DNA of the present invention;
(8) The non-human mammal according to (6), which is a rodent;
(9) The non-human mammal according to (8), wherein the rodent is mouse; and
(10) A method for screening a compound or its salt that enhances or inhibits the promoter activity for the DNA of the present invention, which comprises administering a test compound to the mammal of (7) and detecting expression of the reporter gene.

The non-human mammalian embryonic stem cell, in which the DNA of the present invention is inactivated, refers to a non-human mammalian embryonic stem cell that suppresses the ability of the non-human mammal to express the DNA by artificially mutating the DNA of the present invention possessed in the non-human mammal, or the DNA has no substantial ability to express the polypeptide or receptor of the present invention (hereinafter sometimes referred to as the knockout DNA of the present invention) by substantially inactivating the activities of the polypeptide or receptor of the present invention encoded by the DNA (hereinafter merely referred to as ES cell).

As the non-human mammalian, the same examples as described above apply.

Techniques for artificially mutating the DNA of the present invention include deletion of a part or all of the DNA sequence and insertion of or substitution with other DNA, e.g., by genetic engineering. By these variations, the knockout DNA of the present invention may be prepared, for example, by shifting the reading frame of a codon or by disrupting the function of a promoter or exon.

Specifically, the non-human mammalian embryonic stem cell, in which the DNA of the present invention is inactivated (hereinafter merely referred to as the ES cell with the DNA of the present invention inactivated or the knockout ES cell of the present invention), can be obtained by, for example, isolating the DNA of the present invention possessed by the target non-human mammal, inserting a DNA strand (hereinafter simply referred to as targeting vector) having a DNA sequence constructed so as to eventually destroy the gene by inserting into its exon site a chemical resistant gene such as a neomycin resistant gene or a hygromycin resistant gene, or a reporter gene such as lacZ (β-galactosidase gene) or cat (chloramphenicol acetyltransferase gene), etc. thereby to destroy the functions of exon, or by inserting into the intron site between exons a DNA sequence which terminates gene transcription (e.g., polyA-added signal, etc.) thereby to disable the synthesis of complete mRNA, into a chromosome of the animal cells by, e.g., homologous recombination. The thus-obtained ES cells are analyzed by the Southern hybridization using as a probe a DNA sequence on or near the DNA of the present invention, or by PCR using as primers a DNA sequence on the targeting vector and another DNA sequence near the DNA of the present invention which is not included in the targeting vector, and the knockout ES cell of the present invention is selected.

The parent ES cells to inactivate the DNA of the present invention by homologous recombination, etc. may be of a strain already established as described above, or may be originally established in accordance with a modification of the known method by Evans and Kaufman. For example, in the case of mouse ES cells, currently it is common practice to use ES cells of the 129 strain. However, since their immunological background is obscure, the C57BL/6 mouse or the BDF$_1$ mouse (F$_1$ hybrid between C57BL/6 and DBA/2), wherein the low ovum collection per C57BL/6 mouse or C57BL/6 has been improved-by crossing with DBA/2, may be preferably used, instead of obtaining a pure line of ES cells with the clear immunological genetic background. The BDF$_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes of 3.5 days after fertilization are commonly used. A large number of early stage embryos may be acquired more efficiently, by collecting the embryos of the 8-cell stage and using the same after culturing until the blastocyte stage.

Although the ES cells used may be of either sex, male ES cells are generally more convenient for generation of a germ cell line chimera and are therefore preferred. It is desirable to identify sexes as soon as possible also in order to save painstaking culture time.

As an example of the method for sex identification of the ES cell, mention may be made of a method in which a gene in the sex-determining region on the Y-chromosome is amplified by PCR and detected. When this method is used, ES cells (about 50 cells) corresponding to almost 1 colony are sufficient, whereas karyotype analysis hitherto required about $10^6$ cells; therefore, the first selection of ES cells at the early stage of culture can be based on sex identification, and male cells can be selected early, which saves a significant amount of time at the early stage of culture.

Second selection can be achieved by, for example, number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and about 90% air) in the presence of LIF (1-10000 U/ml) on appropriate feeder cells such as STO fibroblasts, treated with a trypsin/EDTA solution (normally about 0.001 to about 0.5% trypsin/about 0.1 to 5 mM EDTA, preferably about 0.1% trypsin/about 1 mM EDTA) at the time of passage to obtain separate single cells, which are then seeded on freshly prepared feeder cells. This passage is normally conducted every 1 to 3 days; it is desirable that cells be observed at passage and cells found to be morphologically abnormal in culture, if any, be abandoned.

By allowing ES cells to reach a high density in monolayers or to form cell aggregates in suspension under appropriate conditions, it is possible to differentiate them to various cell types, for example, parietal and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtainable from the differentiated ES cells of the present invention, are useful for studying the functions of the polypeptide or the receptor of the present invention in vitro cytologically or molecular biologically.

The non-human mammal deficient in expression of the DNA of the present invention can be identified from a normal animal by measuring the amount of mRNA in the subject animal by a publicly known method, and indirectly comparing the levels of expression.

As the non-human mammal, the same examples described above apply.

With respect to the non-human mammal deficient in expression of the DNA of the present invention, the DNA of the present invention can be made knockout by transfecting a targeting vector, prepared as described above, to mouse embryonic stem cells or mouse oocytes thereof, and conducting homologous recombination in which a targeting vector DNA sequence, wherein the DNA of the present invention is inactivated by the transfection, is replaced with the DNA of the present invention on a chromosome of a mouse embryonic stem cell or mouse oocyte.

The cells, in which the DNA of the present invention is rendered knockout, can be identified by the Southern hybridization analysis using as a probe a DNA sequence on or near the DNA of the present invention, or by PCR analysis using as primers a DNA sequence on the targeting vector and another DNA sequence which is not included in the DNA of the present invention derived from mouse, which is used as the targeting vector. When non-human mammalian embryonic stem cells are used, the cell line wherein the DNA of the present invention is inactivated is cloned by homologous recombination; the resulting cloned cell line is injected to, e.g., a non-human mammalian embryo or blastocyte, at an appropriate stage such as the 8-cell stage. The resulting chimeric embryos are transplanted to the uterus of the pseudo-pregnant non-human mammal. The resulting animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual, in which all tissues are composed of cells having an artificially mutated locus of the DNA of the present invention, can be selected from a series of offspring obtained by crossing between such a chimeric animal and a normal animal, e.g., by coat color identification, etc. The individuals thus obtained are normally deficient in heterozygous expression of the polypeptide or the receptor of the present invention. The individuals deficient in homozygous expression of the polypeptide or the receptor of the present invention can be obtained from offspring of the intercross between the heterozygotes.

When an oocyte is used, a DNA solution may be injected, e.g., to the prenucleus by microinjection thereby to obtain a transgenic non-human mammal having a targeting vector introduced into its chromosome. From such transgenic non-human mammals, those having a mutation at the locus of the DNA of the present invention can be obtained by selection based on homologous recombination.

As described above, individuals wherein the DNA of the present invention is rendered knockout permit passage rearing under ordinary rearing conditions, after it is confirmed that in the animal individuals obtained by their crossing, the DNA has been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammalian embryonic stem cell, in which the DNA of the present invention is inactivated, is very useful for preparing a non-human mammal deficient in expression of the DNA of the present invention.

Since the non-human mammal, in which the DNA of the present invention fails to express, lacks various biological activities induced by the polypeptide or the receptor of the present invention, such an animal can be a disease model suspected of inactivated biological activities of the polypeptide or the receptor of the present invention and thus, offers an effective study to investigate causes for and therapy for these diseases.

(8a) Method for Screening of Compounds Having Therapeutic/Prophylactic Effects for Diseases Caused by Deficiency, Damages, etc. of the DNA of the Present Invention The non-human mammal deficient in expression of the DNA of the present invention can be used to screen the compounds having therapeutic/prophylactic effects for diseases caused by deficiency, damages, and the like of the DNA of the present invention.

That is, the present invention provides a method for screening of a compound or its salt having therapeutic/prophylactic effects for diseases caused by deficiency, damages, etc. of the DNA of the present invention such as adiposis (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), hyperphagia, which comprises administering a test compound to the non-human mammal deficient in expression of the DNA of the present invention, and observing and measuring a change occurred in the animal.

As the non-human mammal deficient in expression of the DNA of the present invention used for the screening method, the same examples as given hereinabove apply.

Examples of the test compounds include peptides, proteins, non-peptide compounds, synthetic compounds, fermentation products, cell extracts, vegetable extracts, animal tissue extracts, blood plasma, etc. and these compounds may be novel compounds or publicly known compounds.

Specifically, the non-human mammal deficient in the expression of the DNA of the present invention is treated with a test compound, comparison is made with an intact animal for control and a change in each organ, tissue, disease conditions, etc. of the animal is used as an indicator to assess the therapeutic/prophylactic effects of the test compound.

For treating an animal to be tested with a test compound, for example, oral administration, intravenous injection, etc. are applied and the treatment is appropriately selected depending upon conditions of the test animal, properties of the test compound, etc. Furthermore, the amount of a test compound administered can be appropriately selected depending on administration route, nature of the test compound, or the like.

For example, in the case of screening a compound having a therapeutic/prophylactic effect for adiposis (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), hyperphagia, the non-human mammal deficient in expression of the DNA of the present invention is subjected to a sugar loading treatment, a test compound is administered before or after the sugar loading treatment and, blood sugar level, body weight change, etc. of the animal is measured with passage of time.

In the screening method, where the test compound was administered to a test animal, the test compound can be selected as a compound having the prophylactic and/or therapeutic effect against the above-mentioned diseases when metastasis of cancer reduced more than about 10%, preferably more than about 30%, more preferably more than about 50%.

The compound obtained using the screening methods is a compound selected from the test compounds described above and exhibits a therapeutic/prophylactic effect for the diseases caused by deficiencies, damages, etc. of the polypeptide of the present invention such as adiposis (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), hyperphagia. Therefore, the compound can be used as a safe and low toxic medicine for the treatment/prevention, etc. for these diseases. Furthermore, compounds derived from such a compound obtained by the above screening can be used as well.

The compound obtained by the screening above may be in the form of salts. As the salts of the compound, there may be used salts with physiologically acceptable acids (e.g., inorganic acids or organic acids) or bases (e.g., alkali metal), preferably physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

A medicine containing the compound or salts thereof obtained by the screening methods may be manufactured in a manner similar to the method for preparing the medicine containing the polypeptide of the present invention described hereinabove.

Since the pharmaceutical product thus obtained is safe and low toxic, it can be administered to human and mammals (e.g., rat, mouse, guinea pig, rabbit, sheep, swine, bovine, horse, cat, dog, monkey, etc.).

The dose of the compound or its salt may vary depending on target disease, subject to be administered, route for administration, etc. When the compound is orally administered, the compound is administered to adult patient with obesity (as 60 kg body weight) generally in a daily dose of approximately 0.1 to 100 mg, preferably approximately 1.0 to 50 mg, more preferably approximately 1.0 to 200 mg, and most preferably approximately 1.0 to 20 mg. In parenteral administration, a single dose of the compound may vary depending on subject to be administered, target disease, etc. When the compound is administered to adult patient with obesity (as 60 kg) in the form of injection, it is desired to intravenously administer the compound in the form of injection, generally in a daily dose of approximately 0.01 to 30 mg, preferably approximately 0.1 to 20 mg, and more preferably approximately 0.1 to 10 mg. For other animal species, the corresponding dose as converted per 60 kg weight can be administered.

(8b) Method of Screening a Compound That Promotes or Inhibits the Activities of a Promoter to the DNA of the Present Invention The present invention provides a method of screening a compound or its salt that promotes or inhibits the activities of a promoter to the DNA of the present invention, which comprises administering a test compound to a non-human mammal deficient in expression of the DNA of the present invention and detecting expression of the reporter gene.

In the screening method described above, the non-human mammal deficient in expression of the DNA of the present invention is selected from the aforesaid non-human mammal deficient in expression of the DNA of the present invention for an animal, in which the DNA of the present invention is inactivated by introducing a reporter gene and the reporter gene can be expressed under control of a promoter to the DNA of the present invention.

The same examples given above for the test compound apply to the test compound.

As the reporter gene, the same specific examples given above apply to the reporter gene, with β-galactosidase (lacZ), soluble alkaline phosphatase gene, luciferase gene, etc. being preferred.

In the non-human mammal deficient in expression of the DNA of the present invention wherein the DNA of the present invention is substituted with a reporter gene, the reporter gene is present under control of a promoter to the DNA of the present invention. Thus, the activity of the promoter can be detected by tracing the expression of a substance encoded by the reporter gene.

For example, when a part of the DNA region encoding the polypeptide of the present invention is substituted with, e.g., β-galactosidase gene (lacZ) derived from *Escherichia coli*, β-galactosidase is expressed in a tissue where the polypeptide of the present invention should originally be expressed, in place of the polypeptide of the present invention. Thus, the expression state of the polypeptide of the present invention can be readily observed in vivo of an animal, by staining with a reagent, e.g., 5-bromo-4-chloro-3-indolyl-β-D-galactopyranoside (X-gal), which is a substrate for β-galactosidase. Specifically, a mouse deficient in the polypeptide of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening methods described above are compounds selected from the test compounds described above, which enhance or inhibit the promoter activity for the DNA of the present invention.

The compound obtained by the screening methods may be in the form of salts. The salts of the compound used are salts with physiologically acceptable acids (e.g., inorganic acids) or bases (e.g., organic acids), and physiologically acceptable acid addition salts are preferred. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

Since the compounds or salts thereof that enhance the promoter activity to the DNA of the present invention can enhance the expression of the polypeptide or the receptor of the present invention, or can enhance the functions of the polypeptide or the receptor, they are useful as low toxic and safe medicines such as a prophylactic/therapeutic agent for adiposis (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), hyperphagia and the like. Alternatively, they are useful for medicines of central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.). Among them, a prophylactic/therapeutic agent for adiposis is preferred.

Since the compounds or salts thereof that inhibit the promoter activity to the DNA of the present invention can inhibit the expression of the polypeptide or the receptor of the present invention, or can inhibit the functions of the polypeptide or the receptor, they are useful as low toxic and safe medicines such as prophylactic/therapeutic agents for cancer (e.g., carcinoma of large intestine, colon cancer, rectum cancer, breast cancer, lung cancer, non-small-cell lung cancer, prostate cancer, esophageal cancer, stomach cancer, liver cancer, carcinoma of biliary tract, spleen cancer, renal cancer, bladder carcinoma, uterine cancer, ovarian cancer, carcinoma of uterine cervix, carcinoma of testis, thyroid carcinoma, pancreatic cancer, brain tumor, blood cancer), feeding (appetite) enhancer, prophylactic/therapeutic agents for anorexia, apoptosis inducer and the like. Alternatively, they are useful for medicines of central dysfunction (e.g., Alzheimer's disease, senile dementia, suppression of eating, etc.), endocrine-related diseases (e.g., hypertension, hypogonadism, hypothyroidism, hypopituitarism, etc.), metabolic disorders (e.g., diabetes mellitus, lipid metabolic disorders, hyperlipemia, etc.). A prophylactic/therapeutic agent for cancer or feeding enhancer is preferred.

In addition, compound derived from the compounds obtained by the screening above may be employed as well.

A medicine containing the compounds or salts thereof obtained by the screening methods described above may be prepared in a manner similar to the method for preparing the medicine containing the compound of the present invention or its salts described above.

Since the pharmaceutical preparation thus obtained is safe and low toxic, it can be administered to human or mammals (e.g., rat, mouse, guinea pig, rabbit, sheep, swine, bovine, horse, cat, dog, monkey, etc.).

The dose of the compound or salts thereof varies depending on target disease, subject to be administered, route for administration, etc.; for example, when the compound that enhances the promoter activity to the DNA of the present invention is orally administered, they may be administered to adult patient with obesity (as 60 kg body weight) normally in a daily dose of about 0.1 to about 100 mg, preferably about 1.0 to about 50 mg, more preferably about 1.0 to about 20 mg. In parenteral administration, a single dose of the compound may vary depending upon subject to be administered, target disease, etc.; when the compound that enhances the promoter activity to the DNA of the present invention is administered in the form of injectable preparation, it is advantageous to administer the compound intravenously to adult patient with obesity (as 60 kg) in a daily dose of about 0.01 to about 30 mg, preferably about 0.1 to about 20 mg, more preferably about 0.1 to about 10 mg. For other animal species, the corresponding dose as converted per 60 kg can be administered.

On the other hand, for example, when the compound that inhibits the promoter activity to the DNA of the present invention is orally administered, the compound is administered to adult patient with cancer (as 60 kg body weight) in a daily dose of approximately 0.1 to 100 mg, preferably approximately 1.0 to 50 mg, more preferably approximately 1.0 to 20 mg. In parenteral administration, a single dose of the compound may vary depending on subject to be administered, target disease, etc.; when the compound that inhibits the promoter activity to the DNA of the present invention is administered to adult patient with cancer (as 60 kg) in the form of injectable preparation, it is advantageous to administer the compound intravenously in a daily dose of approximately 0.01 to 30 mg, preferably approximately 0.1 to 20 mg, more preferably approximately 0.1 to 10 mg. For other animal species, the corresponding dose as converted per 60 kg weight can be administered.

As described above, the non-human mammal deficient in expression of the DNA of the present invention is extremely useful for screening a compound that enhances or inhibits the promoter activity of the DNA of the present invention, or a salt thereof. Therefore, it can greatly contribute for searching causes of, or developing prophylactic/therapeutic agents for various diseases caused by deficiency in expression of the DNA of the present invention.

Further, where so-called transgenic animal (gene-introduced animal) is prepared by using DNA, which contains a promoter region for the polypeptide of the present invention, ligating genes encoding a variety of proteins to downstream thereof and injecting this DNA to animal's egg cell, the polypeptide can be synthesized specifically, so that it will allow to investigate its intravital function. Furthermore, where the cell line expressing an appropriate reporter gene, which binds to the above-mentioned promoter region, leads to establish, it can be used as a screening system of low molecular weight compound having a function that specifically enhances or inhibits intravital producing ability of the polypeptide of the present invention or the receptor of the present invention per se.

(9) As to the "Prophylactic/Therapeutic Agent for Obesity, which Comprises a Compound that Enhances the Activity of the Polypeptide of the Present Invention, or a Salt Thereof" and the "Prophylactic/Therapeutic Agent for Cancer, which Comprises a Compound that Inhibits the Activity of the Polypeptide of the Present Invention, or a Salt Thereof"

The "compound that enhances the activity of the polypeptide of the present invention" may be any compound that enhances the activity of the polypeptide of the present invention, and is useful as a low toxic and safe medicine such as a prophylactic/therapeutic agent for adiposis (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity).

The "compound that inhibits the activity of the polypeptide of the present invention" may be any compound that inhibits the activity of the polypeptide of the present invention, and is useful as a low toxic and safe medicine such as a prophylactic/therapeutic agent for cancer (e.g., carcinoma of large intestine, colon cancer, rectum cancer, breast cancer, lung cancer, non-small-cell lung cancer, prostate cancer, esophageal cancer, stomach cancer, liver cancer, carcinoma of biliary tract, spleen cancer, renal cancer, bladder carcinoma, uterine cancer, ovarian cancer, carcinoma of uterine cervix, carcinoma of testis, thyroid carcinoma, pancreatic cancer, brain tumor, blood cancer).

The prophylactic/therapeutic agent can be manufactured in the similar manner to the above (2).

In the description and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| I | inosine |
| R | adenine (A) or guanine (G) |
| Y | thymine (T) or cytosine (C) |
| M | adenine (A) or cytosine (C) |
| K | guanine (G) or thymine (T) |
| S | guanine (G) or cytosine (C) |
| W | adenine (A) or thymine (T) |
| B | guanine (G), guanine (G) or thymine (T) |
| D | adenine (A), guanine (G) or thymine (T) |
| V | adenine (A), guanine (G) or cytosine (C) |
| N | adenine (A), guanine (G), cytosine (C) or thymine (T), or unknown or other bases |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediamine tetraacetic acid |
| SDS | sodium dodecyl sulfate |
| BHA | benzhydorylamine |
| pMBHA | p-methylbenzhydrylamine |
| Tos | p-toluenesulfonyl |
| Bzl | benzyl |
| Bom | benzyloxymethyl |
| Boc | t-butoxycarbonyl |
| DCM | dichloromethane |
| HOBt | 1-hydroxybenztriazole |
| DCC | N,N'-dicyclohexylcarbodiimido |
| TFA | trifluoroacetic acid |
| DIEA | diisopropylethylamine |
| BSA | bovine serum albumin |
| CHAPS | 3-[(3-cholamidopropyl)dimethylammonio]-1-propanesulfonate |
| Gly or G | glycine |
| Ala or A | alanine |
| Val or V | valine |
| Leu or L | leucine |
| Ile or I | isoleucine |
| Ser or S | serine |
| Thr or T | threonine |
| Cys or C | cysteine |
| Met or M | methionine |
| Glu or E | glutamic acid |
| Asp or D | aspartic acid |
| Lys or K | lysine |
| Arg or R | arginine |
| His or H | histidine |
| Phe or F | phenylalanine |
| Tyr or Y | tyrosine |
| Trp or W | tryptophan |
| Pro or P | proline |
| Asn or N | asparagine |
| Gln or Q | glutamine |
| pGlu | pyroglutamic acid |
| Tyr (I) | 3-iodotyrosine |
| DMF | N,N-dimethylformamide |
| Fmoc | N-9-fluorenyl methoxycarbonyl |
| Trt | trityl |
| Pbf | 2,2,4,6,7-pentamethyldihydrobenzofrane-5-sulfonyl |
| Clt | 2-chlorotrityl |
| Bu$^t$ | t-butyl |
| Met (O) | methionine sulfoxide |
| PAM | phenylacetamidomethyl |
| DIPCI | N,N'-diisopropylcarbodiimide |
| Cl-Z | 2-chlorobenzyloxycarbonyl |
| HOAt | 1-hydroxy-7-azabenzotriazol |
| PyAop | 7-azabenzotriazol-1-iloxytrispirolidinophophonium hexafluorophophate |
| DIPCDI | 1,3-diisopropylcarbodiimide |
| Nle | norleucine |
| PMSF | phenylmethylsulfonyl fluoride |
| Cl-Z | 2-chlorobenzyloxycarbonyl |
| Br-Z | 2-bromobenzyloxycarbonyl |
| Fmoc-Lys(Boc)-Thr(Psi(Me,Me)pro)-OH | (4S,5R)-3-(Fmoc-Lys(Boc)-2,2,5-trimethyl-oxazolidine-4-carboxylic acid |

The sequence identification numbers in the sequence listing of the description indicates the following sequence, respectively.

[SEQ ID NO: 1]
This represents the amino acid sequence of the human-derived G protein-coupled receptor protein TGR23-1 (human TGR23-1).

[SEQ ID NO: 2]
This represents the base sequence of the cDNA encoding the human-derived G protein-coupled receptor protein TGR23-1.

[SEQ ID NO: 3]
This represents the amino acid sequence of the human-derived G protein-coupled receptor protein TGR23-2 (human TGR23-2).

[SEQ ID NO: 4]
This represents the base sequence of the cDNA encoding the human-derived G protein-coupled receptor protein TGR23-2.

[SEQ ID NO: 5]
This represents the base sequence of the primer 1 used in the PCR reaction of Reference Example 1, Example 28, Example 32 and Example 33 described below.

[SEQ ID NO: 6]
This represents the base sequence of the primer 2 used in the PCR reaction of Reference Example 1, Example 28, Example 32 and Example 33 described below.

[SEQ ID NO: 7]
This represents the base sequence of the primer 1 used in the PCR reaction of Example 1 and Example 15 described below.

[SEQ ID NO: 8]
This represents the base sequence of the primer 2 used in the PCR reaction of Example 1 and Example 15 described below.

[SEQ ID NO: 9]
This represents the base sequence of the primer used in the PCR reaction of Example 2, Example 16, Reference Example 2, Example 31, Example 39 and Example 47 described below.

[SEQ ID NO: 10]
This represents the base sequence of the primer used in the PCR reaction of Example 2, Example 16, Reference Example 2, Example 31, Example 39 and Example 47 described below.

[SEQ ID NO: 11]
This represents the base sequence of the probe used in the PCR reaction of Example 2, Example 16, Reference Example 2, Example 31, Example 39 and Example 47 described below.

[SEQ ID NO: 12]
This represents the amino acid sequence of rat TGR23-2 ligand (1-18).

[SEQ ID NO: 13]
This represents the amino acid sequence of rat TGR23-2 ligand (1-15).

[SEQ ID NO: 14]
This represents the amino acid sequence of rat TGR23-2 ligand (1-14).

[SEQ ID NO: 15]
This represents the base sequence of the primer used in the PCR reaction of Example 11 described below.

[SEQ ID NO: 16]
This represents the base sequence of the primer used in the PCR reaction of Example 11 described below.

[SEQ ID NO: 17]
This represents the base sequence of the primer used in the PCR reaction of Example 11 described below.

[SEQ ID NO: 18]
This represents the base sequence of the cDNA encoding human TGR23-2 ligand precursor.

[SEQ ID NO: 19]
This represents the amino acid sequence of the human TGR23-2 ligand precursor.

[SEQ ID NO: 20]
This represents the amino acid sequence of human TGR23-2 ligand (1-18).

[SEQ ID NO: 21]
This represents the amino acid sequence of human TGR23-2 ligand (1-15).

[SEQ ID NO: 22]
This represents the amino acid sequence of human TGR23-2 ligand (1-14).

[SEQ ID NO: 23]
This represents the amino acid sequence of human TGR23-2 ligand (1-20).

[SEQ ID NO: 24]
This represents the base sequence of the primer used in the PCR reaction of Example 12 described below.

[SEQ ID NO: 25]
This represents the base sequence of the primer used in the PCR reaction of Example 12 described below.

[SEQ ID NO: 26]
This represents the base sequence of the primer used in the PCR reaction of Example 12 described below.

[SEQ ID NO: 27]
This represents the base sequence of the cDNA encoding the mouse TGR23-2 ligand precursor.

[SEQ ID NO: 28]
This represents the amino acid sequence of the mouse TGR23-2 ligand precursor.

[SEQ ID NO: 29]
This represents the amino acid sequence of mouse TGR23-2 ligand (1-18).

[SEQ ID NO: 30]
This represents the amino acid sequence of mouse TGR23-2 ligand (1-15).

[SEQ ID NO: 31]
This represents the amino acid sequence of mouse TGR23-2 ligand (1-14).

[SEQ ID NO: 32]
This represents the amino acid sequence of mouse TGR23-2 ligand (1-20).

[SEQ ID NO: 33]
This represents the base sequence of the primer used in the PCR reaction of Example 13 described below.

[SEQ ID NO: 34]
This represents the base sequence of the cDNA encoding a portion of the rat TGR23-2 ligand precursor.

[SEQ ID NO: 35]
This represents the amino acid sequence of the portion of the rat TGR23-2 ligand precursor.

[SEQ ID NO: 36]
This represents the amino acid sequence of rat TGR23-2 ligand (1-20).

[SEQ ID NO: 37]
This represents the base sequence encoding the amino acid sequence represented by SEQ ID NO: 12.

[SEQ ID NO: 38]
This represents the base sequence encoding the amino acid sequence represented by SEQ ID NO: 13.

[SEQ ID NO: 39]
This represents the base sequence encoding the amino acid sequence represented by SEQ ID NO: 14.

[SEQ ID NO: 40]
This represents the base sequence encoding the amino acid sequence represented by SEQ ID NO: 36.

[SEQ ID NO: 41]
This represents the base sequence encoding the amino acid sequence represented by SEQ ID NO: 20.

[SEQ ID NO: 42]
This represents the base sequence encoding the amino acid sequence represented by SEQ ID NO: 21.

[SEQ ID NO: 43]
This represents the base sequence encoding the amino acid sequence represented by SEQ ID NO: 22.

[SEQ ID NO: 44]
This represents the base sequence encoding the amino acid sequence represented by SEQ ID NO: 23.

[SEQ ID NO: 45]
This represents the base sequence encoding the amino acid sequence represented by SEQ ID NO: 29.

[SEQ ID NO: 46]
This represents the base sequence encoding the amino acid sequence represented by SEQ ID NO: 30.

[SEQ ID NO: 47]
This represents the base sequence encoding the amino acid sequence represented by SEQ ID NO. 31.

[SEQ ID NO: 48]
This represents the base sequence encoding the amino acid sequence represented by SEQ ID NO: 32.

[SEQ ID NO: 49]
This represents the amino acid sequence of human TGR23-2 ligand (1-16).

[SEQ ID NO: 50]
This represents the base sequence encoding the amino acid sequence represented by SEQ ID NO: 49.

[SEQ ID NO: 51]
This represents the amino acid sequence of the human-derived G protein-coupled receptor protein.

[SEQ ID NO: 52]
This represents the base sequence encoding the amino acid sequence represented by SEQ ID NO: 51.

[SEQ ID NO: 53]
This represents the amino acid sequence of the human-derived G protein-coupled receptor protein.

[SEQ ID NO: 54]
This represents the base sequence encoding the amino acid sequence represented by SEQ ID NO: 53.

[SEQ ID NO: 55]
This represents the amino acid sequence of the human-derived G protein-coupled receptor protein.

[SEQ ID NO: 56]
This represents the base sequence encoding the amino acid sequence represented by SEQ ID NO: 55.

[SEQ ID NO: 57]
This represents the base sequence of the primer used in the PCR reaction of Example 14 described below.

[SEQ ID NO: 58]
This represents the base sequence of the primer used in the PCR reaction of Example 14 described below.

[SEQ ID NO: 59]
This represents the base sequence of the primer used in the PCR reaction of Example 14 described below.

[SEQ ID NO: 60]
This represents the base sequence of the cDNA encoding the rat TGR23-2 ligand precursor.

[SEQ ID NO: 61]
This represents the amino acid sequence of the rat TGR23-2 ligand precursor.

[SEQ ID NO: 62]
This represents the amino acid sequence of [Nle$^{10}$, Tyr$^{15}$] human TGR3-2 ligand (1-20).

[SEQ ID NO: 63]
This represents the amino acid sequence of novel G protein-coupled receptor protein TGR23-1A (human TGR23-1A).

[SEQ ID NO: 64]
This represents the base sequence of the cDNA encoding the human TGR23-1A.

[SEQ ID NO: 65]
This represents the amino acid sequence of novel G protein-coupled receptor protein TGR23-1B (human TGR23-1B).

[SEQ ID NO: 66]
This represents the base sequence of the cDNA encoding the human TGR23-1B.

[SEQ ID NO: 67]
This represents the amino acid sequence of human-derived G protein-coupled receptor protein.

[SEQ ID NO: 68]
This represents the base sequence encoding the amino acid sequence represented by SEQ ID NO: 67.

[SEQ ID NO: 69]
This represents the amino acid sequence of human-derived G protein-coupled receptor protein.

[SEQ ID NO: 70]
This represents the base sequence encoding the amino acid sequence represented by SEQ ID NO: 69.

[SEQ ID NO: 71]
This represents the amino acid sequence of mouse-derived novel G protein-coupled receptor protein TGR23-A (sometimes referred to as mouse TGR23-A).

[SEQ ID NO: 72]
This represents the base sequence of the cDNA encoding the mouse-derived novel G protein-coupled receptor protein TGR23-A.

[SEQ ID NO: 73]
This represents the base sequence of the primer used in the PCR reaction of Reference Example 3 described below.

[SEQ ID NO: 74]
This represents the base sequence of the primer used in the PCR reaction of Reference Example 3 described below.

[SEQ ID NO: 75]

This represents the amino acid sequence of mouse-derived novel G protein-coupled receptor protein TGR23-B (sometimes referred to as mouse TGR23-B).

[SEQ ID NO: 76]

This represents the base sequence of the cDNA encoding the mouse-derived novel G protein-coupled receptor protein TGR23-B.

[SEQ ID NO: 77]

This represents the amino acid sequence of rat-derived novel G protein-coupled receptor protein TGR23-1 (sometimes referred to as rat TGR23-1).

[SEQ ID NO: 78]

This represents the base sequence of the cDNA encoding the rat-derived novel G protein-coupled receptor protein TGR23-1.

[SEQ ID NO: 79]

This represents the base sequence of the primer used in the PCR reaction of Reference Example 4 and Example 30 described below.

[SEQ ID NO: 80]

This represents the base sequence of the primer used in the PCR reaction of Reference Example 4 and Example 30 described below.

[SEQ ID NO: 81]

This represents the base sequence of the primer used in the PCR reaction of Example 29 described below.

[SEQ ID NO: 82]

This represents the base sequence of the primer used in the PCR reaction of Example 29 described below.

[SEQ ID NO: 83]

This represents the amino acid sequence of the mouse-derived novel G protein-coupled receptor protein TGR23-C of the present invention (sometimes referred to as mouse TGR23-C).

[SEQ ID NO: 84]

This represents the base sequence of the cDNA encoding the mouse-derived novel G protein-coupled receptor protein TGR23-C of the present invention.

[SEQ ID NO: 85]

This represents the amino acid sequence of the rat-derived novel G protein-coupled receptor protein TGR23-2 of the present invention (sometimes referred to as rat TGR23-2).

[SEQ ID NO: 86]

This represents the base sequence of the cDNA encoding the rat-derived novel G protein-coupled receptor protein TGR23-2 of the present invention.

[SEQ ID NO: 87]

This represents the amino acid sequence of the rat-derived novel G protein-coupled receptor protein TGR23-3 of the present invention (sometimes referred to as rat TGR23-3).

[SEQ ID NO: 88]

This represents the base sequence of the cDNA encoding the rat-derived novel G protein-coupled receptor protein TGR23-3 of the present invention.

[SEQ ID NO: 89]

This represents the amino acid sequence of the rat-derived novel G protein-coupled receptor protein TGR23-4 of the present invention (sometimes referred to as rat TGR23-4).

[SEQ ID NO: 90]

This represents the base sequence of the cDNA encoding the rat-derived novel G protein-coupled receptor protein TGR23-4 of the present invention.

[SEQ ID NO: 91]

This represents the amino acid sequence of the rat-derived novel G protein-coupled receptor protein TGR23-5 of the present invention (sometimes referred to as rat TGR23-5).

[SEQ ID NO: 92]

This represents the base sequence of the cDNA encoding the rat-derived novel G protein-coupled receptor protein TGR23-5 of the present invention.

[SEQ ID NO: 93]

This represents the amino acid sequence of the rat-derived novel G protein-coupled receptor protein TGR23-6 of the present invention (sometimes referred to as rat TGR23-2).

[SEQ ID NO: 94]

This represents the base sequence of the cDNA encoding the rat-derived novel G protein-coupled receptor protein TGR23-6 of the present invention.

[SEQ ID NO: 95]

This represents the amino acid sequence of the novel G protein-coupled receptor protein TGR23-1C, which is obtained from human-colon cancer cells LS 174T (human TGR23-1C).

[SEQ ID NO: 96]

This represents the base sequence of the cDNA encoding SEQ ID NO: 95.

[SEQ ID NO: 97]

This represents the amino acid sequence of the novel G protein-coupled receptor protein TGR23-1D, which is obtained from human colon cancer cells LS 180 (human TGR23-1D).

[SEQ ID NO: 98]

This represents the base sequence of the cDNA encoding SEQ ID NO: 97.

[SEQ ID NO: 99]

This represents the base sequence of the cDNA encoding the novel G protein-coupled receptor protein TGR23-1C, which is obtained from human stomach cancer cells KATOIII (human TGR23-1C).

[SEQ ID NO: 100]

This represents the base sequence of the cDNA encoding SEQ ID NO: 95.

[SEQ ID NO: 101]

This represents the base sequence of the cDNA encoding SEQ ID NO: 3.

[SEQ ID NO: 102]

This represents the amino acid sequence of the novel G protein-coupled receptor protein TGR23-1E (human TGR23-1E).

[SEQ ID NO: 103]

This represents the base sequence of the cDNA encoding human TGR23-1E.

[SEQ ID NO: 104]

This represents the amino acid sequence of the novel G protein-coupled receptor protein TGR23-1F (human TGR23-1F).

[SEQ ID NO: 105]
This represents the base sequence of the cDNA encoding human TGR23-1F.

[SEQ ID NO: 106]
This represents the base sequence of the primer used for preparation of the DNA encoding human TGR23-1A.

[SEQ ID NO: 107]
This represents the base sequence of the primer used for preparation of the DNA encoding human TGR23-1A.

[SEQ ID NO: 108]
This represents the base sequence of the primer used for preparation of the DNA encoding human TGR23-1C.

[SEQ ID NO: 109]
This represents the base sequence of the primer used for preparation of the DNA encoding human TGR23-1C.

[SEQ ID NO: 110]
This represents the base sequence of the primer used for preparation of the DNA encoding human TGR23-1D.

[SEQ ID NO: 111]
This represents the base sequence of the primer used for preparation of the DNA encoding human TGR23-1D.

[SEQ ID NO: 112]
This represents the base sequence of the primer used for preparation of the DNA encoding human TGR23-1B.

[SEQ ID NO: 113]
This represents the base sequence of the primer used for preparation of the DNA encoding human TGR23-1B.

[SEQ ID NO: 114]
This represents the base sequence of the primer used for amplification of the partial DNA of the human TGR23-2 in Example 39.

[SEQ ID NO: 115]
This represents the base sequence of the primer used for amplification of the partial DNA of the human TGR23-2 in Example 39.

[SEQ ID NO: 116]
This represents the base sequence of the primer used for preparation of the DNA encoding rat TGR23-5.

[SEQ ID NO: 117]
This represents the base sequence of the primer used for preparation of the DNA encoding rat TGR23-5.

[SEQ ID NO: 118]
This represents the base sequence of the primer used for amplification of the partial DNA of the rat TGR23-1 in Example 43.

[SEQ ID NO: 119]
This represents the base sequence of the primer used for amplification of the partial DNA of the rat TGR23-1 in Example 43.

[SEQ ID NO: 120]
This represents the base sequence of the primer used in Example 43.

[SEQ ID NO: 121]
This represents the base sequence of the primer used in Example 43.

[SEQ ID NO: 122]
This represents the base sequence of the probe used in Example 43.

[SEQ ID NO: 123]
This represents the base sequence of the antisense oligonucleotide used in Example 46 and Example 47.

[SEQ ID NO: 124]
This represents the base sequence of the oligonucleotide used in Example 46 and Example 47.

Transformant *Escherichia coli* TOP10/pTB2173 obtained in Reference Example 1 described below has been deposited with the Institute for Fermentation, Osaka (IFO) located at 2-17-85, Juso-Honmachi, Yodogawa-ku, Osaka-shi, Osaka, Japan (postal code 532-8686) under the Accession Number IFO 16483 since Oct. 24, 2000, and with the National Institute of Advanced Industrial Science and Technology, International Patent Organism Depositary (former NIBH) located at Central 6, 1-1-1 Higashi, Tsukuba, Ibaraki, Japan (postal code 305-8566) under the Accession Number FERM BP-7346 since Nov. 1, 2000.

Transformant *Escherichia coli* TOP10/pTB2174 obtained in Reference Example 1 described below has been deposited with the Institute for Fermentation, Osaka (IFO) located at 2-17-85, Juso-Honmachi, Yodogawa-ku, Osaka-shi, Osaka, Japan (postal code 532-8686) under the Accession Number IFO 16484 since Oct. 24, 2000, and with the National Institute of Advanced Industrial Science and Technology, International Patent Organism Depositary (former NIBH) located at Central 6, 1-1-1 Higashi, Tsukuba, Ibaraki, Japan (postal code 305-8566) under the Accession Number FERM BP-7347 since Nov. 1, 2000.

Transformant *Escherichia coli* JM109/pGEM-T Easy Human TGR23(2) Ligand Precursor obtained in Example 11 described below has been deposited with the Institute for Fermentation, Osaka (IFO) located at 2-17-85, Juso-Honmachi, Yodogawa-ku, Osaka-shi, Osaka, Japan (postal code 532-8686) under the Accession Number IFO 16714 since Oct. 12, 2001, and with the National Institute of Advanced Industrial Science and Technology, International Patent Organism Depositary located at Central 6, 1-1-1 Higashi, Tsukuba, Ibaraki, Japan (postal code 305-8566) under the Accession Number FERM BP-7781 since Oct. 22, 2001.

Transformant *Escherichia coli* JM109/pGEM-T Easy Mouse TGR23(2) Ligand Precursor obtained in Example 12 described below has been deposited with the Institute for Fermentation, Osaka (IFO) located at 2-17-85, Juso-Honmachi, Yodogawa-ku, Osaka-shi, Osaka, Japan (postal code 532-8686) under the Accession Number IFO 16715 since Oct. 12, 2001, and with the National Institute of Advanced Industrial Science and Technology, International Patent Organism Depositary located at Central 6, 1-1-1 Higashi, Tsukuba, Ibaraki, Japan (postal code 305-8566) under the Accession Number FERM BP-7783 since Oct. 22, 2001.

Transformant *Escherichia coli* JM109/pGEM-T Easy Rat TGR23(2) Ligand Precursor obtained in Example 14 described below has been deposited with the Institute for Fermentation, Osaka (IFO) located at 2-17-85, Juso-Honmachi, Yodogawa-ku, Osaka-shi, Osaka, Japan (postal code 532-8686) under the Accession Number IFO 16716 since Oct. 12, 2001, and with the National Institute of Advanced Industrial Science and Technology, International Patent Organism Depositary located at Central 6, 1-1-1 Higashi, Tsukuba, Ibaraki, Japan (postal code 305-8566) under the Accession Number FERM BP-7782 since Oct. 22, 2001.

Transformant *Escherichia coli* DH5α/pCR2.1-mTGR23-B obtained in Example 29 described below has been deposited with the National Institute of Advanced Industrial Science and Technology, International Patent Organism Depositary located at Central 6, 1-1-1 Higashi, Tsukuba, Ibaraki, Japan (postal code 305-8566) under the Accession Number FERM BP-8078 since Jun. 18, 2002.

Transformant *Escherichia coli* DH5α/pCR2.1-rTGR23-1 obtained in Reference Example 4 described below has been deposited with the National Institute of Advanced Industrial Science and Technology, International Patent Organism Depositary located at Central 6, 1-1-1 Higashi, Tsukuba, Ibaraki, Japan (postal code 305-8566) under the Accession Number FERM BP-8079 since Jun. 18, 2002.

Transformant *Escherichia coli* TOP10/pAKKO-hTGR23-1A obtained in Example 36 described below has been deposited with the National Institute of Advanced Industrial Science and Technology, International Patent Organism Depositary located at Central 6, 1-1-1 Higashi, Tsukuba, Ibaraki, Japan (postal code 305-8566) under the Accession Number FERM BP-8092 since Jun. 27, 2002.

Transformant *Escherichia coli* TOP10/pAKKO-hTGR23-1B obtained in Example 37 described below has been deposited with the National Institute of Advanced Industrial Science and Technology, International Patent Organism Depositary located at Central 6, 1-1-1 Higashi, Tsukuba, Ibaraki, Japan (postal code 305-8566) under the Accession Number FERM BP-8093 since Jun. 27, 2002.

Transformant *Escherichia coli* DH5α/pAKKO-hTGR23-1C obtained in Example 36 described below has been deposited with the National Institute of Advanced Industrial Science and Technology, International Patent Organism Depositary located at Central 6, 1-1-1 Higashi, Tsukuba, Ibaraki, Japan (postal code 305-8566) under the Accession Number FERM BP-8094 since Jun. 27, 2002.

Transformant *Escherichia coli* DH5α/pAKKO-hTGR23-1D obtained in Example 36 described below has been deposited with the National Institute of Advanced Industrial Science and Technology, International Patent Organism Depositary located at Central 6, 1-1-1 Higashi, Tsukuba, Ibaraki, Japan (postal code 305-8566) under the Accession Number FERM BP-8095 since Jun. 27, 2002.

Transformant *Escherichia coli* DH5α/pAKKO-rTGR23-5 obtained in Example 41 described below has been deposited with the National Institute of Advanced Industrial Science and Technology, International Patent Organism Depositary located at Central 6, 1-1-1 Higashi, Tsukuba, Ibaraki, Japan (postal code 305-8566) under the Accession Number FERM BP-8178 since Sep. 6, 2002.

EXAMPLES

Hereinafter, the present invention will be described in more detail but is not deemed to limit the scope of the invention.

Human TGR23-1, human TGR23-2, human TGR23-1A, human TGR23-1B, human TGR23-1C and human TGR23-1D are sometimes abbreviated to human TGR23. The human TGR23 includes also variants of the above-mentioned proteins. In addition, a gene encoding the human TGR23 is referred to as human TGR23 gene.

Reference Example 1

Cloning of the cDNA Encoding the Human Colon Cancer-derived G Protein-coupled Receptor Protein and Determination of the Base Sequence Using human colon cancer-derived cDNA (CLONTECH) as a template and two primers, namely, primer 1 (SEQ ID NO: 5) and primer 2 (SEQ ID NO: 6), PCR was carried out. The reaction solution in the above reaction comprised of 5 μl of the above cDNA as a template, 2.5 U of Pfu Turbo DNA Polymerase (Stratagene), 1.0 μM each of primer 1 (SEQ ID NO: 5) and primer 2 (SEQ ID NO: 6), 200 μM of dNTPs, and 25 μl of 2×GC Buffer I attached to the enzyme (Takara) to make the total volume 50 μl. The PCR reaction was carried out by reaction of 95° C. for one minute, then a cycle set to include 95° C. for one minute followed by 60° C. for one minute and 72° C. for 1.5 minutes, which was repeated 38 times, and finally, extension reaction at 72° C. for 10 minutes. The PCR product was subcloned to plasmid vector pCR-BluntII-TOPO (Invitrogen) following the instructions attached to the Zero Blunt TOPO PCR Cloning Kit (Invitrogen). The plasmid was then introduced into *Escherichia coli* TOP10, and the clones containing the cDNA were selected on LB agar plates containing kanamycin. As a result of analysis for sequence of each clone, cDNA sequences encoding the novel G protein-coupled receptor protein were obtained (SEQ ID NO: 2 and SEQ ID NO: 4). The plasmid having the DNA fragment containing the base sequence represented by SEQ ID NO: 2 and the plasmid having the DNA fragment containing the base sequence represented by SEQ ID NO: 4 were designated pTB2173 and pTB2174, respectively. The novel G protein-coupled receptor proteins containing the amino acid sequences (SEQ ID NO: 1 and SEQ ID NO: 3) encoded by the base sequence of these DNA (SEQ ID NO: 2 and SEQ ID NO: 4) were designated TGR23-1 (human TGR23-1) and TGR23-2 (human TGR23-2), respectively. Further, the transformants transformed with plasmids pTH2173 and pTB2174 were designated *Escherichia coli* TOP10/pTB2173 and *Escherichia coli* TOP10/pTB2174, respectively.

In the amino acid sequence of TGR23-2, Asn at 107 and Gln at 344 of the amino acid sequence of TGR23-1 are substituted to Ile and Arg, respectively. Alternatively, in the base sequence of the DNA encoding TGR23-2, A at 320, C at 648, A at 1031 and T at 1071 are substitute to T, T, G and C, respectively.

Figure 2:
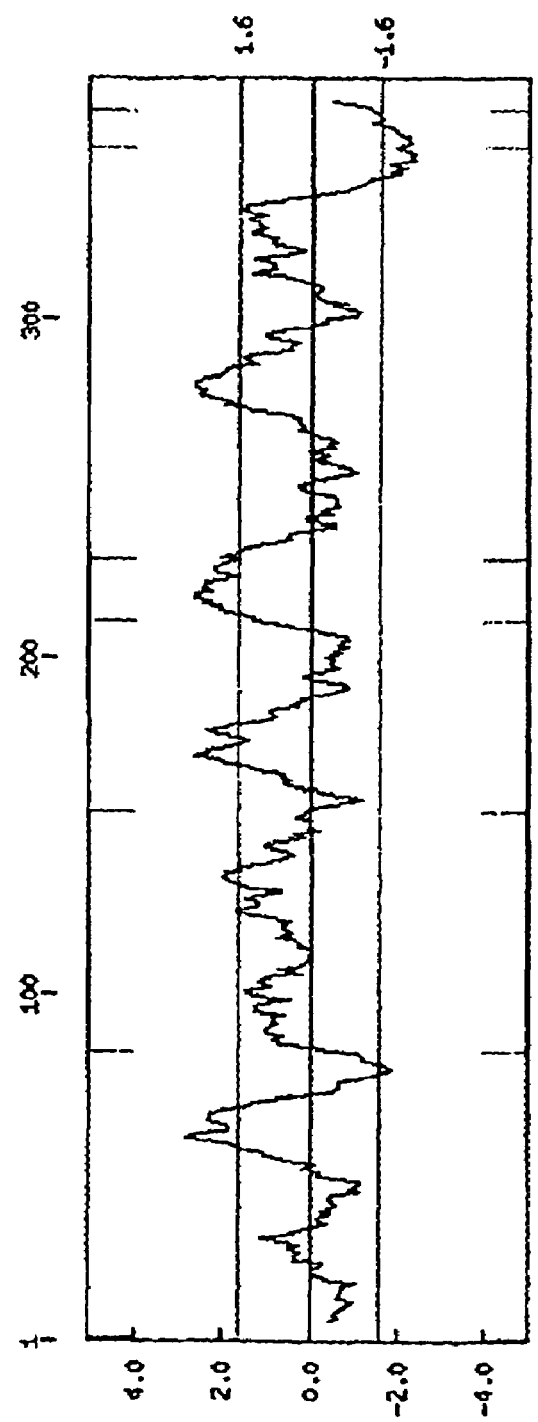
FIG. 2 shows a hydrophobic plot of TGR23-2.

Plots for hydrophobicity of TGR23-1 and TGR23-2 were shown in FIGS. 1 and 2, respectively.

Reference Example 2

Analysis of Expression of Human TGR23-1 and Human TGR23-2 in Cancer Cell Lines

Using cancer cell lines SW620 (derived from human colon cancer), LS123 (derived from human colon cancer), COLO205 (derived from human colon cancer), DU145 (derived from human prostate cancer), ZR75-1 (derived from human breast cancer), NCI-H358 (derived from human bronchoalveolar adenocarcinoma), wherein all are available from American Type Culture Collection (ATCC), an expression level of human TGR23-1 and TGR23-2 was analyzed. SW620 was cultivated with Leibovitz's L15 medium (SIGMA, Cat No. L5520), LS123 with EMEM medium (GIBCO, Cat No. 11090-081), COLO205, ZR75-1 and NCI-H358 with RPMI 1640 medium (GIBCO, Cat No. 11875-093) containing 10 mM HEPES (GIBCO) and 1 mM Sodium Pyruvate (GIBCO), DU145 with EMEM medium (GIBCO, Cat No. 11095-080) containing 1 mM MEM non-essential amino acid solution and 1 mM Sodium Pyruvate (GIBCO), wherein each medium was supplemented with 10% fetal bovine serum (GIBCO) and 0.1 g/L of kanamycin (GIBCO). Cell culture was performed in 10 cm dish. RNA was prepared using RNeasy Mini Kit (Qiagen). Concentration of RNA obtained was calculated by measurement of absorbance at 260 nm. Reverse transcription was performed using 5 ng of each RNA with TaqMan Reverse Transcription Reagents (Applied Biosystems). Using a given amount of the obtained reverse transcripts equivalent to 1 ng or 1 ng of RNA, to which the reverse transcription was not done, as a template, two primers, namely primer 1 (SEQ ID NO: 9) and primer 2 (SEQ ID NO: 10), and probe 1 (SEQ ID NO: 11), PCR reaction was performed. The reaction solution in the above reaction comprised of a given amount of the obtained reverse transcripts equivalent to 1 ng or 1 ng of RNA as a template, 0.5 µM each of primer 1 (SEQ ID NO: 9) and primer 2 (SEQ ID NO: 10), 0.1 µM of probe 1 (SEQ ID NO: 11), and 12.5 µl of TaqMan Universal PCR Master Mix (Applied Biosystems) to make the total volume 25 µl. The PCR reaction was carried out by reaction of 50° C. for 2 minutes and 95° C. for 10 minutes, then a cycle set to include 95° C. for 15 seconds followed by 60° C. for one minute, which was repeated 40 times with ABI7700 (Applied Biosystems). Similarly, using a given amount of the obtained reverse transcripts equivalent to 0.25 ng or 0.25 ng of RNA, to which the reverse transcription was not done, as a template, and TaqMan β-actin Control Reagents (Applied Biosystems), PCR reaction was performed. The reaction solution in the above reaction comprised of a given amount of the obtained reverse transcripts equivalent to 0.25 ng or 0.25 ng of RNA, to which the reverse transcription was not done, as a template, 0.4 µM each of β-actin Forward Primer and β-actin Reverse Primer, 0.5 µM β-actin Probe, and 12.5 µl of TaqMan Universal PCR Master Mix (Applied Biosystems) to make the total volume 25 µl. The PCR reaction was carried out by reaction of 50° C. for 2 minutes and 95° C. for 10 minutes, then a cycle set to include 95° C. for 15 seconds followed by 62° C. for one minute, which was repeated 40 times with ABI7700 (Applied Biosystems). Analysis was performed in the same manner as Example 2, and the expression level was determined by subtracting the value obtained from the reaction without reverse transcription from the value obtained from analysis of the reverse transcripts. In addition, the expression level of human TGR23-1 and TGR23-2 was calculated as a value against that of β-actin. Where the value showed less than zero, the value was replaced with zero. The expression level of human TGR23-1 and TGR23-2 against β-actin was 0.0021% in SW620, 0.0% in LS123, 2.1% in COLO205, 0.0029% in DU145, 0.0012% in ZR75-1 and 0.0% in NCI-H358.

From this result, it is found that the expression of human TGR23-1 and human TGR23-2 was greatly enhanced in COLO205.

Figure 19:
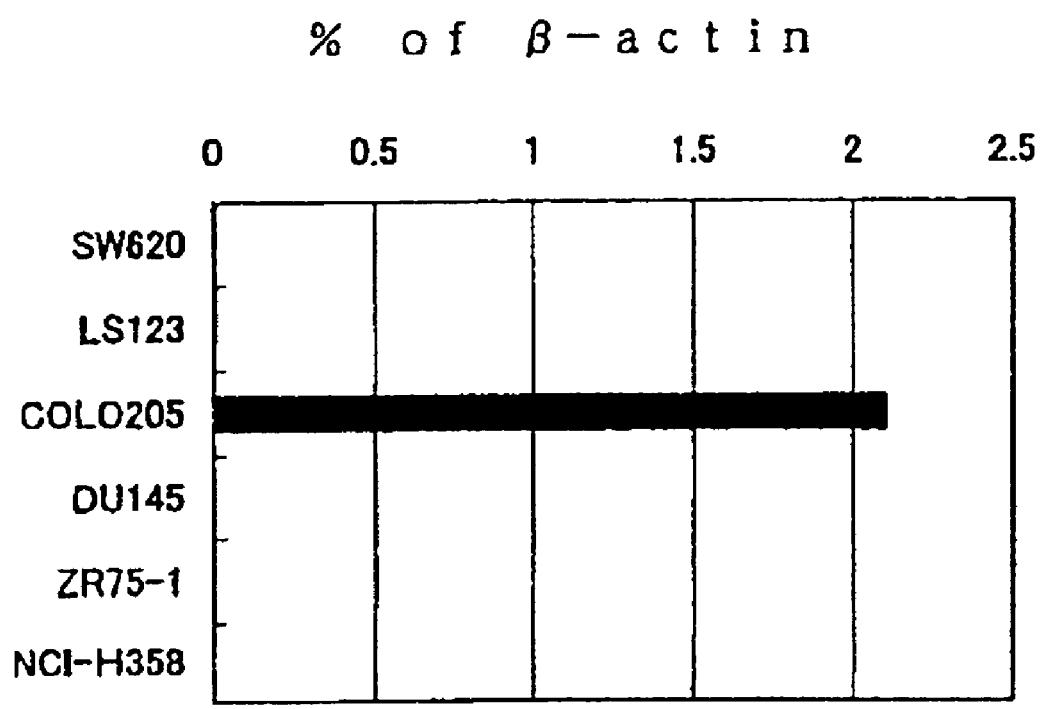
FIG. 19 shows a graph of the expression level of human TGR23-1 and human TGR23-2 in cancer cells.

The graph indicating the expression level of human TGR23-1 and human TGR23-2 in cancer cell lines is shown in FIG. 19.

Reference Example 3

Cloning of the cDNA Encoding the Mouse Brain-derived G Protein-coupled Receptor Protein and Determination of the Base Sequence Using mouse Marathon Ready cDNA (CLONTECH) as a template and two primers, namely, primer 1 (SEQ ID NO: 73) and primer 2 (SEQ ID NO: 74), PCR was carried out. The reaction solution in the above reaction comprised of 1 µl of the above cDNA as a template, 2.5 U of Pfu Turbo DNA Polymerase (STRATAGENE), 1 µM each of primer 1 (SEQ ID NO: 73) and primer 2 (SEQ ID NO: 74), 200 µM of dNTPs, and 25 µl of 2×GC Buffer I (Takara) attached to the enzyme to make the total volume 50 µl. The PCR reaction was carried out by reaction of 95° C. for one minute, then a cycle set to include 95° C. for one minute followed by 60° C. for one minute and 72° C. for 1.5 minutes, which was repeated 38 times, and finally, extension reaction at 72° C. for 10 minutes. Subsequently, agarose gel electrophoresis was done, and the PCR product was purified using Gel Extraction Kit (QIAGEN). This purified product was subcloned to plasmid vector pCR-Blunt II-TOPO (Invitrogen) according to the instructions attached with the Zero Blunt TOPO PCR Cloning Kit (Invitrogen). This plasmid was introduced into *Escherichia coli* TOP10, and the clones harboring the cDNA were selected on LB agar medium containing kanamycin. A sequence of each clone was analyzed, and the base sequence (SEQ ID NO: 72) of the cDNA encoding a novel G protein-coupled receptor protein was obtained. The novel G protein-coupled receptor protein containing the amino acid sequence (SEQ ID NO: 71), which is encoded by the base sequence (SEQ ID NO: 72) of the DNA, was designated mouse TGR23-A.

The plasmid harboring the DNA fragment having the base sequence represented by SEQ ID NO: 72 was designated pTB2237, and the transformant transformed with plasmid pTB2237 was designated *Escherichia coli* TOP10/pTB2237.

Reference Example 4

Cloning of the cDNA Encoding the Rat Brain-derived G Protein-coupled Receptor Protein and Determination of the Base Sequence Using rat Marathon Ready cDNA (CLONTECH) as a template and two primers, namely, primer 1 (SEQ ID NO: 79) and primer 2 (SEQ ID NO: 80), PCR was carried out. The reaction solution in the above reaction comprised of 2.5 µl of the above cDNA as a template, 1 µl of Advantage 2 Polymerase Mix (CLONTECH), 0.2 µM each of primer 1 (SEQ ID NO: 79) and primer 2 (SEQ ID NO: 80), 800 µM of dNTPs, and 2 µL of DMSO to make the total volume 50 µl. The PCR reaction was carried out by reaction of 95° C. for one minute, then a cycle set to include 95° C. for 30 seconds followed by 72° C. for 4 minutes, which was repeated 5 times, 95° C. for 30 seconds followed by 70° C. for 4 minutes, which was repeated 5 times, 95° C. for 30 seconds followed by 68° C. for 4 minutes, which was repeated 30 times, and finally, extension reaction at 68° C. for 3 minutes. Subsequently, agarose gel electrophoresis was done, and the PCR product was purified using GENECLEAN SPIN Kit (BIO101). This purified product was subcloned to plasmid vector pCR2.1-TOPO (Invitrogen) according to the instructions attached with the TOPO TA Cloning Kit (Invitrogen). This plasmid was introduced into *Escherichia coli* DH5α, and the clones harboring the cDNA were selected on LB agar medium containing ampicillin. A sequence of each clone was analyzed, and the base sequence (SEQ ID NO: 78) of the cDNA encoding a novel G protein-coupled receptor protein was obtained. The novel G protein-coupled receptor protein containing the amino acid sequence (SEQ ID NO: 77), which is encoded by the base sequence (SEQ ID NO: 78) of the DNA, was designated rat TGR23-1.

The plasmid harboring the DNA fragment having the base sequence represented by SEQ ID NO: 78 was designated pCR2.1-rTGR23-1, and the transformant transformed with plasmid pCR2.1-rTGR23-1 was designated *Escherichia coli* DH5α/pCR2.1-rTGR23-1.

Example 1

Preparation of TGR23-2 (Hereinafter Human TGR23-2 is Sometimes Merely Referred to as TGR23-2) Expressing CHO Cells Using the plasmid pTB2174 obtained in Reference Example 1 as a template and two primers, namely, primer 1 attached to Sal I recognition sequence (SEQ ID NO: 7) and primer 2 attached to Spe I recognition sequence (SEQ ID NO: 8), PCR was carried out. The reaction solution in the above reaction comprised of 10 ng of the plasmid as a template, 2.5 U of Pfu Turbo DNA Polymerase (STRATAGENE), 1.0 µM each of primer 1 (SEQ ID NO: 7) and primer 2 (SEQ ID NO: 8), 200 µM of dNTPs, and 25 µl of 2×GC Buffer I (Takara) to make the total volume 50 µl. The PCR reaction was carried out by reaction of 95° C. for 60 seconds, then a cycle set to include 95° C. for 60 seconds followed by 55° C. for 60 seconds and 72° C. for 70 seconds, which was repeated 25 times, and finally, extension reaction at 72° C. for 10 minutes. The PCR product was subcloned into plasmid vector pCR-Blunt II-TOPO (Invitrogen) following the instructions attached to the Zero Blunt TOPO PCR Cloning Kit (Invitrogen). The plasmid was then introduced into *Escherichia coli* TOP10 (Invitrogen), and the clones having the cDNA of TGR23-2, which is contained in pTB2174, were selected on LB agar plates containing kanamycin. From *E. coli* clones transformed by the plasmid thus obtained, in which the TGR23-2 was introduced, the plasmid was prepared using Plasmid Miniprep Kit (BIO RAD) and digested with the restriction enzymes Sal I and Spe I to excise the insert, wherein TGR23-2 was attached to Sal I recognition sequence at 5' end and Spe I recognition sequence at 3' end. The insert DNA was electrophoresed to excise from agarose gel and recovered using the Gel Extraction Kit (Qiagen). This insert DNA was added to the expression vector plasmid for animal cells, pAKKO-111H (the same vector plasmid as pAKKO1.11H described in Biochim. Biophys. Acta, Vol. 1219, pp. 251-259 (1994) by Hinuma, S. et al.), which has been cleaved with Sal I and Spe I, and both DNAs were ligated by the DNA Ligation Kit Ver. 2 (Takara Shuzo). Thus, the plasmid pAKKO-TGR23-2 for protein expression was constructed. After cultivating *E. coli* TOP10 transformed with this pAKKO-TGR23-2, plasmid DNA of pAKKO-TGR23-2 was prepared using Plasmid Miniprep Kit (BIO RAD). $1 \times 10^5$ cells of hamster CHO/dhfr$^-$ cell were seeded in Falcon dish (3.5 cm diameter) with α-MEM medium (with ribonucleosides and deoxyribonucleosides, GIBCO, Cat No. 12571) containing 10% Fetal Bovine Serum, and cultivated at 37° C. for overnight in 5% $CO_2$ incubater. Two µg of the above-mentioned expression plasmid, pAKKO-TGR23-2 was transfected using Transfection Reagent FuGENE 6 (Roche) in accordance with the procedures described in the attached instruction. After 18 hours of cultivation, the medium was exchanged to a fresh medium for growth. Further cultivation for 10 hours, the transfected cells were harvested by treatment with Trypsin-EDTA, and seeded to 10 of 96-well flat bottomed plates with a selection medium (α-MEM medium (without ribonucleosides and deoxyribonucleosides, GIBCO, Cat No. 12561) containing 10% dialyzed Fetal Bovine Serum). Cultivation was continued while the selection medium was exchanged every 3 or 4 days, and 79 clones of DHFR$^+$ cell, which grew as a colony, were acquired after 2 or 3 weeks.

Example 2

Quantification of TGR23-2 Expression Level in TGR23-2 Expressing CHO Cell Lines Using TaqMan PCR Method The 79 clones of TGR23-2 expressing CHO cells obtained in Example 1 were cultured in the 96-well plate, and total RNA was prepared using RNeasy 96 Kit (Qiagen). Using 50 to 200 ng of total RNA obtained and TaqMan Gold RT-PCR Kit (PE Biosystems), a reverse transcription reaction was performed. Using 25 µl of the reaction mixture containing a reverse transcript corresponding to 5 to 20 ng of the total RNA obtained or a standard cDNA prepared as described below, 1×Universal PCR Master Mix (PE Biosystems), 500 µM each of primers represented by SEQ ID NO: 9 and SEQ ID NO: 10, and 100 nM TaqMan probe represented by SEQ ID NO: 11 (Fam-acctggtttg ccgagtggtc cgctattt-Tamra; in the sequence, Fam and Tamra represent 6-carboxy-fluorescein and 6-carboxy-tetramethyl-rhodamine, respectively), PCR was performed with ABI PRISM 7700 Sequence Detector (PE Biosystems). The PCR was carried out by reaction of 50° C. for 2 minutes and 95° C. for 10 minute, then a cycle set to include 95° C. for 15 seconds followed by 60° C. for 60 seconds, which was repeated 40 times.

By measuring absorbance of the plasmid pTB2174 obtained in Reference Example at 260 nm, the concentration was calculated and accurate copy numbers were calculated. Then, 2 to $2 \times 10^6$ copies of standard cDNA solution were prepared by diluting with 10 mM Tris-HCl (pH8.0) containing 1 mM EDTA. Further, probe and primers for TaqMan PCR were designed by the Primer Express Version 1.0 (PE Biosystems).

The expression level was calculated by the ABI PRISM 7700 SDS Software. Using cycle numbers at the moment when fluorescent intensity of reporter comes to preset values indicated as a vertical axis, and logarithm of an initial concentration of the standard cDNA as a horizontal axis, standard curve was prepared. From this standard curve, the expression level of TGR23-2 gene per total RNA of each clone was determined by calculating an initial concentration of each reverse transcript. As a result, 21 clones of CHO cell lines, in which the expression of TGR23-2 was high, were selected and cultured in 24-well plate. For these cells, the expression level of TGR23-2 was re-examined. After preparation of total RNA with RNeasy Mini Kits (Qiagen), the RNA was treated with DNase by RNase-free DNase Set (Qiagen). From total RNA obtained, the reverse transcription reaction was carried out in the same manner as described above, and the expression level of TGR23-2 gene per total RNA of each clone was determined by the TaqMan PCR method. From this, it was revealed that the clones No. 53 and No. 58 of CHO cell lines expressing TGR23-2 were highly expressed.

In Examples described below, these two clones of the TGR23-2 expressing cells were used.

Example 3

Assay for Enhancing/Inhibiting Activity of Intracellular cAMP Production Using TGR23-2 Expressing CHO Cells The CHO/TGR23-2 cells prepared in Example 1 and selected in Example 2 were plated on 24-well plate at $7 \times 10^4$ cells/well and cultured for 48 hours. The cells were washed with αMEM medium (pH7.5) containing 0.2 mM 3-isobutyl-methylxanthine, 0.05% BSA and 20 mM HEPES (hereafter, αMEM medium (pH7.5) containing 0.2 mM 3-isobutyl-methylxanthine, 0.05% BSA and 20 mM HEPES may be referred to as a reaction buffer). Subsequently, 0.5 ml of the reaction buffer was added, and the solution was incubated for 30 minutes in the incubator. The reaction buffer was removed and 0.25 ml of the reaction buffer was freshly added to the cells. Then, the cells were admixed with a sample and 0.25 ml of the reaction buffer containing 2 µM forskoline, and incubated at 37° C. for 30 minutes. Intracellular cAMP was extracted by removing the reaction solution and adding 0.5 ml of the solution for cell lysis attached with cAMP EIA Kit (Applied Biosystems). The cAMP level in the extract was quantified with the same kit. Based on this measured value, a calculation was made using the following formula, and the enhancing/inhibiting activity for cAMP production was represented by % of control. The activity of the sample-adding group was calculated using a control value configured in each plate.

% of control=$(X-C)/(T-C) \times 100$

X: The cAMP level in the sample-adding group

T: The means of the cAMP level in 3 wells of positive control (no sample, with stimulus of forskoline)

C: The means of the cAMP level in 3 wells of negative control (no sample, without stimulus of forskoline)

Example 4

Assay for Enhancing Activity of Arachidonic Acid Metabolite Release Using TGR23-2 Expressing CHO Cells The CHO/TGR23-2 cells prepared in Example 1 and selected in Example 2 were plated on 24-well plate at $5 \times 10^4$ cells/well and cultured for 24 hours. After removing the medium, αMEM medium (pH7.4) supplemented with 0.5 µCi/ml [$^3$H] arachidonic acid, 10% dialyzed FBS, 20 mM HEPES and 0.5% BSA was added to the cells at 500 µl/well. Subsequently, the cells were incubated for 16 hours in the incubator. After the culture medium containing [$^3$H] arachidonic acid was discarded, 500 µl/well of αMEM medium (pH7.4) supplemented with 20 mM HEPES and 0.5% BSA were added, and the cells were incubated for 4 hours in the incubator. The culture medium was removed, and the cells were washed twice with 750 µl/well of Hanks' solution (pH7.4) supplemented with 0.05% BSA and 20 mM HEPES (hereafter, Hanks' solution (pH7.4) supplemented with 0.05% BSA and 20 mM HEPES was referred to as a reaction buffer). After washing, the cells were admixed with 750 µl/well of the reaction buffer and incubated for 40 minutes in the incubator. The reaction buffer was removed and 250 µl of the reaction buffer was freshly added. Then, a sample and 250 µl of the reaction buffer were added to the cells, and the cells were incubated at 37° C. for 40 minutes. After reaction, 350 µl of the supernatant were fractionated. Three milliliters of liquid scintilator were added to the supernatant described above to measure the radioactivity. Based on this measured value, a calculation was made using the following formula, and the promoting activity of arachidonic acid metabolite release was represented by % of control. The activity of the sample-adding group was calculated using a control value configured in each plate.

% of control=$(X-C) \times 100$

X: The radioactivity in the sample-adding group

C: The means of the radioactivity in 4 wells of control (no sample)

Example 5

Assay for Enhancing Activity of Intracellular $Ca^{2+}$ Release Using TGR23-2 Expressing CHO Cells An enhancing activity of intracellular $Ca^{2+}$ release was assayed using FLIPR (Molecular Devices, Inc.). The CHO/TGR23-2 cells prepared in Example 1 and selected in Example 2 were plated on 96-well plate at $3 \times 10^4$ cells/well and cultured for 24 hours. A loading buffer was prepared by adding 1 vial of Fluo 3-AM to 10 ml of Hanks' solution (pH7.4) containing 2.5 mM Probenecid and 20 mM HEPES (hereafter, Hanks' solution (pH7.4) containing 2.5 mM Probenecid and 20 mM HEPES may be referred to as a washing buffer). The culture medium was discarded from the culture plate and 100 µl/well of the loading buffer were added to the cells. Then, the cells were incubated for 60 minutes in the incubator. After the loading buffer was removed from the culture plate and the cells were washed with the washing buffer, the plate was put in place of FLIPR. A sample was prepared by adding a sample buffer, which 2 mg/ml BSA and 1 mg/ml CHAPS were added to the washing buffer, to lyophilized product, stirring and treating by ultrasonication for 30 minutes, and transferred to 96-well sample plate. This sample plate was also put in place for assay. The enhancing activity of intracellular $Ca^{2+}$ release was measured as an increase of fluorescent intensity, which is raised by addition of the sample.

Example 6

Purification of an Active Substance, which Specifically Exhibits a Promoting Activity of cAMP Production on TGR23-2 Expressing CHO Cells, from Rat Whole Brain Extracts A substance, which exhibits a ligand activity specific to TGR23-2 was purified from rat whole brain using a enhancing activity of cAMP production on TGR23-2 expressing CHO cells as an index.

High Performance Liquid Chromatography (HPLC) fraction from rat whole brain extracts was prepared by the method described below. Four hundreds grams of a whole brain of 8 weeks old male Wistar rat (corresponding to 200 rats) available from Charles River Japan, Inc., were sequentially extirpated and boiled for 10 minutes in boiling distilled water (300 ml) in increments of 25 rats. After boiling, the samples were immediately chilled in ice and all of 200 samples were put together (2.4 L). One hundred and eighty milliliter of acetic acid was added to the samples to make the final concentration 1.0 M. Then the sample was homogenized with polytron (10,000 rpm, 2 minutes) under low temperature. The homogenized solution was centrifuged at 8,000 rpm for 30 minutes to get supernatant. To precipitate, 2.4 L of 1.0 M acetic acid was added, and homogenization was carried out again with polytron. After stirring for overnight, supernatant was acquired by centrifugation (8,000 rpm, 30 minutes). Two volumes of cold acetone (4.8 L) were dropped at 4° C. to each supernatant obtained from centrifugation. The supernatant obtained from the 1st centrifugation was stirred for overnight and the 2nd supernatant was stirred for 4 hours. The extract, to which acetone was added, was centrifuged at 8,000 rpm for 30 minutes to discard precipitate. Acetone was removed from the supernatant obtained with evaporator under vacuum pressure. Equal volumes of diethylether were added to the extract after removal of acetone. Then the aqeous phase was recovered by isolating the ether phase containing lipids using separatory funnel. The extract, which was defatted with ether, was concentrated with evaporator under vacuum pressure, and ether was completely removed. After the concentrate was filtered through glass fiber filter paper (Advantech, DP70 (90 mmΦ)), the filtrate was applied to ODS column (Daiso, Daisogel IR-120-ODS-A 63/210 μm), which was filled in glass column (30Φ×240 mm). The column was washed with 400 ml of 1.0 M acetic acid and eluted with 500 ml of 60% acetonitrile containing 0.1% trifluoracetic acid. The eluate was concentrated under vacuum pressure to remove solvent. Subsequently, the concentrate was lyophilized. The obtained white powder, 1.2 g, was dissolved in 30 ml of 10% acetonitrile containing 0.1% trifluoracetic acid. The solution obtained as described above, 12.5 ml each was applied to fractionated HPLC using ODS column (Toso, TSKgel ODS-80Ts (21.5Φ×300 mm)) by elution with concentration gradient from 10% to 60% of acetonitrile containing 0.1% trifluoracetic acid. HPLC was carried out twice. The eluate was fractionated into 60 every 2 minutes, and the resultant was put together. Each fraction was concentrated and evaporated under vacuum pressure, and to the residual 0.4 ml of dimethylsulfoxide (DMSO) was added. Then the residual was completely dissolved using Vortex mixer and ultrasonicator.

Where the DMSO solution of HPLC fraction obtained as described above was administered to TGR23-2 expressing CHO cells according to the method shown in Example 3, and a production level of intracellular cAMP was determined, a significant enhancing activity for cAMP production was observed in the fraction numbers 18, 20 and 22 to 23. In addition, for the same sample, in accordance with the method shown in Example 4, an arachidonic acid metabolite releasing activity was assayed. As the result, a siginificant activity was confirmed.

Since these activities were not observed in other receptor-expressing cells, it was shown that a ligand active substance specific to TGR23-2 is presented in rat whole brain extract. The three active fractions, which were obtained, were further purified by the following methods (a) to (c), respectively. Moreover, for each active fraction, the fraction observing a enhancing activity for cAMP production, which was obtained in the purification process using the first cation exchange column, coincidentally possessed an intracellular calcium releasing activity specific to receptor, which was detected with FLIPR described in Example 5. Thus, for confirmation of the activity in the subsequent purification processes, the intracellular calcium releasing activity with FLIPR was used as an index. The fact that the active fraction exhibits an enhancing activity for cAMP production was appropriately confirmed.

(a) Fraction Number 18

Figure 7:
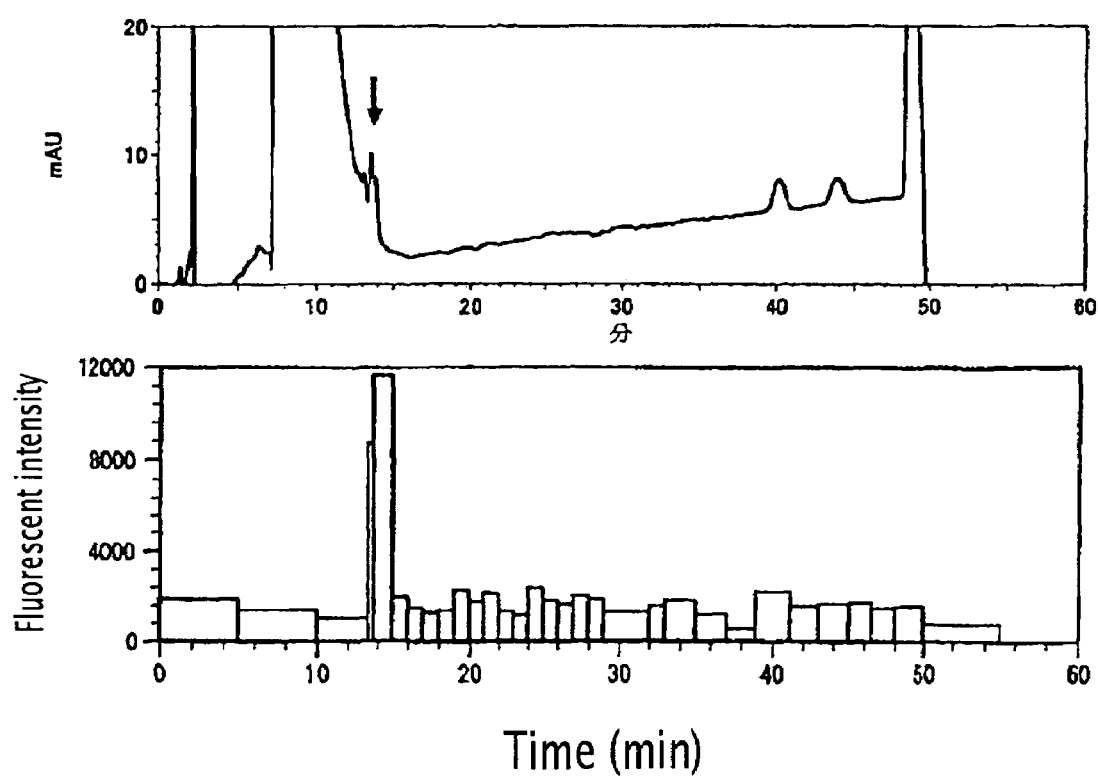
FIG. 7 shows UV absorption of HPLC at the final step of purification of rat TGR23-2 ligand using Wakosil-II 3C18HG column and cAMP production enhancing activity in each peak. The activity was recovered in the peak indicated by arrows (fraction number 18).

The fraction number 18 was dissolved in 10 ml of 10 mM ammonium formate containing 10% acetonitrile, applied to cation exchange column (Toso, TSKgel SP-5PW (20 mmΦ×150 mm) and eluted with concentration gradient from 10 mM to 1.0 M of ammonium formate containing 10% acetonitrile. The activity was recovered from around 0.4 M ammonium formate. After lyophilization, the active fraction was dissolved in 0.8 ml of 10% acetonitrile containing 0.1% trifluoracetic acid. Where the solution was applied to ODS column (Toso, TSKgel ODS-80Ts (4.6Φ×250 mm)) and eluted with concentration gradient from 10% to 25% of acetonitrile containing 0.1% trifluoracetic acid, the activity was detected at around 13% acetonitrile. After lyophilization, the obtained active fraction was dissolved in 0.1 ml of DMSO. Further, 0.7 ml of 10% acetonitrile containing 0.1% heptafluor butyric acid was added to the above solution, and the solution thus obtained was applied to ODS column (Wako Pure Chemicals, Wakosil-II 3C18HG (2.0 mmΦ×150 mm)). The elution was carried out by concentration gradient of acetonitrile containing 0.1% heptafluor butyric acid from 10% to 37.5%, and each peak was manually fractionated. The activity was detected at around 26% acetonitrile. To the active fraction, 0.7 ml of 10% acetonitrile containing 0.1% trifluor acetic acid was added, and the fraction was applied to ODS column (Wako Pure Chemicals, Wakosil-II 3C18HG). The elution was carried out by concentration gradient of acetonitrile containing 0.1% trifluor acetic acid from 10% to 20%, and each peak was manually fractionated. The activity was recovered as a single peak at around 11% acetonitrile (FIG. 7). Structure of an active substance, which is contained in this fraction, was determined as shown in Example 10 described below.

(b) Fraction Number 20

Figure 5:
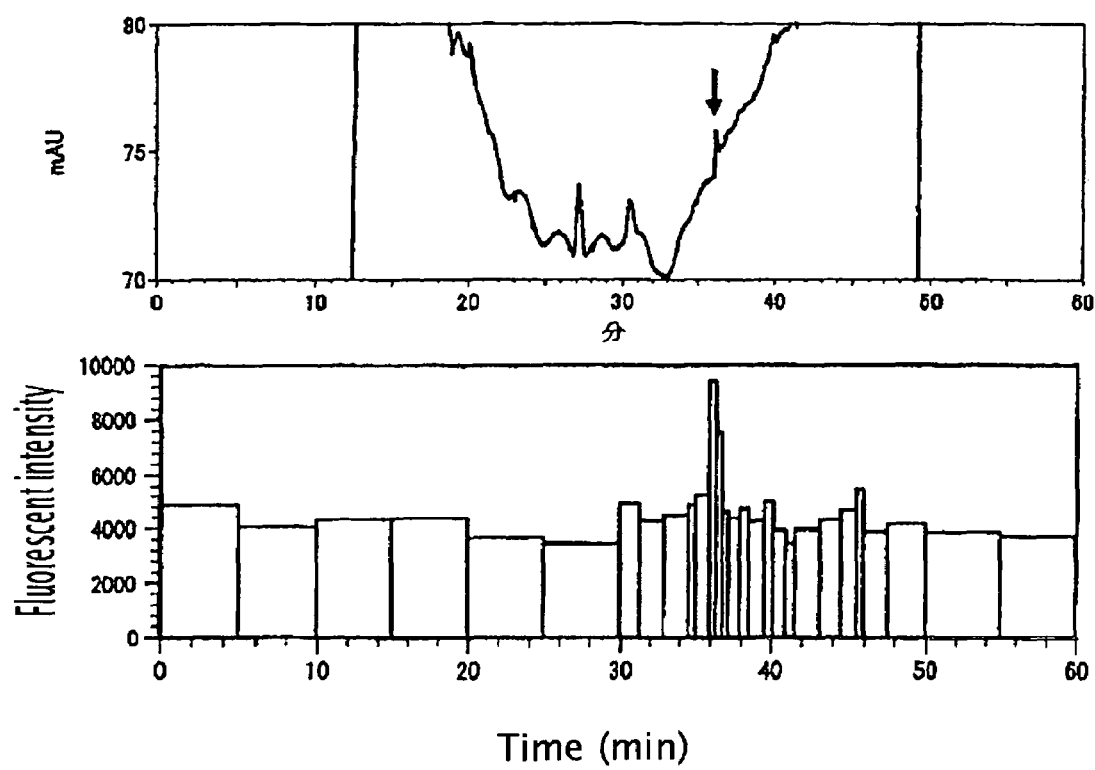
FIG. 5 shows UV absorption of HPLC at the final step of purification of rat TGR23-2 ligand using Wakosil-II 3C18HG column and cAMP production enhancing activity in each peak. The activity was recovered in the peak indicated by arrows (fraction number 20).

The fraction number 20 was dissolved in 10 ml of 10 mM ammonium formate containing 10% acetonitrile, applied to cation exchange column (Toso, TSKgel SP-5PW (20 mmΦ×150 mm) and eluted with concentration gradient from 10 mM to 1.0 M of ammonium formate containing 10% acetonitrile. The activity was recovered from around 0.6 M ammonium formate. After lyophilization, the active fraction was dissolved in 0.8 ml of 10% acetonitrile containing 0.1% trifluoracetic acid. Where the solution was applied to CN column (Nomura Chemicals, Develosil CN-UG-5 (4.6Φ×250 mm) and eluted with concentration gradient from 10% to 25% of acetonitrile containing 0.1% trifluoracetic acid, the activity was detected at around 12% acetonitrile. After lyophilization, 0.7 ml of 10% acetonitrile containing 0.1% trifluor acetic acid was added to the active fraction, and the fraction was applied to ODS column (Wako Pure Chemicals, Wakosil-II 3C18HG (2.0 mmΦ×150 mm)). The elution was carried out by concentration gradient of acetonitrile containing 0.1% trifluor acetic acid from 10% to 20%, and each peak of the eluate was manually fractionated. The activity was recovered as a single peak at around 15% acetonitrile (FIG. 5). Structure of an active substance, which is contained in this fraction, was determined as shown in Example 8 described below.

(c) Fraction Numbers 22 to 23

Figure 6:
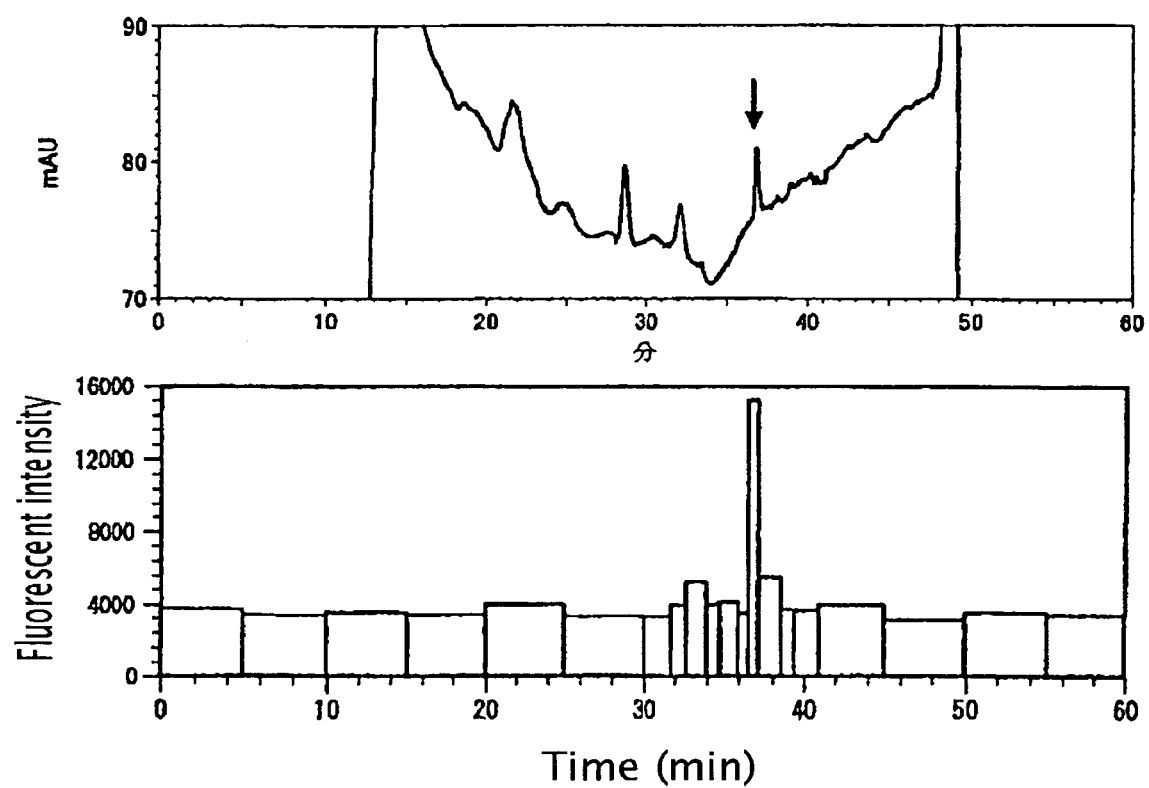
FIG. 6 shows UV absorption of HPLC at the final step of purification of rat TGR23-2 ligand using Wakosil-II 3C18HG column and cAMP production enhancing activity in each peak. The activity was recovered in the peak indicated by arrows (fraction number 22-23).

The fraction numbers 22 to 23 were dissolved in 10 ml of 10 mM ammonium formate containing 10% acetonitrile, applied to cation exchange column (Toso, TSKgel SP-5PW (20 mmΦ×150 mm) and eluted with concentration gradient from 10 mM to 1.0 M of ammonium formate containing 10% acetonitrile. The activity was recovered from around 0.4 M ammonium formate. After lyophilization, the active fraction was dissolved in 0.8 ml of 10% acetonitrile containing 0.1% trifluoracetic acid. Where the solution was applied to CN column (Nomura Chemicals, Develosil CN-UG-5 (4.6 mmΦ×250 mm) and eluted with concentration gradient from 10% to 25% of acetonitrile containing 0.1% trifluoracetic acid, the activity was detected at around 13% acetonitrile. After lyophilization, the active fraction was dissolved in 0.1 ml of DMSO and 0.7 ml of 10% acetonitrile containing 0.1% trifluor acetic acid was added thereto. Further the fraction was applied to ODS column (Wako Pure Chemicals, Wakosil-II 3C18HG (2.0 mmΦ×150 mm)). The elution was carried out by concentration gradient of acetonitrile containing 0.1% trifluor acetic acid from 10% to 20%, and each peak was manually fractionated. The activity was recovered as a single peak at around 16% acetonitrile. To the active fraction, 0.7 ml of 10% acetonitrile containing 0.1% heptafluor butyric acid was further added, and the solution thus obtained was applied to ODS column (Wako Pure Chemicals, Wakosil-II 3C18HG). The elution was carried out by concentration gradient of acetonitrile containing 0.1% heptafluor butyric acid from 10% to 37.5%, and each peak of the eluate was manually fractionated. The activity was obtained as a single peak at around 28% acetonitrile (FIG. 6). Structure of an active substance, which is contained in this fraction, was determined as shown in Example 9 described below.

Example 7

Inactivation of an Active Substance in Rat Whole Brain Extracts, which Specifically Exhibits an Enhancing Activity of cAMP Production on TGR23-2 Expressing CHO Cells, by Pronase The HPLC fractions 18, 20 and 22 to 23 exhibiting an enhancing activity for intracellular cAMP production on TGR23-2 expressing CHO cells in Example 6 were treated with proteolytic enzyme, Pronase (Sigma, protease Type XIV (P5147)) in order to investigate whether the active substances may be protein, or not.

Four microlitters each of the above-mentioned HPLC active fractions of rat whole brain extracts (Fraction numbers 18, 20 and 22 to 23) was added to 100 μl of 0.2 M ammonium acetate and incubated at 37° C. for 2 hours with 3 μg of Pronase. Subsequently, Pronase added, was inactivated by heating in boiling water for 10 minutes. To this solution, one ml of distilled water containing 0.05 mg of BSA and 0.05 mg of CHAPS was added. Further, it was lyophilized. For the lyophilized sample, enhancing activity for intracellular cAMP production was assayed by adding to TGR23-2 expressing CHO cells according to the method shown in Example 3.

As the result, an activity of each fraction was completely diminished by treatment with Pronase.

Therefore, it was clarified that the active substances in rat whole brain extracts, which specifically exhibits an enhancing activity of cAMP production on TGR23-2 expressing CHO cells are protein or peptide, respectively.

Example 8

Determination of an Amino Acid Sequence of an Active Substance Obtained from the Fraction Number 20 in Rat Whole Brain Extracts, which Specifically Exhibits an Enhancing Activity for cAMP Production on TGR23-2 Expressing CHO Cells As shown in Example 7, since it was expected that the active substances specifically exhibiting enhancing activity for cAMP production on TGR23-2 expressing CHO cells, which are contained in the three fractions of rat whole brain extracts, may be protein, respectively, an amino acid sequence for each fraction was analyzed as follows.

Determination of an amino acid sequence and mass spectrometry for the active substance obtained from the fraction number 20 in rat whole brain extracts as shown in Example 6, which specifically exhibits an enhancing activity for cAMP production on TGR23-2 expressing CHO cells, were carried out. As the result of amino acid sequence analysis of the amino terminus using eluate containing the active peak with Procise 491c LC Protein Sequencer (Applied Biosystems), the amino acid sequence from N terminus to the 18th residue having SFRNGVGSGVKKTSFRRA (SEQ ID NO: 12) was obtained. Where mass spectrometry was carried out using Thermo Finnigan LCQ ion trap mass spectrometer (ThermoQuest) equipped with nano spray ion sources (Protana), the mass weight calculating from the amino acid sequence represented by SEQ ID NO: 12 was found (the found value: 1954.9; the calculated value: 1954.2).

From the results, it was determined that the active substance obtained from the fraction number 20 in rat whole brain extracts, which specifically exhibits an enhancing activity for cAMP production on TGR23-2 expressing CHO cells, have the amino acid sequence represented by SEQ ID NO: 12.

Example 9

Determination of an Amino Acid Sequence of an Active Substance Obtained from the Fraction Numbers 22 to 23 in Rat Whole Brain Extracts, which Specifically Exhibits an Enhancing Activity of cAMP Production on TGR23-2 Expressing CHO Cells Determination of an amino acid sequence and mass spectrometry for the active substance obtained from the fraction numbers 22 to 23 in rat whole brain extracts as shown in Example 6, which specifically exhibits a promoting activity for cAMP production on TGR23-2 expressing CHO cells, were carried out. As the result of amino acid sequence analysis of the amino terminus using eluate containing the active peak with Procise 491c LC Protein Sequencer (Applied Biosystems), the amino acid sequence from N terminus to the 15th residue having SFRNGVGS-GVKKTSF (SEQ ID NO: 13) was obtained. Where mass spectrometry was carried out using Thermo Finnigan LCQ ion trap mass spectrometer (ThermoQuest) equipped with nano spray ion sources (Protana), the mass weight calculating from the amino acid sequence represented by SEQ ID NO: 13 was found (the found value: 1570.8; the calculated value: 1570.8).

From the results, it was determined that the active substance obtained from the fraction numbers 22 to 23 in rat whole brain extracts, which specifically exhibits an enhancing activity for cAMP production on TGR23-2 expressing CHO cells, have the amino acid sequence represented by SEQ ID NO: 13.

Example 10

Determination of an Amino Acid Sequence of an Active Substance Obtained from the Fraction Number 18 in Rat Whole Brain Extracts, which Specifically Exhibits an Enhancing Activity of cAMP Production on TGR23-2 Expressing CHO Cells Determination of an amino acid sequence and mass spectrometry for the active substance obtained from the fraction number 18 in rat whole brain extracts as shown in Example 6, which specifically exhibits an enhancing activity for cAMP production on TGR23-2 expressing CHO cells, were carried out. As the result of amino acid sequence analysis of the amino terminus using eluate containing the active peak with Procise 491c LC Protein Sequencer (Applied Biosystems), the amino acid sequence from N terminus to the 14th residue having SFRNGVGSGVKKTS (SEQ ID NO: 14) was obtained. Where mass spectrometry was carried out using Thermo Finnigan LCQ ion trap mass spectrometer (ThermoQuest) equipped with nano spray ion sources (Protana), the mass weight calculating from the amino acid sequence represented by SEQ ID NO: 14 was found (the found value: 1424.1; the calculated value: 1423.6).

From the results, it was determined that the active substance obtained from the fraction number 18 in rat whole brain extracts, which specifically exhibits an enhancing activity for cAMP production on TGR23-2 expressing CHO cells, have the amino acid sequence represented by SEQ ID NO: 14.

Example 11

Cloning of cDNA Encoding Human TGR23-2 Ligand Precursor

In order to clone cDNA encoding a precursor of human homologue (in the description, sometimes referred to as human TGR23-2 ligand) for an active peptide exhibiting an enhancing activity for cAMP production specific to TGR23-2 expressing CHO cells, which is obtained from rat whole brain extracts (in the description, referred to as rat TGR23-2 ligand), using cDNA derived from human hypothalamus as a template, PCR was carried out.

Using the following synthetic DNA primers and cDNA derived from human hypothalamus as a template, amplification by PCR method was performed. The reaction solution in the above reaction comprised of 0.8 μl of human hypothalamus Marathon Ready cDNA (CLONTECH), 1.0 μM each of synthetic DNA primers represented by SEQ ID NO: 15 and SEQ ID NO: 16, 0.2 mM dNTPs, 0.1 μl of ExTaq (Takara Shuzo) and ExTaq Buffer attached to the enzyme to make the total volume 20 μl. The PCR reaction was carried out using a thermal cycler (PE Biosystems) by heating of 94° C. for 300 seconds, then a cycle set to include 94° C. for 10 seconds followed by 55° C. for 30 seconds and 72° C. for 30 seconds, which was repeated 35 times, and finally, extension reaction at 72° C. for 5 minutes. Subsequently, 2 μl of the PCR reaction solution diluted by 50-fold with DNase, Rnase-free distilled water, 1.0 μM each of synthetic DNA primers represented by SEQ ID NO: 15 and SEQ ID NO: 17, 0.2 mM dNTPs, 0.1 μl of ExTaq polymerase (Takara Shuzo) and ExTaq Buffer attached to the enzyme were made to 20 μl of total volume. The reaction solution was incubated using a thermal cycler (PE Biosystems) by heating of 94° C. for 300 seconds, then a cycle set to include 94° C. for 10 seconds followed by 55° C. for 30 seconds and 72° C. for 30 seconds, which was repeated 35 times, and finally, extension reaction at 72° C. for 5 minutes. The amplified DNA was separated by 2.0% agarose gel electrophoresis and the band of the DNA was excised by razor blade. The DNA was recovered using QIAquick Gel Extraction Kit (Qiagen). This DNA was cloned to pGEM-T Easy vector in accordance with the protocol of pGEM-T Easy Vector System (Promega). After transformation of Escherichia coli JM109 competent cell (Takara Shuzo) by introducing the above-mentioned vector, clones harboring cDNA insert fragment was selected on LB agar medium containing ampicillin and X-gal. All the white-colored clones were isolated with sterilized toothpick, and then the transformants were obtained. This transformant was designated Escherichia coli JM109/pGEM-T Easy Human TGR23(2) Ligand Precursor. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 18, was obtained.

Since in the base sequence of the DNA represented by SEQ ID NO: 18, a frame encoding extremely similar amino acid sequence to that of rat TGR23-2 ligand obtained from rat whole brain, which are represented by SEQ ID NO: 12, SEQ ID NO: 13 and SEQ ID NO: 14 exits, it was presumed that the DNAs are cDNA encoding a precursor or a portion of human TGR23-2 ligand.

In the frame encoding an amino acid sequence that is considered to be human TGR23-2 ligand, there exists two ATG, which are expected to be a translation initiation codon, upstream of 5'-end of the amino acid sequence translated from the sequence represented by SEQ ID NO: 18. When hydrophobicity was plotted, since high hydrophobic region, which was expected to be a signal sequence, was appeared in the case when it was translated from ATG located further upstream of 5'-end, it was presumed that this ATG was an initiation codon. In 3'-end, there was a termination codon downstream of the sequence, which was considered that human TGR23-2 ligand was encoded. The amino acid sequence of human TGR23-2 ligand precursor deduced from these results is shown as SEQ ID NO: 19. In this sequence, there exists Lys-Arg sequence, wherein it is considered that physiologically active substances are generally excised from its precursor protein (Seidah, N. G. et al., Ann. N. Y. Acad. Sci., Vol. 839, pp. 9-24, 1998) in the N-terminus of the amino acid sequence corresponding to human TGR23-2 ligand. On the other hand, although there exists a termination codon in the C-terminus, there exists two more residues between termination codon and the sequence corresponding to rat TGR23-2 ligand having an amino acid sequence represented by SEQ ID NO: 12.

From these results, it was presumed that the amino acid sequence of human TGR23-2 ligand was the amino acid sequences represented by SEQ ID NO: 20 [human TGR23-2 ligand (1-18)], SEQ ID NO: 21 [human TGR23-2 ligand (1-15)] and SEQ ID NO: 22 [human TGR23-2 ligand (1-14)], wherein the above-mentioned sequences were corresponded to the amino acid sequences of rat TGR23-2 ligand: SEQ ID NO: 12 [rat TGR23-2 ligand (1-18)], SEQ ID NO: 13 [rat TGR23-2 ligand (1-15)] and SEQ ID NO: 14 [rat TGR23-2 ligand (1-14)], respectively; and further the amino acid sequence represented by SEQ ID NO: 23 [human TGR23-2 ligand (1-20)], to which two residues were extended in the C-terminus of the sequence represented by SEQ ID NO: 20. In addition, since the sequence of human TGR23-2 ligand has not Arg-Arg sequence, but Glu-Arg sequence, which characteristic is different from that of the sequences of mouse TGR23-2 ligand and rat TGR23-2 ligand, it was presumed that the amino acid sequence having 16 residues represented is by SEQ ID NO: 49 [human TGR23-2 ligand (1-16)] was also a ligand sequence.

Example 12

Cloning of cDNA Encoding Mouse TGR23-2 Ligand Precursor

In order to clone cDNA encoding a precursor of mouse homologue (in the description, sometimes referred to as mouse TGR23-2 ligand) for rat TGR23-2 ligand, which is obtained from rat whole brain extracts, using cDNA derived from mouse whole brain as a template, PCR was carried out.

Using the following synthetic DNA primers and cDNA derived from mouse whole brain as a template, amplification by PCR method was performed. The reaction solution in the above reaction comprised of 0.8 µl of mouse whole brain Marathon Ready cDNA (CLONTECH), 1.0 µM each of synthetic DNA primers represented by SEQ ID NO: 24 and SEQ ID NO: 25, 0.2 mM dNTPs, 0.1 µl of ExTaq (Takara Shuzo) and ExTaq Buffer attached to the enzyme to make the total volume 20 µl. The PCR reaction was carried out using a thermal cycler (PE Biosystems) by heating of 94° C. for 5 minutes, then a cycle set to include 94° C. for 10 seconds followed by 65° C. for 30 seconds and 72° C. for 30 seconds, which was repeated 35 times, and finally, extension reaction at 72° C. for 5 minutes. Subsequently, 2 µl of the PCR reaction solution diluted by 100-fold with DNase, Rnase-free distilled water, 1.0 µM each of synthetic DNA primers represented by SEQ ID NO: 24 and SEQ ID NO: 26, 0.2 mM dNTPs, 0.1 µl of ExTaq polymerase (Takara Shuzo) and ExTaq Buffer attached to the enzyme were made to 20 µl of total volume. The reaction solution was incubated using a thermal cycler (PE Biosystems) by heating of 94° C. for 5 minutes, then a cycle set to include 94° C. for 10 seconds followed by 60° C. for 30 seconds and 72° C. for 30 seconds, which was repeated 30 times, and finally, extension reaction at 72° C. for 5 minutes. The amplified DNA was separated by 2.0% agarose gel electrophoresis and the DNA having about 440 bases length was excised by razor blade. The DNA was recovered using QIAquick Gel Extraction Kit (Qiagen). This DNA was cloned to pGEM-T Easy vector in accordance with the protocol of pGEM-T Easy Vector System (Promega). After transformation of *Escherichia coli* JM109 competent cell (Takara Shuzo) by introducing the above-mentioned vector, clones harboring cDNA insert fragment was selected on LB agar medium containing ampicillin and X-gal. All the white-colored clones were isolated with sterilized toothpick, and then the transformants were obtained. The transformant was designated *Escherichia coli* JM109/pGEM-T Easy Mouse TGR23(2) Ligand Precursor. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 27, was obtained.

Since in the base sequence of the DNA represented by SEQ ID NO: 27, a frame encoding extremely similar amino acid sequence to that of rat TGR23-2 ligand obtained from rat whole brain, which are represented by SEQ ID NO: 12, SEQ ID NO: 13 and SEQ ID NO: 14 exits, it was presumed that the DNA are cDNA encoding a precursor or a portion of mouse TGR23-2 ligand.

In the frame encoding an amino acid sequence that is considered to be mouse TGR23-2 ligand, there exists two ATG, which are expected to be a translation initiation codon, upstream of 5'-end of the amino acid sequence translated from the sequence represented by SEQ ID NO: 27. When hydrophobicity was plotted, since high hydrophobic region, which was expected to be a signal sequence, was appeared in the case when it was translated from ATG located further upstream of 5'-end, it was presumed that this ATG was an initiation codon. In 3'-end, there was a termination codon downstream of the sequence, which was considered that mouse TGR23-2 ligand was encoded. The amino acid sequence of mouse TGR23-2 ligand precursor deduced from these results is shown as SEQ ID NO: 28. In this sequence, there exists Lys-Arg sequence, wherein it is considered that physiologically active substances are generally excised from its precursor protein (Seidah, N. G. et al., Ann. N. Y. Acad. Sci., Vol. 839, pp. 9-24, 1998) in the N-terminus of the amino acid sequence corresponding to human TGR23-2 ligand. On the other hand, although there exists a termination codon in the C-terminus, there exists two more residues between termination codon and the sequence corresponding to rat TGR23-2 ligand having an amino acid sequence represented by SEQ ID NO: 12.

From these results, it was presumed that the amino acid sequence of mouse TGR23-2 ligand was the amino acid sequences represented by SEQ ID NO: 29 [mouse TGR23-2 ligand (1-18)], SEQ ID NO: 30 [mouse TGR23-2 ligand (1-15)] and SEQ ID NO: 31 [mouse TGR23-2 ligand (1-14)], wherein the above-mentioned sequences were corresponded to the amino acid sequences of rat TGR23-2 ligand: SEQ ID NO: 12 [rat TGR23-2 ligand (1-18)], SEQ ID NO: 13 [rat TGR23-2 ligand (1-15)] and SEQ ID NO: 14 [rat TGR23-2 ligand (1-14)], respectively; and further the amino acid sequence represented by SEQ ID NO: 32 [mouse TGR23-2 ligand (1-20)], to which two residues were extended in the C-terminus of the sequence represented by SEQ ID NO: 29.

Example 13

Cloning of cDNA Encoding a Portion of Rat TGR23-2 Ligand Precursor

In order to clone cDNA encoding a precursor of rat TGR23-2 ligand, using cDNA derived from rat whole brain as a template, PCR was carried out.

Using the following synthetic DNA primers and cDNA derived from rat whole brain as a template, amplification by PCR method was performed. The reaction solution in the above reaction comprised of 0.8 µl of rat whole brain Marathon Ready cDNA (CLONTECH), 1.0 µM each of synthetic DNA primers represented by SEQ ID NO: 33 and SEQ ID NO: 25, 0.2 mM dNTPs, 0.1 µl of ExTaq (Takara Shuzo) and ExTaq Buffer attached to the enzyme to make the total volume 20 µl. The PCR reaction was carried out using a thermal cycler (PE Biosystems) by heating of 94° C. for 5 minutes, then a cycle set to include 94° C. for 10 seconds followed by 65° C. for 30 seconds and 72° C. for 30 seconds, which was repeated 35 times, and finally, extension reaction at 72° C. for 5 minutes. Subsequently, 2 µl of the PCR reaction solution diluted by 100-fold with DNase, Rnase-free distilled water, 1.0 µM of primer represented by SEQ ID NO: 33, 0.2 µM of primer represented by SEQ ID NO: 26, 0.2 mM dNTPs, 0.1 µl of ExTaq polymerase (Takara Shuzo) and ExTaq Buffer attached to the enzyme were made to 20 µl of total volume. The reaction solution was incubated using a thermal cycler (PE Biosystems) by heating of 94° C. for 5 minutes, then a cycle set to include 94° C. for 10 seconds followed by 60° C. for 30 seconds and 72° C. for 30 seconds, which was repeated 30 times, and finally, extension reaction at 72° C. for 5 minutes. The amplified DNA was separated by 2.0% agarose gel electrophoresis and the DNA having about 200 bases length was excised by razor blade. The DNA was recovered using QIAquick Gel Extraction Kit (Qiagen). This DNA was cloned to pGEM-T Easy vector in accordance with the protocol of pGEM-T Easy Vector System (Promega). After transformation of *Escherichia coli* JM109 competent cell (Takara Shuzo) by introducing the above-mentioned vector, clones harboring cDNA insert fragment was selected on LB agar medium containing ampicillin and X-gal. All the white-colored clones were isolated with sterilized toothpick, and then the transformants were obtained. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 34, was obtained.

In the base sequence of the DNA represented by SEQ ID NO: 34, there exists a frame encoding an amino acid sequence of rat TGR23-2 ligand obtained from rat whole brain, which are represented by SEQ ID NO: 12, SEQ ID NO: 13 and SEQ ID NO: 14. Where the DNA sequence was translated using this frame as a reading frame, the amino acid sequence represented by SEQ ID NO: 35 was obtained. As compared this sequence with the amino acid sequence of mouse TGR23-2 ligand precursor (SEQ ID NO: 27) that was obtained in Example 12, it was presumed that this sequence corresponds to a sequence consisting of 54 amino acids at the C-terminus, which is a portion of rat TGR23-2 ligand precursor. In 3'-end, there was a termination codon downstream of the sequence, which was considered that rat TGR23-2 ligand was encoded. In this sequence, there exists Lys-Arg sequence, which physiologically active substances are generally excised from its precursor protein (Seidah, N. G. et al., Ann. N. Y. Acad. Sci., Vol. 839, pp. 9-24, 1998) in the N-terminus of the amino acid sequence corresponding to human TGR23-2 ligand. On the other hand, although there exists a termination codon in the C-terminus, there exists two more residues between termination codon and the sequence corresponding to rat TGR23-2 ligand having an amino acid sequence represented by SEQ ID NO: 12.

From these results, it was presumed that the amino acid sequence of rat TGR23-2 ligand was the amino acid sequences represented by SEQ ID NO: 12 [rat TGR23-2 ligand (1-18)], SEQ ID NO: 13 [rat TGR23-2 ligand (1-15)] and SEQ ID NO: 14 [rat TGR23-2 ligand (1-14)], and further the amino acid sequence represented by SEQ ID NO: 36 [rat TGR23-2 ligand (1-20)], to which two residues were extended in the C-terminus of the sequence represented by SEQ ID NO: 12.

Example 14

Cloning of cDNA Encoding Rat TGR23-2 Ligand Precursor

In order to clone cDNA encoding a precursor of rat TGR23-2 ligand, using cDNA derived from rat whole brain as a template, PCR was carried out.

Using the following synthetic DNA primers and cDNA derived from rat whole brain as a template, amplification by PCR method was performed. The reaction solution in the above reaction comprised of 0.8 µl of rat whole brain Marathon Ready cDNA (CLONTECH), 1.0 µM each of synthetic DNA primers represented by SEQ ID NO: 57 and SEQ ID NO: 58, 0.2 mM dNTPs, 0.1 µl of ExTaq (Takara Shuzo) and ExTaq Buffer attached to the enzyme to make the total volume 20 µl. The PCR reaction was carried out using a thermal cycler (PE Biosystems) by heating of 94° C. for 5 minutes, then a cycle set to include 94° C. for 10 seconds followed by 65° C. for 30 seconds and 72° C. for 30 seconds, which was repeated 35 times, and finally, extension reaction at 72° C. for 5 minutes. Subsequently, 2 µl of the PCR reaction solution diluted by 50-fold with DNase, Rnase-free distilled water, 1.0 µM of primer represented by SEQ ID NO: 59, 0.2 µM of primer represented by SEQ ID NO: 58, 0.2 mM dNTPs, 0.1 µl of ExTaq polymerase (Takara Shuzo) and ExTaq Buffer attached to the enzyme were made to 20 µl of total volume. The reaction solution was incubated using a thermal cycler (PE Biosystems) by heating of 94° C. for 5 minutes, then a cycle set to include 94° C. for 10 seconds followed by 65° C. for 30 seconds and 72° C. for 30 seconds, which was repeated 30 times, and finally, extension reaction at 72° C. for 5 minutes. The amplified DNA was separated by 2.0% agarose gel electrophoresis and the DNA having about 350 bases length was excised by razor blade. The DNA was recovered using QIAquick Gel Extraction Kir (Qiagen). This DNA was cloned to pGEM-T Easy vector in accordance with the protocol of pGEM-T Easy Vector System (Promega). After transformation of *Escherichia coli* JM109 competent cell (Takara Shuzo) by introducing the above-mentioned vector, clones harboring cDNA insert fragment was selected on LB agar medium containing ampicillin and X-gal. All the white-colored clones were isolated with sterilized toothpick, and then the transformants were obtained. The transformant was designated *Escherichia coli* JM109/pGEM-T Easy Rat TGR23(2) Ligand Precursor. Respective clones were cultured in LB medium containing ampicillin for overnight. Subsequently, the plasmid DNA was prepared using QIAwell 8 Plasmid Kit (Qiagen). The reaction for determination of the base sequence was carried out using BigDye Terminator Cycle Sequencing Ready Reaction Kit (PE Biosystems). As a result, after decoding with the fluorescent automated sequencer, the DNA sequence represented by SEQ ID NO: 60, was obtained.

The base sequence of the DNA represented by SEQ ID NO: 60, was a sequence, wherein the DNA sequence encoding a portion of rat TGR23-2 ligand precursor obtained in Example 13 (SEQ ID NO: 34) was further extended to 5' direction. Where the DNA sequence was translated using a frame encoding an amino acid sequence identical to that of rat TGR23-2 ligand precursor obtained from rat whole brain, which are represented by SEQ ID NO: 12, SEQ ID NO: 13 and SEQ ID NO: 14 as a reading frame, there was one site of ATG in 5' upstream at the position corresponding to ATG, which is presumed to be an initiation codon of protein translation that located in cDNA (SEQ ID NO: 18 and SEQ ID NO: 27) being expected to encode human TGR23-2 ligand precursor and mouse TGR23-2 ligand precursor. In addition, in further upstream of 5'-end of this ATG codon, a termination codon was appeared on the same frame. In 3'-end, there was a termination codon downstream of the sequence, which was considered that mouse TGR23-2 ligand was encoded. From these results, it was presumed that the sequence represented by SEQ ID NO: 60 was the cDNA sequence encoding rat TGR23-2 ligand precursor. The amino acid sequence translated from the base sequence of cDNA represented by SEQ ID NO: 60 is shown as SEQ ID NO: 61.

Example 15

Preparation of TGR23-1 (Hereinafter, Sometimes Human TGR23-1 Is Merely Referred to as TGR23-1) Expressing CHO Cells Using the plasmid pTB2173 obtained in Reference Example 1 as a template and two primers, namely, primer 1 attached to Sal I recognition sequence (SEQ ID NO: 7) and primer 2 attached to Spe I recognition sequence (SEQ ID NO: 8), PCR was carried out. The reaction solution in the above reaction comprised of 10 ng of the above plasmid as a template, 2.5 U of Pfu Turbo DNA Polymerase (STRATAGENE), 1.0 μM each of primer 1 (SEQ ID NO: 7) and primer 2 (SEQ ID NO: 8), 200 μM of dNTPs, and 25 μl of 2×GC Buffer I (Takara) to make the total volume 50 μl. The PCR reaction was carried out by reaction of 95° C. for 60 seconds, then a cycle set to include 95° C. for 60 seconds followed by 55° C. for 60 seconds and 72° C. for 70 seconds, which was repeated 25 times, and finally, extension reaction at 72° C. for 10 minutes. The PCR product was subcloned into plasmid vector pCR-Blunt II-TOPO (Invitrogen) following the instructions attached to the Zero Blunt TOPO PCR Cloning Kit (Invitrogen). The plasmid was then introduced into *Escherichia coli* TOP10 (Invitrogen), and the clones having the cDNA of TGR23-1, which is contained in pTB2173, were selected on LB agar plates containing kanamycin. From *E. coli* clones transformed by the plasmid thus obtained, in which the TGR23-1 was introduced, the plasmid was prepared using Plasmid Miniprep Kit (BIO RAD) and digested with the restriction enzymes Sal I and Spe I to excise the insert, wherein TGR23-1 was attached to Sal I recognition sequence at 5' end and Spe I recognition sequence at 3' end. The insert DNA was electrophoresed to excise from agarose gel and recovered using the Gel Extraction Kit (Qiagen). This insert DNA was added to the expression vector plasmid for animal cells, pAKKO-111H (the same vector plasmid as pAKKO1.11 H described in Biochim. Biophys. Acta, Vol. 1219, pp. 251-259 (1994) by Hinuma, S. et al.), which has been cleaved with Sal I and Spe I, and both DNAs were ligated by the DNA Ligation Kit Ver. 2 (Takara Shuzo). Thus, the plasmid pAKKO-TGR23-1 for protein expression was constructed. After cultivating *E. coli* TOP10 transformed with this pAKKO-TGR23-1, plasmid DNA of pAKKO-TGR23-1 was prepared using Plasmid Miniprep Kit (BIO RAD).

With α-MEM medium (with ribonucleosides and deoxyribonucleosides, GIBCO, Cat No. 12571) containing 10% Fetal Bovine Serum, 1×10$^5$ cells of hamster CHO/dhfr$^-$ cell were seeded in Falcon dish (3.5 cm diameter) and cultivated at 37° C. for overnight in 5% CO$_2$ incubater. Two μg of the above-mentioned expression plasmid, pAKKO-TGR23-1 was transfected using Transfection Reagent FuGENE 6 (Roche) in accordance with the procedures described in the attached instruction. After 18 hours of cultivation, the medium was exchanged to a fresh medium for growth. Further cultivation for 10 hours, the transfected cells were harvested by treatment with Trypsin-EDTA, and seeded to 10 of 96-well flat bottomed plates with a selection medium (α-MEM medium (without ribonucleosides and deoxyribonucleosides, GIBCO, Cat No. 12561) containing 10% dialyzed Fetal Bovine Serum). Cultivation was continued while the selection medium was exchanged every 3 or 4 days, and 81 clones of DHFR$^+$ cell, which grew as a colony, were acquired after 2 or 3 weeks.

Example 16

Quantification of TGR23-1 Expression Level in TGR23-1 Expressing CHO Cell Lines Using TaqMan PCR Method The 81 clones of TGR23-1 expressing CHO cells obtained in Example 15 were cultured in the 96-well plate, and total RNA was prepared using RNeasy 96 Kit (Qiagen). Using 50 to 200 ng of total RNA obtained and TaqMan Gold RT-PCR Kit (PE Biosystems), a reverse transcription reaction was performed. Using 25 μl of the reaction mixture containing a reverse transcript corresponding to 5 to 20 ng of the total RNA obtained or a standard cDNA prepared as described below, 1× Universal PCR Master Mix (PE Biosystems), 500 nM each of primers represented by SEQ ID NO: 9 and SEQ ID NO: 10, and 100 nM TaqMan probe represented by SEQ ID NO: 11 (Fam-acctggtttg ccgagtggtc cgctattt-Tamra; in the sequence, Fam and Tamra represent 6-carboxy-fluorescein and 6-carboxy-tetramethyl-rhodamine, respectively), PCR was performed with ABI PRISM 7700 Sequence Detector (PE Biosystems). The PCR was carried out by reaction of 50° C. for 2 minutes and 95° C. for 10 minutes, then a cycle set to include 95° C. for 15 seconds followed by 60° C. for 60 seconds, which was repeated 40 times.

After concentration of the plasmid pTB2174 obtained in Reference Example 1 was calculated by measuring absorbance at 260 nm and accurate copy numbers were calculated, 2 to 2×10$^6$ copies of standard cDNA solution were prepared by diluting with 10 mM Tris-HCl (pH8.0) containing 1 mM EDTA. Further, probe and primers for TaqMan PCR were designed by the Primer Express Version 1.0 (PE Biosystems).

The expression level was calculated using the ABI PRISM 7700 SDS Software. By representing cycle numbers at the moment when fluorescent intensity of reporter comes to preset values indicated as a vertical axis, and logarithm of an initial concentration of the standard cDNA as a horizontal axis, standard curve was prepared. From this standard curve, the expression level of TGR23-1 gene per total RNA of each clone was found by calculating an initial concentration of each reverse transcript. As a result, 11 clones of CHO cell lines, in which the expression of TGR23-1 was high, were selected and cultured in 24-well plate. For these cells, the expression level of TGR23-1 was re-examined. After preparation of total RNA with RNeasy Mini Kits (Qiagen), the RNA was treated with DNase by RNase-free DNase Set (Qiagen). From total RNA obtained, the reverse transcription reaction was carried out in the same manner as described above, and the expression level of TGR23-1 gene per total RNA of each clone was found by the TaqMan PCR method. From this, it was revealed that the clones No. 49 and No. 52 of CHO cell lines expressing TGR23-1 were highly expressed.

In the Examples described below, these two clones of the TGR23-1 expressing cells were used.

Example 17

Manufacture of Human TGR23-2 Ligand (1-20): Ser-Phe-Arg-Asn-Gly-Val-Gly-Thr-Gly-Met-Lys-Lys-Thr-Ser-Phe-Gln-Arg-Ala-Lys-Ser (SEQ ID NO: 23)

Commercially available Boc-Ser(Bzl)-OCH$_2$-PAM resin was charged in a reaction tank of peptide synthesizer, ACT90. After swelling with DCM, the resin was treated with TFA to remove Boc and neutralized with DEIA. The resin was suspended in NMP and Boc-Lys(Cl-Z) was condensed to the amino group by the HOBt-DIPCI. Ninhydrin test was conducted to examine if any unreacted amino group was present. Where the ninhydrin test was positive, the same amino acid was condensed again. Where the ninhydrin test was also positive after re-condensation, peptide was acethylated with acetic anhydrite. By repeating this cycle, Boc-Ala, Boc-Arg(Tos), Boc-Gln, Boc-Phe, Boc-Ser(Bzl), Boc-Thr(Bzl), Boc-Lys(Cl-Z), Boc-Lys(Cl-Z), Boc-Met, Boc-Gly, Boc-Thr(Bzl), Boc-Gly, Boc-Val, Boc-Gly, Boc-Asn, Boc-Arg(Tos), Boc-Phe and Boc-Ser(Bzl) were condensed in this order. As a result, 0.24 g of protected peptide resin, which was desired, was obtained. The resin was reacted in about 15 ml of hydrogen fluoride together with 1.5 ml of p-cresol at 0° C. for 60 minutes. After removing the hydrogen fluoride by distillation in vacuum, diethyl ether was added to the residue, and filtrated. Water and acetic acid were added to the filtrate in order to extract the peptide. Finally, it was separated from the resin. The extract was concentrated, and the concentrate obtained was applied to a column of Sephadex (trade mark) G-25 (2.0×80 cm) equilibrated with 50% acetic acid, developed with the same solvent. Main fractions were collected and lyophilized. The part of the peptide (45 mg) was applied to a reversed phase column (2.6×60 cm) filled up with LiChroprep (trade name) RP-18 followed by carrying out the washing with 200 ml of 0.1% aqueous TFA and the linear gradient elution using 300 ml of 0.1% aqueous TFA and 300 ml of 25% acetonitrile aqueous solution containing 0.1% TFA. Main fractions were collected and lyophilized to give 12.7 mg of objective peptide.

ESI-MS: molecular weight MW 2188.0 (theoretical value 2187.5)

Elution time on HPLC: 10.6 minutes

Column Conditions:
Column: Wakosil 5C18T (4.6×100 mm)
Eluant: linear density gradient elution (25 minutes) with A/B: 95/5 to 45/55, using solution A (0.1% TFA) and solution B (acetonitrile solution containing 0.1% TFA)
Flow rate: 1.0 ml/min.

Example 18

Figure 8:
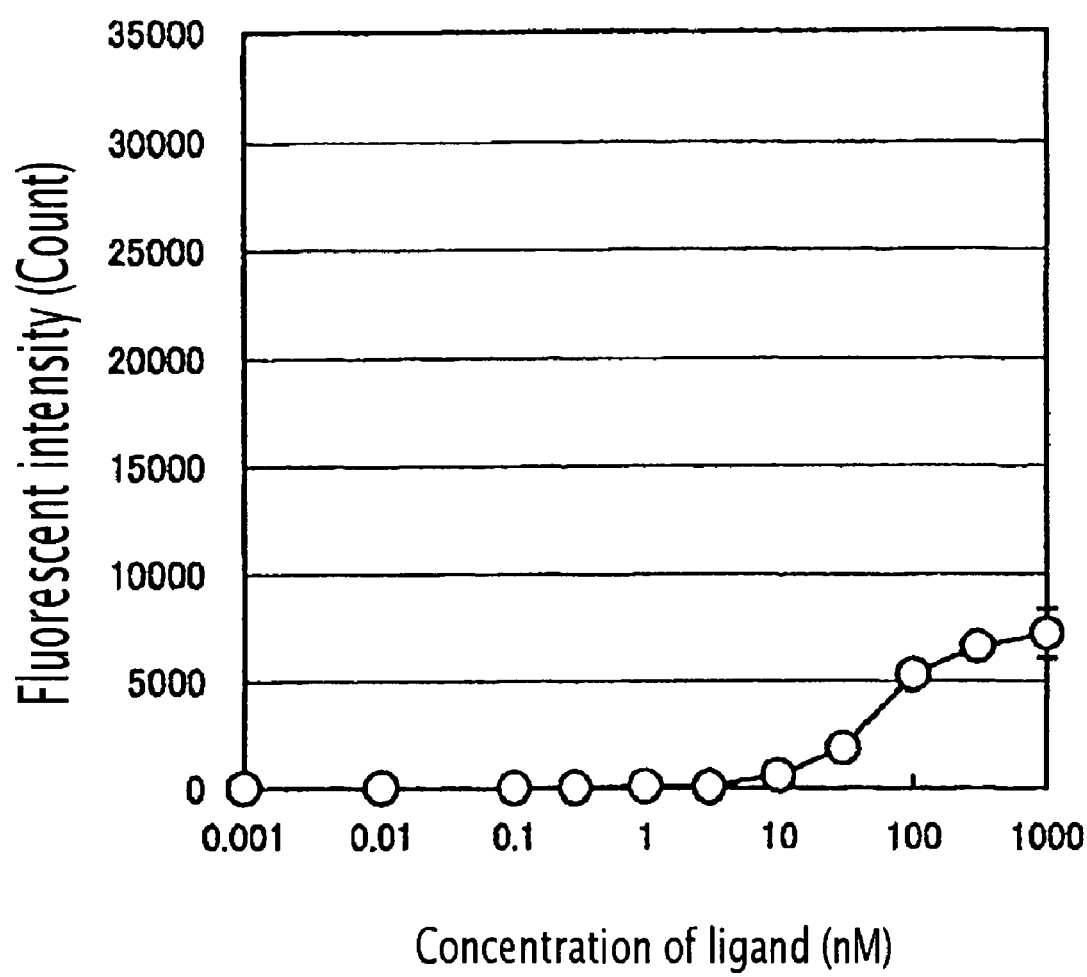
FIG. 8 shows the intracellular Ca ion concentration increasing activity in TGR23-1 expressing CHO cells by various concentration of human TGR23-2 ligand (1-20), which is measured using FLIPR.
Figure 9:
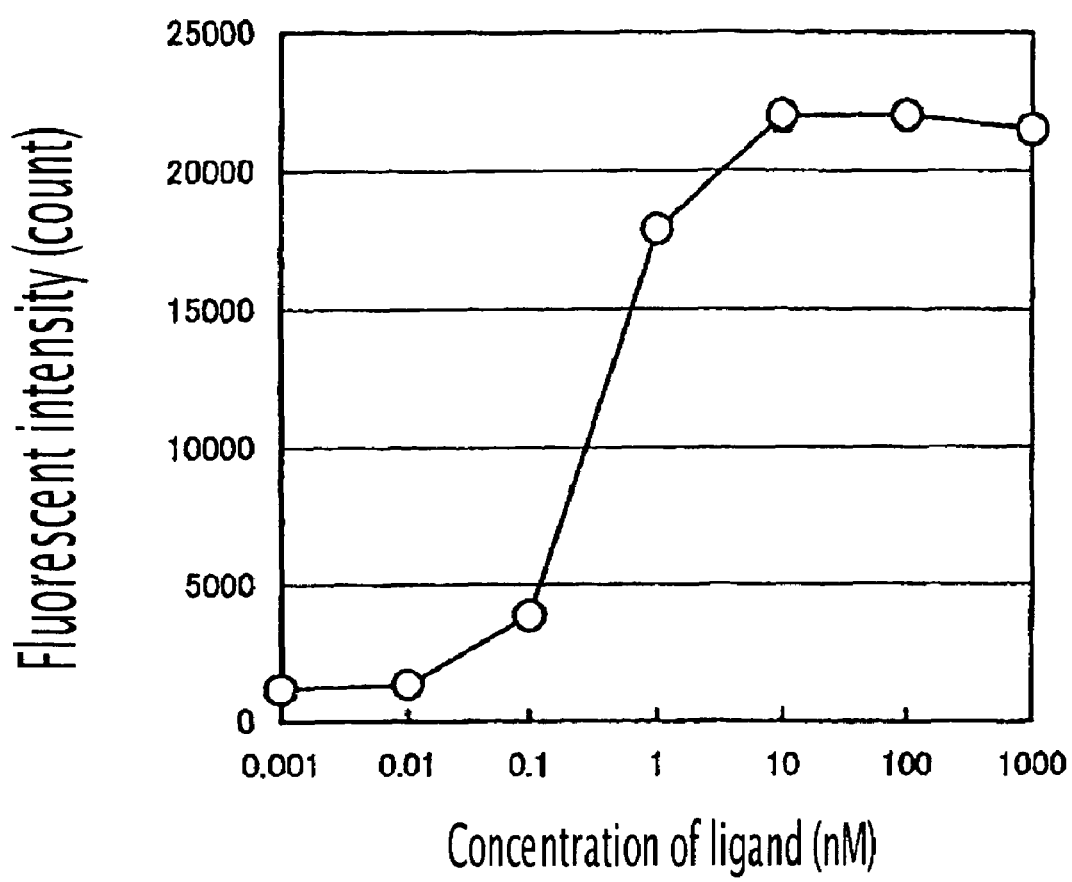
FIG. 9 shows the intracellular Ca ion concentration increasing activity in TGR23-2 expressing CHO cells by various concentration of human TGR23-2 ligand (1-20), which is measured using FLIPR.
Figure 10:
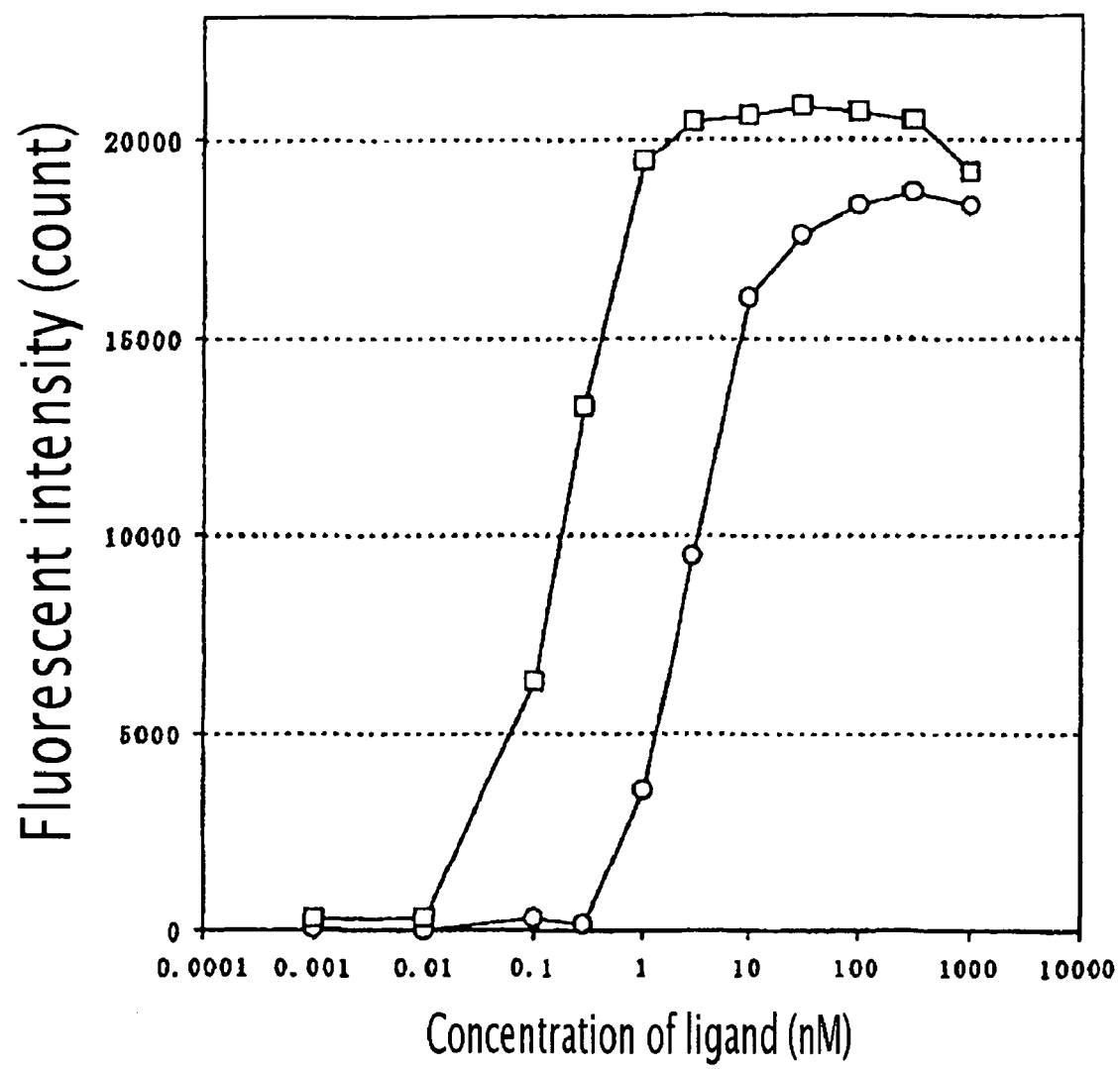
FIG. 10 shows the intracellular Ca ion concentration increasing activity in TGR23-1 expressing CHO cells and TGR23-2 expressing CHO cells by various concentration of human TGR23-2 ligand (1-18), which is measured using FLIPR. In the figure, open circle and open square represent the intracellular Ca ion concentration increasing activity in TGR23-1 expressing CHO cells and that in TGR23-2 expressing CHO cells, respectively.
Figure 11:
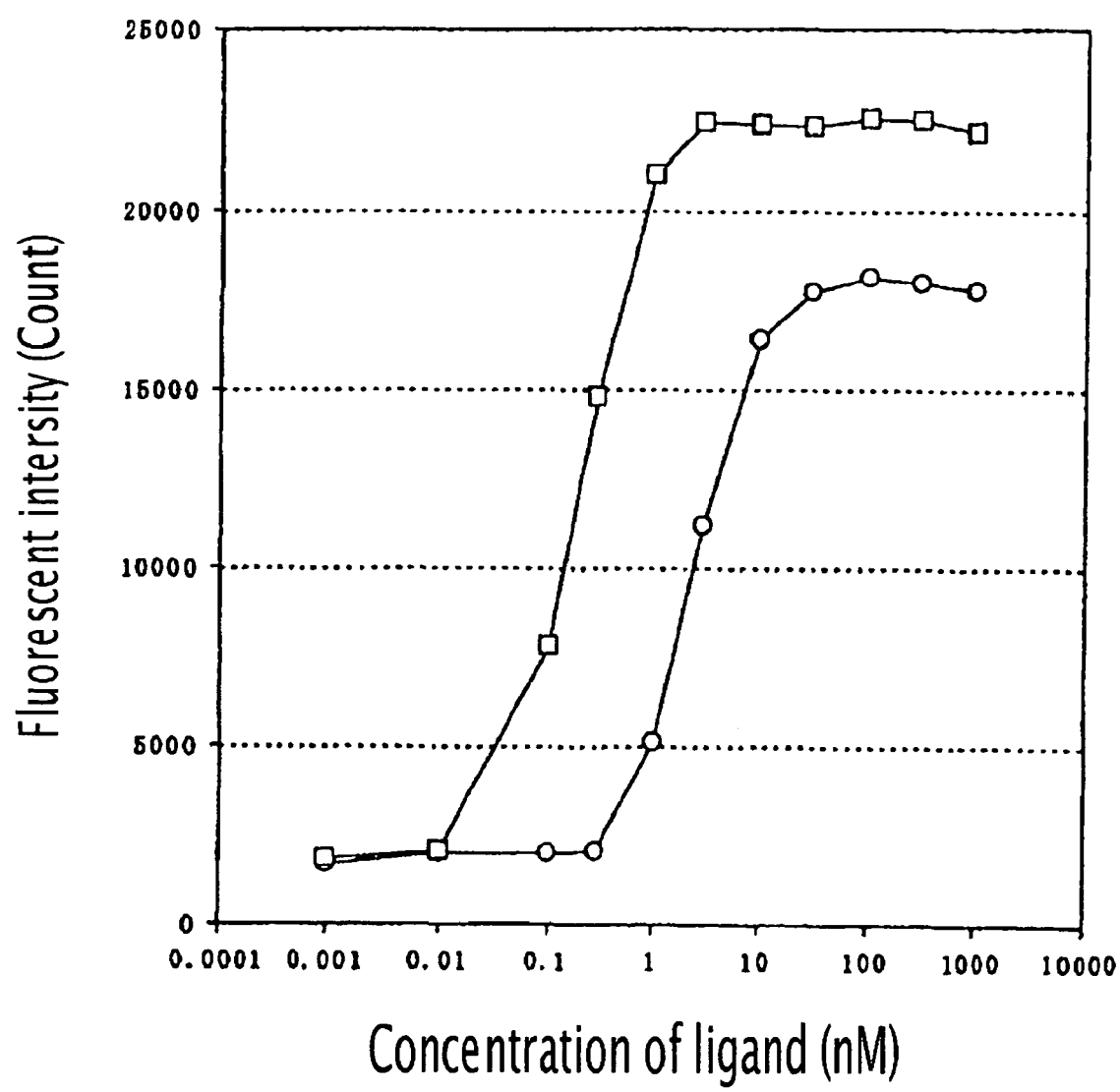
FIG. 11 shows the intracellular Ca ion concentration increasing activity in TGR23-1 expressing CHO cells and TGR23-2 expressing CHO cells by various concentration of human TGR23-2 ligand (1-20), which is measured using FLIPR. In the figure, open circle and open square represent the intracellular Ca ion concentration increasing activity in TGR23-1 expressing CHO cells and that in TGR23-2 expressing CHO cells, respectively.

Assay for Increasing Activity of Intracellular Ca Ion Concentration on TGR23-1 Expressing CHO Cells and TGR23-2 Expressing CHO Cells by Human TGR23-2 Ligand (1-20) Using FLIPR Human TGR23-2 ligand (1-20) obtained in Example 17 was administered to TGR23-1 expressing CHO cells and TGR23-2 expressing CHO cells at a variety of concentrations according to the method described in Example 5, and the increasing activity of intracellular Ca ion concentration was determined using FLIPR. As a result, human TGR23-2 ligand (1-20) enhances an increase of intracellular Ca ion concentration on TGR23-1 expressing CHO cells and TGR23-2 expressing CHO cells depending on the concentration. The results are shown in FIG. 8 and FIG. 9.

From these results, it is clear that the polypeptide having an amino acid sequence represented by SEQ ID NO: 23 [human TGR23-2 ligand (1-20)] possesses an increasing activity of intracellular Ca ion concentration on TGR23-1 expressing CHO cells and TGR23-2 expressing CHO cells.

Example 19

Manufacture of Rat TGR23-2 Ligand (1-18): Ser-Phe-Arg-Asn-Gly-Val-Gly-Ser-Gly-Val-Lys-Lys-Thr-Ser-Phe-Arg-Arg-Ala (SEQ ID NO: 12)

The corresponding to 0.25 mmol of Fmoc-Ala-O-Clt resin (0.638 mmol/g), wherein Fmoc-Ala-OH is introduced to 2-chlorotrityl resin (Clt resin, 1.33 mmol/g) commercially available, was charged in a reaction tank of peptide synthesizer, ABI433A. By Fmoc/DCC/HOBt method, a solid phase synthesis was performed. For protecting group of the side chain of Fmoc amino acid, Pbf group, Bu$^t$ group, Boc group and Trt group corresponded to Arg, Ser, Lys and Asn, respectively. For other amino acids, amino acids, wherein the side chain is not protected, were used. Then the peptide chain was introduced from Arg at 17 of the sequence indicated above to Ser at 14 for the N-terminus in order. The obtained Fmoc-rat TGR23-2 ligand (14-18) O-Clt resin (0.25 mmol) was treated with 381.1 mg (0.625 mmol) of Fmoc-Lys(Boc)-Thr(Psi(Me,Me)pro)-OH (Nova, Product No. 05-20-1116), 326.1 mg (0.625 mmol) of PyAOP, 85.1 mg (0.625 mmol) of HOAt and 435.5 ml (2.5 mmol) of DIEA to give Lys at 12 and Thr at 13. Subsequently, using the obtained Fmoc-Lys(Boc)-Thr(Psi(Me,Me)pro)$^{13}$]-rat-TGR23-2 ligand (12-18)-O-Clt resin, the solid phase synthesis was restarted with peptide synthesize. Then the peptide chain was introduced from Lys at 11 of the sequence indicated above to Ser at 1 for the N-terminus in order to give 573.5 mg of the desired protecting peptide resin.

All the resin (0.25 mmol) was stirred at room temperature for 90 minutes in 9 ml of mixture consisting of TFA, thioanisole, m-cresol, water, triisopropylsilane and ethandithiol (80:5:5:5:2.5:2.5). Then ether was added to the reaction mixture to give a white powder. By centrifugation, the supernatant was discarded. This procedure was repeated three times. The residues were extracted with water, and the extract was lyophilized to give 219.4 mg of white powder. The crude peptide obtained was loaded to fractionated HPLC using YMC Pack R&D-ODS-5-B S-5, 120A column (30×250 mm), and eluted with a linear gradient (60 minutes) from A/B: 90/10 to 70/30 wherein A solution is 0.1% TFA-water and B solution is acetonitrile containing 0.1% TFA. The fractions containing the objective substance were collected, lyophilized to give white powder.

All the powder obtained was dissolved in water and admixed. Subsequently, 3 ml of ion exchange resin AG1×8 100-200 mesh chloride form, which is acetated, were added to the solution. After stirring for 20 minutes, resin and impurities were removed. After lyophilization, 107.0 mg of white powder was obtained as acetate.

ESI-MS: M$^+$ 1954.2 (theoretical value 1954.2)

Elution time on HPLC: 15.2 minutes

Column Conditions:
Column: YMC AM 301 (4.6×100 mm)
Eluant: linear density gradient elution (25 minutes) with A/B: 100/0 to 50/50, using solution A (0.1% TFA-water) and solution B (acetonitrile solution containing 0.1% TFA)
Flow rate: 1.0 ml/min.

Example 20

Manufacture of Mouse TGR23-2 Ligand (1-20): Ser-Phe-Arg-Asn-Gly-Val-Gly-Ser-Gly-Ala-Lys-Lys-Thr-Ser-Phe-Arg-Arg-Ala-Lys-Gln (SEQ ID NO: 32)

Using 0.25 mmol of Fmoc-Gln(Trt)-O-Clt resin (0.408 mmol/g), wherein Fmoc-Gln(Trt)-OH is introduced to 2-chlorotrityl resin (Clt resin, 1.12 mmol/g) commercially available, solid phase synthesis was done in the similar manner to the manufacturing of rat TGR23-2 ligand (1-18) described in Example 19 to give 324.7 mg of the objective protection peptide.

One hundred milligrams of the resin was treated as with Example 19 to give 50.0 mg of white powder. The crude peptide obtained was loaded to fractionated HPLC using YMC SH-343-5 S-5, 120A column (20×250 mm), and eluted with a linear gradient (60 minutes) from A/B: 92/8 to 72/28 wherein A solution is 0.1% TFA-water and B solution is acetonitrile containing 0.1% TFA. The fractions containing the objective substance were collected, lyophilized to give 22.6 mg of white powder.

ESI-MS: M⁺ 2182.8 (theoretical value 2182.5)
Elution time on HPLC: 14.1 minutes
Column Conditions:
Column: YMC AM 301 (4.6×100 mm)
Eluant: linear density gradient elution (25 minutes) with A/B: 100/0 to 50/50, using solution A (0.1% TFA-water) and solution B (acetonitrile solution containing 0.1% TFA)
Flow rate: 1.0 ml/min.

Example 21

Figure 14:
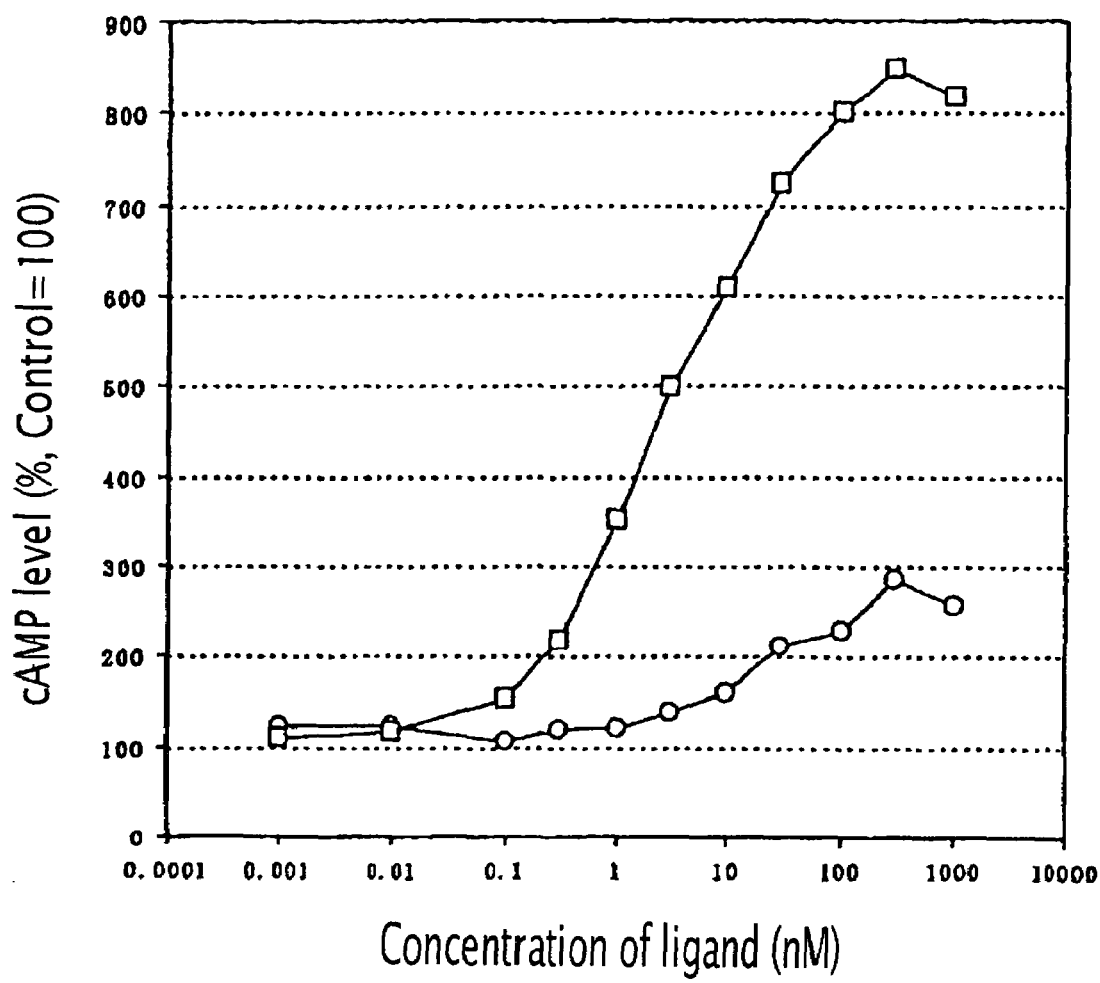
FIG. 14 shows the intracellular cAMP production enhancing activity of various concentration of the rat TGR23-2 ligand (1-18) on TGR23-1 expressing CHO cells and TGR23-2 expressing CHO cells, wherein both cells were on the condition of no forskolin. In the figure, open circle and open square represent the intracellular cAMP production enhancing activity in TGR23-1 expressing CHO cells and that in TGR23-2 expressing CHO cells, respectively.
Figure 15:
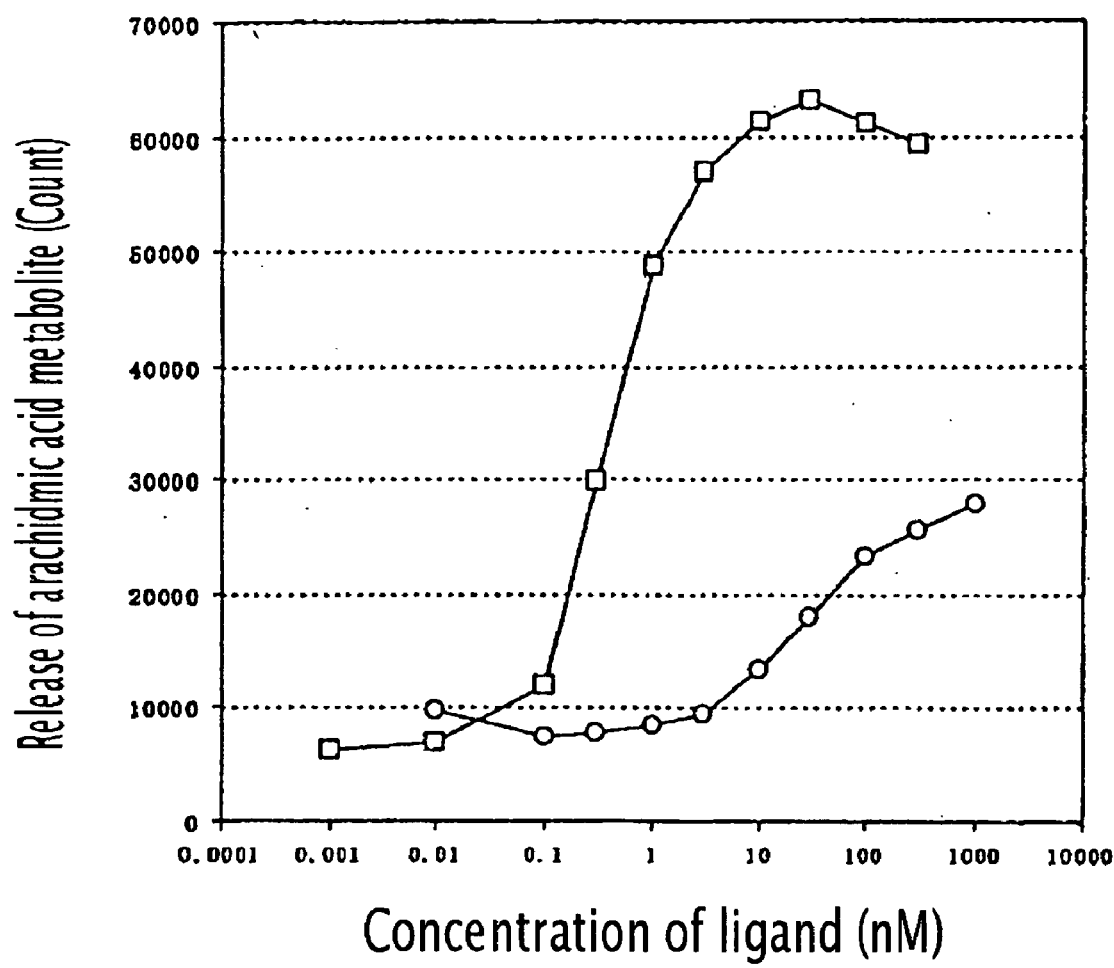
FIG. 15 shows the arachidonic acid metabolite releasing activity of various concentration of the human TGR23-2 ligand (1-20) on TGR23-1 expressing CHO cells and TGR23-2 expressing CHO cells. In the figure, open circle and open square represent the arachidonic acid metabolite releasing activity in TGR23-1 expressing CHO cells and that in TGR23-2 expressing CHO cells, respectively.

Assay for Increasing Activity of Intracellular Ca ion Concentration on TGR23-1 Expressing CHO Cells and TGR23-2 Expressing CHO Cells by Rat TGR23-2 Ligand (1-18) and Mouse TGR23-2 Ligand (1-20) Using FLIPR Rat TGR23-2 ligand (1-18) prepared by the method described in Example 19 and mouse TGR23-2 ligand (1-20) prepared by the method described in Example 20 were administered to TGR23-1 expressing CHO cells and TGR23-2 expressing CHO cells at a variety of concentrations according to the method described in Example 5, and the increasing activity of intracellular Ca ion concentration was determined using FLIPR. The results are shown in FIG. 14 and FIG. 15. Rat TGR23-2 ligand (1-18) and mouse TGR23-2 ligand (1-20) clearly enhance an increase of intracellular Ca ion concentration on TGR23-1 expressing CHO cells and TGR23-2 expressing CHO cells depending on the concentration. From these results, it becomes clear that the peptide having the structure represented by SEQ ID NO: 12 and SEQ ID NO: 32 possesses an increasing activity of intracellular Ca ion concentration on TGR23-1 expressing CHO cells and TGR23-2 expressing CHO cells.

Example 22

Assay for Enhancing Activities of Intracellular cAMP Production in TGR23-1 Expressing CHO Cells and TGR23-2 Expressing Cells by Human TGR23-2 Ligand (1-20) and Rat TGR23-2 Ligand (1-18)

Figure 12:
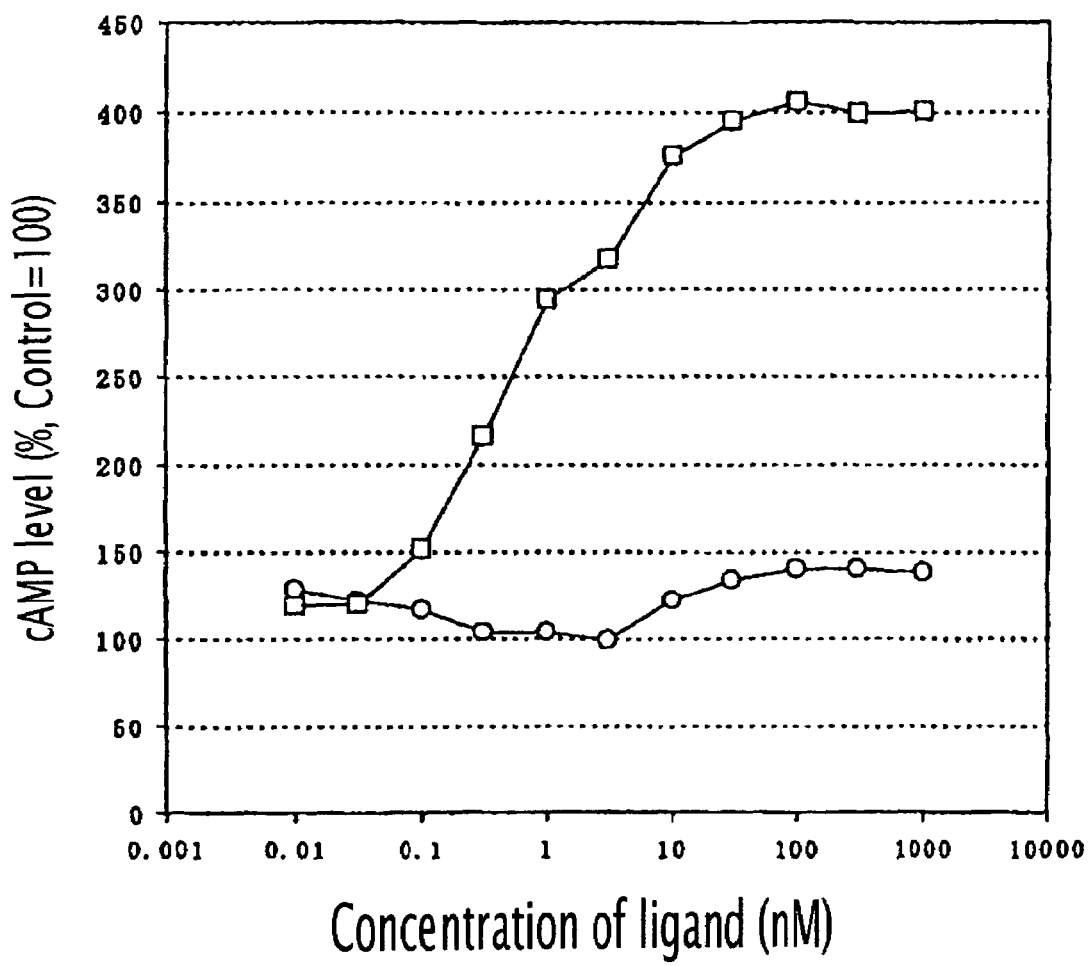
FIG. 12 shows the intracellular cAMP production enhancing activity of various concentration of the human TGR23-2 ligand (1-20) on TGR23-1 expressing CHO cells and TGR23-2 expressing CHO cells, wherein both cells were stimulated by forskolin. In the figure, open circle and open square represent the intracellular cAMP production enhancing activity in TGR23-1 expressing CHO cells and that in TGR23-2 expressing CHO cells, respectively.

Human TGR23-2 ligand (1-20) prepared by the method described in Example 17 was administered to TGR23-1 expressing CHO cells and TGR23-2 expressing CHO cells at a variety of concentrations according to the method described in Example 3, and the enhancing activity of intracellular cAMP production was determined. The results are shown in FIG. 12.

Human TGR23-2 ligand (1-20) clearly enhances cAMP production on TGR23-1 expressing CHO cells and TGR23-2 expressing CHO cells depending on the concentration.

Further, human TGR23-2 ligand (1-20) and rat TGR23-2 ligand (1-18) prepared by the method described in Example 19 were administered to TGR23-1 expressing CHO cells and TGR23-2 expressing CHO cells at a variety of concentrations, and the same assay as described above was carried out under the condition of no forskolin. A calculation was made using the following formula, and the enhancing activity for cAMP production was represented by % of control:

% of control=$X/C$×100;

X: The cAMP level in the sample-adding group; and
C: Control (no sample, without stimulus of forskoline).

Figure 13:
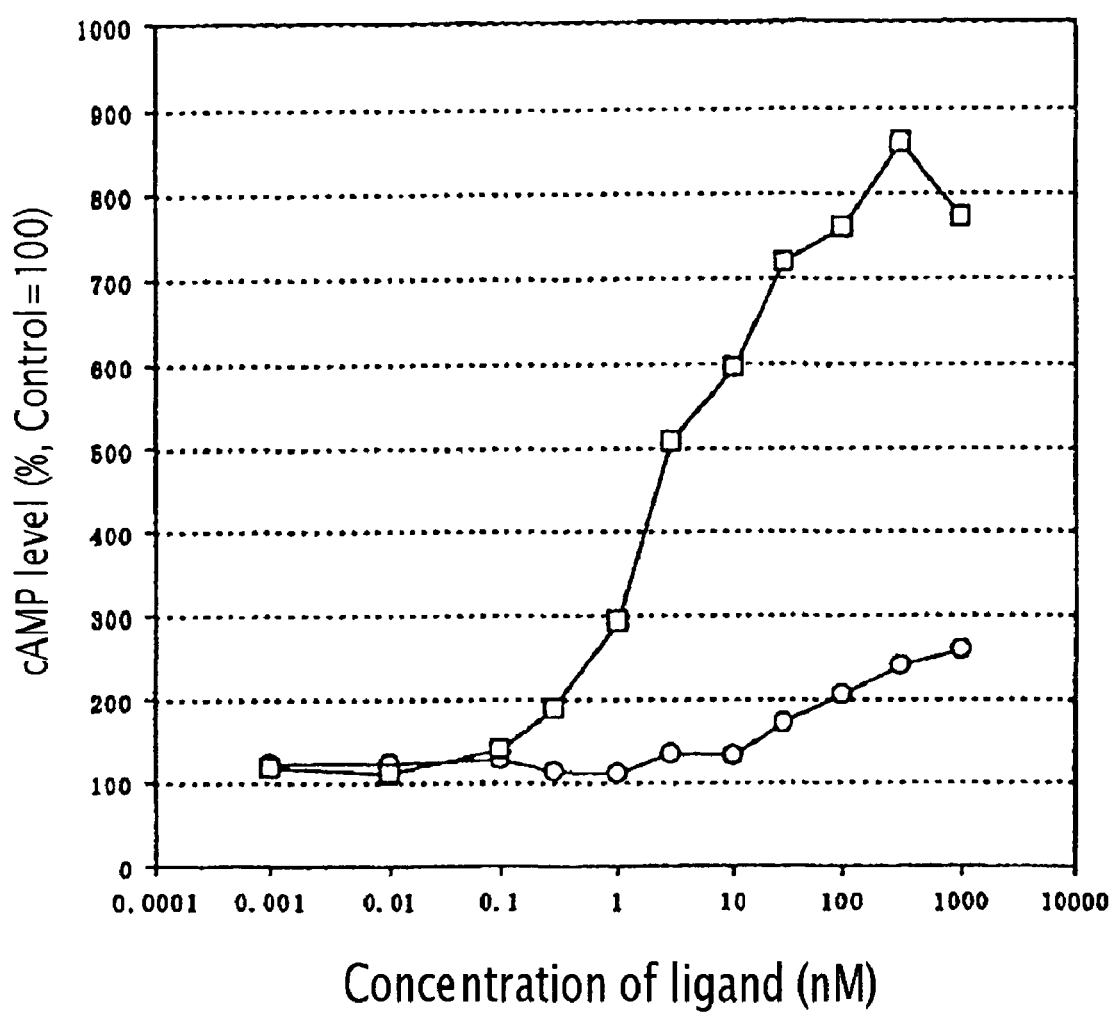
FIG. 13 shows the intracellular cAMP production enhancing activity of various concentration of the human TGR23-2 ligand (1-20) on TGR23-1 expressing CHO cells and TGR23-2 expressing CHO cells, wherein both cells were on the condition of no forskolin. In the figure, open circle and open square represent the intracellular cAMP production enhancing activity in TGR23-1 expressing CHO cells and that in TGR23-2 expressing CHO cells, respectively.

Using the above, the means for cAMP level of two wells are shown in FIG. 13 and FIG. 14. Clearly, under the condition of no forskolin, human TGR23-2 ligand (1-20) and rat TGR23-2 ligand (1-18) enhance the intracellular cAMP production in TGR23-1 expressing CHO cells and TGR23-2 expressing CHO cells depending on the concentration.

Example 23

Assay for Enhancing Activities of Arachidonic Acid Metabolite Release in TGR23-1 Expressing CHO Cells and TGR23-2 Expressing Cells by Human TGR23-2 Ligand (1-20) and Rat TGR23-2 Ligand (1-18)

Figure 16:
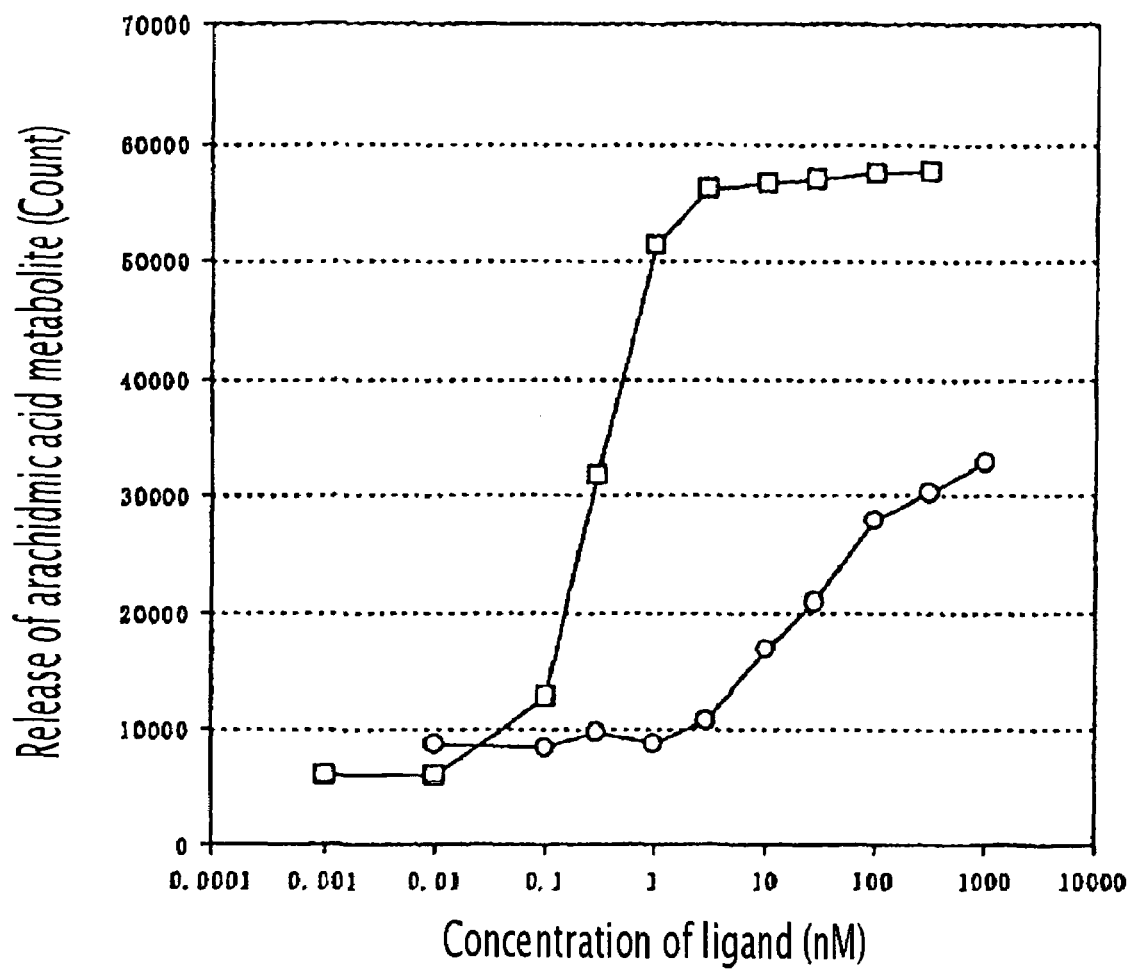
FIG. 16 shows the arachidonic acid metabolite releasing activity of various concentration of the rat TGR23-2 ligand (1-18) on TGR23-1 expressing CHO cells and TGR23-2 expressing CHO cells. In the figure, open circle and open square represent the arachidonic acid metabolite releasing activity in TGR23-1 expressing CHO cells and that in TGR23-2 expressing CHO cells, respectively.

Human TGR23-2 ligand (1-20) prepared by the method described in Example 17 and rat TGR23-2 ligand (1-18) prepared by the method described in Example 19 were administered to TGR23-1 expressing CHO cells and TGR23-2 expressing CHO cells at a variety of concentrations according to the method described in Example 4, and the enhancing activity of arachidonic acid metabolite release was determined. The results are shown in FIG. 15 and FIG. 16.

Clearly, under the condition of no forskolin, human TGR23-2 ligand (1-20) and rat TGR23-2 ligand (1-18) enhance the arachidonic acid metabolite release in TGR23-1 expressing CHO cells and TGR23-2 expressing CHO cells depending on the concentration.

Example 24

Assay for GTPγS Binding Activity in the Membrane Fraction of TGR23-2 Expressing Cells by Human TGR23-2 Ligand (1-20), Rat TGR23-2 Ligand (1-18) and Mouse TGR23-2 Ligand (1-20)

Enhancing activity of binding of [$^{35}$S]-Guanosine 5'-(γ-thio) triphosphate in the membrane fraction of TGR23-2 expressing CHO cells was measured by the following method. Firstly, it is described about preparation of membrane fraction. Twenty (20) ml of homogenation buffer (10 mM HEPES (pH7.3), 5 mM EDTA, 0.52 mM PMSF, 10 μg/ml pepstatin, 8 μg/ml E64, 20 μg/ml leupeptin) was added to 8×10⁷ of TGR23-2 expressing CHO cells, and the cells were disrupted using Polytron (12,000 rpm, 30 seconds×3 times). The cell-disrupted fluids were centrifuged (1,000 g for 15 minutes) to get supernatant. Subsequently the supernatant was ultracentrifuged (Beckman type 30 rotor, 30,000 rpm, one hour), and the precipitate obtained was collected as a membrane fraction of TGR23-2 expressing CHO cells.

The GTPγS binding activity was assayed as follows. The membrane fraction of TGR23-2 expressing CHO cells was diluted with membrane dilution buffer (50 mM Tris-HCl buffer (pH7.4), 5 mM MgCl$_2$, 150 mM NaCl, 0.03% NaN$_3$, 0.1% BSA, 1 μM GDP) to get cell membrane fraction solution for assay at the protein concentration of 30 mg/ml. Two (2) μl of 50 nM [$^{35}$S]-guanosine 5'-(γ-thio) triphosphate (NEN) and sample were added to 200 μl of cell membrane fraction solution for assay, and the mixture was incubated at 25° C. for one (1) hour. The mixture was filtered, and the filter was washed twice with 1.5 ml of washing buffer (50 mM Tris-HCl buffer (pH7.4), 5 mM MgCl$_2$, 1 mM EDTA, 0.03% NaN$_3$, 0.1% BSA). Then the radioactivity on the filter was measured by liquid scintillation counter.

Figure 17:
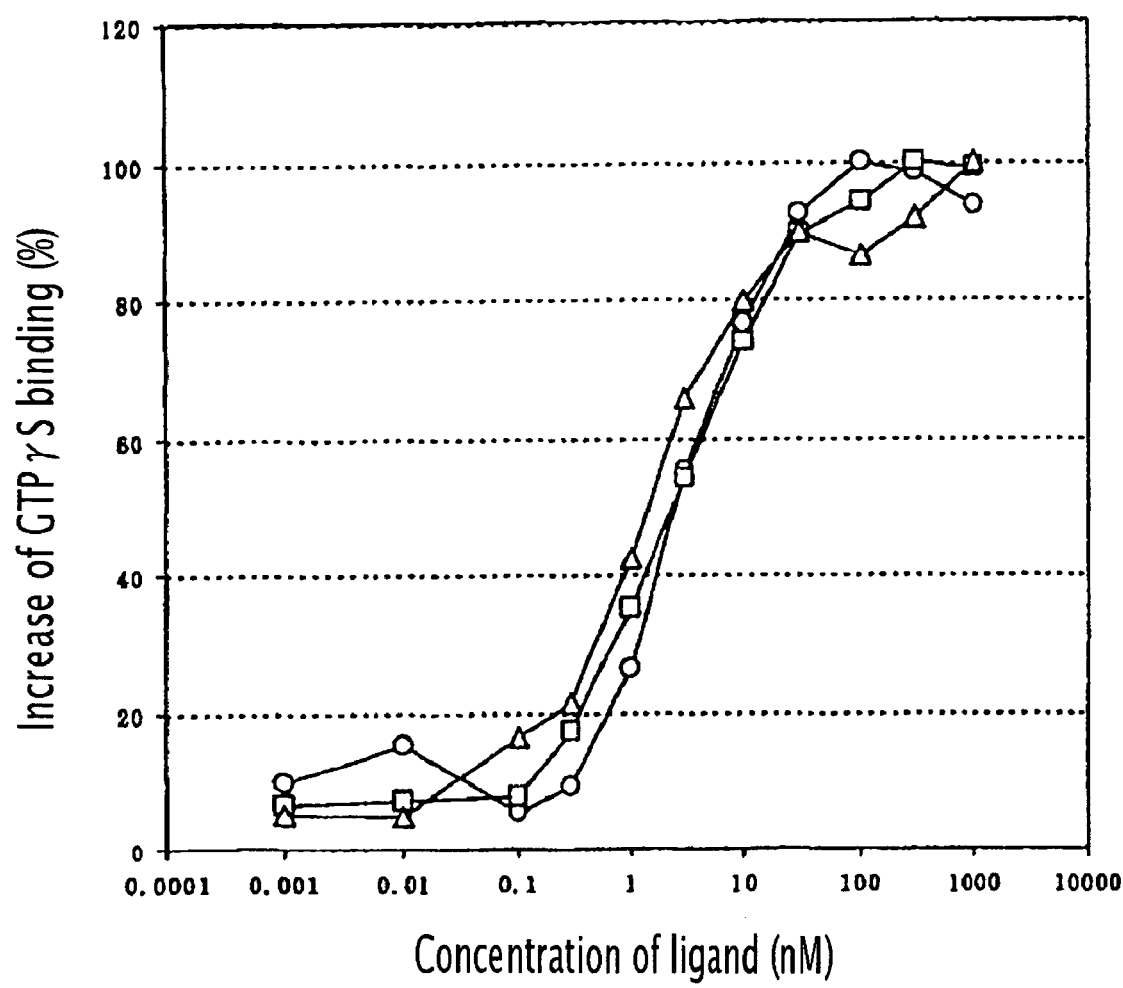
FIG. 17 shows the GTPγS binding enhancing activity of various concentration of the human TGR23-2 ligand (1-20), the rat TGR23-2 ligand (1-18) and the mouse TGR23-2 ligand (1-20) on cell membrane fraction of TGR23-2 expressing CHO cells. In the figure, open circle, open square and open triangle represent the GTPγS binding enhancing activity of the human TGR23-2 ligand (1-20), the rat TGR23-2 ligand (1-18) and the mouse TGR23-2 ligand (1-20), respectively.

Human TGR23-2 ligand (1-20) prepared by the method described in Example 17, rat TGR23-2 ligand (1-18) prepared by the method described in Example 19 and mouse TGR23-2 ligand (1-20) prepared by the method described in Example 20 were administered to TGR23-2 expressing CHO cells at a variety of concentrations according to the method described above, and the GTPγS binding activity was determined. The results are shown in FIG. 17. Clearly, human TGR23-2 ligand (1-20), rat TGR23-2 ligand (1-18) and mouse TGR23-2 ligand (1-20) enhance the GTPγS binding activity in the membrane fraction prepared from TGR23-2 expressing CHO cells depending on the concentration.

Example 25

Preparation of [Nle$^{10}$, Tyr$^{15}$] Human TGR23-2 Ligand (1-20): Ser-Phe-Arg-Asn-Gly-Val-Gly-Thr-Gly-Nle-Lys-Lys-Thr-Ser-Tyr-Gln-Arg-Ala-Lys-Ser (SEQ ID NO: 62)

Commercially available Boc-Ser(Bzl)-OCH$_2$-PAM resin was charged in a reaction tank of peptide synthesizer, ACT90. After swelling with DCM, the resin was treated with TFA to remove Boc and neutralized with DIEA. The resin was suspended in NMP and Boc-Lys(Cl-Z) was condensed to the amino group by the HOBt-DIPCI. After reaction, ninhydrin test was conducted to examine if any free amino group was present. Where the ninhydrin test was positive, the same amino acid was condensed again. Where the ninhydrin test was also positive after re-condensation, peptide was acethylated with acetic anhydrite. By repeating this cycle, Boc-Ala, Boc-Arg(Tos), Boc-Gln, Boc-Tyr(Br-Z), Boc-Ser(Bzl), Boc-Thr(Bzl), Boc-Lys(Cl-Z), Boc-Lys (Cl-Z), Boc-Nle, Boc-Gly, Boc-Thr(Bzl), Boc-Gly, Boc-Val, Boc-Gly, Boc-Asn, Boc-Arg(Tos), Boc-Phe, Boc-Seq(Bzl) were condensed in this order. As a result, 0.14 g of protected peptide resin, which was desired, was obtained. The resin was reacted in about 15 ml of hydrogen fluoride together with 2.0 ml of p-cresol at 0° C. for 60 minutes. After removing the hydrogen fluoride by distillation in vacuum, diethyl ether was added to the residue, and filtrated. Water and acetic acid were added to the filtrate in order to extract the peptide. Finally, it was separated from the resin. The extract was concentrated, and the concentrate obtained was applied to a column of Sephadex (trade mark) G-25 (2.0×80 cm) equilibrated with 50% acetic acid, developed with the same solvent. Main fractions were collected and lyophilized. The part of the peptide (10.3 mg) was applied to a reversed phase column (2.6×60 cm) filled up with LiChroprep (trade name) RP-18 followed by carrying out the washing with 200 ml of 0.1% aqueous TFA and the linear gradient elution using 300 ml of 0.1% aqueous TFA and 300 ml of 25% acetonitrile aqueous solution containing 0.1% TFA. Main fractions were collected and lyophilized to give 3.96 mg of objective peptide.

ESI-MS: M$^+$ 2186.1 (theoretical value 2185.5)
Elution time on HPLC: 10.4 minutes Column Conditions:
Column: Wakosil 5C18HG (4.6×100 mm)
Eluant: linear density gradient elution (25 minutes) with A/B: 95/5 to 55/45, using solution A (0.1% TFA) and solution B (acetonitrile solution containing 0.1% TFA)
Flow rate: 1.0 ml/min.

Example 26

Preparation of [Nle$^{10}$, Tyr$^{15}$] Human TGR23-2 Ligand (1-20) Using Lactoperoxidase Method One nmol of [Nle$^{10}$, Tyr$^{15}$] human TGR23-2 ligand (1-20) (the polypeptide consisting of the amino acid sequence represented by SEQ ID NO: 62) dissolved in 10 µl of DMSO was mixed with 10 µl of 0.001% hydrogen peroxide dissolved in 0.1 M HEPES (pH7), 10 µl of 10 µg/ml lactoperoxidase (Sigma) dissolved in 0.1 M HEPES (pH7), and 10 µl of [$^{125}$I] NaI (37 MBq, Perkin Elmer Life Science). The reaction mixture was incubated at room temperature for 15 minutes, and then [Nle$^{10}$, $^{125}$I-Tyr$^{15}$] human TGR23-2 ligand (1-20) produced was fractionated by HPLC under the following conditions.

As a column, ODS-80TM (4.6 mm×15 cm) (Toso) was used, and as an eluent A and eluent B, 10% acetonitrile/0.1% TFA and 60% acetonitrile/0.1% TFA were used, respectively. Elution was performed by gradient elution of 5-5 (2 minutes), 5-29 (40 minutes) of % B/A+B. Flow rate was 1 mL/min. Column temperature was 40° C. Detection of absorbance at 220 nm was used. Under the condition utilized, [Nle$^{10}$, $^{125}$I-Tyr$^{15}$] human TGR23-2 ligand (1-20) was eluted at around 24 minutes.

Example 27

The Receptor Binding Assay Using [Nle$^{10}$, $^{125}$I-Tyr$^{15}$] Human TGR3-2 Ligand (1-20)

Using using [Nle$^{10}$, $^{125}$I-Tyr$^{15}$] human TGR23-2 ligand (1-20) prepared by the method described in Example 26, and a cell membrane fraction prepared from TGR23-2 expressing CHO cells as described in Example 24 and a cell membrane fraction prepared from TGR23-1 expressing CHO cells by the similar method to that described in Example 24 using TGR23-1 expressing CHO cells instead of TGR23-2 expressing CHO cells, a receptor binding assay was carried out as follows.

Cell membrane fraction prepared from TGR23-1 expressing CHO cells and TGR23-2 expressing CHO cells was diluted to various concentration with assay buffer (20 mM Tris-HCl, 5 mM EDTA, 0.1% BSA, 0.5 mM PMSF, 1 µg/ml Pepstatin, 4 µg/ml E-64, 20 µg/ml Leupeptin, pH7.4), and 200 µl each of the diluent was dispensed into polypropylene test tube (Falcon 2053). In order to determine an amount of maximum binding, 2 µl of DMSO and 2 µl of 10 nM [Nle$^{10}$, $^{125}$I-Tyr$^{15}$] human TGR23-2 ligand (1-20) were added to the membrane fraction solution. Further, in order to determine a non-specific binding, 2 µl of 1 µM [Nle$^{10}$, Tyr$^{15}$] human TGR23-2 ligand (1-20)/DMSO solution was added to the membrane fraction solution. The reaction was done at 25° C. for 90 minutes, and the reaction mixture was filtered by suction filtration using Whatman glassfilter (GF-F) treated with polyethyleneimine. After filtration, a radioactivity remaining on the filter was counted using γ-counter, and an amount of specific binding was estimated by subtracting an amount of non-specific binding from an amount of maximum binding. When the concentration of membrane fraction was changed, a specific binding of [Nle$^{10}$, $^{125}$I-Tyr$^{15}$] human TGR23-2 ligand (1-20) was perceived depending on the concentration of membrane fraction. An inhibition of binding activity of the test specimen to TGR23-1 receptor or TGR23-2 receptor (inhibition rate (%)) was represented by a ratio of the value to the specific binding (SB), wherein the value is calculated by subtracting the radioactivity remaining on the filter (X) in the case of adding the test sample and [Nle$^{10}$, $^{125}$I-Tyr$^{15}$] human TGR3-2 ligand (1-20) from the total binding (TB) ((TB–X)/SB×100 (%)).

For the membrane fraction prepared from the TGR23-2 expressing CHO cells at the concentration of 1 µg/ml, from the inhibition rate, the concentration, at which 50% inhibition was occurred, (IC$_{50}$) of human TGR23-2 ligand (1-20), rat TGR23-2 ligand (1-18) and mouse TGR23-2 ligand (1-20) was calculated. As a result, $IC_{50}$ values are 105 pM (human TGR23-2 ligand (1-20)), 92.8 pM (rat TGR23-2 ligand (1-18) and 24.5 pM (mouse TGR23-2 ligand (1-20)), respectively.

Figure 18:
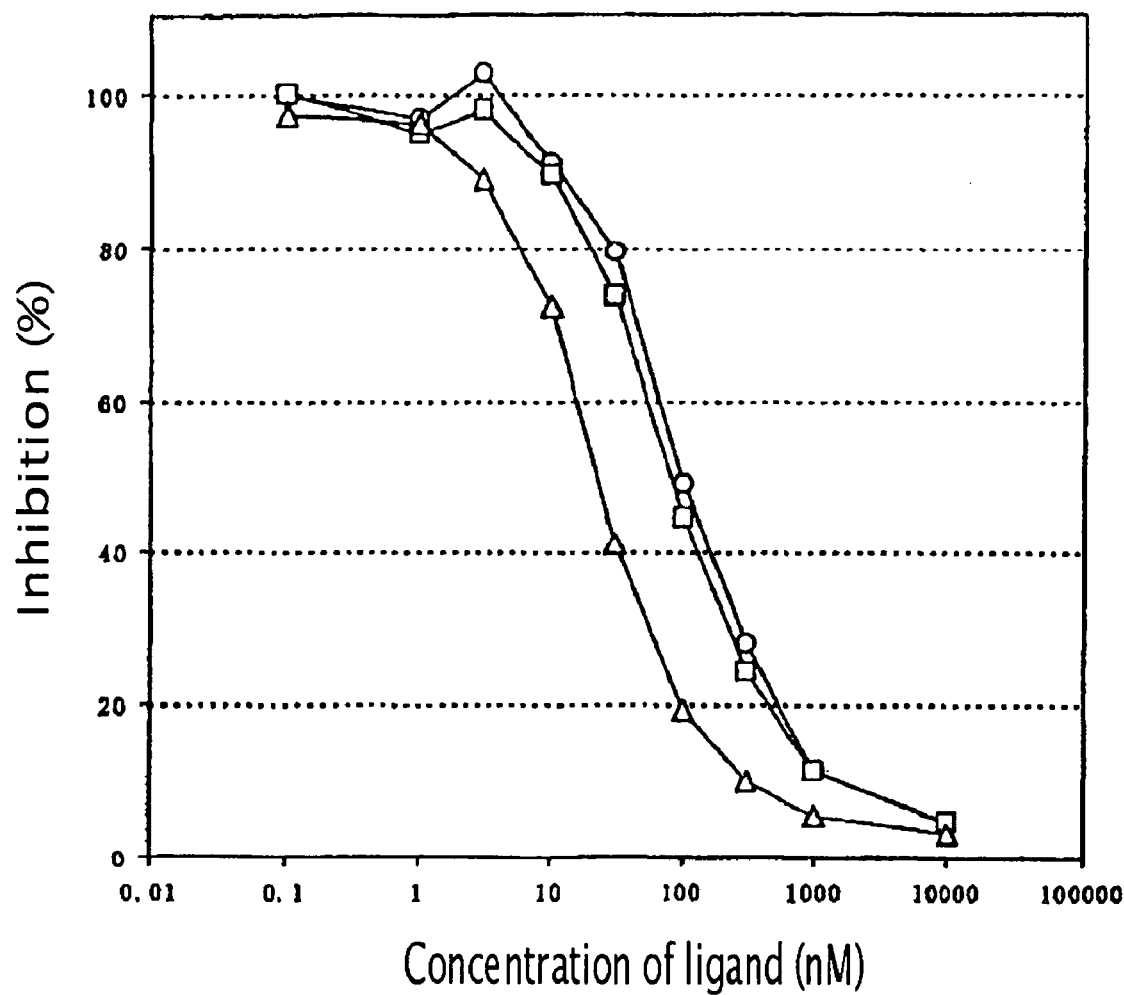
FIG. 18 shows the binding inhibiting activity of human TGR23-2 ligand (1-20), rat TGR23-2 ligand (1-18) and mouse TGR3-2 ligand (1-20) on [$Nle^{10}$, $^{125}I$-$tyr^{15}$] human TGR23-2 ligand (1-20), using the cell membrane fraction prepared from TGR23-2 expressing CHO cells. In the figure, open circle, open square and open triangle represent the binding inhibiting activity of human TGR23-2 ligand (1-20), rat TGR23-2 ligand (1-18) and mouse TGR23-2 ligand (1-20), respectively.

Inhibition of binding activity of human TGR23-2 ligand (1-20), rat TGR23-2 ligand (1-18) and mouse TGR23-2 ligand (1-20) at a variety of concentrations is shown in FIG. 18.

Example 28

Cloning of TGR23 Gene Derived from Human Colon Carcinoma Cells COLO 205

The COLO 205 cells acquired from ATCC were cultured in 75 cm² of flask. From the cells grew, using ISOGEN (Nippon Gene), total RNA fraction was prepared. Using 0.5 µg of total RNA from COLO 205 cells as a template, ReverTra Ace-α-(TOYOBO), and random primers, a reverse transcription reaction was carried out and cDNA was prepared. Using cDNA from COLO 205 cells prepared as a template and two primers, i.e., primer 1 (SEQ ID NO: 5) and primer 2 (SEQ ID NO: 6), PCR reaction was carried out. The reaction solution for PCR was composed of 50 µl consisting of the above cDNA used as a template corresponding to 12.5 ng of mRNA, 0.2 µM each of primers, 0.2 mM dNTPs, 0.5 M GC-Melt, 1/50 volume of Advantage-GC 2 Polymerase Mix (CLONTECH) and 1/5 volume of the 5× buffer. PCR was carried out, after reacting at 96° C. for 2 minutes, by repeating 35 times the cycle set to include 96° C. for 30 seconds, 54° C. for 30 seconds and 72° C. for one minute, and finally extension was performed at 72° C. for 10 minutes. Using the reaction mixture obtained, the PCR product was subcloned to plasmid vector pCR2.1-TOPO with the TOPO TA Cloning Kit (Invitrogen), and the vector was introduced into *Escherichia coli* DH5α-T1. From the transformant appeared, with QIAwell 8 Ultra Plasmid Kit (QIAGEN), plasmid DNA was purified. The reaction for determination of the base sequence was carried out using BigDye Terminator Cycle Sequencing Ready Reaction Kit (Perkin Elmer). Then the sequence was decoded with the fluorescent automated sequencer.

As a result, the base sequences represented by SEQ ID NO: 64 and SEQ ID NO: 66 were obtained.

In the base sequences represented by SEQ ID NO: 64 and SEQ ID NO: 66, translation frame from the initiation codon, ATG to the termination codon, TGA was present. The amino acid sequences of protein translated from this frame are shown in SEQ ID NO: 63 and SEQ ID NO: 65, respectively. Novel G protein-coupled receptor proteins containing the amino acid sequence represented by SEQ ID NO: 63 and SEQ ID NO: 65 were designated TGR23-1A and TGR23-1B, respectively.

In the base sequence represented by SEQ ID NO: 64, C at the 723rd position of the base sequence represented by SEQ ID NO: 2 (TGR23-1) is substituted to G.

In the base sequence represented by SEQ ID NO: 66, A at the 320th position of the base sequence represented by SEQ ID NO: 2 (TGR23-1) is substituted to T, and also C at the 723rd position to G.

In the amino acid sequence represented by SEQ ID NO: 63, Ser at the 241st position of the amino acid sequence represented by SEQ ID NO: 1 (TGR23-1) is substituted to Arg.

In the amino acid sequence represented by SEQ ID NO: 65, Asn at the 107th position of the amino acid sequence represented by SEQ ID NO: 1 (TGR23-1) is substituted to Ile, and also Ser at the 241st position to Arg.

Example 29

Cloning of the cDNA Encoding the Mouse Brain-derived G Protein-coupled Receptor Protein and Determination of the Base Sequence Using mouse Marathon Ready cDNA (CLONTECH) as a template and two primers, namely, primer 1 (SEQ ID NO: 81) and primer 2 (SEQ ID NO: 82), PCR was carried out. The reaction solution in the above reaction comprised of 2.5 µl of the above cDNA as a template, 1 µl of Advantage 2 Polymerase Mix (CLONTECH), 0.2 µM each of primer 1 (SEQ ID NO: 81) and primer 2 (SEQ ID NO: 82), 800 µM of dNTPs to make the total volume 50 µl. The PCR reaction was carried out by reaction of 95° C. for one minute, then a cycle set to include 95° C. for 30 seconds followed by 72° C. for 4 minutes, which was repeated 3 times, a cycle set to include 95° C. for 30 seconds followed by 70° C. for 4 minutes, which was repeated 3 times, a cycle set to include 95° C. for 30 seconds followed by 68° C. for 4 minutes, which was repeated 30 times, and finally, extension reaction at 68° C. for 4 minutes. Subsequently, agarose gel electrophoresis was done, and the PCR product was purified using GENECLEAN SPIN Kit (BIO101). This purified product was subcloned to plasmid vector pCR2.1-TOPO (Invitrogen) according to the instructions attached with the TOPO TA Cloning Kit (Invitrogen). This plasmid was introduced into *Escherichia coli* DH5α, and the clones harboring the cDNA were selected on LB agar medium containing ampicillin. A sequence of each clone was analyzed, and cDNA sequence encoding a G protein-coupled receptor protein (SEQ ID NO: 76) was obtained (SEQ ID NO: 15 described in WO 02/31145). The G protein-coupled receptor protein containing the amino acid sequence (SEQ ID NO: 75), which is encoded by the DNA sequence, was designated mouse TGR23-B (SEQ ID NO: 14 described in WO 02/31145).

When the mouse TGR23-B is compared with the mouse TGR23-A described in Reference Example 3, 54 bases are inserted behind G at the 280th position of the mouse TGR23-A, thus 18 amino acid residues are inserted.

Further, cDNa sequence (SEQ ID NO: 84) encoding a variant receptor of the mouse TGR23-B was obtained simultaneously. In this sequence, three bases, i.e., CAG is inserted just behind G at the 478th position of the DNA sequence of mouse TGR23-B, thus Ala is inserted just prior to Glu at the 160th position of amino acid sequence. A novel G protein-coupled receptor protein encoded by this sequence (SEQ ID NO: 84), wherein Ala is inserted just prior to Glu at the 160th position, was designated mouse TGR23-C.

A plasmid harboring a DNA fragment having the base sequence represented by SEQ ID NO: 76 was designated pCR2.1-mTGR23-B, and a transformant, in which the plasmid pCR2.1-mTGR23-B is introduced, was designated *Escherichia coli* DH5α/pCR2.1-mTGR23-B.

Example 30

Cloning of the cDNA Encoding the Rat Brain-derived G Protein-coupled Receptor Protein and Determination of the Base Sequence Using rat Marathon Ready cDNA (CLONTECH) as a template and two primers, namely, primer 1 (SEQ ID NO: 79) and primer 2 (SEQ ID NO: 80), PCR was carried out.

The reaction solution in the above reaction comprised of 2.5 µl of the above cDNA as a template, 1 µl of Advantage 2 Polymerase Mix (CLONTECH), 0.2 µM each of primer 1 (SEQ ID NO: 79) and primer 2 (SEQ ID NO: 80), 800 µM of dNTPs and 2 µl of DMSO to make the total volume 50 µl. The PCR reaction was carried out by reaction of 95° C. for one minute, then a cycle set to include 95° C. for 30 seconds followed by 72° C. for 4 minutes, which was repeated 5 times, a cycle set to include 95° C. for 30 seconds followed by 70° C. for 4 minutes, which was repeated 5 times, a cycle set to include 95° C. for 30 seconds followed by 68° C. for 4 minutes, which was repeated 30 times, and finally, extension reaction at 68° C. for 3 minutes. Subsequently, agarose gel electrophoresis was done, and the PCR product was purified using GENECLEAN SPIN Kit (BIO101). This purified product was subcloned to plasmid vector pCR2.1-TOPO (Invitrogen) according to the instructions attached with the TOPO TA Cloning Kit (Invitrogen). This plasmid was introduced into Escherichia coli DH5α, and the clones harboring the cDNA were selected on LB agar medium containing ampicillin. A sequence of each clone was analyzed, and cDNA sequence encoding five rat TGR23 variant receptors, which are other than cDNA sequence (SEQ ID NO: 78) encoding the rat TGR23-1 (SEQ ID NO: 77) described in Reference Example 4, was obtained. Where comparing with rat TGR23-1, they included the sequence wherein A at the 1031st position of the base sequence is substitute to G (SEQ ID NO: 86), the sequence wherein T at the 772nd position of the base sequence is substitute to C (SEQ ID NO: 88), the sequence wherein T at the 653th position of the base sequence is substitute to C (SEQ ID NO: 90), the sequence wherein three bases, i.e., CAG is inserted just behind G at the 478th position of the base sequence (SEQ ID NO: 92), and the sequence wherein three bases, i.e., CAG is inserted just behind G at the 478th position of the base sequence and A at the 1031st position of the base sequence is substitute to G (SEQ ID NO: 94).

Novel G protein-coupled receptor proteins containing the amino acid sequences encoded by these DNA sequences were designated rat TGR23-2 (SEQ ID NO: 85), rat TGR23-3 (SEQ ID NO: 87), rat TGR23-4 (SEQ ID NO: 89), rat TGR23-5 (SEQ ID NO: 91) and rat TGR23-6 (SEQ ID NO: 93), respectively.

Where the amino acid sequence of each variant is compared with that of the rat TGR23-1, Gln at the 344th position of the amino acid sequence of the rat TGR23-2 is substituted with Arg. In the rat TGR23-3, Cys at the 258th position of the amino acid sequence is substituted with Arg. In the rat TGR23-4, Val at the 218th position of the amino acid sequence is substituted with Ala. In the rat TGR23-5, Ala is inserted just before Glu at the 160th position of the amino acid sequence. In the rat TGR23-6, Ala is inserted just before Glu at the 160th position of the amino acid sequence and further Gin at the 344th position of the amino acid sequence of the rat TGR23-2 is substituted with Arg.

Plasmids harboring the DNA fragments having the base sequences represented by SEQ ID NO: 86, SEQ ID NO: 88, SEQ ID NO: 90 and SEQ ID NO: 92, respectively, were designated pCR2.1-rTGR23-2, pCR2.1-rTGR23-3, pCR2.1-rTGR23-4, pCR2.1-rTGR23-5 and pCR2.1-rTGR23-6, respectively. Escherichia coli transformants, in which the plasmids are introduced, were designated Escherichia coli DH5α/pCR2.1-rTGR23-2, Escherichia coli DH5α/pCR2.1-rTGR23-3, Escherichia coli DH5α/pCR2.1-rTGR23-4, Escherichia coli DH5α/pCR2.1-rTGR23-5 and Escherichia coli DH5α/pCR2.1-rTGR23-6, respectively.

Example 31

Quantification of Expression Level of Human TGR23 Gene in Human Colon Cancer Cell Lines and Human Stomach Cancer Cell Lines Using TaqMan PCR Method Human colon cancer cell lines DLD-1, HCT 116, COLO 320DM, COLO 201, COLO 205, LoVo, SW 403, SW 48, SW 948, Caco-2, HT-29, SK-CO-1, T84 and SNU-C1 were acquired from American Type Culture Collection. Human colon cancer cell lines COLO 320HSR, HCT-15, LS 174T, LS 180, SW 480, SW 1116, SW1417, WiDr and human stomach cancer cell lines AGS and KATOIII were acquired from Dainippon Pharmaceutical, Co. Ltd. Each cell was cultured in 75 cm$^2$ flask, and total RNA fraction was prepared from the grown cells using ISOGEN (Nippon Gene). Using 0.5 µg of total RNA of each cell as a template, ReverTra Ace-α-(TOYOBO) and random primers, in accordance with the manual attached, cDNA was prepared by reverse transcription. Using 25 µl of the reaction mixture containing the obtained reverse transcript corresponding to 25 ng of total RNA or standard cDNA prepared as described later, 1× Universal PCR Master Mix (PE Biosystems), 500 nM each of the primer represented by SEQ ID NO: 9 and the primer represented by SEQ ID NO: 10, and 100 nM TaqMan probe represented by SEQ ID NO: 11 (Fam-acctggttg ccgagtggtc cgctat-Tanra; in the sequence, Fam and Tamra indicate 6-carboxy-fluorescein and 6-carboxy-tetramethyl-rhodamine, respectively), with ABI PRISM 7700 Sequence Detector (PE Biosystems), PCR was carried out. PCR was performed by reaction at 50° C. for 2 minutes and at 95° C. for 10 minutes, then a cycle set to include 95° C. for 15 seconds followed by 60° C. for 60 seconds, which was repeated 40 times.

After concentration of the plasmid pTB2174 obtained in Reference Example 1 was calculated by measuring absorbance at 260 nm and accurate copy numbers were calculated, 1 to 1×10$^6$ copies of standard cDNA solution were prepared by diluting with 10 mM Tris-HCl (pH8.0) containing 1 mM EDTA. Further, probe and primers for TaqMan PCR were designed by the Primer Express Version 1.0 (PE Biosystems).

The expression level was calculated by the ABI PRISM 7700 SDS Software. Using cycle numbers at the moment when fluorescent intensity of reporter comes to preset values indicated as a vertical axis, and logarithm of an initial concentration of the standard cDNA as a horizontal axis, standard curve was prepared. From this standard curve, the expression level of human TGR23 gene per 25 ng of total RNA of each clone was determined by calculating an initial concentration of each reverse transcript. In addition, by calculating expression level of GAPDH for each sample with GAPDH Control Reagents (PE Biosystems) by the TaqMan PCR method, the expression level of human TGR23 gene was corrected.

As a result, the expression level of human TGR23 against GAPDH was 0.000022% for DLD-1, 0.0013% for HCT 116, 0.0017% for COLO 320DM, 1.0% for COLO 201, 3.7% for COLO 205, 0.031% for LoVo, 0.95% for SW 403, 0.00031% for SW 48, 0.0001% for SW 948, 0.0001% for Caco-2, 0.034% for HT-29, 0.51% for SK-CO-1, 0.0027% for T84, 0.26% for SNU-C1, 0.0001% for COLO 320HSR, 0.0001% for HCT-15, 1.0% for LS 174T, 0.85% for LS 180, 0.0001% for SW 480, 0.0018% for SW 1116, 0.0055% for SW 1417, 0.00082% for WiDr, 0.0002% for AGS and 1.2% for KATOIII.

From these results, it was found that in particular, the expression of human TGR23 was accentuated in the colon cancer cell lines COLO 201, COLO 205, LoVo, SW 403, HT-29, SK-CO-1, LS 174T, LS 180 and the stomach cancer cell line KATOIII.

Figure 20:
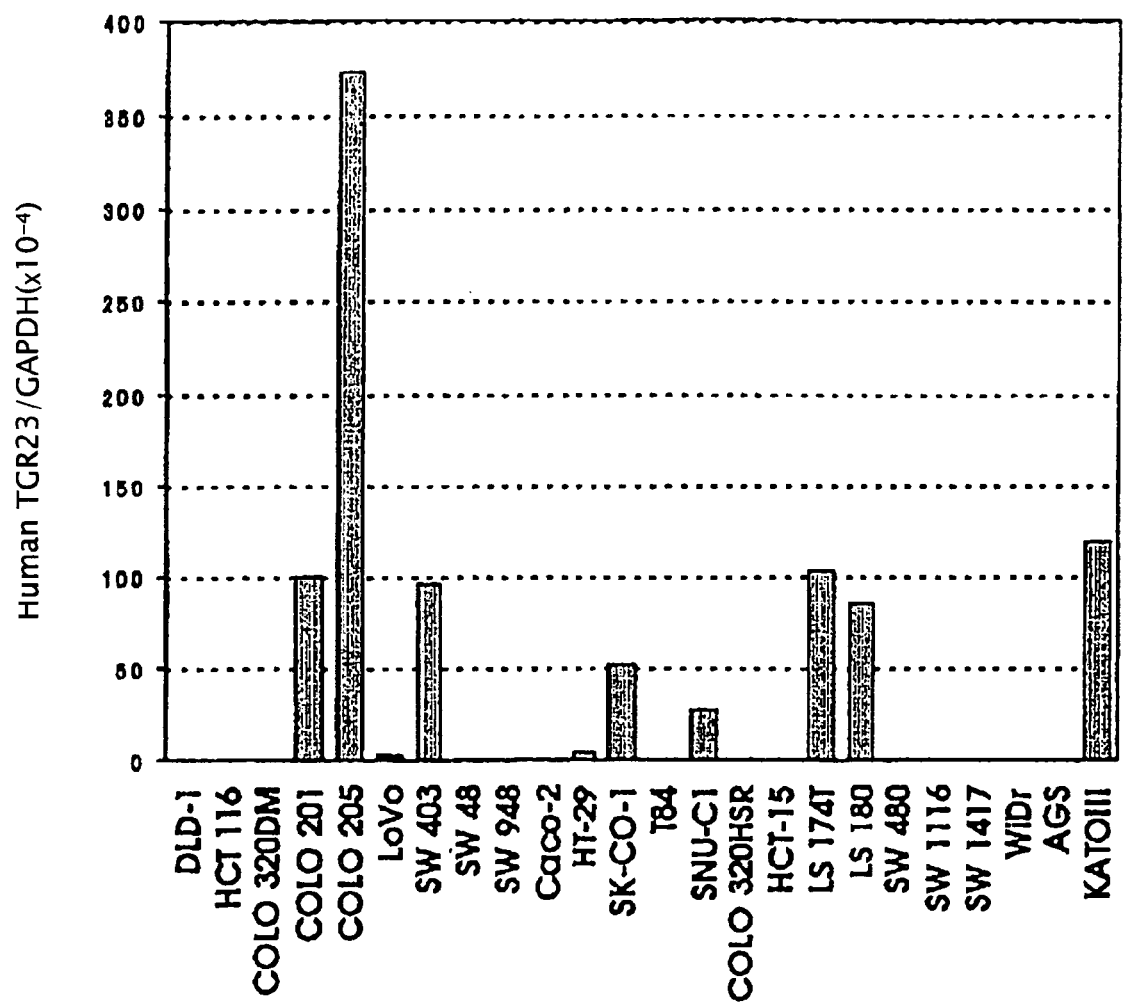
FIG. 20 shows a graph of the expression level of human TGR23 in cancer cells.

A graph for the expression level of human TGR23 in Cancer cell lines is shown in FIG. 20.

In addition, it was perceived that human colon cancer cell line COLO 205 exhibits high expression by measuring the expression level of TGR23 in Reference Example 2. The expression level for β-actin was 2.1%.

Example 32

Clonong of Human TGR23 Gene Derived from Human Colon Cancer Cells LS 174T, LS 180, SW 403, and Human Stomach Cancer Cell KATOIII The LS 174T cells acquired from Dainippon Pharmaceutical, Co. Ltd., were cultured in the 75 cm² flask, and from the grown cells, using ISOGEN (Nippon Gene), total RNA fraction was prepared. Using 0.5 µg of total RNA of LS 174T cells as a template, ReverTra Ace-α-(TOYOBO) and random primers, in accordance with the manual attached, cDNA was prepared by reverse transcription. Using the obtained cDNA from LS 174T cells as a template, primer 1 (SEQ ID NO: 5) and primer 2 (SEQ ID NO: 6), PCR reaction was carried out. Using 50 µl of the reaction mixture, it consisted of the cDNA solution corresponding to 12.5 ng of total RNA prepared, 0.2 µM each of primers, 0.2 mM dNTPs, 0.5 M GC-Melt, 1/50 volume of Advantage-GC 2 Polymerase Mix (CLONTECH), and 1/5 volume of 5× Buffer. PCR was performed by reaction at 96° C. for 2 minutes, then a cycle set to include 96° C. for 30 seconds followed by 54° C. for 30 seconds and 72° C. for one minute, which was repeated 35 times, and finally incubation at 72° C. for 10 minutes. Subsequently, the obtained PCR reaction solution was electrophoresed, and the objective band was purified using Gel Extraction Kit (QIAGEN). The obtained reaction solution was subcloned to plasmid vector pCR2.1-TOPO (Invitrogen) using the TOPO TA Cloning Kit (Invitrogen). This plasmid was introduced into *Escherichia coli* DH5α-T1. From the transformant appeared, using QIAwell 8 Ultra Plasmid Kit (QIAGEN), plasmid DNA was prepared. The reaction for determination of sequence was carried out using BigDye Terminator Cycle Sequence Ready Reaction Kit (Perkin Elmer), and the sequence was decoded using fluorescence autosequencer.

As a result, the base sequences represented by SEQ ID NO: 2 and SEQ ID NO: 96 were obtained, respectively. In the base sequence represented by SEQ ID NO: 96, a translation frame from the initiation codon, ATG to the termination codon, TGA was present. The amino acid sequence of the protein, which is translated from the translation frame, is represented by SEQ ID NO: 95.

In the base sequence represented by SEQ ID NO: 96, A at the 320th position of the base sequence represented by SEQ ID NO: 2 (TGR23-1) is substituted with T.

In the amino acid sequence represented by SEQ ID NO: 95, Asn at the 107th position of the amino acid sequence represented by SEQ ID NO: 1 (TGR23-1) is substituted with Ile.

A novel G protein-coupled receptor protein containing the amino acid sequence represented by SEQ ID NO: 95, was designated human TGR23-1C.

Concerning the SW 403 cells acquired from American Type Culture Collection, cloning of human TGR23 gene was also performed. As a result of decoding the sequence, the base sequence represented by SEQ ID NO: 2 was obtained.

Concerning the LS 180 cells and KATOIII cells acquired from Dainippon Pharmaceutical, cloning of human TGR23 gene was also performed. As a result of decoding the sequence, the base sequence represented by SEQ ID NO: 98 was obtained from LS 180 cells, as well as the base sequence represented by SEQ ID NO: 99 was obtained from KATOIII cells. In addition, the PCR reaction consisted of the prepared cDNA solution corresponding to 12.5 ng of mRNA as a template, 0.2 µM each of primers, 0.2 mM dNTPs, 2 mM MgCl₂, 1.25 units of Ex Taq Polymerase (TOYOBO) and 1/10 volume of 10× Buffer.

In the base sequence represented by SEQ ID NO: 98, a translation frame from the initiation codon, ATG to the termination codon, TGA was present. The amino acid sequence of the protein, which is translated from the translation frame, is represented by SEQ ID NO: 97.

In the base sequence represented by SEQ ID NO: 99, a translation frame from the initiation codon, ATG to the termination codon, TGA was present. The amino acid sequence of the protein, which is translated from the translation frame, is represented by SEQ ID NO: 95.

In the base sequence represented by SEQ ID NO: 98, A at the 1031st position of the base sequence represented by SEQ ID NO: 2 (TGR23-1) is substituted with G, as well as T at the 1071st position with C.

In the base sequence represented by SEQ ID NO: 99, A at the 320th position of the base sequence represented by SEQ ID NO: 2 (TGR23-1) is substituted with T, as well as C at the 648th position with T.

In the amino acid sequence represented by SEQ ID NO: 97, Gln at the 344th position of the amino acid sequence represented by SEQ ID NO: 1 is substituted with Arg.

A novel G protein-coupled receptor protein containing the amino acid sequence represented by SEQ ID NO: 97 was designated human TGR23-1D.

Example 33

Cloning of TGR23 Gene Derived from Human Hypothalamus

Using human hypothalamus-derived Marathon-Ready cDNA (CLONTECH) as a template, primer 1 (SEQ ID NO: 5) and primer 2 (SEQ ID NO: 6), PCR reaction was carried out. Using 50 µl of the reaction mixture, it consisted of 1/10 volume of the cDNA solution, 0.2 µM each of primers, 0.2 mM dNTPs, 2 mM MgCl₂, 1.25 units of Ex Taq Polymerase (TOYOBO), and 1/10 volume of 10× Buffer. The reaction was performed by incubating at 96° C. for 2 minutes, then a cycle set to include 96° C. for 30 seconds followed by 54° C. for 30 seconds and 72° C. for one minute, which was repeated 35 times, and finally incubation at 72° C. for 10 minutes. Subsequently, the obtained PCR reaction solution was electrophoresed, and the objective band was purified using Gel Extraction Kit (QIAGEN). The obtained reaction solution was subcloned to plasmid vector pCR2.1-TOPO (Invitrogen) using the TOPO TA Cloning Kit (Invitrogen). This plasmid was introduced into *Escherichia coli* DH5α-T1. From the transformant appeared, using QIAwell 8 Ultra Plasmid Kit (QIAGEN), plasmid DNA was prepared. The reaction for determination of sequence was carried out using BigDye Terminator Cycle Sequence Ready Reaction Kit (Perkin Elmer), and the sequence was decoded using fluorescence autosequencer.

As a result, the five base sequences represented by SEQ ID NO: 2, SEQ ID NO: 4, SEQ ID NO: 98, SEQ ID NO: 100 and SEQ ID NO: 101 were obtained, respectively.

In the base sequence represented by SEQ ID NO: 100, A at the 320th position of the base sequence represented by SEQ ID NO: 2 (TGR23-1) is substituted with T, as well as C at the 396th with G.

In the base sequence represented by SEQ ID NO: 101, A at the 320th position of the base sequence represented by SEQ ID NO: 2 (TGR23-1) is substituted with T, as well as A at the 1031st with G and T at the 1071st with C.

In the base sequences represented by SEQ ID NO: 2, SEQ ID NO: 4, SEQ ID NO: 98, SEQ ID NO: 100 and SEQ ID NO: 101, a translation frame from the initiation codon, ATG to the termination codon, TGA was present, respectively. The proteins, which are translated from the translation frames, are human TGR23-1 (SEQ ID NO: 1), human TGR23-2 (SEQ ID NO: 3), human TGR23-1D (SEQ ID NO: 97), human TGR23-1C (SEQ ID NO: 95) and human TGR23-2 (SEQ ID NO: 3), respectively.

Example 34

Effects on the feeding level by administration of the human TGR23-2 ligand (1-20) into rat lateral ventricle were studied.

Rats were bred for lightning hours from eight to twenty o'clock at 25° C. Male Wistar rats at eight weeks old (260 through 280 g of weight at the time of operation) were anesthetized with 50 mg/kg of pentobarbital, i.p., and each rat was immobilized in a rat brain stereotaxic apparatus. The incisor bar was set 3.3 mm lower from the interaural line. The skull was exposed, and using a dental drill a hole was made on the bone for implantation of a guide cannula AG-8 (0.4 mm inner diameter, 0.5 mm outer diameter, EICOM Co., Ltd.). In addition, three anchor screws were buried around the hole. A stainless-steel guide cannula, AG-8 was inserted in such a manner that its tip would be situated in the upper part of the lateral ventricle. Following the atlas of Paxinos and Watson (1986), the stereotaxic coordinates were set to AP: −0.8 mm, L: 1.5 mm, and H: −4.5 mm from the bregma. The guide cannula was secured to the skull using an instant adhesive, dental cement and anchor screws. A stainless-steel dummy cannula, AD-8 (0.35 mm outer diameter, EICOM Co., Ltd.), was then passed through the guide cannula and locked in position with a cap nut (EICOM Co., Ltd.). After the operation the rats were housed in individual cages and naturalized to powder feed for one week.

For about one week after embedding of guide cannula, rats were bred to be postoperatively recuperative and be naturalized to powder feed. The cap nut and dummy cannula were removed from the rat skull and instead, a stainless steel microinjection cannula AMI-9 (0.17 mm inner diameter, 0.35 mm outer diameter, EICOM Co., Ltd.) connected to a PTFE (polytetrafluoroethylene) tube (50 cm long, 0.1 mm inner diameter, 0.35 mm outer diameter, EICOM Co., Ltd.) was inserted. The length of the microinjection cannula was adjusted beforehand so that its tip would be exposed from the guide cannula by 1 mm. One end of the PTFE tube was connected to a microsyringe pump and Otsuka distilled water and the distilled water, in which the human TGR23-2 ligand (1-20) was dissolved, were injected, in a total volume of 10 µl (10 nmol/rat), into the lateral ventricle at a flow rate of 5 µl/min. After two minutes standby time following the infusion, the microinjection cannula was disconnected and the dummy cannula was locked in position again with a cap nut. The infusion was carried out between 19 o'clock and 20 o'clock. Feeding level after infusion was measured with time using Feed-Scale (Columbus) every 30 minutes until four hours after administration.

Figure 21:
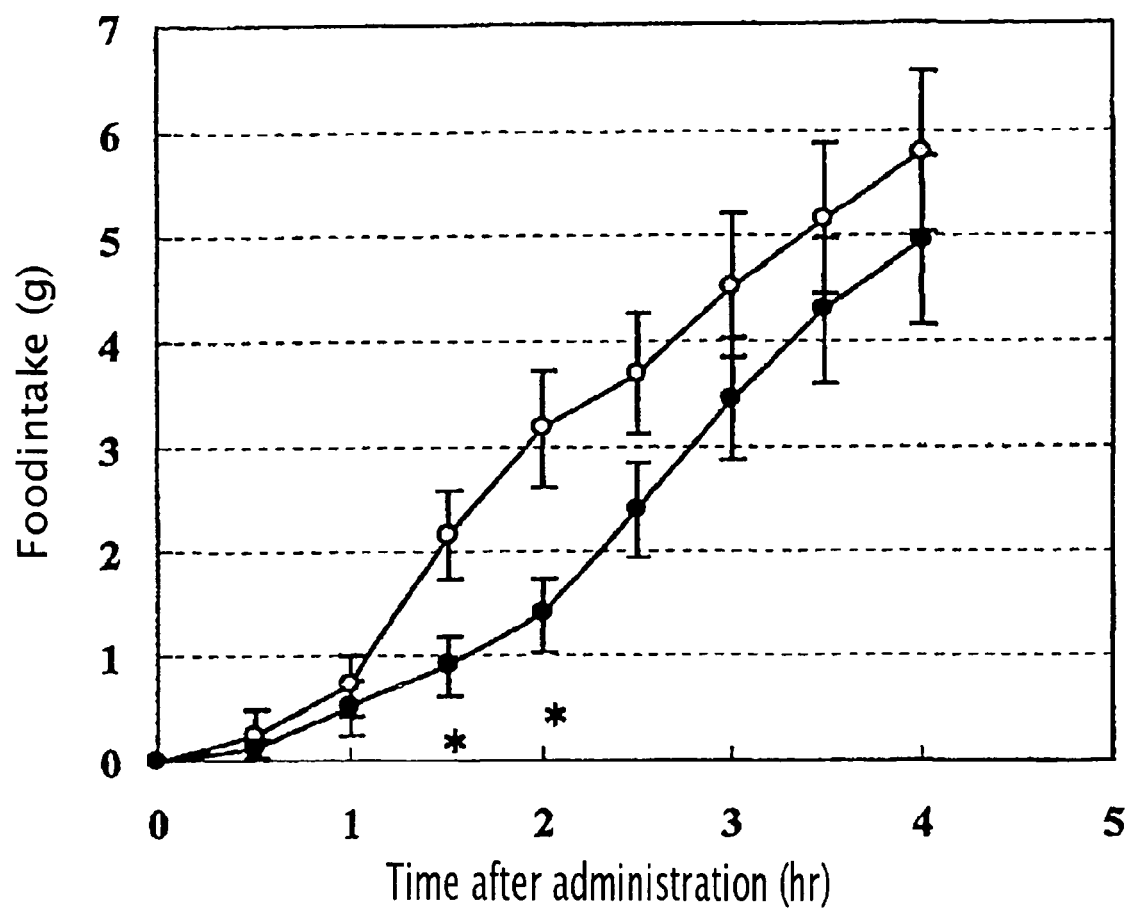
FIG. 21 shows sequential changes of feeding for every 30 minutes up to four hours after administration of the human TGR23 ligand (1-20) or distilled water to lateral ventricle. In the figure, closed circle and open circle represent the group wherein the human TGR23-2 ligand (1-20) was administered, and the group wherein distilled water was administered, respectively. * indicates a significant difference ($p<0.05$) against the group wherein distilled water was administered.

The result was shown in FIG. 21. From the result, it is perceived that a group with the human TGR23-2 ligand (1-20) exhibits a significant decrease of feeding level ($p<0.05$) at 1.5 hours and two hours after administration, compared to the control group.

Example 35

Effects on the growth of carcinomas by the human TGR23-2 ligand (1-20) in nude mice of human colon cancer cell line LS 174T were investigated.

The LS 174T dissolved in PBS (phosphate buffered saline) was subcutaneously administered at the ratio of $4 \times 10^6$ cells/200 µl/mouse to left abdominal of female nude mice (BALB/cAnN-nu, six weeks old). After three hours of administration, 100 µl of the human TGR23-2 ligand (1-20) dissolved in Otsuka distilled water at the concentration of 2 mM, or Otsuka distilled water was filled in the Micro-Osmotic Pump (alza, model 1002), and further embedded under the skin in the back of mouse under anesthesia (n=10 per each group). From this day, the human TGR23-2 ligand (1-20) was continuously released for 14 days at 48 nmol/day. From the third day of administration, dimensions of the carcinoma were measured, and carcinoma volume was calculated based on the formula: (major axis)×(minor axis)$^2$/2.

Figure 22:
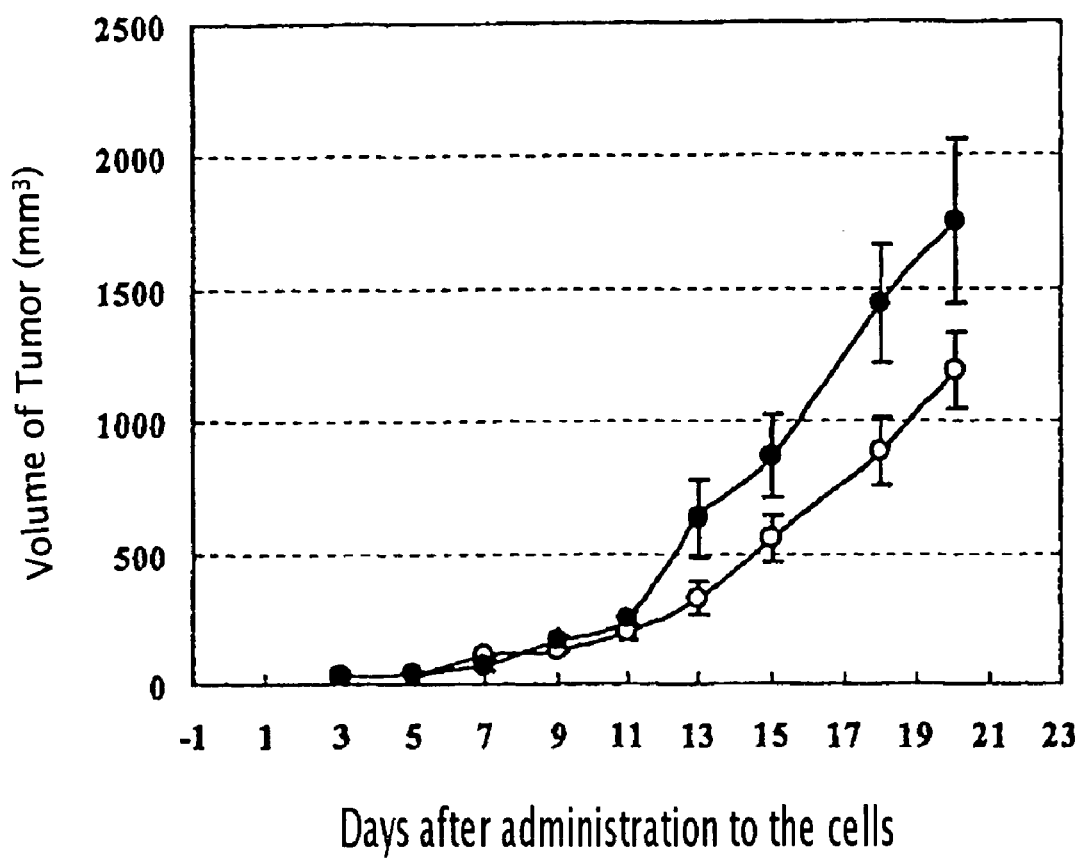
FIG. 22 shows sequential changes of carcinoma size of LS174T in nude mice when the human TGR23 ligand (1-20) or distilled water was continuously administered using MICRO-OSMOTIC PUMP. In the figure, closed circle and open circle represent the group wherein the human TGR23-2 ligand (1-20) was administered, and the group wherein distilled water was administered, respectively. The values indicate means±standard error (n=10).
Figure 23:
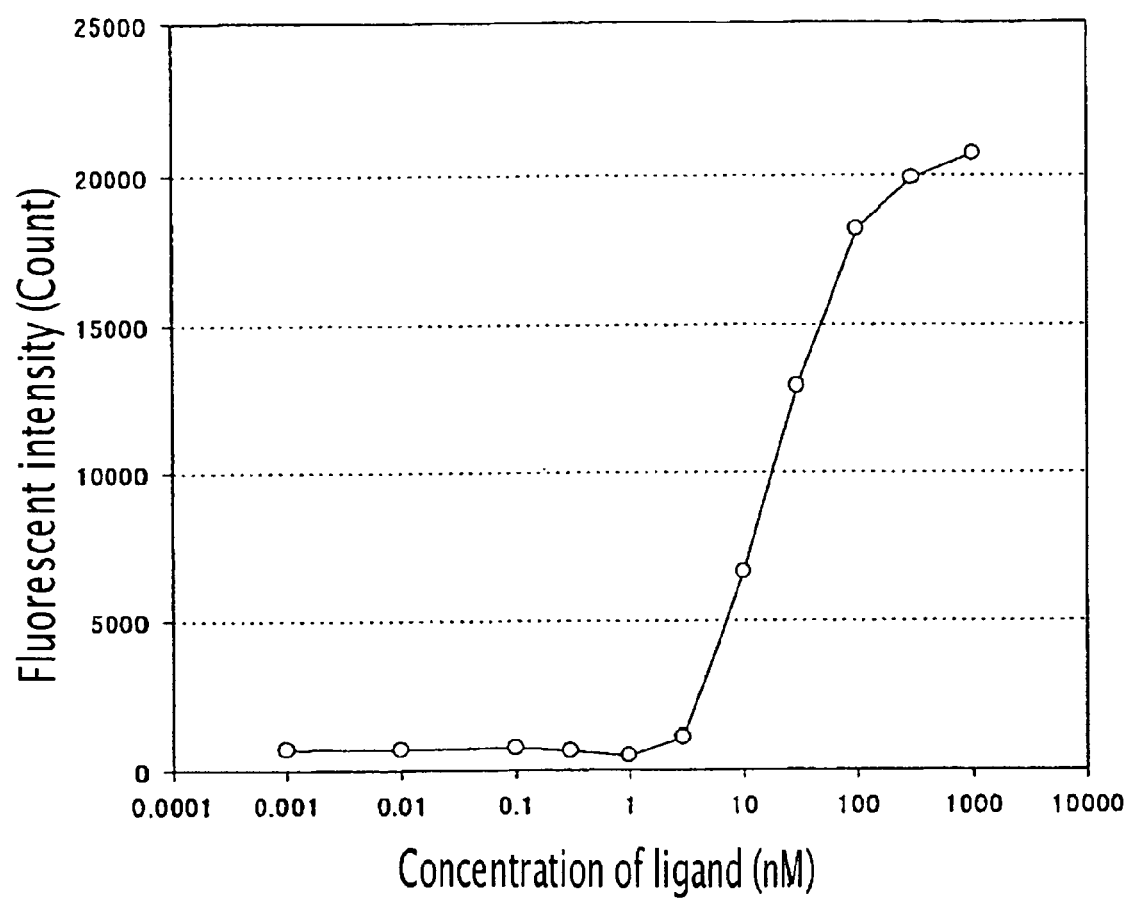
FIG. 23 shows the intracellular Ca ion concentration increasing activity in the human TGR23-1A expressing CHO cells by various concentration of human TGR23-2 ligand (1-20), which was measured using FLIPR.
Figure 24:
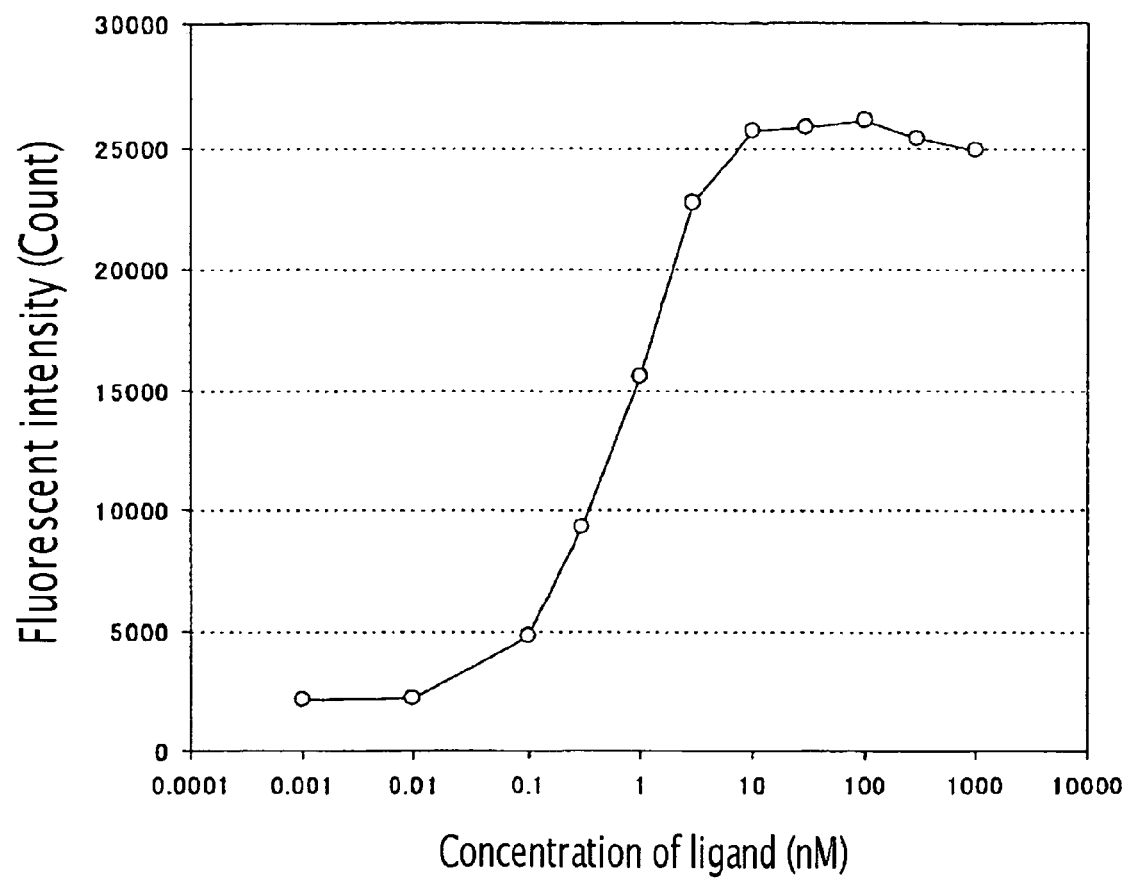
FIG. 24 shows the intracellular Ca ion concentration increasing activity in the human TGR23-1B expressing CHO cells by various concentration of human TGR23-2 ligand (1-20), which was measured using FLIPR.
Figure 25:
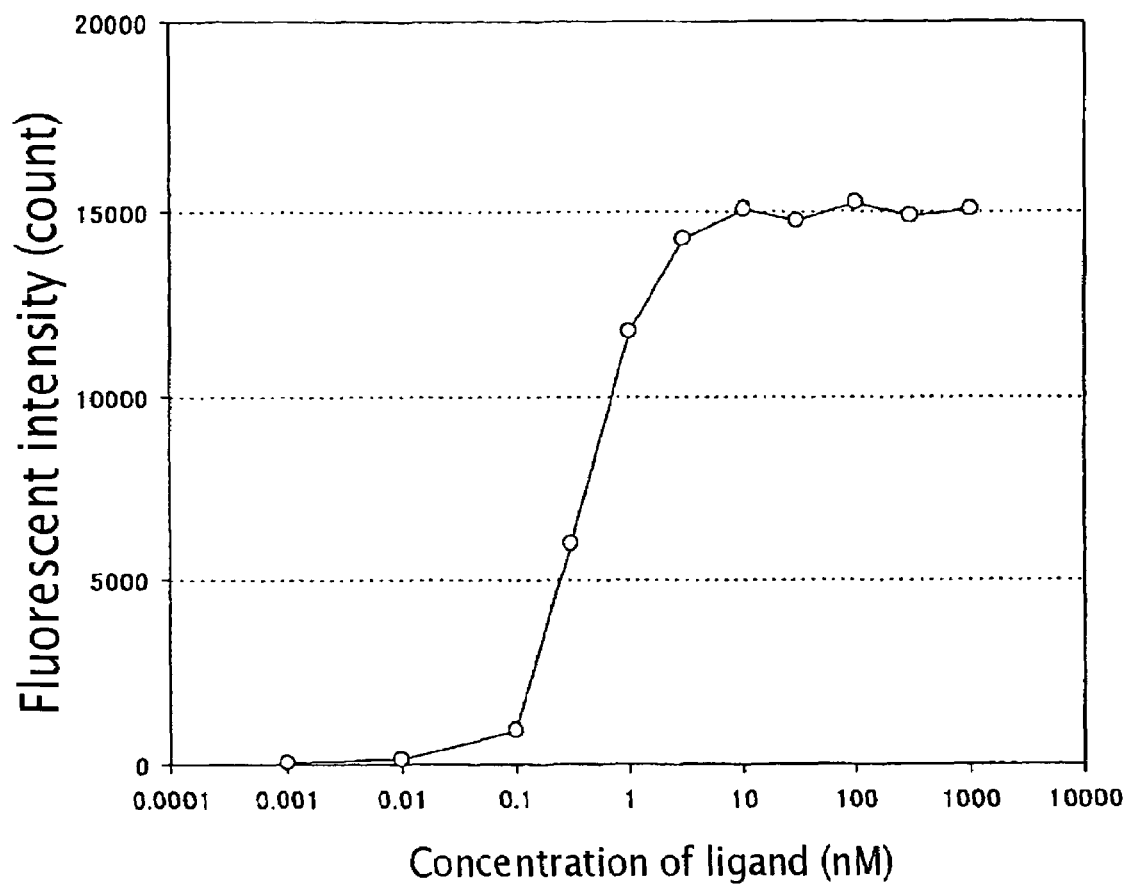
FIG. 25 shows the intracellular Ca ion concentration increasing activity in the human TGR23-1C expressing CHO cells by various concentration of human TGR23-2 ligand (1-20), which was measured using FLIPR.
Figure 26:
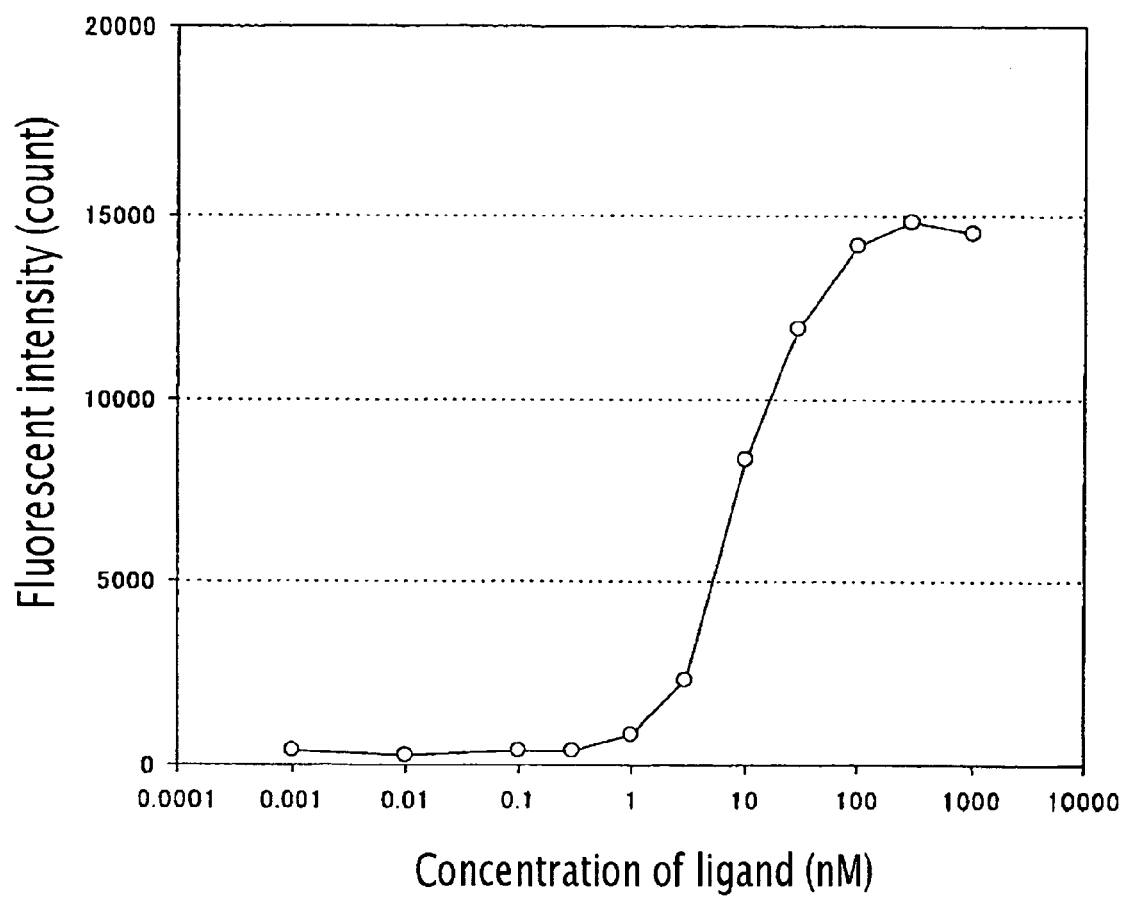
FIG. 26 shows the intracellular Ca ion concentration increasing activity in the human TGR23-1D expressing CHO cells by various concentration of human TGR23-2 ligand (1-20), which was measured using FLIPR.

The result was shown in FIG. 22. From the result, it was observed that from 11th to 20th day, in the group with the human TGR23-2 ligand (1-20), carcinoma volume of LS 174T has a tendency to increase.

Example 36

Construction of Expression Vector for Human TGR23-1A, Human TGR23-1C and Human TGR23-1D DNAs encoding human TGR23-1A (SEQ ID NO: 63), human TGR23-1C (SEQ ID NO: 95) and human TGR23-1D (SEQ ID NO: 97) were prepared from human TGR23-1 DNA using Quick Change Site-directed Mutagenesis Kit (Stratagene). To the human TGR23-1 DNA, as follows, by PCR method, the site-directed mutagenesis was carried out. The PCR reaction solution consisted of 5 ng of pAKKO-TGR23-1 described in Example 15, 2 mM dNTPs, 0.4 µM each of forward primer and reverse primer for mutagenesis [forward primer for pAKKO-TGR23-1A (SEQ ID NO: 106), reverse primer for pAKKO-TGR23-1A (SEQ ID NO: 107), forward primer for pAKKO-TGR23-1C (SEQ ID NO: 108), reverse primer for pAKKO-TGR23-1C (SEQ ID NO: 109), forward primer for pAKKO-TGR23-1D (SEQ ID NO: 110), reverse primer for pAKKO-TGR23-1D (SEQ ID NO: 111)], 2.5 units of pfu polymerase and the buffer for PCR reaction attached to the kit to make total volume 50 µl. The reaction solution was applied to the reaction, which comprises incubating at 95° C. for 30 seconds, then a cycle set to include 95° C. for 30 seconds followed by 55° C. for 60 seconds and 68° C. for 14 minutes, which was repeated 12 times. After the completion of the reaction, to degrade pAKKO-TGR23-1 as a template, 1 µl of Dpn I (10 units/µl) was added to the reaction solution, and the incubation at 37° C. for one hour was performed. TOP10, the competent cells (Invitrogen) was transformed with the Dpn I reaction mixture by heat-shock method. From the transformant *Escherichia coli*, plasmid DNAs were acquires using QIAwell 8 Ultra Plasmid Kit (QIAGEN). The reaction for determination of the base sequence is carried out using DyeDeoxy-Terminator Cycle Sequence Kit (Applied Biosystems). Subsequently, the base sequence of each DNA was analyzed using ABI PRISM 377 DNA Sequencer (Applied Biosystems) and confirmed to introduce the mutation.

The expression vectors for human TGR23-1A, human TGR23-1C and human TGR23-1D were constructed by ligating human TGR23-1A, human TGR23-1C and human TGR23-1D, which is confirmed to be mutagenized, into Sal I-Spe I site of pAKKO, the expression vector for animal cells. The plasmid DNA, in which the mutagenesis was confirmed by the DNA sequence analysis, was digested with Sal I and Spe I. The DNA solution was electrophoresed on 1.5% agarose gel, and DNA fragments of human TGR23-1A, human TGR23-1C and human TGR23-1D harboring Sal I cleavage site at the 5'-terminus and Spe I cleavage site at the 3'-terminus were recovered using DNA Extraction Kit (QIAGEN). The DNA fragment was ligated to the Sal I-Spe I site of pAKKO using Takara Ligation Kit Ver. 2 (Takara). The competent cells, *Escherichia coli* TOP10 (Invitrogen) or DH5α (TOYOBO) was transformed with the ligation mixture to give transformants. The obtained transformants were designated *Escherichia coli* TOP10/pAKKO-TGR23-1A, *Escherichia coli* DH5α/pAKKO-TGR23-1C and *Escherichia coli* DH5α/pAKKO-TGR23-1D, respectively.

Example 37

Construction of Expression Vector for Human TGR23-1B

DNA encoding human TGR23-1B (SEQ ID NO: 65) was prepared using Quick Change Site-directed Mutagenesis Kit (Stratagene). To the human TGR23-1C DNA, as follows, by PCR method, the site-directed mutagenesis was carried out. The PCR reaction solution consisted of 5 ng of pAKKO-TGR23-1C (the plasmid obtained in Example 36), 2 mM dNTPs, 0.4 µM each of forward primer and reverse primer for mutagenesis [forward primer for pAKKO-TGR23-1B (SEQ ID NO: 112), reverse primer for pAKKO-TGR23-1B (SEQ ID NO: 113)], 2.5 units of pfu polymerase and the buffer for PCR reaction attached to the kit to make total volume 50 µl. The reaction solution was applied to the reaction, which comprises incubating at 95° C. for 30 seconds, then a cycle set to include 95° C. for 30 seconds followed by 55° C. for 60 seconds and 68° C. for 14 minutes, which was repeated 12 times. After the completion of the reaction, to degrade pAKKO-TGR23-1C as a template, 1 µl of Dpn I (10 units/µl) was added to the reaction solution, and the incubation at 37° C. for one hour was performed. TOP10, the competent cells (Invitrogen) was transformed with the Dpn I reaction mixture by heat-shock method. From the transformant *Escherichia coli*, plasmid DNAs were acquires using QIAwell 8 Ultra Plasmid Kit (QIAGEN). The reaction for determination of the base sequence is carried out using DyeDeoxyTerminator Cycle Sequence Kit (Applied Biosystems). Subsequently, the base sequence of human TGR23-1B DNA was analyzed using ABI PRISM 377 DNA Sequencer (Applied Biosystems) and confirmed to introduce the mutation.

The expression vectors for human TGR23-1B was constructed by ligating human TGR23-1B, which is confirmed to be mutagenized, into Sal I-Spe I site of pAKKO, the expression vector for animal cells. The plasmid DNA, in which the mutagenesis was confirmed by the DNA sequence analysis, was digested with Sal I and Spe I. The DNA solution was electrophoresed on 1.5% agarose gel, and DNA fragments of human TGR23-1B harboring Sal I cleavage site at the 5'-terminus and Spe I cleavage site at the 3'-terminus were recovered using DNA Extraction Kit (QIAGEN). The DNA fragment was ligated to the Sal I-Spe I site of pAKKO using Takara Ligation Kit Ver. 2 (Takara). The competent cell, *Escherichia coli* TOP10 (Invitrogen) was transformed with the ligation mixture to give transformants. The obtained transformant was designated *Escherichia coli* TOP10/pAKKO-TGR23-1B.

Example 38

Preparation of CHO Cell Lines, in which Human TGR23-1A, Human TGR23-1C and Human TGR23-1D are Expressed

*Escherichia coli* TOP10/pAKKO-TGR23-1A, *Escherichia coli* TOP 10/pAKKO-TGR23-1B, *Escherichia coli* DH5α/pAKKO-TGR23-1C and *Escherichia coli* DH5α/pAKKO-TGR23-1D were cultured. From the *E. coli* cells, using the Plasmid Midi Kit (QIAGEN), each plasmid DNA was prepared. These plasmid DNAs were transfected using the Effectene Transfection Reagent (QIAGEN) in accordance with the attached protocol to CHO dhfr⁻ cells. The mixture of 2 µg of plasmid DNA with the transfection reagents was added to Petri dish with 10 cm diameter, on which 1×10⁶ CHO dhfr⁻ cells had been seeded before 48 hours. The cells were cultured in MEMα medium containing 10% fetal bovine serum for one day, and subcultured in MEMα medium containing 10% fetal bovine serum and no nucleic acid as a selection medium. Colonies of human TGR23-1A expressing cells, human TGR23-1B expressing cells, human TGR23-1C expressing cells and human TGR23-1D expressing cells, which appeared in the selection medium were selected up to 40.

Example 39

Measurement of Expression Level of the Transfected Gene in the CHO Cell Lines, in which Human TGR23-1A, Human TGR23-1C and Human TGR23-1D are Expressed, Using TaqMan PCR Method The CHO cell lines prepared in Example 38, in which human TGR23-1A, human TGR23-1C and human TGR3-1D are expressed, were cultured in 25 cm² flask, respectively. From the grown cells, using Rneasy Protect Kit (QIAGEN), total RNA was prepared. The reaction mixture for cDNA synthesis using total RNA as a template consisted of 0.5 µg of total RNA, 25 pmol random nonamer (Takara), 1 mM dNTPs, 1 µl of ReverTra Ace (TOYOBO) and the reaction buffer attached to the kit, and the total volume is 20 µl. Reverse transcription was performed using thermal cycler (Takara) by the reaction at 30° C. for 10 minutes, 42° C. for 60 minutes and 99° C. for five minutes.

Standaard partial DNA of human TGR23-2 was prepared by purifying PCR-amplified DNA with whole length human TGR23-2 DNA as a template. The PCR reaction solution consisted of 10 ng of pTB2174 (Reference Example 1), 1 µM synthetic DNA forward primer (SEQ ID NO: 114), 1 µM synthetic DNA reverse primer (SEQ ID NO: 115), 0.2 mM dNTPs, 2.5 U of Pfu Turbo DNA Polymerase (Stratagene) and 25 µl of 2×GC buffer I (Takara) to make total volume 50 µl. The reaction for amplification was carried out by reaction of 95° C. for 60 seconds, then a cycle set to include 95° C. for 60 seconds followed by 55° C. for 60 seconds and 72° C. for 70 seconds, which was repeated 25 times, and finally, extension reaction at 72° C. for 10 minutes. The PCR amplified DNA was electrophoresed on agarose gel, and recovered using the QIAquick Gel Extraction Kit (QIAGEN). The PCR product was subcloned into pCR-BluntII-TOPO (Invitrogen). This plasmid was introduced into *Escherichia coli* TOP 10 (Invitrogen), and the transformant harboring the TGR23-2 cDNA was on LB agar medium containing kanamycin. From the obtained *Escherichia coli* harboring human TGR23-2 cDNA, using Quantum Prep Plasmid Miniprep Kit (Bio Rad), the plasmid was recovered. Based on the amount of DNA calculated from the absorbance at 260 nm and DNA base contents, copy number of human TGR23-2 partial DNA, which contains in the DNA solution, was calculated. The human TGR23-2 partial DNA, wherein the copy number was found, was used as a standard human TGR23-2 partial DNA for quantitative TaqMan PCR.

The copy number of the transfected and expressed gene in the cell lines, in which human TGR23-1A, human TGR23-1B, human TGR23-1C and human TGR-1D were expressed, respectively, was determined by the TaqMan PCR method. The reaction solution for TaqMan PCR consisted of 2 μl of reverse transcribed cDNA solution or 1 μl of standard human TGR23-2 partial DNA having various concentrations, 0.2 μM synthetic DNA forward primer (SEQ ID NO: 9), 0.2 μM synthetic DNA reverse primer (SEQ ID NO: 10), 0.2 μM TaqMan probe (SEQ ID NO: 11) and TaqMan Universal PCR Master Mix (Applied Biosystems). The total volume of the reaction solution was 25 μl. The PCR reaction was performed using ABI PRISM 7700 Sequence Detector System (Applied Biosystems) by the incubation at 50° C. for two minutes and 95° C. for 10 minutes, followed by 95° C. for 15 seconds and 60° C. for 60 seconds, which was repeated 40 times. A level of expression of the gene in the cell lines, in which human TGR23-1A, human TGR23-1B, human TGR23-1C and human TGR-1D were expressed, was calculated with ABI PRISM 7700 SDS Software. Using cycle numbers at the moment when fluorescent intensity of reporter comes to preset values indicated as a vertical axis, and logarithm of copy numbers of the standard human TGR23-2 partial cDNA as a horizontal axis, standard curve was prepared. From this standard curve, the expression level of the transfected gene per 1 ng of total RNA was determined by calculating copy numbers of the transfected gene, which is contained in reverse transcribed cDNA. For highly expressed cell lines of human TGR23-1A, human TGR23-1B, human TGR23-1C and human TGR23-1D, clones No. 60, 59, 9 and 12 were selected, respectively.

Example 40

Measurement for the Intracellular Ca Ion Concentration Increasing Activity of the CHO Cells, in which Human TGR23-1A, Human TGR23-1B, Human TGR23-1C and Human TGR23-1D are Expressed, by the Human TGR23-2 Ligand (1-20) Using FLIPR The human TGR23-2 ligand (1-20) having various concentrations was administered in accordance with the method described in Example 5, to the CHO cells, in which human TGR23-1A, human TGR23-1B, human TGR23-1C and human TGR23-1D are expressed. Subsequently, the intracellular Ca ion concentration increasing activity was measured using FLIPR. The results were shown in FIGS. 23, 24, 25 and 26.

It is clear that the CHO cells, in which human TGR23-1A, human TGR23-1B, human TGR23-1C and human TGR23-1D are expressed, responded to the human TGR23-2 ligand (1-20), and the intracellular Ca ion level increased depending on the concentration of this ligand.

Example 41

Construction of Expression Vector for Rat TGR23-1 and Rat TGR23-5

DNA encoding rat TGR23-5 (SEQ ID NO: 91) was prepared using Quick Change Site-directed Mutagenesis Kit (Stratagene). To the rat TGR23-1 DNA, as follows, by PCR method, the site-directed mutagenesis was carried out. The PCR reaction solution consisted of 5 ng of pAKKO-rTGR23-1, which is described in Reference Example 4, 2 mM dNTPs, 0.4 μM each of forward primer and reverse primer for mutagenesis [forward primer for pAKKO-TGR23-5 (SEQ ID NO: 116), reverse primer for pAKKO-TGR23-5 (SEQ ID NO: 117)], 2.5 units of pfu polymerase and the buffer for PCR reaction attached to the kit to make total volume 50 μl. The reaction solution was applied to the reaction, which comprises incubating at 95° C. for 30 seconds, then a cycle set to include 95° C. for 30 seconds followed by 55° C. for 60 seconds and 68° C. for 10 minutes, which was repeated 18 times. After the completion of the reaction, to degrade pAKKO-rTGR23-1 as a template, 1 μl of Dpn I (10 units/μl) was added to the reaction solution, and the incubation at 37° C. for one hour was performed. TOP10, the competent cells (Invitrogen) was transformed with the Dpn I reaction mixture by heat-shock method. From the transformant *Escherichia coli*, plasmid DNAs were acquires using QIAwell 8 Ultra Plasmid Kit (QIAGEN). The reaction for determination of the base sequence is carried out using DyeDeoxyTerminator Cycle Sequence Kit (Applied Biosystems). Subsequently, the base sequence of human TGR23-1B DNA was analyzed using ABI PRISM 377 DNA Sequencer (Applied Biosystems) and confirmed to introduce the mutation.

The expression vectors for rat TGR23-5 was constructed by ligating rat TGR23-5, which is confirmed to be mutagenized, into Sal I-Spe I site of pAKKO, the expression vector for animal cells. The plasmid DNA, in which the mutagenesis was confirmed by the DNA sequence analysis, was digested with Sal I and Spe I. The DNA solution was electrophoresed on 1.5% agarose gel, and DNA fragments of rat TGR23-5 harboring Sal I cleavage site at the 5'-terminus and Spe I cleavage site at the 3'-terminus were recovered using DNA Extraction Kit (QIAGEN). The DNA fragment was ligated to the Sal I-Spe I site of pAKKO using Takara Ligation Kit Ver. 2 (Takara). The competent cell, *Escherichia coli* DH5α (TOYOBO) was transformed with the ligation mixture to give transformants. The obtained transformant was designated *Escherichia coli* DH5α/pAKKO-rTGR23-5.

The rat TGR23-1 expressing vector was constructed by digestion of plasmid pCR2.1-rTGR23-1 with Sal I and Spe I, and ligating the fragment to the Sal I-Spe I site of pAKKO, the expression vector for animal cells in accordance with the same method as the case of rat TGR23-5. Then with this plasmid, the competent cell, *Escherichia coli* DH5α (TOYOBO) was transformed to give *Escherichia coli* DH5α/pAKKO-rTGR23-1.

Example 42

Preparation of CHO Cell Lines, in which Rat TGR23-1 and Rat TGR23-5 are Expressed

*Escherichia coli* DH5α/pAKKO-rTGR23-1 and *Escherichia coli* DH5α/pAKKO-rTGR23-5 were cultured. From these *E. coli* cells, using the Plasmid Midi Kit (QIAGEN), each plasmid DNA was prepared. These plasmid DNAs were transfected using the Effectene Transfection Reagent (QIAGEN) in accordance with the attached protocol to CHO dhfr⁻ cells. The mixture of 2 μg of plasmid DNA with the transfection reagents was added to Petri dish with 10 cm diameter, on which $1 \times 10^6$ CHO dhfr⁻ cells had been seeded before 48 hours. The cells were cultured in MEMα medium containing 10% fetal bovine serum for one day, and subcultured in MEMα medium containing 10% fetal bovine serum and no nucleic acid as a selection medium. Colonies of rat TGR23-1 expressing cells and rat TGR23-5 expressing cells, which appeared in the selection medium, were selected up to 30, respectively.

Example 43

Measurement of Expression Level of the Transfected Gene in the CHO Cell Lines, in which Rat TGR23-1 and Rat TGR23-5 are Expressed, Using TaqMan PCR Method The CHO cell lines prepared in Example 42, in which rat TGR23-1 and rat TGR23-5 are expressed, were cultured in 25 cm² flask, respectively. From the grown cells, using Rneasy Protect Kit (QIAGEN), total RNA was prepared. The reaction mixture for cDNA synthesis using total RNA as a template consisted of 0.5 μg of total RNA, 25 pmol random nonamer (Takara), 1 mM dNTPs, 1 μl of ReverTra Ace (TOYOBO) and the reaction buffer attached to the kit, and the total volume is 20 μl. Reverse transcription was performed using thermal cycler (Takara) by the reaction at 30° C. for 10 minutes, 42° C. for 60 minutes and 99° C. for five minutes.

Standaard partial DNA of rat TGR23-1 was prepared by purifying PCR-amplified DNA with whole length rat TGR23-1 DNA as a template. The PCR reaction solution consisted of 680 pg of pCR2.1-TGR23-1 (Reference Example 4), 1 μM synthetic DNA forward primer (SEQ ID NO: 118), 1 μM synthetic DNA reverse primer (SEQ ID NO: 119), 0.8 mM dNTPs, 2 μl of Advantage II Polymerase (CLONTECH) and buffer attached to the enzyme to make total volume 100 μl. The reaction for amplification was carried out by reaction of 95° C. for 60 seconds, then a cycle set to include 95° C. for 20 seconds followed by 72° C. for 120 seconds, which was repeated 5 times, a cycle set to include 95° C. for 20 seconds followed by 72° C. for 120 seconds, which was repeated 5 times, a cycle set to include 95° C. for 20 seconds followed by 68° C. for 120 seconds, which was repeated 20 times, and finally, extension reaction at 68° C. for three minutes. The PCR amplified DNA was recovered using the QIAquick Gel Extraction Kit (QIAGEN). Based on the amount of DNA calculated from the absorbance at 260 nm of the amplified rat TGR23-1 partial DNA solution and DNA base contents of the amplified rat TGR23-1 partial DNA, copy number of rat TGR23-1 partial DNA, which contains in the DNA solution, was calculated. The rat TGR23-1 partial DNA, wherein the copy number was found, was used as a standard rat TGR23-1 partial DNA for quantitative TaqMan PCR.

The copy number of the transfected and expressed gene in the cell lines, in which rat TGR23-1 and rat TGR-5 were expressed, respectively, was determined by the TaqMan PCR method. The reaction solution for TaqMan PCR consisted of 2 μl of reverse transcribed cDNA solution or 1 μl of standard rat TGR23-1 partial DNA having various concentrations, 0.2 μM synthetic DNA forward primer (SEQ ID NO: 120), 0.2 μM synthetic DNA reverse primer (SEQ ID NO: 121), 0.2 μM TaqMan probe for rat TGR23 (SEQ ID NO: 122, Fam-ttggagttat ccggtcctct cttccaag-Tamra; in the sequence, Fam and Tamra represent 6-carboxy-fluorescein and 6-carboxy-tetramethyl-rhodamine, respectively) and TaqMan Universal PCR Master Mix (Applied Biosystems). The total volume of the reaction solution was 25 μl. The PCR reaction was performed using ABI PRISM 7700 Sequence Detector System (Applied Biosystems) by the incubation at 50° C. for two minutes and 95° C. for 10 minutes, followed by 95° C. for 15 seconds and 60° C. for 60 seconds, which was repeated 40 times. A level of expression of the gene in the cell lines, in which rat TGR23-1 and rat TGR-5 were expressed, was calculated with ABI PRISM 7700 SDS Software. Using cycle numbers at the moment when fluorescent intensity of reporter comes to preset values indicated as a vertical axis, and logarithm of copy numbers of the standard rat TGR23-1 partial cDNA as a horizontal axis, standard curve was prepared. From this standard curve, the expression level of the transfected gene per 1 ng of total RNA was determined by calculating copy numbers of the transfected gene, which is contained in reverse transcribed cDNA. For highly expressed cell lines of rat TGR23-1 and rat TGR23-5, clones No. 34 and 29 were selected, respectively.

Example 44

Figure 27:
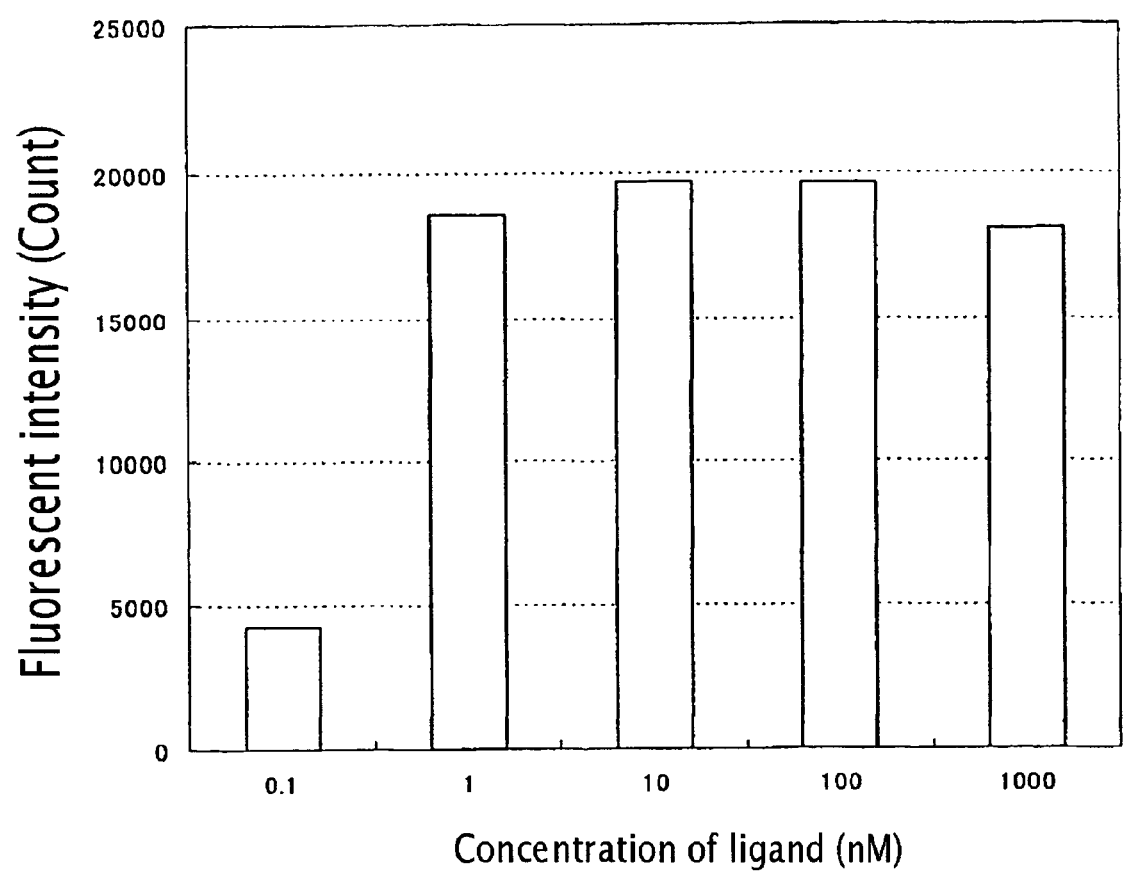
FIG. 27 shows the intracellular Ca ion concentration increasing activity in the rat TGR23-1 expressing CHO cells by various concentration of rat TGR23-2 ligand (1-18), which was measured using FLIPR.
Figure 28:
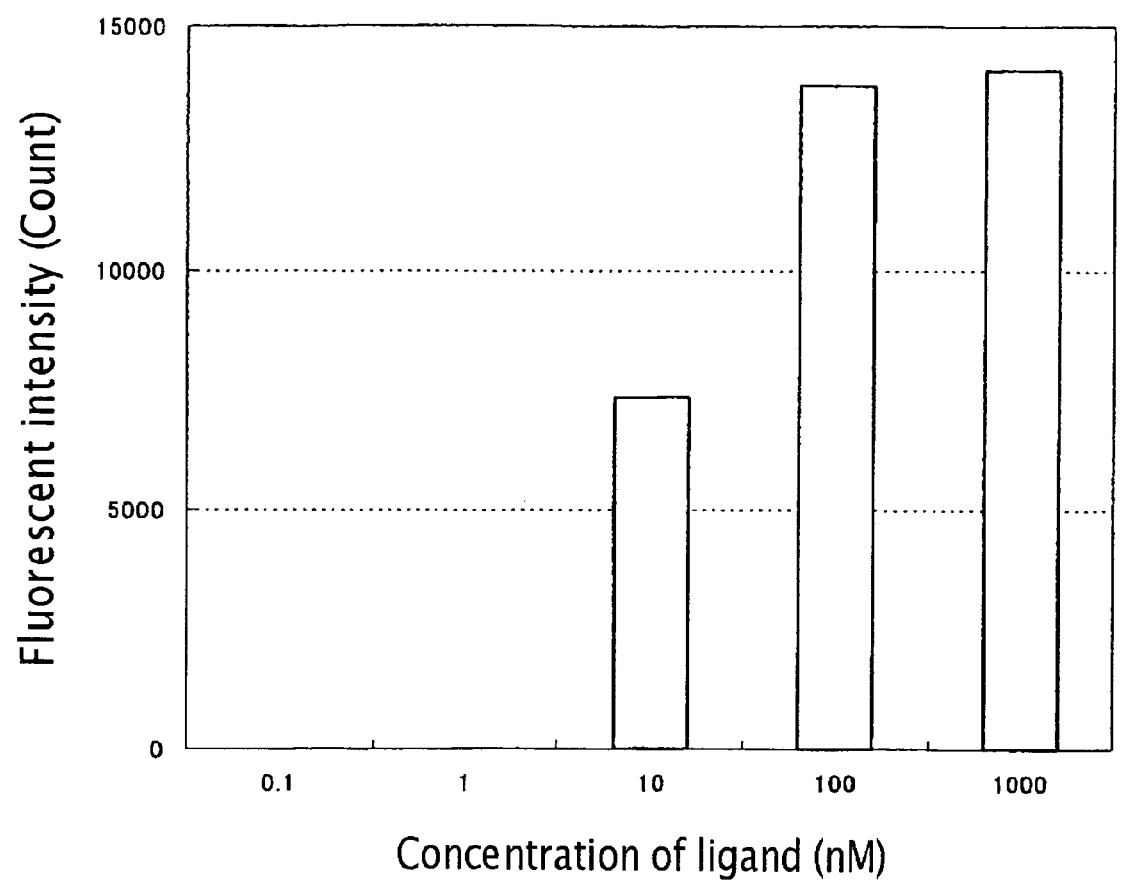
FIG. 28 shows the intracellular Ca ion concentration increasing activity in the rat TGR23-5 expressing CHO cells by various concentration of rat TGR23-2 ligand (1-18), which was measured using FLIPR.

Measurement for the Intracellular Ca Ion Concentration Increasing Activity of the CHO Cells, in which Rat TGR23-1 and Rat TGR23-5 are Expressed, by the Rat TGR23-2 Ligand (1-18) Using FLIPR The rat TGR23-2 ligand (1-18) having various concentrations was administered in accordance with the method described in Example 5, to the CHO cells, in which rat TGR23-1 and rat TGR23-5 are expressed. Subsequently, the intracellular Ca ion concentration increasing activity was measured using FLIPR. The results were shown in FIGS. 27 and 28. It is clear that the CHO cells, in which rat TGR23-1 and rat TGR23-5 are expressed, responded to the rat TGR23-2 ligand (1-18), and the intracellular Ca ion level increased depending on the concentration of this ligand. $EC_{50}$ values of rat TGR23-2 ligand (1-18) to the rat TGR23-1 expressing cells and the rat TGR23-5 expressing cells in the intracellular Ca ion concentration increasing activity, which are calculated from the graph shown in FIGS. 27 and 28, were 0.19 nM (rat TGR23-1) and 14 nM (rat TGR23-5), respectively.

Example 45

Comparison of Binding Affinity for [$Nle^{10}$, $^{125}I$-$Tyr^{15}$] Human TGR3-2 Ligand (1-20) to Rat TGR23-1 or Rat TGR23-5 by Binding Saturation Experiment The binding affinity of the cell membrane fraction prepared from rat TGR23-1 expressing CHO cells and rat TGR23-5 expressing CHO cells to [$Nle^{10}$, $^{125}I$-$Tyr^{15}$] human TGR23-2 ligand (1-20) was measured as follows.

Firstly, membrane fraction was prepared from rat TGR23-1 expressing CHO cells and rat TGR23-5 expressing CHO cells. The rat TGR23-1 expressing CHO cells and the rat TGR23-5 expressing CHO cells were cultured. After washing the cells with phosphate buffered saline, the cells were peeled off from the flask and clod of the cells was harvested by centrifugation. The cells were suspended in cell disruption buffer (20 mM Tris-HCl (pH7.4), 5 mM EDTA, 0.5 mM PMSF, 0.1 μg/ml of pepstatin, 20 μg/ml of leupeptine and 4 μg/ml of E-64) and disrupted by Polytron homogenizer. The cell disrupting fluid was applied to centrifugation (4° C., 1000×g, 5 minutes) and the supernatant was recovered. Subsequently, the supernatant was ultracentrifuged (4° C., 30000×g, 60 minutes) and the precipitate was recovered as a membrane fraction. This membrane fraction was suspended in cell disruption buffer and the protein concentration in the suspension was determined. Then the membrane fraction was stored at −80° C. until use.

The membrane fractions of rat TGR23-1 expressing CHO cells and rat TGR23-5 expressing CHO cells, which were prepared as described above, were suspended in binding buffer (20 mM Tris-HCl (pH7.4), 5 mM EDTA, 0.1% BSA, 0.5 mM PMSF, 0.1 μg/ml of pepstatin, 20 μg/ml of leupeptine and 4 μg/ml of E-64). The concentration was adjusted to 10 μg/ml. The solution was used as a membrane fraction solution for binding saturation. Total binding of [$Nle^{10}$, $^{125}I$-$Tyr^{15}$] human TGR23-2 ligand (1-20), which was prepared by the method described in Example 26, to the membrane fractions, was obtained by the following method.

To 200 μl of the membrane fraction solution for binding saturation, 2 μl of dimethylsulfoxide (DMSO) and 2 μl of [$Nle^{10}$, $^{125}I$-$Tyr^{15}$] human TGR23-2 ligand (1-20) having various concentrations, were added, and then the mixture was incubated at 25° C. for 90 minutes. The [$Nle^{10}$, $^{125}I$-$Tyr^{15}$] human TGR23-2 ligand (1-20) bound to the membrane fractions was separated from non-binding [$Nle^{10}$, $^{125}I$-$Tyr^{15}$] human TGR23-2 ligand (1-20) by filtration of the reaction mixture with glass filter. Specifically, the reaction mixture was filtered through GF/F filter (Whatman), which is previously soaked to 20 mM Tris-HCl (pH7.4) buffer containing 0.3% polyethyleneimine, and the filter was washed three times with 1.5 ml of ice-cooled binding buffer. The radioactivity of [$Nle^{10}$, $^{125}I$-$Tyr^{15}$] human TGR23-2 ligand (1-20) trapped on the glass filter was measured by γ-counter, and the obtained value was determined as the total binding. On the other hand, non-specific binding of [$Nle^{10}$, $^{125}I$-$Tyr^{15}$] human TGR23-2 ligand (1-20) to the membrane fractions was aquired by using 2 μl of 100 μM human TGR23-2 ligand (1-20) (SEQ ID NO: 23) instead of 2 μl of DMSO in the reaction mixture for the total binding. A specific binding at a given concentration of [$Nle^{10}$, $^{125}I$-$Tyr^{15}$] human TGR23-2 ligand (1-20) is calculated by subtracting the non-specific binding from the total binding at the same concentration.

Figure 29:
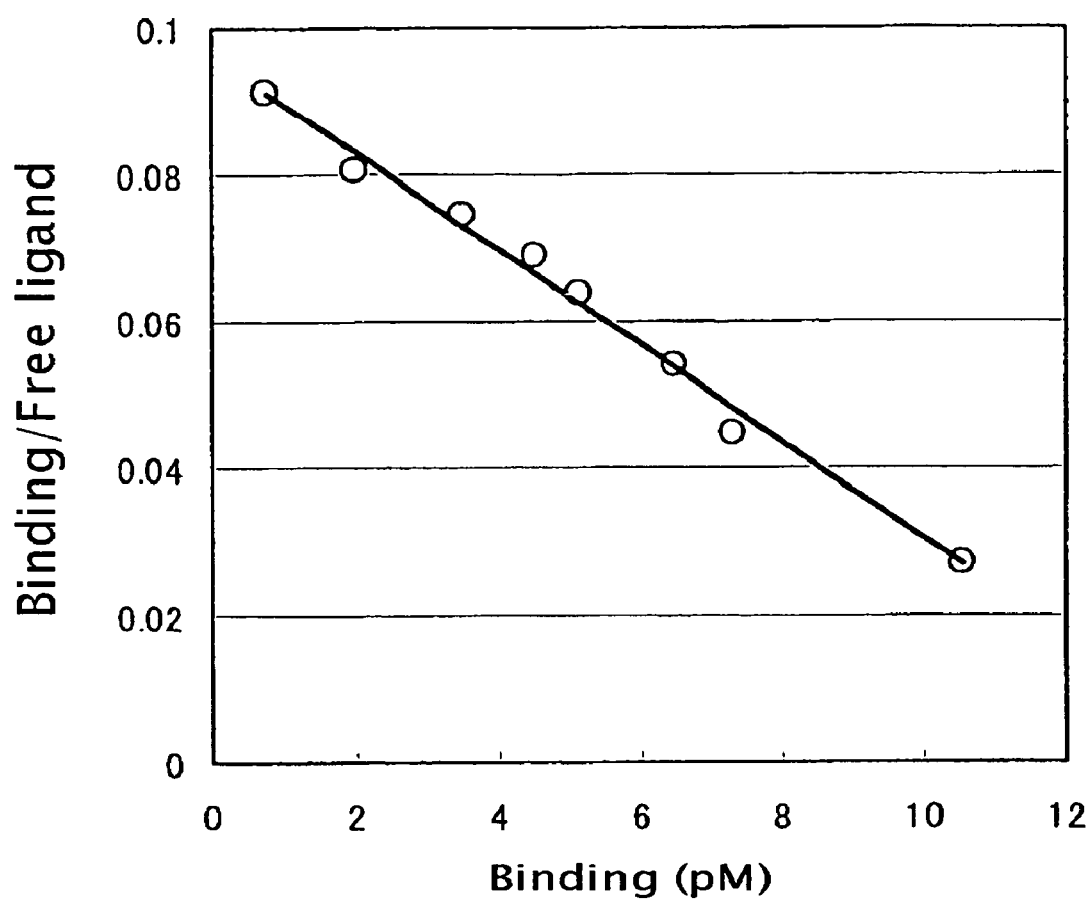
FIG. 29 shows a Scatchard plot for calculating dissociation constant [Nle$^{10}$, $^{125}$I-tyr$^{15}$] human TGR23-2 ligand (1-20) for rat TGR23-1.
Figure 30:
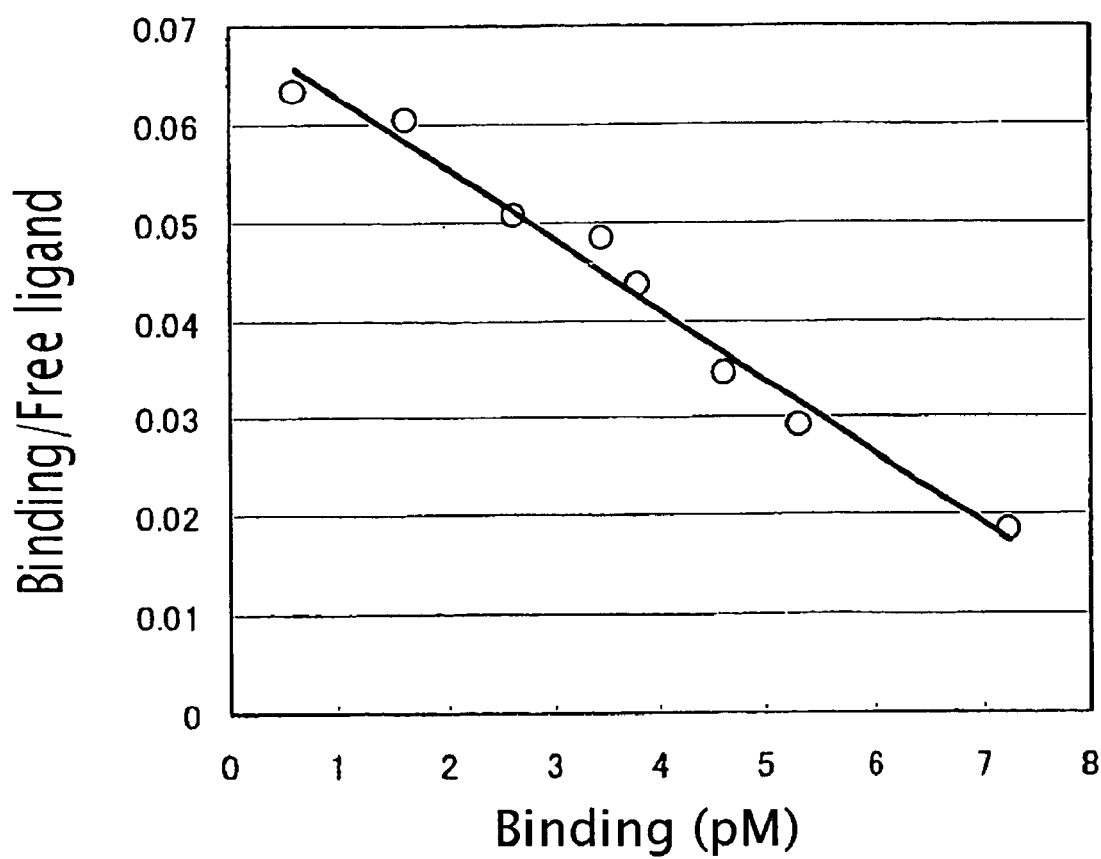
FIG. 30 shows a Scatchard plot for calculating dissociation constant [Nle$^{10}$, $^{125}$I-tyr$^{15}$] human TGR23-2 ligand (1-20) for rat TGR23-5.

The binding manner of [$Nle^{10}$, $^{125}I$-$Tyr^{15}$] human TGR23-2 ligand (1-20) to the membrane fraction of rat TGR23-1 expressing CHO cells or rat TGR23-5 expressing CHO cells in the above-described binding saturation experiment was analyzed by Scatchard method. By representing the specific binding of [$Nle^{10}$, $^{125}I$-$Tyr^{15}$] human TGR23-2 ligand (1-20) per 1 mg protein of the membrane fraction at a given concentration of [$Nle^{10}$, $^{125}I$-$Tyr^{15}$] human TGR23-2 ligand (1-20) as a horizontal axis, and the specific binding of [$Nle^{10}$, $^{125}I$-$Tyr^{15}$] human TGR3-2 ligand (1-20) per 1 mg protein of the membrane fraction divided by non-bound [$Nle^{10}$, $^{125}I$-$Tyr^{15}$] human TGR23-2 ligand (1-20) in the reaction mixture as a vertical axis, the value obtained was plotted. As shown in FIGS. 29 and 30, a plot in the binding saturation experiment of [$Nle^{10}$, $^{125}I$-$Tyr^{15}$] human TGR23-2 ligand (1-20) to the membrane fraction of rat TGR23-1 expressing CHO cells or rat TGR23-5 expressing CHO cells was approximate to linear line. This fact indicated that unique binding site of [$Nle^{10}$, $^{125}I$-$Tyr^{15}$] human TGR23-2 ligand (1-20) is present in the membrane fraction of rat TGR23-1 expressing CHO cells or rat TGR23-5 expressing CHO cells. In this experiment, dissociation constant between the rat TGR23-1 and [$Nle^{10}$, $^{125}I$-$Tyr^{15}$] human TGR23-2 ligand (1-20) was 141±8.71 (pM). Also, maximum binding sites of rat TGR23-1 to [$Nle^{10}$, $^{125}I$-$Tyr^{15}$] human TGR23-2 ligand (1-20) was 1.41±0.04 pmol/mg protein. On the other hand, dissociation constant between the rat TGR23-1 and [$Nle^{10}$, $^{125}I$-$Tyr^{15}$] human TGR23-2 ligand (1-20) was 125±8.36 (pM). Also, maximum binding sites of rat TGR23-1 to [$Nle^{10}$, $^{125}I$-$Tyr^{15}$] human TGR23-2 ligand (1-20) was 0.93±0.03 pmol/mg protein. [$Nle^{10}$, $^{125}I$-$Tyr^{15}$] human TGR23-2 ligand (1-20) was bound to both rat TGR23-1 and rat TGR23-5 with almost identical affinity.

Table 1 shows the affinity of rat TGR23-1 and rat TGR23-5 to TGR23-2 ligand and the intracellular Ca ion concentration increasing activity of each receptor expressing cells by TGR23-2 ligand.

Whereas the rat TGR23-5 posesses a high affinity to the TGR23-2 ligand as that of the rat TGR23-1, the response of the rat TGR23-5 to the TGR23-2 ligand was about 1/100 of that of the rat TGR23-1. This fact suggests that the response of rat TGR23-1, mouse TGR23-B or human TGR23 to the TGR23-2 ligand can be attenuated by coexistence of rat TGR23-5 with rat TGR23-1, mouse TGR23-B or human TGR23 in the same cell.

TABLE 1

|  | Rat TGR23-1 | Rat TGR23-5 |
|---|---|---|
| Binding Constant | 141 pM | 125 pM |
| Intracellular Ca increasing activity ($EC_{50}$) | 0.19 nM | 14 nM |

Example 46

Induction of Apoptosis in Human Colon Cancer Cell Lines by Suppression of TGR23 Gene Expression Human colon cancer cell line COLO 205 acquired from ATCC was suspended in the RPMI-1640 medium (containing 25 mM HEPES) supplemented with 10% fetal calf serum (ATCC), and seeded at the cell density of 4000 per well in 96-well collagen type I coated plate (IWAKI). Human colon cancer cell line LS 174T acquired from ATCC was suspended in the Eagle's MEM, which is supplied from Invitrogen, supplemented with 10% fetal calf serum (ATCC), and seeded at the cell density of 3000 per well in 96-well flat bottom culture plate (BD Falcon). Human colon cancer cell line HCT 116 (ATCC) was suspended in D-MEM medium (containing 10 mM HEPES), which is supplied from Invitrogen, supplemented with 10% fetal calf serum (ATCC), and seeded at the cell density of 3000 per well in 96-well flat bottom culture plate (BD Falcon). After incubation under 5% $CO_2$ gas flow at 37° C. for overnight, antisense oligonucleotide was transfected.

Antisense oligonucleotide sequence (SEQ ID NO: 123), which hybridizes to the translation region of TGR23 gene, was designed. Phosphorothioate-oligonucleotide was synthesized and purified by HPLC to use the transfection experiment (hereinafter, referred to as antisense oligonucleotide). For control, a reverse sequence (SEQ ID NO: 124) of the base sequence represented by SEQ ID NO: 123 was phosphorothioated and purified by HPLC to use (hereinafter, referred to as control oligonucleotide).

Specifically, in the case of COLO 205, to FuGENE™6 Transfection Reagent (Roche Diagnostics), which was diluted 167 fold with Opti-MEM I (Invitrogen), antisense oligonucleotide or control oligonucleotide was added. The mixed oligonucleotide solution was added to the plate at the ratio of 65 µl per well. The final concentration of oligonucleotide was adjusted to 200 nM. In the case of LS 174T, to Lipofectamine™2000 (Invitrogen), which was diluted 32 fold with Opti-MEM I (Invitrogen), antisense oligonucleotide or control oligonucleotide, which was diluted with Opti-MEM I (Invitrogen), was added at the ratio of 1:1. The mixed oligonucleotide solution was added to the plate at the ratio of 50 µl per well. The final concentration of oligonucleotide was adjusted to 33 nM. In the case of HCT 116, to OLIGOFECTAMINE™ Reagent (Invitrogen), which was diluted 5 fold with Opti-MEM I (Invitrogen), antisense oligonucleotide or control oligonucleotide, which was diluted with Opti-MEM I (Invitrogen), was added at the ratio of 3:8. The mixed oligonucleotide solution was added to the plate at the ratio of 40 µl per well. The final concentration of oligonucleotide was adjusted to 520 nM.

Under the above conditions, culture was continued for further three days. Using Cell Death Detection ELISA$^{PLUS}$ Kit (Roche Diagnostics), in accordance with the attached protocol, apopyosis induction activity by the above oligonucleotide was measured.

As a result, the antisense oligonucleotide (SEQ ID NO: 123) exhibited an apoptosis induction activity 1.6 fold (in the case of COLO 205) or 1.3 fold (in the case of LS 174T) as the case of control oligonucleotide (SEQ ID NO: 124). This result shows a statistically significant difference (in COLO 205, $p \leq 0.05$; in LS 174T, $p \leq 0.01$) (Tables 2 and 3). In addition, in HCT 116, in which the TGR23 is not expressed, antisense oligonucleotide did not exhibit a significant apoptosis induction activity compared with control oligonucleotide as a negative control.

TABLE 2

| COLO 205 | Apoptosis inducing activity ($A_{405}$-$A_{492}$) | |
| --- | --- | --- |
| | Average | Standard deviation |
| Blank | 0.23 | 0.012 |
| Control oligonucleotide | 0.52 | 0.046 |
| Antisense oligonucleotide | 0.83 | 0.11 |

TABLE 3

| LS174T | Apoptosis inducing activity ($A_{405}$-$A_{492}$) | |
| --- | --- | --- |
| | Average | Standard deviation |
| Blank | 0.43 | 0.016 |
| Control oligonucleotide | 0.88 | 0.0099 |
| Antisense oligonucleotide | 1.1 | 0.024 |

TABLE 4

| HCT 116 | Apoptosis inducing activity ($A_{405}$-$A_{492}$) | |
| --- | --- | --- |
| | Average | Standard deviation |
| Blank | 0.59 | 0.054 |
| Control oligonucleotide | 0.72 | 0.026 |
| Antisense oligonucleotide | 0.68 | 0.10 |

Example 47

Investigation of Reduction of TGR23 Gene Expression by Adminostration of Antisense Oligonucleotide The human colon cancer cell lines COLO 205 and LS 174T, wherein both were used in Example 46, were suspended in the same medium as that used in Example 46. The COLO 205 was seeded at the cell density of 24,000 per well to 24-well collagen type I coated plate (IWAKI), and the LS 174T was seeded at the cell density of 18,000 per well to 24-well flat bottom tissue culture plate (BD Falcon). After cell culture under 5% $CO_2$ gas flow at 37° C. for overnight, in accordance with the method described in Example 46, the antisense oligonucleotide and control oligonucleotide, wherein both were used in Example 46, were transfected. Herein, adding volume of the oligonucleotide solution per well was 390 µl for COLO 205 and 300 µl for LS 174T. After transfection, the cells were cultured under 5% $CO_2$ gas flow at 37° C. for overnight. Subsequently, using RNeasy Mini Total RNA Kit (QIAGEN), total RNA was extracted. Using the thus obtained total RNA as a template and TaqMan Reverse Transcription Reagents (Applied Biosystems), according to the attached protocol, reverse transcription reaction was carried out. Then using TaqMan Universal PCR Master Mix (Applied Biosystems), to the reaction sixture, cDNA corresponding 1.5 to 3 ng of total RNA as a template, 500 nM each of two primers (SEQ ID NO: 9 and SEQ ID NO: 10) and 100 nM FM-labeled probe (SEQ ID NO: 11) were added. The expressed copy numbers of the TGR23 gene were measured. The PCR reaction comprised the incubation at 50° C. for 2 minutes and 95° C. for 10 minutes, followed by the cycle set to include at 95° C. for 15 seconds and at 60° C. for one minute, which is repeated 40 times. When the antisense oligonucleotide and the control oligonucleotide were not transfected, an expression level of the TGR23 gene per 1 ng of total RNA was 620 copies for COLO 205 and 290 copies for LS 174T, whereas in the group with antisense oligonucleotide, it was 210 copies for COLO 205 and 150 copies for LS 174T. From this result, it was perceived that there is a statistically significant reduction of expression ($p \leq 0.01$ for COLO 205; $p \leq 0.05$ for LS 174T). On the other hand, in the group with control oligonucleotide used as a negative control, the expression was 590 copies for COLO 205 and 280 copies for LS 174T, wherein it was not observed a statistically significant reduction of expression level, compared with non-transfection group.

As a result, it was indicated that due to the reduction of the TGR23 gene expression, apoptosis in the human colon cancer cell line was induced.

Example 48

A Method for Screening a Compound that Binds to Human TGR23-2, Using [Nle$^{10}$, $^{125}$I-Tyr$^{15}$] Human TGR23-2 Ligand (1-20) and Membrane Fraction of Human TGR23-2 Expressing CHO Cells Using [Nle$^{10}$, $^{125}$I-Tyr$^{15}$] human TGR3-2 ligand (1-20) prepared by the method described in Example 26 and membrane fraction of human TGR23-2 expressing CHO cells prepared from human TGR23-2 expressing CHO cells by the method described in Example 24, screening of a compound that binds to human TGR23 is carried out as follows.

The membrane fraction prepared from the human TGR23-2 expressing CHO cells was diluted to 1 µg/ml of concentration of membrane fraction with assay buffer (20 mM Tris-HCl, 5 mM EDTA, 0.1% BSA, 0.5 mM PMSF, 1 µg/ml of pepstatin, 4 µg/ml of E-64 and 20 µg/ml of leupeptine, pH7.4), and then 200 µl of aliquot is dispensed into polypropylene test tube (Falcon 2053). To measure maximum binding (TB), 2 µl of DMSO and 2 µl of 10 nM [Nle$^{10}$, $^{125}$I-Tyr$^{15}$] human TGR23-2 ligand (1-20) are added to the membrane fraction solution. Further, to measure the non-specific binding, 2 µl of 1 µM [Nle$^{10}$, $^{125}$I-Tyr$^{15}$] human TGR23-2 ligand (1-20) dissolved in DMSO and 2 µl of 10 nM [Nle$^{10}$, $^{125}$I-Tyr$^{15}$] human TGR23-2 ligand (1-20) are added to the membrane fraction solution. Further, to investigate the binding activity of a test compound to the human TGR23, 2 µl of test compound dissolved in DMSO, which has various concentration, and 2 µl of 10 nM [Nle$^{10}$, $^{125}$I-Tyr$^{15}$] human TGR-23-2 ligand (1-20) are added to the membrane fraction solution. The mixture is reacted at 25° C. for 90 minutes, and then using polyethyleneimine-treated Whatman glass filter (GF/F), the reaction mixture is filtered by suction. After filtration, using γ-counter, radioactivity remained on the filter is measured. Value subtracted the non-specific binding from the maximum binding is estimated as the specific binding (SB). Binding inhibition activity of the test compound to the human TGR23-2 (inhibition rate (%)) is represented by a ratio of the value to the specific binding (SB), wherein the value is calculated by subtracting the radioactivity remaining on the filter (X) in the case of adding the test sample and [Nle$^{10}$, $^{125}$I-Tyr$^{15}$] human TGR23-2 ligand (1-20) from the total binding (TB) ((TB−X)/SB×100 (%)). By comparing the binding inhibition rate of the test compound at various concentrations, a compound that exhibits higher binding inhibition activity at lower concentration is selected as a compound, which has a high ability to bind to the human TGR23.

Concerning the compound bound to the human TGR23, which is selected as described above, by the methods described in Examples 3, 4 or 5, intracellular cAMP production enhancing activity (Example 3), arachidonic acid metabolite release enhancing activity (Example 4) or intracellular Ca$^{2+}$ release enhancing activity (Example 5) is measured. A compound, which exhibits any of activities, is pegged at TGR23 agonist. In addition, for a compound, which exhibits no activity, the assays described in Examples 3, 4 or 5 are performed under the condition of coexistence with TGR23-2 ligand. Thus, a compound that exhibits inhibition activity against the activity shown by the TGR23-2 ligand is pegged at the TGR23 antagonist.

INDUSTRIAL APPLICABILITY

The polypeptide of the present invention, the receptor of the present invention, the polynucleotide of the present invention encoding the polypeptide or the receptor of the present invention, the antibody of the present invention against the polypeptide or the receptor of the present invention, the antisense polynucleotide of the present invention for the polynucleotide or the receptor of the present invention and the like are useful for (i) a prophylactic/therapeutic agent for various diseases associated with the polypeptide or the receptor of the present invention; (ii) screening a compound that enhances or inhibits the activity of the polypeptide or the receptor of the present invention (e.g., a compound that alters the binding property to the protein of the present invention), a compound that enhances or inhibits the expression of the polypeptide or the receptor of the present invention, or salts thereof; (iii) quantification of the polypeptide or the receptor of the present invention; (iv) a gene diagnostic product for the polypeptide or the receptor of the present invention; (v) a medicine containing the antisense DNA; (vi) a medicine containing the antibody of the present invention; (vii) preparation of non-human animals bearing the DNA of the present invention; (viii) preparation of non-human animals wherein the DNA of the present invention is inactivated; (ix) drug design based on comparison with structurally similar ligands/receptors, and the like.

The polypeptide of the present invention, the receptor of the present invention, the polynucleotide of the present invention, the compound or salts thereof that enhances the activity of the polypeptide or the receptor of the present invention, and the compound or salts thereof that enhances the expression of the polypeptide or the receptor of the present invention are useful as a low toxic and safe medicine such as a prophylactic/therapeutic agent for adiposis (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), hyperphagia and the like.

The compound or salts thereof that enhances the activity of the polypeptide or the receptor of the present invention, the compound or salts thereof that enhances the expression of the polypeptide or the receptor of the present invention, the antibody of the present invention (neutralizing antibody), and the antisense polynucleotide of the present invention are useful as a low toxic and safe medicine such as a prophylactic/therapeutic agent for cancer (e.g., carcinoma of large intestine, colon cancer, rectum cancer, breast cancer, lung cancer, non-small-cell lung cancer, prostate cancer, esophageal cancer, stomach cancer, liver cancer, carcinoma of biliary tract, spleen cancer, renal cancer, bladder carcinoma, uterine cancer, ovarian cancer, carcinoma of uterine cervix, carcinoma of testis, thyroid carcinoma, pancreatic cancer, brain tumor, blood cancer), feeding (appetite) enhancer, a prophylactic/therapeutic agent for anorexia, apoptosis inducing agent.

The invention claimed is:

1. An isolated polypeptide, which is a ligand for and has an ability to bind to a G protein-coupled receptor protein comprising the amino acid sequence represented by SEQ ID NO: 1 or SEQ ID NO: 3, or a salt thereof, its amide or its ester, or salts thereof, and wherein the isolated polypeptide comprises the amino acid sequence represented by SEQ ID NO: 23, its amide or its ester, or salts thereof.

2. A pharmaceutical composition comprising the polypeptide of SEQ ID NO: 23, its amide or its ester, or salts thereof.

3. A kit for screening a compound that enhances or inhibits the activity of the polypeptide of SEQ ID NO: 23, its amide or its ester, or salts thereof, which comprises the polypeptide according to claim 1, its amid or its ester, or salts thereof.

4. The kit for screening according to claim 3, which further comprises a protein comprising the amino acid sequence represented by SEQ ID NO: 1 or SEQ ID NO: 3, its amide or its ester, or salts thereof.

5. The kit for screening according to claim 4, which comprises the protein comprising the amino acid sequence represented by SEQ ID NO: 3, its amide or its ester, or salts thereof.

6. The kit for screening according to claim 4, which comprises cells that contain the protein comprising the amino acid sequence represented by SEQ ID NO: 1 or SEQ ID NO: 3, its amide or its ester, or salts thereof.

7. The kit for screening according to claim 4, which comprises a membrane fraction of cells that contain a protein comprising the amino acid sequence represented by SEQ ID NO: 1 or SEQ ID NO: 3, its amide or its ester, or salts thereof.

8. The kit for screening according to claim 4, which comprises the protein that is expressed in the cell membrane of the transformant which is transformed with a recombinant vector, wherein said vector comprises a polynucleotide encoding the polypeptide of SEQ ID NO: 23 by culturing the transformant.

9. The kit for screening according to claim 3, which comprises a protein comprising the amino acid sequence represented by SEQ ID NO: 1 and SEQ ID NO: 3, their amide or its ester, or salts thereof.

* * * * *

SEQUENCE LISTING

<160> NUMBER OF SEQ ID NOS: 124

<210> SEQ ID NO 1
<211> LENGTH: 371
<212> TYPE: PRT
<213> ORGANISM: Human

<400> SEQUENCE: 1

Met Pro Ala Asn Phe Thr Glu Gly Ser Phe Asp Ser Ser Gly Thr Gly
            5                  10                 15

Gln Thr Leu Asp Ser Ser Pro Val Ala Cys Thr Glu Thr Val Thr Phe
            20                 25                 30

Thr Glu Val Val Glu Gly Lys Glu Trp Gly Ser Phe Tyr Tyr Ser Phe
            35                 40                 45

Lys Thr Glu Gln Leu Ile Thr Leu Trp Val Leu Phe Val Phe Thr Ile
 50                 55                 60

Val Gly Asn Ser Val Val Leu Phe Ser Thr Trp Arg Arg Lys Lys Lys
 65                 70                 75                 80

Ser Arg Met Thr Phe Phe Val Thr Gln Leu Ala Ile Thr Asp Ser Phe
            85                 90                 95

Thr Gly Leu Val Asn Ile Leu Thr Asp Ile Asn Trp Arg Phe Thr Gly
            100                105                110

Asp Phe Thr Ala Pro Asp Leu Val Cys Arg Val Val Arg Tyr Leu Gln
            115                120                125

Val Val Leu Leu Tyr Ala Ser Thr Tyr Val Leu Val Ser Leu Ser Ile
 130                135                140

Asp Arg Tyr His Ala Ile Val Tyr Pro Met Lys Phe Leu Gln Gly Glu
145                 150                155                160

Lys Gln Ala Arg Val Leu Ile Val Ile Ala Trp Ser Leu Ser Phe Leu
            165                170                175

Phe Ser Ile Pro Thr Leu Ile Ile Phe Gly Lys Arg Thr Leu Ser Asn
            180                185                190

Gly Glu Val Gln Cys Trp Ala Leu Trp Pro Asp Asp Ser Tyr Trp Thr
            195                200                205

Pro Tyr Met Thr Ile Val Ala Phe Leu Val Tyr Phe Ile Pro Leu Thr
            210                215                220

Ile Ile Ser Ile Met Tyr Gly Ile Val Ile Arg Thr Ile Trp Ile Lys
225                 230                235                240

Ser Lys Thr Tyr Glu Thr Val Ile Ser Asn Cys Ser Asp Gly Lys Leu
            245                250                255

Cys Ser Ser Tyr Asn Arg Gly Leu Ile Ser Lys Ala Lys Ile Lys Ala
            260                265                270

Ile Lys Tyr Ser Ile Ile Ile Leu Ala Phe Ile Cys Cys Trp Ser
            275                280                285

Pro Tyr Phe Leu Phe Asp Ile Leu Asp Asn Phe Asn Leu Leu Pro Asp
            290                295                300

Thr Gln Glu Arg Phe Tyr Ala Ser Val Ile Ile Gln Asn Leu Pro Ala
305                 310                315                320

Leu Asn Ser Ala Ile Asn Pro Leu Ile Tyr Cys Val Phe Ser Ser Ser
            325                330                335

Ile Ser Phe Pro Cys Arg Glu Gln Arg Ser Gln Asp Ser Arg Met Thr
            340                345                350

Phe Arg Glu Arg Thr Glu Arg His Glu Met Gln Ile Leu Ser Lys Pro
            355                360                365

Glu Phe Ile
 370

<210> SEQ ID NO 2
<211> LENGTH: 1113
<212> TYPE: DNA
<213> ORGANISM: Human

-continued

```
<400> SEQUENCE: 2
atgccagcca acttcacaga gggcagcttc gattccagtg ggaccgggca gacgctggat      60
tcttccccag tggcttgcac tgaaacagtg acttttactg aagtggtgga aggaaaggaa    120
tggggttcct tctactactc ctttaagact gagcaattga taactctgtg ggtcctcttt    180 gttttacca ttgttggaaa ctccgttgtg cttttttcca catggaggag aaagaagaag     240
tcaagaatga ccttctttgt gactcagctg ccatcacaga ttctttcac aggactggtc     300 aacatcttga cagatattaa ttggcgattc actggagact tcacggcacc tgacctggtt    360
tgccgagtgg tccgctattt gcaggttgtg ctgctctacg cctctaccta cgtcctggtg    420
tccctcagca tagacagata ccatgccatc gtctaccca tgaagttcct tcaaggagaa    480
aagcaagcca gggtcctcat tgtgatcgcc tggagcctgt cttttctgtt ctccattccc    540
accctgatca tatttgggaa gaggacactg tccaacggtg aagtgcagtg ctgggccctg    600
tggcctgacg actcctactg acccccatac atgaccatcg tggccttcct ggtgtacttc    660
atccctctga caatcatcag catcatgtat ggcattgtga tccgaactat ttggattaaa    720
agcaaaacct acgaaacagt gatttccaac tgctcagatg ggaaactgtg cagcagctat    780
aaccgaggac tcatctcaaa ggcaaaaatc aaggctatca gtatagcat catcatcatt     840 cttgccttca tctgctgttg gagtccatac ttcctgtttg acattttgga caatttcaac    900
ctccttccag acacccagga gcgtttctat gcctctgtga tcattcagaa cctgccagca    960
ttgaatagtg ccatcaaccc cctcatctac tgtgtcttca gcagctccat ctctttcccc   1020
tgcagggagc aaagatcaca ggattccaga atgacgttcc gggagagaac tgagaggcat   1080
gagatgcaga ttctgtccaa gccagaattc atc                                1113

<210> SEQ ID NO 3
<211> LENGTH: 371
<212> TYPE: PRT
<213> ORGANISM: Human

<400> SEQUENCE: 3

Met Pro Ala Asn Phe Thr Glu Gly Ser Phe Asp Ser Ser Gly Thr Gly
                 5                  10                  15

Gln Thr Leu Asp Ser Ser Pro Val Ala Cys Thr Glu Thr Val Thr Phe
             20                  25                  30

Thr Glu Val Val Glu Gly Lys Glu Trp Gly Ser Phe Tyr Tyr Ser Phe
         35                  40                  45

Lys Thr Glu Gln Leu Ile Thr Leu Trp Val Leu Phe Val Phe Thr Ile
     50                  55                  60

Val Gly Asn Ser Val Val Leu Phe Ser Thr Trp Arg Arg Lys Lys Lys
 65                  70                  75                  80

Ser Arg Met Thr Phe Phe Val Thr Gln Leu Ala Ile Thr Asp Ser Phe
                 85                  90                  95

Thr Gly Leu Val Asn Ile Leu Thr Asp Ile Ile Trp Arg Phe Thr Gly
            100                 105                 110

Asp Phe Thr Ala Pro Asp Leu Val Cys Arg Val Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Glu
145                 150                 155                 160

Lys Gln Ala Arg Val Leu Ile Val Ile Ala Trp Ser Leu Ser Phe Leu
```

-continued

```
                    165                 170                 175
Phe Ser Ile Pro Thr Leu Ile Ile Phe Gly Lys Arg Thr Leu Ser Asn
                180                 185                 190
Gly Glu Val Gln Cys Trp Ala Leu Trp Pro Asp Asp Ser Tyr Trp Thr
            195                 200                 205
Pro Tyr Met Thr Ile Val Ala Phe Leu Val Tyr Phe Ile Pro Leu Thr
        210                 215                 220
Ile Ile Ser Ile Met Tyr Gly Ile Val Ile Arg Thr Ile Trp Ile Lys
225                 230                 235                 240
Ser Lys Thr Tyr Glu Thr Val Ile Ser Asn Cys Ser Asp Gly Lys Leu
                245                 250                 255
Cys Ser Ser Tyr Asn Arg Gly Leu Ile Ser Lys Ala Lys Ile Lys Ala
            260                 265                 270
Ile Lys Tyr Ser Ile Ile Ile Leu Ala Phe Ile Cys Cys Trp Ser
        275                 280                 285
Pro Tyr Phe Leu Phe Asp Ile Leu Asp Asn Phe Asn Leu Leu Pro Asp
        290                 295                 300
Thr Gln Glu Arg Phe Tyr Ala Ser Val Ile Ile Gln Asn Leu Pro Ala
305                 310                 315                 320
Leu Asn Ser Ala Ile Asn Pro Leu Ile Tyr Cys Val Phe Ser Ser Ser
                325                 330                 335
Ile Ser Phe Pro Cys Arg Glu Arg Ser Gln Asp Ser Arg Met Thr
            340                 345                 350
Phe Arg Glu Arg Thr Glu Arg His Glu Met Gln Ile Leu Ser Lys Pro
        355                 360                 365
Glu Phe Ile
    370

<210> SEQ ID NO 4
<211> LENGTH: 1113
<212> TYPE: DNA
<213> ORGANISM: Human

<400> SEQUENCE: 4
atgccagcca acttcacaga gggcagcttc gattccagtg ggaccgggca gacgctggat      60
tcttccccag tggcttgcac tgaaacagtg acttttactg aagtggtgga aggaaaggaa     120
tggggttcct tctactactc ctttaagact gagcaattga taactctgtg ggtcctcttt     180
gttttacca ttgttggaaa ctccgttgtg cttttttcca catggaggag aaagaagaag      240
tcaagaatga ccttctttgt gactcagctg gccatacag attctttcac aggactggtc      300
aacatcttga cagatattat ttggcgattc actggagact tcacggcacc tgacctggtt     360
tgccgagtgg tccgctattt gcaggttgtg ctgctctacg cctctaccta cgtcctggtg     420
tccctcagca tagacagata ccatgccatc gtctacccca tgaagttcct tcaaggagaa     480
aagcaagcca gggtcctcat tgtgatcgcc tggagcctgt ctttctgtt ctccattccc      540
accctgatca tatttgggaa gaggacactg tccaacggtg aagtgcagtg ctgggccctg     600
tggcctgacg actcctactg gacccatac atgaccatcg tggcctttct ggtgtacttc      660
atccctctga caatcatcag catcatgtat ggcattgtga tccgaactat ttggattaaa     720
agcaaaacct acgaaacagt gatttccaac tgctcagatg ggaaactgtg cagcagctat     780
aaccgaggac tcatctcaaa ggcaaaaatc aaggctatca gtatagcat catcatcatt     840
cttgccttca tctgctgttg gagtccatac ttcctgtttg acattttgga caatttcaac     900
```

```
ctccttccag acacccagga gcgtttctat gcctctgtga tcattcagaa cctgccagca      960
ttgaatagtg ccatcaaccc cctcatctac tgtgtcttca gcagctccat ctctttcccc     1020
tgcagggagc gaagatcaca ggattccaga atgacgttcc gggagagaac cgagaggcat     1080
gagatgcaga ttctgtccaa gccagaattc atc                                  1113
```

<210> SEQ ID NO 5
<211> LENGTH: 22
<212> TYPE: DNA
<213> ORGANISM: Artificial Sequence
<220> FEATURE:
<223> OTHER INFORMATION: Designed oligonucleotide primer to amplify DNA encoding TGR23-1 or TGR23-2

<400> SEQUENCE: 5

```
atgccagcca acttcacaga gg                                                22
```

<210> SEQ ID NO 6
<211> LENGTH: 24
<212> TYPE: DNA
<213> ORGANISM: Artificial Sequence
<220> FEATURE:
<223> OTHER INFORMATION: Designed oligonucleotide primer to amplify DNA encoding TGR23-1 or TGR23-2

<400> SEQUENCE: 6

```
ctagatgaat tctggcttgg acag                                              24
```

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7

```
tatagtcgac atgccagcca acttcac                                           27
```

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8

```
tgtcactagt ctagatgaat tctggctt                                          28
```

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9

```
ttcactggag acttcacggc a                                                 21
```

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10

```
tagaggcgta gagcagcaca ac                                          22

<210> SEQ ID NO 11
<211> LENGTH: 28
<212> TYPE: DNA
<213> ORGANISM: Artificial Sequence
<220> FEATURE:
<223> OTHER INFORMATION: Probe

<400> SEQUENCE: 11
acctggtttg ccgagtggtc cgctattt                                    28

<210> SEQ ID NO 12
<211> LENGTH: 18
<212> TYPE: PRT
<213> ORGANISM: Rat

<400> SEQUENCE: 12

Ser Phe Arg Asn Gly Val Gly Ser Gly Val Lys Lys Thr Ser Phe Arg
            5                   10                  15
Arg Ala

<210> SEQ ID NO 13
<211> LENGTH: 15
<212> TYPE: PRT
<213> ORGANISM: Rat

<400> SEQUENCE: 13

Ser Phe Arg Asn Gly Val Gly Ser Gly Val Lys Lys Thr Ser Phe
            5                   10                  15

<210> SEQ ID NO 14
<211> LENGTH: 14
<212> TYPE: PRT
<213> ORGANISM: Rat

<400> SEQUENCE: 14

Ser Phe Arg Asn Gly Val Gly Ser Gly Val Lys Lys Thr Ser
            5                   10

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
cagattttgg gaagtccaaa atga                                        24

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
gagtacgtca gtcacactct acag                                        24

<210> SEQ ID NO 17
<211> LENGTH: 24
<212> TYPE: DNA
<213> ORGANISM: Artificial Sequence
```

```
<220> FEATURE:
<223> OTHER INFORMATION: Primer

<400> SEQUENCE: 17
agattaattc cccgagtcct ttgc                                           24

<210> SEQ ID NO 18
<211> LENGTH: 322
<212> TYPE: DNA
<213> ORGANISM: Human

<400> SEQUENCE: 18
cagattttgg gaagtccaaa atgattagct cagtaaaact caatctcatc ctagttctgt    60
cgctgtccac aatgcatgtg ttttggtgtt atccagttcc atcttctaag gtgtctggaa   120
aatctgatta ctttctcatt ctgctgaaca gctgcccaac cagattggac aggagcaaag   180
aactagcttt tctaaagcca attttggaga agatgtttgt gaaaaggtcc tttcgcaatg   240
gagttggcac agggatgaaa aaaacttcct ttcaaagagc aaaatcatga ctaagtgtgc   300
aaaggactcg gggaattaat ct                                           322

<210> SEQ ID NO 19
<211> LENGTH: 89
<212> TYPE: PRT
<213> ORGANISM: Human

<400> SEQUENCE: 19

Met Ile Ser Ser Val Lys Leu Asn Leu Ile Leu Val Leu Ser Leu Ser
                  5                  10                  15

Thr Met His Val Phe Trp Cys Tyr Pro Val Pro Ser Ser Lys Val Ser
             20                  25                  30

Gly Lys Ser Asp Tyr Phe Leu Ile Leu Leu Asn Ser Cys Pro Thr Arg
         35                  40                  45

Leu Asp Arg Ser Lys Glu Leu Ala Phe Leu Lys Pro Ile Leu Glu Lys
     50                  55                  60

Met Phe Val Lys Arg Ser Phe Arg Asn Gly Val Gly Thr Gly Met Lys
 65                  70                  75                  80

Lys Thr Ser Phe Gln Arg Ala Lys Ser
                 85

<210> SEQ ID NO 20
<211> LENGTH: 18
<212> TYPE: PRT
<213> ORGANISM: Human

<400> SEQUENCE: 20

Ser Phe Arg Asn Gly Val Gly Thr Gly Met Lys Lys Thr Ser Phe Gln
                  5                  10                  15

Arg Ala

<210> SEQ ID NO 21
<211> LENGTH: 15
<212> TYPE: PRT
<213> ORGANISM: Human

<400> SEQUENCE: 21

Ser Phe Arg Asn Gly Val Gly Thr Gly Met Lys Lys Thr Ser Phe
                  5                  10                  15

<210> SEQ ID NO 22
```

```
<211> LENGTH: 14
<212> TYPE: PRT
<213> ORGANISM: Human

<400> SEQUENCE: 22

Ser Phe Arg Asn Gly Val Gly Thr Gly Met Lys Lys Thr Ser
                5                   10

<210> SEQ ID NO 23
<211> LENGTH: 20
<212> TYPE: PRT
<213> ORGANISM: Human

<400> SEQUENCE: 23

Ser Phe Arg Asn Gly Val Gly Thr Gly Met Lys Lys Thr Ser Phe Gln
                5                   10                  15

Arg Ala Lys Ser
            20

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
ccagtcacac aggagggatc tcaa                                           24

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
gcacatcagt cacactctac atag                                           24

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
agattaattc ccagagtcct ttgc                                           24

<210> SEQ ID NO 27
<211> LENGTH: 443
<212> TYPE: DNA
<213> ORGANISM: Mouse

<400> SEQUENCE: 27
ccagtcacac aggagggatc tcaatgacat ttttacttct gaactttttct aatataaaag    60 ggccacccaa gcaggctcag acagcaaacg tgaggaaatt ggcaataaaa acccatctgc   120
gcaggtctcg gaaaatccaa aatgattggc tcgttaaaac tcagcttcgt cttagctctg   180
tcgctgtctg taatgcacgt gctttggtgt tatccggtcc tctcttccaa ggtgcctggg   240
aagcctgatt actttctcat cttgctgagc agctgcccag ccaggctgga ggggagcgac   300
aggctagctt ttctaaagcc aatttttggag aagacatcga tgaaaaggtc ctttcgcaac   360
```

```
ggagtcggct caggggcgaa aaaaacttcg tttcgaagag caaagcaatg aataagtgtg    420
caaaggactc tgggaattaa tct                                            443
```

<210> SEQ ID NO 28
<211> LENGTH: 89
<212> TYPE: PRT
<213> ORGANISM: Mouse

<400> SEQUENCE: 28

Met Ile Gly Ser Leu Lys Leu Ser Phe Val Leu Ala Leu Ser Leu Ser
            5                   10                  15

Val Met His Val Leu Trp Cys Tyr Pro Val Leu Ser Ser Lys Val Pro
        20                  25                  30

Gly Lys Pro Asp Tyr Phe Leu Ile Leu Leu Ser Ser Cys Pro Ala Arg
    35                  40                  45

Leu Glu Gly Ser Asp Arg Leu Ala Phe Leu Lys Pro Ile Leu Glu Lys
50                  55                  60

Thr Ser Met Lys Arg Ser Phe Arg Asn Gly Val Gly Ser Gly Ala Lys
65                  70                  75                  80

Lys Thr Ser Phe Arg Arg Ala Lys Gln
                85

<210> SEQ ID NO 29
<211> LENGTH: 18
<212> TYPE: PRT
<213> ORGANISM: Mouse

<400> SEQUENCE: 29

Ser Phe Arg Asn Gly Val Gly Ser Gly Ala Lys Lys Thr Ser Phe Arg
            5                   10                  15

Arg Ala

<210> SEQ ID NO 30
<211> LENGTH: 15
<212> TYPE: PRT
<213> ORGANISM: Mouse

<400> SEQUENCE: 30

Ser Phe Arg Asn Gly Val Gly Ser Gly Ala Lys Lys Thr Ser Phe
            5                   10                  15

<210> SEQ ID NO 31
<211> LENGTH: 14
<212> TYPE: PRT
<213> ORGANISM: Mouse

<400> SEQUENCE: 31

Ser Phe Arg Asn Gly Val Gly Ser Gly Ala Lys Lys Thr Ser
            5                   10

<210> SEQ ID NO 32
<211> LENGTH: 20
<212> TYPE: PRT
<213> ORGANISM: Mouse

<400> SEQUENCE: 32

Ser Phe Arg Asn Gly Val Gly Ser Gly Ala Lys Lys Thr Ser Phe Arg
            5                   10                  15

Arg Ala Lys Gln
            20

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
ctgattactt tctcatyytg ctga                                          24

<210> SEQ ID NO 34
<211> LENGTH: 199
<212> TYPE: DNA
<213> ORGANISM: Rat

<400> SEQUENCE: 34
ctgattactt tctcattttg ctgagtacct gcccagccag gctggagggg agcgacgggc    60
tagcttttct aaagccaatt ttggagaaga cgtcgatgaa aaggtccttt cgcaacggag   120
tcggctcagg ggtgaaaaaa acttcatttc gaagagcaaa gcaatgaata agtgtgcaaa   180
ggactctggg aattaatct                                                199

<210> SEQ ID NO 35
<211> LENGTH: 54
<212> TYPE: PRT
<213> ORGANISM: Rat

<400> SEQUENCE: 35

Asp Tyr Phe Leu Ile Leu Leu Ser Thr Cys Pro Ala Arg Leu Glu Gly
                5                  10                  15
Ser Asp Gly Leu Ala Phe Leu Lys Pro Ile Leu Glu Lys Thr Ser Met
            20                  25                  30
Lys Arg Ser Phe Arg Asn Gly Val Gly Ser Gly Val Lys Lys Thr Ser
        35                  40                  45
Phe Arg Arg Ala Lys Gln
    50

<210> SEQ ID NO 36
<211> LENGTH: 20
<212> TYPE: PRT
<213> ORGANISM: Rat

<400> SEQUENCE: 36

Ser Phe Arg Asn Gly Val Gly Ser Gly Val Lys Lys Thr Ser Phe Arg
                5                  10                  15
Arg Ala Lys Gln
            20

<210> SEQ ID NO 37
<211> LENGTH: 54
<212> TYPE: DNA
<213> ORGANISM: Rat

<400> SEQUENCE: 37
tcctttcgca acggagtcgg ctcaggggtg aaaaaaactt catttcgaag agca          54

<210> SEQ ID NO 38
<211> LENGTH: 45
<212> TYPE: DNA
<213> ORGANISM: Rat

<400> SEQUENCE: 38

```
tcctttcgca acggagtcgg ctcaggggtg aaaaaaactt cattt          45

<210> SEQ ID NO 39
<211> LENGTH: 42
<212> TYPE: DNA
<213> ORGANISM: Rat

<400> SEQUENCE: 39
tcctttcgca acggagtcgg ctcaggggtg aaaaaaactt ca             42

<210> SEQ ID NO 40
<211> LENGTH: 60
<212> TYPE: DNA
<213> ORGANISM: Rat

<400> SEQUENCE: 40
tcctttcgca acggagtcgg ctcaggggtg aaaaaaactt catttcgaag agcaaagcaa  60

<210> SEQ ID NO 41
<211> LENGTH: 54
<212> TYPE: DNA
<213> ORGANISM: Human

<400> SEQUENCE: 41
tcctttcgca atggagttgg cacagggatg aaaaaaactt cctttcaaag agca       54

<210> SEQ ID NO 42
<211> LENGTH: 45
<212> TYPE: DNA
<213> ORGANISM: Human

<400> SEQUENCE: 42
tcctttcgca atggagttgg cacagggatg aaaaaaactt cctttt       45

<210> SEQ ID NO 43
<211> LENGTH: 42
<212> TYPE: DNA
<213> ORGANISM: Human

<400> SEQUENCE: 43
tcctttcgca atggagttgg cacagggatg aaaaaaactt cc             42

<210> SEQ ID NO 44
<211> LENGTH: 60
<212> TYPE: DNA
<213> ORGANISM: Human

<400> SEQUENCE: 44
tcctttcgca atggagttgg cacagggatg aaaaaaactt cctttcaaag agcaaaatca  60

<210> SEQ ID NO 45
<211> LENGTH: 54
<212> TYPE: DNA
<213> ORGANISM: Mouse

<400> SEQUENCE: 45
tcctttcgca acggagtcgg ctcaggggcg aaaaaaactt cgtttcgaag agca       54

<210> SEQ ID NO 46
<211> LENGTH: 45
<212> TYPE: DNA
<213> ORGANISM: Mouse
```

-continued

<400> SEQUENCE: 46
tcctttcgca acggagtcgg ctcagggggcg aaaaaaactt cgttt                45

<210> SEQ ID NO 47
<211> LENGTH: 42
<212> TYPE: DNA
<213> ORGANISM: Mouse

<400> SEQUENCE: 47
tcctttcgca acggagtcgg ctcagggggcg aaaaaaactt cg                   42

<210> SEQ ID NO 48
<211> LENGTH: 60
<212> TYPE: DNA
<213> ORGANISM: Mouse

<400> SEQUENCE: 48
tcctttcgca acggagtcgg ctcagggggcg aaaaaaactt cgtttcgaag agcaaagcaa   60

<210> SEQ ID NO 49
<211> LENGTH: 16
<212> TYPE: PRT
<213> ORGANISM: Human

<400> SEQUENCE: 49

Ser Phe Arg Asn Gly Val Gly Thr Gly Met Lys Lys Thr Ser Phe Gln
              5                  10                  15

<210> SEQ ID NO 50
<211> LENGTH: 48
<212> TYPE: DNA
<213> ORGANISM: Human

<400> SEQUENCE: 50
tcctttcgca atggagttgg cacagggatg aaaaaaactt cctttcaa              48

<210> SEQ ID NO 51
<211> LENGTH: 371
<212> TYPE: PRT
<213> ORGANISM: Human
<220> FEATURE:
<221> NAME/KEY: VARIANT
<222> LOCATION: 273
<223> OTHER INFORMATION: Xaa is Val or Ile.
<220> FEATURE:
<221> NAME/KEY: VARIANT
<222> LOCATION: 308
<223> OTHER INFORMATION: Xaa is Arg or His.

<400> SEQUENCE: 51

Met Pro Ala Asn Phe Thr Glu Gly Ser Phe Asp Ser Ser Gly Thr Gly
              5                  10                  15

Gln Thr Leu Asp Ser Ser Pro Val Ala Cys Thr Glu Thr Val Thr Phe
             20                  25                  30

Thr Glu Val Val Glu Gly Lys Glu Trp Gly Ser Phe Tyr Tyr Ser Phe
         35                  40                  45

Lys Thr Glu Gln Leu Ile Thr Leu Trp Val Leu Phe Val Phe Thr Ile
     50                  55                  60

Val Gly Asn Ser Val Val Leu Phe Ser Thr Trp Arg Arg Lys Lys Lys
 65                  70                  75                  80

Ser Arg Met Thr Phe Phe Val Thr Gln Leu Ala Ile Thr Asp Ser Phe
                 85                  90                  95

-continued

```
Thr Gly Leu Val Asn Ile Leu Thr Asp Ile Asn Trp Arg Phe Thr Gly
            100                 105                 110

Asp Phe Thr Ala Pro Asp Leu Val Cys Arg Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Glu
145                 150                 155                 160

Lys Gln Ala Arg Val Leu Ile Val Ile Ala Trp Ser Leu Ser Phe Leu
                165                 170                 175

Phe Ser Ile Pro Thr Leu Ile Ile Phe Gly Lys Arg Thr Leu Ser Asn
            180                 185                 190

Gly Glu Val Gln Cys Trp Ala Leu Trp Pro Asp Asp Ser Tyr Trp Thr
        195                 200                 205

Pro Tyr Met Thr Ile Val Ala Phe Leu Val Tyr Phe Ile Pro Leu Thr
    210                 215                 220

Ile Ile Ser Ile Met Tyr Gly Ile Val Ile Arg Thr Ile Trp Ile Lys
225                 230                 235                 240

Ser Lys Thr Tyr Glu Thr Val Ile Ser Asn Cys Ser Asp Gly Lys Leu
                245                 250                 255

Cys Ser Ser Tyr Asn Arg Gly Leu Ile Ser Lys Ala Lys Ile Lys Ala
            260                 265                 270

Xaa Lys Tyr Ser Ile Ile Ile Leu Ala Phe Ile Cys Cys Trp Ser
        275                 280                 285

Pro Tyr Phe Leu Phe Asp Ile Leu Asp Asn Phe Asn Leu Leu Pro Asp
    290                 295                 300

Thr Gln Glu Xaa Phe Tyr Ala Ser Val Ile Ile Gln Asn Leu Pro Ala
305                 310                 315                 320

Leu Asn Ser Ala Ile Asn Pro Leu Ile Tyr Cys Val Phe Ser Ser Ser
                325                 330                 335

Ile Ser Phe Pro Cys Arg Glu Arg Ser Gln Asp Ser Arg Met Thr
            340                 345                 350

Phe Arg Glu Arg Thr Glu Arg His Glu Met Gln Ile Leu Ser Lys Pro
        355                 360                 365

Glu Phe Ile
    370
```

<210> SEQ ID NO 52
<211> LENGTH: 1113
<212> TYPE: DNA
<213> ORGANISM: Human

<400> SEQUENCE: 52

```
atgccagcca acttcacaga gggcagcttc gattccagtg ggaccgggca gacgctggat    60
tcttccccag tggcttgcac tgaaacagtg acttttacta agtggtggaa ggaaaaggaa   120
tggggttcct tctactactc ctttaagact gagcaattga taactctgtg ggtcctcttt   180
gtttttacca ttgttggaaa ctccgttgtg ctttttttcca catggaggag aaagaagaag   240
tcaagaatga ccttctttgt gactcagctg ccatcacag attctttcac aggactggtc   300
aacatcttga cagatattaa ttggcgattc actggagact tcacggcacc tgacctggtt   360
tgccgagtgg tccgctattt gcaggttgtg ctgctctacg cctctaccta cgtcctggtg   420
tccctcagca tagacagata ccatgccatc gtctacccca tgaagttcct tcaaggagaa   480
aagcaagcca gggtcctcat tgtgatcgcc tggagcctgt cttttctgtt ctccattccc   540
```

-continued

```
acccctgatca tatttgggaa gaggacactg tccaacggtg aagtgcagtg ctgggccctg      600
tggcctgacg actcctactg gaccccatac atgaccatcg tggccttcct ggtgtacttc      660
atccctctga caatcatcag catcatgtat ggcattgtga tccgaactat ttggattaaa      720
agcaaaacct acgaaacagt gatttccaac tgctcagatg ggaaactgtg cagcagctat      780
aaccgaggac tcatctcaaa ggcaaaaatc aaggctrtca agtatagcat catcatcatt      840
cttgccttca tctgctgttg gagtccatac ttcctgtttg acattttgga caatttcaac      900
ctccttccag acacccagga gcrtttctat gcctctgtga tcattcagaa cctgccagca      960
ttgaatagtg ccatcaaccc cctcatctac tgtgtcttca gcagctccat ctctttcccc     1020
tgcagggagc gaagatcaca ggattccaga atgacgttcc gggagagaac cgagaggcat     1080
gagatgcaga ttctgtccaa gccagaattc atc                                  1113
```

<210> SEQ ID NO 53
<211> LENGTH: 371
<212> TYPE: PRT
<213> ORGANISM: Human

<400> SEQUENCE: 53

```
Met Pro Ala Asn Phe Thr Glu Gly Ser Phe Asp Ser Ser Gly Thr Gly
                5                   10                  15
Gln Thr Leu Asp Ser Ser Pro Val Ala Cys Thr Glu Thr Val Thr Phe
            20                  25                  30
Thr Glu Val Val Glu Gly Lys Glu Trp Gly Ser Phe Tyr Tyr Ser Phe
        35                  40                  45
Lys Thr Glu Gln Leu Ile Thr Leu Trp Val Leu Phe Val Phe Thr Ile
    50                  55                  60
Val Gly Asn Ser Val Val Leu Phe Ser Thr Trp Arg Arg Lys Lys Lys
65                  70                  75                  80
Ser Arg Met Thr Phe Phe Val Thr Gln Leu Ala Ile Thr Asp Ser Phe
                85                  90                  95
Thr Gly Leu Val Asn Ile Leu Thr Asp Ile Asn Trp Arg Phe Thr Gly
            100                 105                 110
Asp Phe Thr Ala Pro Asp Leu Val Cys Arg Val Val Arg Tyr Leu Gln
        115                 120                 125
Val Val Leu Leu Tyr Ala Ser Thr Tyr Val Leu Val Ser Leu Ser Ile
    130                 135                 140
Asp Arg Tyr His Ala Ile Val Tyr Pro Met Lys Phe Leu Gln Gly Glu
145                 150                 155                 160
Lys Gln Ala Arg Val Leu Ile Val Ile Ala Trp Ser Leu Ser Phe Leu
                165                 170                 175
Phe Ser Ile Pro Thr Leu Ile Ile Phe Gly Lys Arg Thr Leu Ser Asn
            180                 185                 190
Gly Glu Val Gln Cys Trp Ala Leu Trp Pro Asp Asp Ser Tyr Trp Thr
        195                 200                 205
Pro Tyr Met Thr Ile Val Ala Phe Leu Val Tyr Phe Ile Pro Leu Thr
    210                 215                 220
Ile Ile Ser Ile Met Tyr Gly Ile Val Ile Arg Thr Ile Trp Ile Lys
225                 230                 235                 240
Ser Lys Thr Tyr Glu Thr Val Ile Ser Asn Cys Ser Asp Gly Lys Leu
                245                 250                 255
Cys Ser Ser Tyr Asn Arg Gly Leu Ile Ser Lys Ala Lys Ile Lys Ala
            260                 265                 270
```

```
Ile Lys Tyr Ser Ile Ile Ile Leu Ala Phe Ile Cys Cys Trp Ser
        275                 280                 285

Pro Tyr Phe Leu Phe Asp Ile Leu Asp Asn Phe Asn Leu Leu Pro Asp
    290                 295                 300

Thr Gln Glu Arg Phe Tyr Ala Ser Val Ile Ile Gln Asn Leu Pro Ala
305                 310                 315                 320

Leu Asn Ser Ala Ile Asn Pro Leu Ile Tyr Cys Val Phe Ser Ser Ser
                325                 330                 335

Ile Ser Phe Pro Cys Arg Glu Gln Arg Ser Gln Asp Ser Arg Met Thr
                340                 345                 350

Phe Arg Glu Arg Thr Glu Arg His Glu Met Gln Ile Leu Ser Lys Pro
            355                 360                 365

Glu Phe Ile
    370
```

<210> SEQ ID NO 54
<211> LENGTH: 1113
<212> TYPE: DNA
<213> ORGANISM: Human

<400> SEQUENCE: 54

```
atgccagcca acttcacaga gggcagcttc gattccagtg ggaccgggca gacgctggat      60
tcttccccag tggcttgcac tgaaacagtg acttttactg aagtggtgga aggaaaggaa     120
tggggttcct tctactactc ctttaagact gagcaattga taactctgtg ggtcctcttt     180
gttttaccca ttgttggaaa ctccgttgtg ctttttttcca catggaggag aaagaagaag     240
tcaagaatga ccttctttgt gactcagctg ccatcacag attctttcac aggactggtc     300
aacatcttga cagatattaa ttggcgattc actggagact tcacggcacc tgacctggtt     360
tgccgagtgg tccgctattt gcaggttgtg ctgctctacg cctctaccta cgtcctggtg     420
tccctcagca tagacagata ccatgccatc gtctacccca tgaagttcct tcaaggagaa     480
aagcaagcca gggtcctcat tgtgatcgcc tggagcctgt cttttctgtt ctccattccc     540
accctgatca tatttgggaa gaggacactg tccaacggtg aagtgcagtg ctgggccctg     600
tggcctgacg actcctactg gaccccatac atgaccatcg tggccttcct ggtgtacttc     660
atccctctga caatcatcag catcatgtat ggcattgtga tccgaactat ttggattaaa     720
agcaaaacct acgaaacagt gatttccaac tgctcagatg ggaaactgtg cagcagctat     780
aaccgaggac tcatctcaaa ggcaaaaatc aaggctatca gtatagcat catcatcatt     840
cttgccttca tctgctgttg gagtccatac ttcctgtttg acattttgga caatttcaac     900
ctccttccag acacccagga gcgtttctat gcctctgtga tcattcagaa cctgccagca     960
ttgaatagtg ccatcaaccc cctcatctac tgtgtcttca gcagctccat ctctttcccc    1020
tgcagggagc aaagatcaca ggattccaga atgacgttcc gggagagaac tgagaggcat    1080
gagatgcaga ttctgtccaa gccagaattc atc                                  1113
```

<210> SEQ ID NO 55
<211> LENGTH: 371
<212> TYPE: PRT
<213> ORGANISM: Human

<400> SEQUENCE: 55

```
Met Pro Ala Asn Phe Thr Glu Gly Ser Phe Asp Ser Ser Gly Thr Gly
                5                   10                  15
```

```
Gln Thr Leu Asp Ser Ser Pro Val Ala Cys Thr Glu Thr Val Thr Phe
                 20                  25                  30
Thr Glu Val Val Glu Gly Lys Glu Trp Gly Ser Phe Tyr Tyr Ser Phe
             35                  40                  45
Lys Thr Glu Gln Leu Ile Thr Leu Trp Val Leu Phe Val Phe Thr Ile
         50                  55                  60
Val Gly Asn Ser Val Val Leu Phe Ser Thr Trp Arg Arg Lys Lys Lys
 65                  70                  75                  80
Ser Arg Met Thr Phe Phe Val Thr Gln Leu Ala Ile Thr Asp Ser Phe
                 85                  90                  95
Thr Gly Leu Val Asn Ile Leu Thr Asp Ile Ile Trp Arg Phe Thr Gly
            100                 105                 110
Asp Phe Thr Ala Pro Asp Leu Val Cys Arg Val Val Arg Tyr Leu Gln
            115                 120                 125
Val Val Leu Leu Tyr Ala Ser Thr Tyr Val Leu Val Ser Leu Ser Ile
130                 135                 140
Asp Arg Tyr His Ala Ile Val Tyr Pro Met Lys Phe Leu Gln Gly Glu
145                 150                 155                 160
Lys Gln Ala Arg Val Leu Ile Val Ile Ala Trp Ser Leu Ser Phe Leu
                165                 170                 175
Phe Ser Ile Pro Thr Leu Ile Ile Phe Gly Lys Arg Thr Leu Ser Asn
            180                 185                 190
Gly Glu Val Gln Cys Trp Ala Leu Trp Pro Gly Asp Ser Tyr Trp Thr
            195                 200                 205
Pro Tyr Met Thr Ile Val Ala Phe Leu Val Tyr Phe Ile Pro Leu Thr
        210                 215                 220
Ile Ile Ser Ile Met Tyr Gly Ile Val Ile Arg Thr Ile Trp Ile Lys
225                 230                 235                 240
Ser Lys Thr Tyr Glu Thr Val Ile Ser Asn Cys Ser Asp Gly Lys Leu
                245                 250                 255
Cys Ser Ser Tyr Asn Arg Gly Leu Ile Ser Lys Ala Lys Ile Lys Ala
            260                 265                 270
Ile Lys Tyr Ser Ile Ile Ile Leu Ala Phe Ile Cys Cys Trp Ser
            275                 280                 285
Pro Tyr Phe Leu Phe Asp Ile Leu Asp Asn Phe Asn Leu Leu Pro Asp
        290                 295                 300
Thr Gln Glu Arg Phe Tyr Ala Ser Val Ile Ile Gln Asn Leu Pro Ala
305                 310                 315                 320
Leu Asn Ser Ala Ile Asn Pro Pro Ile Tyr Cys Val Phe Ser Ser Ser
                325                 330                 335
Ile Ser Phe Pro Cys Arg Glu Gln Arg Ser Gln Asp Ser Arg Met Thr
            340                 345                 350
Phe Arg Glu Arg Thr Glu Arg His Glu Met Gln Ile Leu Ser Lys Pro
        355                 360                 365
Glu Phe Ile
    370

<210> SEQ ID NO 56
<211> LENGTH: 1113
<212> TYPE: DNA
<213> ORGANISM: Human

<400> SEQUENCE: 56
atgccagcca acttcacaga gggcagcttc gattccagtg ggaccgggca gacgctggat    60
```

```
tcttccccag tggcttgcac tgaaacagtg acttttactg aagtggtgga aggaaaggaa      120
tggggttcct tctactactc ctttaagact gagcaattga taactctgtg ggtcctcttt      180
gtttttacca ttgttggaaa ctccgttgtg ctttttccca catggaggag aaagaagaag      240
tcaagaatga ccttctttgt gactcagctg ccatcacag attctttcac aggactggtc       300
aacatcttga cagatattat ttggcgattc actggagact tcacggcacc tgacctggtt      360
tgccgagtgg tccgctattt gcaggttgtg ctgctctacg cctctaccta cgtcctggtg      420
tccctcagca tagacagata ccatgccatc gtctacccca tgaagttcct tcaaggagaa      480
aagcaagcca gggtcctcat tgtgatcgcc tggagcctgt cttttctgtt ctccattccc      540
accctgatca tatttgggaa gaggacactg tccaacggtg aagtgcagtg ctgggccctg      600
tggcctggcg actcctactg gacccccatac atgaccatcg tggccttcct ggtgtacttc      660
atccctctga caatcatcag catcatgtat ggcattgtga tccgaactat ttggattaaa      720
agcaaaacct acgaaacagt gatttccaac tgctcagatg ggaaactgtg cagcagctat      780
aaccgaggac tcatctcaaa ggcaaaaatc aaggctatca agtatagcat tatcatcatt      840
cttgccttca tctgctgttg gagtccatac ttcctgtttg acattttgga caatttcaac      900
ctccttccag acacccagga gcgtttctat gcctctgtga tcattcagaa cctgccagca      960
ttgaatagtg ccatcaaccc ccccatctac tgtgtcttca gcagctccat ctctttcccc     1020
tgcagggagc aaagatcaca ggattccaga atgacgttcc gggagagaac tgagaggcat     1080
gagatgcaga ttctgtccaa gccagaattc atc                                  1113

<210> SEQ ID NO 57
<211> LENGTH: 24
<212> TYPE: DNA
<213> ORGANISM: Artificial Sequence
<220> FEATURE:
<223> OTHER INFORMATION: Primer

<400> SEQUENCE: 57
cttaacaaga acaaaaggcc acag                                              24

<210> SEQ ID NO 58
<211> LENGTH: 26
<212> TYPE: DNA
<213> ORGANISM: Artificial Sequence
<220> FEATURE:
<223> OTHER INFORMATION: Primer

<400> SEQUENCE: 58
ttattcattg ctttgctctt cgaaat                                            26

<210> SEQ ID NO 59
<211> LENGTH: 26
<212> TYPE: DNA
<213> ORGANISM: Artificial Sequence
<220> FEATURE:
<223> OTHER INFORMATION: Primer

<400> SEQUENCE: 59
ccacccaagc aggctcagac agcgag                                            26

<210> SEQ ID NO 60
<211> LENGTH: 353
<212> TYPE: DNA
<213> ORGANISM: Rat

<400> SEQUENCE: 60
```

-continued

```
ccacccaagc aggctcagac agcgagcgtg aggaatttgg caataaaaac ccatctgcac      60
agatctcgga aaatccaaaa tgattggctc attaaaactc aacctcatct tagctctgtc     120
gctgtccgtg gtacacgtga tttggagtta tccggtcctc tcttccaagg tgcctgggaa     180
gcctgattac tttctcattt tgctgagtac ctgcccagcc aggctggagg ggagcgacgg     240
gctagctttt ctaaagccaa ttttggagaa gacgtcgatg aaaaggtcct ttcgcaacgg     300
agtcggctca ggggtgaaaa aaacttcatt tcgaagagca aagcaatgaa taa            353
```

<210> SEQ ID NO 61
<211> LENGTH: 89
<212> TYPE: PRT
<213> ORGANISM: Rat

<400> SEQUENCE: 61

Met Ile Gly Ser Leu Lys Leu Asn Leu Ile Leu Ala Leu Ser Leu Ser
              5                  10                  15

Val Val His Val Ile Trp Ser Tyr Pro Val Leu Ser Ser Lys Val Pro
         20                  25                  30

Gly Lys Pro Asp Tyr Phe Leu Ile Leu Leu Ser Thr Cys Pro Ala Arg
     35                  40                  45

Leu Glu Gly Ser Asp Gly Leu Ala Phe Leu Lys Pro Ile Leu Glu Lys
 50                  55                  60

Thr Ser Met Lys Arg Ser Phe Arg Asn Gly Val Gly Ser Gly Val Lys
65                  70                  75                  80

Lys Thr Ser Phe Arg Arg Ala Lys Gln
                85

<210> SEQ ID NO 62
<211> LENGTH: 20
<212> TYPE: PRT
<213> ORGANISM: Artificial Sequence
<220> FEATURE:
<221> NAME/KEY: MUTAGEN
<222> LOCATION: 10
<223> OTHER INFORMATION: Nle

<400> SEQUENCE: 62

Ser Phe Arg Asn Gly Val Gly Thr Gly Xaa Lys Lys Thr Ser Tyr Gln
              5                  10                  15

Arg Ala Lys Ser
         20

<210> SEQ ID NO 63
<211> LENGTH: 371
<212> TYPE: PRT
<213> ORGANISM: Human

<400> SEQUENCE: 63

Met Pro Ala Asn Phe Thr Glu Gly Ser Phe Asp Ser Ser Gly Thr Gly
              5                  10                  15

Gln Thr Leu Asp Ser Ser Pro Val Ala Cys Thr Glu Thr Val Thr Phe
         20                  25                  30

Thr Glu Val Val Glu Gly Lys Glu Trp Gly Ser Phe Tyr Tyr Ser Phe
     35                  40                  45

Lys Thr Glu Gln Leu Ile Thr Leu Trp Val Leu Phe Val Phe Thr Ile
 50                  55                  60

Val Gly Asn Ser Val Val Leu Phe Ser Thr Trp Arg Arg Lys Lys Lys
65                  70                  75                  80

-continued

Ser Arg Met Thr Phe Phe Val Thr Gln Leu Ala Ile Thr Asp Ser Phe
                85                  90                  95

Thr Gly Leu Val Asn Ile Leu Thr Asp Ile Asn Trp Arg Phe Thr Gly
            100                 105                 110

Asp Phe Thr Ala Pro Asp Leu Val Cys Arg Val Arg Tyr Leu Gln
            115                 120                 125

Val Val Leu Leu Tyr Ala Ser Thr Tyr Val Leu Val Ser Leu Ser Ile
        130                 135                 140

Asp Arg Tyr His Ala Ile Val Tyr Pro Met Lys Phe Leu Gln Gly Glu
145                 150                 155                 160

Lys Gln Ala Arg Val Leu Ile Val Ile Ala Trp Ser Leu Ser Phe Leu
                165                 170                 175

Phe Ser Ile Pro Thr Leu Ile Ile Phe Gly Lys Arg Thr Leu Ser Asn
            180                 185                 190

Gly Glu Val Gln Cys Trp Ala Leu Trp Pro Asp Asp Ser Tyr Trp Thr
        195                 200                 205

Pro Tyr Met Thr Ile Val Ala Phe Leu Val Tyr Phe Ile Pro Leu Thr
210                 215                 220

Ile Ile Ser Ile Met Tyr Gly Ile Val Ile Arg Thr Ile Trp Ile Lys
225                 230                 235                 240

Arg Lys Thr Tyr Glu Thr Val Ile Ser Asn Cys Ser Asp Gly Lys Leu
                245                 250                 255

Cys Ser Ser Tyr Asn Arg Gly Leu Ile Ser Lys Ala Lys Ile Lys Ala
            260                 265                 270

Ile Lys Tyr Ser Ile Ile Ile Leu Ala Phe Ile Cys Cys Trp Ser
        275                 280                 285

Pro Tyr Phe Leu Phe Asp Ile Leu Asp Asn Phe Asn Leu Leu Pro Asp
290                 295                 300

Thr Gln Glu Arg Phe Tyr Ala Ser Val Ile Ile Gln Asn Leu Pro Ala
305                 310                 315                 320

Leu Asn Ser Ala Ile Asn Pro Leu Ile Tyr Cys Val Phe Ser Ser Ser
                325                 330                 335

Ile Ser Phe Pro Cys Arg Glu Gln Arg Ser Gln Asp Ser Arg Met Thr
            340                 345                 350

Phe Arg Glu Arg Thr Glu Arg His Glu Met Gln Ile Leu Ser Lys Pro
        355                 360                 365

Glu Phe Ile
    370

<210> SEQ ID NO 64
<211> LENGTH: 1113
<212> TYPE: DNA
<213> ORGANISM: Human

<400> SEQUENCE: 64
atgccagcca acttcacaga gggcagcttc gattccagtg ggaccgggca gacgctggat      60
tcttccccag tggcttgcac tgaaacagtg acttttactg aagtggtgga aggaaaggaa     120
tggggttcct tctactactc ctttaagact gagcaattga taactctgtg ggtcctcttt     180 gttttacca ttgttggaaa ctccgttgtg cttttttcca catggaggag aaagaagaag     240
tcaagaatga ccttctttgt gactcagctg gccatcacag attctttcac aggactggtc     300
aacatcttga cagatattaa ttggcgattc actggagact tcacggcacc tgacctggtt     360
tgccgagtgg tccgctattt gcaggttgtg ctgctctacg cctctaccta cgtcctggtg     420

-continued

| | |
|---|---|
| tccctcagca tagacagata ccatgccatc gtctacccca tgaagttcct tcaaggagaa | 480 |
| aagcaagcca gggtcctcat tgtgatcgcc tggagcctgt cttttctgtt ctccattccc | 540 |
| accctgatca tatttgggaa gaggacactg tccaacggtg aagtgcagtg ctgggccctg | 600 |
| tggcctgacg actcctactg gaccccatac atgaccatcg tggccttcct ggtgtacttc | 660 |
| atccctctga caatcatcag catcatgtat ggcattgtga tccgaactat ttggattaaa | 720 |
| aggaaaacct acgaaacagt gatttccaac tgctcagatg ggaaactgtg cagcagctat | 780 |
| aaccgaggac tcatctcaaa ggcaaaaatc aaggctatca agtatagcat catcatcatt | 840 |
| cttgccttca tctgctgttg gagtccatac ttcctgtttg acatttgga caatttcaac | 900 |
| ctccttccag acacccagga gcgtttctat gcctctgtga tcattcagaa cctgccagca | 960 |
| ttgaatagtg ccatcaaccc cctcatctac tgtgtcttca gcagctccat ctctttcccc | 1020 |
| tgcagggagc aaagatcaca ggattccaga atgacgttcc gggagagaac tgagaggcat | 1080 |
| gagatgcaga ttctgtccaa gccagaattc atc | 1113 |

<210> SEQ ID NO 65
<211> LENGTH: 371
<212> TYPE: PRT
<213> ORGANISM: Human

<400> SEQUENCE: 65

Met Pro Ala Asn Phe Thr Glu Gly Ser Phe Asp Ser Ser Gly Thr Gly
                5                   10                  15

Gln Thr Leu Asp Ser Ser Pro Val Ala Cys Thr Glu Thr Val Thr Phe
            20                  25                  30

Thr Glu Val Val Glu Gly Lys Glu Trp Gly Ser Phe Tyr Tyr Ser Phe
        35                  40                  45

Lys Thr Glu Gln Leu Ile Thr Leu Trp Val Leu Phe Val Phe Thr Ile
    50                  55                  60

Val Gly Asn Ser Val Val Leu Phe Ser Thr Trp Arg Arg Lys Lys Lys
65                  70                  75                  80

Ser Arg Met Thr Phe Phe Val Thr Gln Leu Ala Ile Thr Asp Ser Phe
                85                  90                  95

Thr Gly Leu Val Asn Ile Leu Thr Asp Ile Ile Trp Arg Phe Thr Gly
            100                 105                 110

Asp Phe Thr Ala Pro Asp Leu Val Cys Arg Val Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Glu
145                 150                 155                 160

Lys Gln Ala Arg Val Leu Ile Val Ile Ala Trp Ser Leu Ser Phe Leu
                165                 170                 175

Phe Ser Ile Pro Thr Leu Ile Ile Phe Gly Lys Arg Thr Leu Ser Asn
            180                 185                 190

Gly Glu Val Gln Cys Trp Ala Leu Trp Pro Asp Asp Ser Tyr Trp Thr
        195                 200                 205

Pro Tyr Met Thr Ile Val Ala Phe Leu Val Tyr Phe Ile Pro Leu Thr
    210                 215                 220

Ile Ile Ser Ile Met Tyr Gly Ile Val Ile Arg Thr Ile Trp Ile Lys
225                 230                 235                 240

Arg Lys Thr Tyr Glu Thr Val Ile Ser Asn Cys Ser Asp Gly Lys Leu

```
                        245                 250                 255
Cys Ser Ser Tyr Asn Arg Gly Leu Ile Ser Lys Ala Lys Ile Lys Ala
                260                 265                 270
Ile Lys Tyr Ser Ile Ile Ile Leu Ala Phe Ile Cys Cys Trp Ser
            275                 280                 285
Pro Tyr Phe Leu Phe Asp Ile Leu Asp Asn Phe Asn Leu Leu Pro Asp
        290                 295                 300
Thr Gln Glu Arg Phe Tyr Ala Ser Val Ile Ile Gln Asn Leu Pro Ala
305                 310                 315                 320
Leu Asn Ser Ala Ile Asn Pro Leu Ile Tyr Cys Val Phe Ser Ser Ser
                325                 330                 335
Ile Ser Phe Pro Cys Arg Glu Gln Arg Ser Gln Asp Ser Arg Met Thr
            340                 345                 350
Phe Arg Glu Arg Thr Glu Arg His Glu Met Gln Ile Leu Ser Lys Pro
        355                 360                 365
Glu Phe Ile
    370

<210> SEQ ID NO 66
<211> LENGTH: 1113
<212> TYPE: DNA
<213> ORGANISM: Human

<400> SEQUENCE: 66
atgccagcca acttcacaga gggcagcttc gattccagtg ggaccgggca gacgctggat      60
tcttccccag tggcttgcac tgaaacagtg acttttactg aagtggtgga aggaaaggaa     120
tggggttcct tctactactc ctttaagact gagcaattga taactctgtg ggtcctcttt     180
gtttttacca ttgttggaaa ctccgttgtg cttttttcca catggaggag aaagaagaag     240
tcaagaatga ccttctttgt gactcagctg ccatcacag attctttcac aggactggtc      300
aacatcttga cagatattat ttggcgattc actggagact tcacggcacc tgacctggtt     360
tgccgagtgg tccgctattt gcaggttgtg ctgctctacg cctctaccta cgtcctggtg     420
tccctcagca tagacagata ccatgccatc gtctacccca tgaagttcct tcaaggagaa     480
aagcaagcca gggtcctcat tgtgatcgcc tggagcctgt cttttctgtt ctccattccc     540
accctgatca tatttgggaa gaggacactg tccaacggtg aagtgcagtg ctgggccctg     600
tggcctgacg actcctactg gacccccatac atgaccatcg tggccttcct ggtgtacttc     660
atccctctga caatcatcag catcatgtat ggcattgtga tccgaactat ttggattaaa     720
aggaaaacct acgaaacagt gatttccaac tgctcagatg ggaaactgtg cagcagctat     780
aaccgaggac tcatctcaaa ggcaaaaatc aaggctatca gtatagcat catcatcatt       840
cttgccttca tctgctgttt gagtccatac ttcctgtttg acattttgga caatttcaac     900
ctccttccag acacccagga gcgtttctat gcctctgtga tcattcagaa cctgccagca     960
ttgaatagtg ccatcaaccc cctcatctac tgtgtcttca gcagctccat ctctttcccc    1020
tgcagggagc aaagatcaca ggattccaga atgacgttcc gggagagaac tgagaggcat    1080
gagatgcaga ttctgtccaa gccagaattc atc                                1113

<210> SEQ ID NO 67
<211> LENGTH: 371
<212> TYPE: PRT
<213> ORGANISM: Human

<400> SEQUENCE: 67
```

```
Met Pro Ala Asn Phe Thr Glu Gly Ser Phe Asp Ser Ser Gly Thr Gly
                  5                  10                 15
Gln Thr Leu Asp Ser Ser Pro Val Ala Cys Thr Glu Thr Val Thr Phe
             20                 25                 30
Thr Glu Val Val Glu Gly Lys Glu Trp Gly Ser Phe Tyr Tyr Ser Phe
         35                 40                 45
Lys Thr Glu Gln Leu Ile Thr Leu Trp Val Leu Phe Val Phe Thr Ile
     50                 55                 60
Val Gly Asn Ser Val Val Leu Phe Ser Thr Trp Arg Arg Lys Lys Lys
 65                 70                 75                 80
Ser Arg Met Thr Phe Phe Val Thr Gln Leu Ala Ile Thr Asp Ser Phe
                 85                 90                 95
Thr Gly Leu Val Asn Ile Leu Thr Asp Ile Asn Trp Arg Phe Thr Gly
             100                105                110
Asp Phe Thr Ala Pro Asp Leu Val Cys Arg Val Val Arg Tyr Leu Gln
             115                120                125
Val Val Leu Leu Tyr Ala Ser Thr Tyr Val Leu Val Ser Leu Ser Ile
130                135                140
Asp Arg Tyr His Ala Ile Val Tyr Pro Met Lys Phe Leu Gln Gly Glu
145                150                155                160
Lys Gln Ala Arg Val Leu Ile Val Ile Ala Trp Ser Leu Ser Phe Leu
                165                170                175
Phe Ser Ile Pro Thr Leu Ile Ile Phe Gly Lys Arg Thr Leu Ser Asn
             180                185                190
Gly Glu Val Gln Cys Trp Ala Leu Trp Pro Asp Asp Ser Tyr Trp Thr
             195                200                205
Pro Tyr Met Thr Ile Val Ala Phe Leu Val Tyr Phe Ile Pro Leu Thr
     210                215                220
Ile Ile Ser Ile Met Tyr Gly Ile Val Ile Arg Thr Ile Trp Ile Lys
225                230                235                240
Ser Lys Thr Tyr Glu Thr Val Ile Ser Asn Cys Ser Asp Gly Lys Leu
             245                250                255
Cys Ser Ser Tyr Asn Arg Gly Leu Ile Ser Lys Ala Lys Ile Lys Ala
             260                265                270
Ile Lys Tyr Ser Ile Ile Ile Leu Ala Phe Ile Cys Cys Trp Ser
     275                280                285
Pro Tyr Phe Leu Phe Asp Ile Leu Asp Asn Phe Asn Leu Leu Pro Asp
     290                295                300
Thr Gln Glu Arg Phe Tyr Ala Ser Val Ile Ile Gln Asn Leu Pro Ala
305                310                315                320
Leu Asn Ser Ala Ile Asn Pro Leu Ile Tyr Cys Val Phe Ser Ser Ser
                325                330                335
Ile Ser Phe Pro Cys Arg Glu Gln Arg Ser Gln Asp Ser Arg Met Thr
             340                345                350
Phe Arg Glu Arg Thr Glu Arg His Glu Met Gln Ile Leu Ser Lys Pro
         355                360                365
Glu Phe Ile
     370

<210> SEQ ID NO 68
<211> LENGTH: 1113
<212> TYPE: DNA
<213> ORGANISM: Human
```

-continued

```
<400> SEQUENCE: 68
atgccagcca acttcacaga gggcagcttc gattccagtg ggaccgggca gacgctggat      60
tcttccccag tggcttgcac tgaaacagtg acttttactg aagtggtgga aggaaaggaa     120
tggggttcct tctactactc ctttaagact gagcaattga taactctgtg ggtcctcttt     180
gtttttacca ttgttggaaa ctccgttgtg cttttttcca catggaggag aaagaagaag     240
tcaagaatga ccttctttgt gactcagctg ccatcacaga ttctttcac aggactggtc      300
aacatcttga cagatattaa ttggcgattc actggagact tcacggcacc tgacctggtt     360
tgccgagtgg tccgctattt gcaggttgtg ctgctctacg cctctaccta cgtcctggtg     420
tccctcagca tagacagata ccatgccatc gtctacccca tgaagttcct tcaaggagaa     480
aagcaagcca gggtcctcat tgtgatcgcc tggagcctgt cttttctgtt ctccattccc     540
accctgatca tatttgggaa gaggacactg tccaacggtg aagtgcagtg ctgggccctg     600
tggcctgacg actcctactg daccccatac atgaccatcg tggccttcct ggtgtacttc     660
atccctctga caatcatcag catcatgtat ggcattgtga tccgaactat ttggattaaa     720
agcaaaacct acgaaacagt gatttccaac tgctcagatg ggaaactgtg cagcagctat     780
aaccgaggac tcatctcaaa ggcaaaaatc aaggctatca agtatagcat catcatcatt     840
cttgccttca tctgctgttg gagtccatac ttcctgtttg acattttgga caatttcaac     900
ctccttccag acacccagga gcgtttctat gcctctgtga tcattcagaa cctgccagca     960
ttgaatagtg ccatcaaccc cctcatctac tgtgtcttca gcagctccat ctctttcccc    1020
tgcagggagc aaagatcaca ggattccaga atgacgttcc gggagagaac tgagaggcat    1080
gagatgcaga ttctgtccaa gccagaattc atc                                 1113

<210> SEQ ID NO 69
<211> LENGTH: 348
<212> TYPE: PRT
<213> ORGANISM: Human

<400> SEQUENCE: 69

Met Pro Ala Asn Phe Thr Glu Gly Ser Phe Asp Ser Ser Gly Thr Gly
                5                   10                  15

Gln Thr Leu Asp Ser Ser Pro Val Ala Cys Thr Glu Ala Val Thr Phe
            20                  25                  30

Thr Glu Val Val Lys Gly Lys Glu Trp Gly Ser Phe Tyr Tyr Ser Phe
        35                  40                  45

Lys Thr Glu Gln Leu Ile Thr Leu Trp Val Leu Phe Val Phe Thr Ile
    50                  55                  60

Val Gly Asn Ser Val Val Leu Phe Ser Thr Trp Arg Arg Lys Lys Lys
65                  70                  75                  80

Ser Arg Met Thr Phe Phe Val Thr Gln Leu Ala Ile Thr Asp Ser Phe
                85                  90                  95

Thr Gly Leu Val Asn Ile Leu Thr Asp Ile Ile Trp Arg Phe Thr Gly
            100                 105                 110

Asp Phe Thr Ala Pro Asp Leu Val Cys Arg Val Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Glu
145                 150                 155                 160

Lys Gln Ala Arg Val Leu Ile Val Ile Ala Trp Ser Leu Ser Phe Leu
```

|     |     |     |     |     | 165 |     |     |     |     | 170 |     |     |     |     | 175 |     |
| --- | --- | --- | --- | --- | --- | --- | --- | --- | --- | --- | --- | --- | --- | --- | --- | --- |
| Phe | Ser | Ile | Pro | Thr | Leu | Ile | Ile | Phe | Gly | Lys | Arg | Thr | Leu | Ser | Asn |     |
|     |     |     |     | 180 |     |     |     |     | 185 |     |     |     |     | 190 |     |     |

Gly Glu Val Gln Cys Trp Ala Leu Trp Pro Asp Asp Ser Tyr Trp Thr
            195                      200                      205

Pro Tyr Met Thr Ile Val Ala Phe Leu Val Tyr Phe Ile Pro Leu Thr
      210                      215                      220

Ile Ile Ser Ile Met Tyr Gly Ile Val Ile Arg Thr Ile Trp Ile Lys
225                      230                      235                      240

Arg Lys Thr Tyr Glu Thr Val Ile Ser Asn Cys Ser Asp Gly Lys Leu
            245                      250                      255

Cys Ser Ser Tyr Asn Arg Gly Leu Ile Ser Lys Ala Lys Ile Lys Ala
      260                      265                      270

Ile Lys Tyr Ser Ile Ile Ile Leu Ala Phe Ile Cys Cys Trp Ser
            275                      280                      285

Pro Tyr Phe Leu Phe Asp Ile Leu Asp Asn Phe Asn Leu Leu Pro Asp
      290                      295                      300

Thr Gln Glu Arg Phe Tyr Ala Ser Val Ile Ile Gln Asn Leu Pro Ala
305                      310                      315                      320

Leu Asn Ser Ala Ile Asn Pro Leu Ile Tyr Cys Val Phe Ser Ser Ser
            325                      330                      335

Ile Ser Phe Pro Cys Arg Ile Ile Asp Gly Asn Asp
            340                      345

```
<210> SEQ ID NO 70
<211> LENGTH: 1044
<212> TYPE: DNA
<213> ORGANISM: Human

<400> SEQUENCE: 70
atgccagcca acttcacaga gggcagcttc gattccagtg ggaccgggca gacgctggat      60
tcttccccag tggcttgcac tgaagcagtg acttttactg aagtggtgaa aggaaaggaa     120
tggggttcct tctactactc ctttaagact gagcaattga taactctgtg ggtcctcttt     180
gtttttacca ttgttggaaa ctccgttgtg cttttttcca catggaggag aaagaagaag     240
tcaagaatga ccttctttgt gactcagctg ccatcacag attctttcac aggactggtc     300
aacatcttga cagatattat ttggcgattc accggagact tcacggcacc tgacctggtt     360
tgccgagtgg tccgctattt gcaggttgtg ctgctgtacg cctctaccta cgtcctggtg     420
tccctcagca tagacagata ccatgccatc gtctacccca tgaagttcct tcaaggagaa     480
aagcaagcca gggtcctcat tgtgatcgcc tggagcctgt cttttctgtt ctccattccc     540
accctgatca tatttgggaa gaggacactg tccaacggtg aagtgcagtg ctgggccctg     600
tggcctgacg actcctactg gacccatac atgaccatcg tggccttcct ggtgtacttc     660
atccctctga caatcatcag catcatgtat ggcattgtga tccgaactat ttggattaaa     720
aggaaaacct acgaaacagt gatttccaac tgctcagatg ggaaactgtg cagcagctat     780
aaccgaggac tcatctcaaa ggcaaaaatc aaggctatca gtatagcat catcatcatt     840 cttgccttca tctgctgttg gagtccatac ttcctgtttg acattttgga caatttcaac     900
ctccttccag acacccagga gcgtttctat gcctctgtga tcattcagaa cctgccagca     960
ttgaatagtg ccatcaaccc cctcatctac tgtgtcttca gcagctccat ctctttcccc    1020
tgcaggatca tagatggaaa tgac                                          1044
```

<210> SEQ ID NO 71
<211> LENGTH: 353
<212> TYPE: PRT
<213> ORGANISM: Mouse

<400> SEQUENCE: 71

Met Pro Ala Asn Leu Thr Glu Gly Ser Phe His Ala Asn Gln Thr Val
                 5                  10                  15
Pro Met Leu Asp Ser Ser Pro Val Ala Cys Thr Glu Ile Val Thr Phe
             20                  25                  30
Thr Glu Ala Leu Val Ala Glu Glu Trp Gly Ser Phe Tyr Ser Ser Phe
         35                  40                  45
Lys Thr Glu Gln Leu Ile Thr Leu Trp Val Leu Phe Val Val Thr Ile
     50                  55                  60
Val Gly Asn Ser Val Val Leu Phe Ser Thr Cys Arg Arg Lys Arg Lys
 65                  70                  75                  80
Ser Arg Met Thr Phe Phe Val Thr Gln Leu Ala Ile Thr Gly Asp Phe
                 85                  90                  95
Met Ala Pro Asp Leu Val Cys Arg Val Val Arg Tyr Leu Gln Val Val
            100                 105                 110
Leu Leu Tyr Ala Ser Thr Tyr Val Leu Val Ser Leu Ser Ile Asp Arg
        115                 120                 125
Tyr His Ala Ile Val Tyr Pro Met Lys Phe Leu Gln Gly Glu Lys Gln
    130                 135                 140
Ala Lys Val Leu Ile Gly Ile Ala Trp Ser Leu Ser Phe Leu Phe Ser
145                 150                 155                 160
Ile Pro Thr Leu Ile Ile Phe Gly Lys Arg Thr Leu Ser Asn Gly Glu
                165                 170                 175
Val Gln Cys Trp Ala Leu Trp Pro Asp Asp Ser Tyr Trp Thr Pro Tyr
            180                 185                 190
Met Thr Ile Val Ala Phe Leu Val Tyr Phe Ile Pro Leu Ala Ile Ile
        195                 200                 205
Ser Val Ile Tyr Gly Leu Val Ile Arg Thr Ile Trp Met Lys Ser Lys
    210                 215                 220
Thr His Glu Thr Val Ile Ser Asn Cys Ser Asp Gly Lys Leu Cys Cys
225                 230                 235                 240
Ser Tyr Asn Arg Gly Leu Ile Ser Lys Ala Lys Ile Lys Ala Ile Lys
                245                 250                 255
Tyr Ser Ile Val Ile Ile Leu Ala Phe Ile Cys Cys Trp Ser Pro Tyr
            260                 265                 270
Phe Leu Phe Asp Ile Leu Asp Asn Phe Asn Val Leu Pro Asp Thr Lys
        275                 280                 285
Glu Arg Phe Tyr Ala Ser Val Ile Ile Gln Asn Leu Pro Ala Leu Asn
    290                 295                 300
Ser Ala Ile Asn Pro Leu Ile Tyr Cys Ile Phe Ser Ser Ser Ile Cys
305                 310                 315                 320
Ser Pro Cys Lys Met Gln Arg Ser Gln Asp Ser Arg Met Thr Tyr Arg
                325                 330                 335
Glu Arg Ser Glu Arg His Glu Met Gln Ile Leu Ser Lys Pro Glu Phe
            340                 345                 350
Ile

<210> SEQ ID NO 72
<211> LENGTH: 1059

―continued

```
<212> TYPE: DNA
<213> ORGANISM: Mouse

<400> SEQUENCE: 72
atgccagcca acctcacaga gggcagcttt catgccaacc agactgtgcc gatgctagat      60
tcttccccag tagcttgcac tgaaattgtg acgttcactg aagcactggt ggctgaggag     120
tggggctcct tctactcctc ctttaagaca gaacagctga taaccctgtg ggtcctgttt     180
gtcgtcacta ttgtgggaaa ctctgttgtg ctgttctcca cgtgcagaag aaaaagaaag     240
tccagaatga ccttctttgt gacacaattg gccatcacag gagacttcat ggcccctgac     300
ctggtttgca gagtcgtccg ctacttgcag gttgtcctgc tgtatgcctc tacctacgtc     360
ctggtgtccc tcagcataga cagataccat gccatcgttt acccatgaa gtttcttcaa      420
ggagagaagc aagccaaagt cctcatcgga atagcgtgga gcctctcgtt cctgttctcc     480
attcccacgc tgatcatatt tgggaaaagg acactttcca atggtgaggt gcagtgctgg     540
gcactgtggc cggatgactc ctactggacc ccgtacatga ccatcgtcgc ctttctggtg     600
tacttcattc ccttggcaat tatcagcgtt atctatggcc ttgtgatccg aactatttgg     660
atgaaaagca aacccatga gacggtgatt tccaactgct cagatggcaa actatgctgc     720
agctacaacc gagggctcat ctctaaggca aaaatcaagg ccatcaagta tagcatcgtc     780
ataatccttg ctttcatctg ctgctggagc ccatacttcc tctttgacat attagacaac     840
ttcaacgtcc ttccagacac caaggagcgt ttctatgcct ctgtgattat ccagaacctg     900
cccgccttga acagtgccat taccccctc atctactgca tcttcagcag ctccatctgt     960
tccccctgca agatgcaaag atcacaggat tccagaatga cataccgaga gagaagcgag    1020
agacacgaga tgcagattct ctccaagccg gaattcatc                           1059

<210> SEQ ID NO 73
<211> LENGTH: 21
<212> TYPE: DNA
<213> ORGANISM: Artificial Sequence
<220> FEATURE:
<223> OTHER INFORMATION: Designed oligonucleotide primer to amplify DNA
      encoding mouse TGR23-A

<400> SEQUENCE: 73
tgcagagaca gtgagacctg a                                                21

<210> SEQ ID NO 74
<211> LENGTH: 24
<212> TYPE: DNA
<213> ORGANISM: Artificial Sequence
<220> FEATURE:
<223> OTHER INFORMATION: Designed oligonucleotide primer to amplify DNA
      encoding mouse TGR23-A

<400> SEQUENCE: 74
aagttcagcc tagcactact gcct                                             24

<210> SEQ ID NO 75
<211> LENGTH: 371
<212> TYPE: PRT
<213> ORGANISM: Mouse

<400> SEQUENCE: 75

Met Pro Ala Asn Leu Thr Glu Gly Ser Phe His Ala Asn Gln Thr Val
              5                  10                  15

Pro Met Leu Asp Ser Ser Pro Val Ala Cys Thr Glu Ile Val Thr Phe
```

```
                     20                  25                  30
Thr Glu Ala Leu Val Ala Glu Glu Trp Gly Ser Phe Tyr Ser Ser Phe
            35                  40                  45

Lys Thr Glu Gln Leu Ile Thr Leu Trp Val Leu Phe Val Thr Ile
        50                  55                  60

Val Gly Asn Ser Val Val Leu Phe Ser Thr Cys Arg Arg Lys Arg Lys
 65                  70                  75                  80

Ser Arg Met Thr Phe Phe Val Thr Gln Leu Ala Ile Thr Asp Ser Phe
                85                  90                  95

Thr Gly Leu Ile Asn Ile Leu Thr Asp Ile Ile Trp Arg Phe Thr Gly
            100                 105                 110

Asp Phe Met Ala Pro Asp Leu Val Cys Arg Val Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Glu
145                 150                 155                 160

Lys Gln Ala Lys Val Leu Ile Gly Ile Ala Trp Ser Leu Ser Phe Leu
                165                 170                 175

Phe Ser Ile Pro Thr Leu Ile Ile Phe Gly Lys Arg Thr Leu Ser Asn
            180                 185                 190

Gly Glu Val Gln Cys Trp Ala Leu Trp Pro Asp Asp Ser Tyr Trp Thr
        195                 200                 205

Pro Tyr Met Thr Ile Val Ala Phe Leu Val Tyr Phe Ile Pro Leu Ala
    210                 215                 220

Ile Ile Ser Val Ile Tyr Gly Leu Val Ile Arg Thr Ile Trp Met Lys
225                 230                 235                 240

Ser Lys Thr His Glu Thr Val Ile Ser Asn Cys Ser Asp Gly Lys Leu
                245                 250                 255

Cys Cys Ser Tyr Asn Arg Gly Leu Ile Ser Lys Ala Lys Ile Lys Ala
            260                 265                 270

Ile Lys Tyr Ser Ile Val Ile Ile Leu Ala Phe Ile Cys Cys Trp Ser
        275                 280                 285

Pro Tyr Phe Leu Phe Asp Ile Leu Asp Asn Phe Asn Val Leu Pro Asp
    290                 295                 300

Thr Lys Glu Arg Phe Tyr Ala Ser Val Ile Ile Gln Asn Leu Pro Ala
305                 310                 315                 320

Leu Asn Ser Ala Ile Asn Pro Leu Ile Tyr Cys Ile Phe Ser Ser Ser
                325                 330                 335

Ile Cys Ser Pro Cys Lys Met Gln Arg Ser Gln Asp Ser Arg Met Thr
            340                 345                 350

Tyr Arg Glu Arg Ser Glu Arg His Glu Met Gln Ile Leu Ser Lys Pro
        355                 360                 365

Glu Phe Ile
    370

<210> SEQ ID NO 76
<211> LENGTH: 1113
<212> TYPE: DNA
<213> ORGANISM: Mouse

<400> SEQUENCE: 76
atgccagcca acctcacaga gggcagcttt catgccaacc agactgtgcc gatgctagat    60
tcttccccag tagcttgcac tgaaattgtg acgttcactg aagcactggt ggctgaggag   120
```

```
                                                                -continued tggggctcct tctactcctc ctttaagaca gaacagctga taaccctgtg ggtcctgttt      180
gtcgtcacta ttgtgggaaa ctctgttgtg ctgttctcca cgtgcagaag aaaaagaaag      240
tccagaatga ccttctttgt gacacaattg gccatcacag actccttcac gggcctgatc      300
aacatcttga cagacattat ttggcgattc acaggagact tcatggcccc tgacctggtt      360
tgcagagtcg tccgctactt gcaggttgtc ctgctgtatg cctctaccta cgtcctggtg      420
tccctcagca tagacagata ccatgccatc gtttacccca tgaagtttct tcaaggagag      480
aagcaagcca aagtcctcat cggaatagcg tggagcctct cgttcctgtt ctccattccc      540
acgctgatca tatttgggaa aaggacactt tccaatggtg aggtgcagtg ctgggcactg      600
tggccggatg actcctactg gaccccgtac atgaccatcg tcgcctttct ggtgtacttc      660
attcccttgg caattatcag cgttatctat ggccttgtga tccgaactat ttggatgaaa      720
agcaaaaccc atgagacggt gatttccaac tgctcagatg caaactatg ctgcagctac       780 aaccgagggc tcatctctaa ggcaaaaatc aaggccatca gtatagcat cgtcataatc       840 cttgctttca tctgctgctg gagcccatac ttcctctttg acatattaga caacttcaac      900
gtccttccag acaccaagga gcgtttctat gcctctgtga ttatccagaa cctgcccgcc      960
ttgaacagtg ccattaaccc cctcatctac tgcatcttca gcagctccat ctgctccccc     1020
tgcaagatgc aaagatcaca ggattccaga atgcataccc gagagagaag cgagagacac     1080
gagatgcaga ttctctccaa gccggaattc atc                                  1113

<210> SEQ ID NO 77
<211> LENGTH: 371
<212> TYPE: PRT
<213> ORGANISM: Rat

<400> SEQUENCE: 77

Met Pro Ala Asn Leu Thr Glu Gly Ser Phe His Ala Asn Gln Thr Val
              5                  10                  15

Pro Met Leu Asp Ser Ser Pro Val Ala Cys Thr Glu Ile Val Thr Phe
         20                  25                  30

Thr Glu Ala Leu Glu Ala Glu Glu Trp Gly Ser Phe Tyr Ser Ser Phe
     35                  40                  45

Lys Thr Glu Gln Leu Ile Thr Leu Trp Val Leu Val Phe Thr Ile
 50                  55                  60

Val Gly Asn Ser Val Val Leu Phe Ser Thr Trp Arg Arg Lys Arg Lys
 65                  70                  75                  80

Ser Arg Met Thr Phe Phe Val Thr Gln Leu Ala Ile Thr Asp Ser Phe
                 85                  90                  95

Thr Gly Leu Ile Asn Ile Leu Thr Asp Ile Ile Trp Arg Phe Thr Gly
            100                 105                 110

Asp Phe Met Ala Pro Asp Leu Val Cys Arg Ile Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Glu
145                 150                 155                 160

Lys Gln Ala Lys Val Leu Ile Gly Ile Ala Trp Ser Leu Ser Phe Leu
                165                 170                 175

Phe Ser Ile Pro Thr Leu Ile Ile Phe Gly Lys Arg Thr Leu Ser Asn
            180                 185                 190
```

```
Gly Glu Val Gln Cys Trp Ala Leu Trp Pro Asp Asp Ser Tyr Trp Thr
            195                 200                 205
Pro Tyr Met Thr Ile Val Ala Phe Leu Val Tyr Phe Ile Pro Leu Thr
        210                 215                 220
Ile Ile Ser Val Ile Tyr Gly Leu Val Ile Arg Thr Ile Trp Ile Lys
225                 230                 235                 240
Ser Lys Ala His Glu Thr Val Ile Ser Asn Cys Ser Asp Gly Glu Leu
                245                 250                 255
Cys Cys Ser Tyr Asn Arg Gly Leu Ile Ser Lys Ala Lys Ile Lys Ala
            260                 265                 270
Ile Lys Tyr Ser Ile Val Ile Ile Leu Ala Phe Ile Cys Cys Trp Ser
        275                 280                 285
Pro Tyr Phe Leu Phe Asp Met Leu Asp Asn Phe Asn Leu Leu Pro Asp
        290                 295                 300
Thr Lys Glu Arg Phe Tyr Ala Ser Val Ile Ile Gln Asn Leu Pro Ala
305                 310                 315                 320
Leu Asn Ser Ala Ile Asn Pro Leu Ile Tyr Cys Ile Phe Ser Gly Ser
                325                 330                 335
Leu Cys Ser Pro Cys Lys Val Gln Arg Ser Gln Asp Ser Arg Met Thr
            340                 345                 350
Tyr Arg Glu Arg Ser Glu Arg His Glu Met Gln Ile Leu Ser Lys Pro
        355                 360                 365
Glu Phe Ile
    370

<210> SEQ ID NO 78
<211> LENGTH: 1113
<212> TYPE: DNA
<213> ORGANISM: Rat

<400> SEQUENCE: 78
atgccggcca acctcacaga gggcagcttt catgccaacc agactgtgcc gatgctagat        60 tcttccctg tagcttgcac tgaaattgtg actttcactg aagcgctgga ggctgaggag        120
tggggctcct tctactcgtc ctttaagaca gagcagctga taaccctgtg ggtcctgttt       180
gtcttcacta ttgtgggaaa ctcggtcgtg ctgttctcca catggagaag aaaaagaaag       240
tccagaatga ccttctttgt gactcaattg ccatcacag actccttcac aggcctgatc        300
aacatcctga cagacattat ttggcgattc acgggagact tcatggcccc tgacctggtc      360
tgcagaatcg tccgctactt acaggttgtc ctgctttatg cctctaccta tgtcctggtg      420
tccctcagca tagacagata ccatgccatc gtttacccca tgaaattcct tcaaggagag      480
aagcaagcca aagtcctcat cggaatagca tggagcctct ccttcctgtt ctccatcccc      540
acactgatca tatttgggaa aaggacactt tccaatggtg aggtacagtg ctgggcactg      600
tggccagacg actcctactg gaccccatat atgaccatct tgcctttct ggtgtacttc      660 atccccttga caattatcag cgtcatctat ggccttgtga tccgaactat ttggattaaa      720
agcaaagccc atgagacggt gatttccaac tgctcagatg agaactatg ctgcagctac      780 aaccgaggcc tcatctcaaa agcaaaaatc aaggccatca gtacagcat cgtcataatc       840 cttgctttca tctgctgctg gagtccatac ttcctctttg acatgttaga caacttcaac      900
ctccttccag acaccaagga gcgtttctat gcctctgtga ttatccagaa cctgcctgcc      960
ttgaacagtg ccattaaccc cctcatctac tgcatcttca gcggctccct ctgctccccc     1020
tgcaaggtgc aaagatccca ggattccaga atgacgtacc gagagagaag cgagaggcat     1080
```
gagatgcaga ttctctccaa gcctgaattc atc                                    1113

<210> SEQ ID NO 79
<211> LENGTH: 36
<212> TYPE: DNA
<213> ORGANISM: Artificial Sequence
<220> FEATURE:
<223> OTHER INFORMATION: Designed oligonucleotide primer to amplify DNA
      encoding rat TGR23

<400> SEQUENCE: 79
gtcgacatgc cggccaacct cacagagggc agcttt                                 36

<210> SEQ ID NO 80
<211> LENGTH: 36
<212> TYPE: DNA
<213> ORGANISM: Artificial Sequence
<220> FEATURE:
<223> OTHER INFORMATION: Designed oligonucleotide primer to amplify DNA
      encoding rat TGR23

<400> SEQUENCE: 80
actagtttag atgaattcag gcttggagag aatctg                                 36

<210> SEQ ID NO 81
<211> LENGTH: 36
<212> TYPE: DNA
<213> ORGANISM: Artificial Sequence
<220> FEATURE:
<223> OTHER INFORMATION: Designed oligonucleotide primer to amplify DNA
      encoding mouse TGR23-B and mouse TGR23-C

<400> SEQUENCE: 81
gtcgacatgc cagccaacct cacagagggc agcttt                                 36

<210> SEQ ID NO 82
<211> LENGTH: 36
<212> TYPE: DNA
<213> ORGANISM: Artificial Sequence
<220> FEATURE:
<223> OTHER INFORMATION: Designed oligonucleotide primer to amplify DNA
      encoding mouse TGR23-B and mouse TGR23-C

<400> SEQUENCE: 82
actagtttag atgaattccg gcttggagag aatctg                                 36

<210> SEQ ID NO 83
<211> LENGTH: 372
<212> TYPE: PRT
<213> ORGANISM: Mouse

<400> SEQUENCE: 83

Met Pro Ala Asn Leu Thr Glu Gly Ser Phe His Ala Asn Gln Thr Val
                5                   10                  15

Pro Met Leu Asp Ser Ser Pro Val Ala Cys Thr Glu Ile Val Thr Phe
            20                  25                  30

Thr Glu Ala Leu Val Ala Glu Glu Trp Gly Ser Phe Tyr Ser Ser Phe
        35                  40                  45

Lys Thr Glu Gln Leu Ile Thr Leu Trp Val Leu Phe Val Val Thr Ile
    50                  55                  60

Val Gly Asn Ser Val Val Leu Phe Ser Thr Cys Arg Arg Lys Arg Lys
65                  70                  75                  80

Ser Arg Met Thr Phe Phe Val Thr Gln Leu Ala Ile Thr Asp Ser Phe

```
                85                  90                  95
Thr Gly Leu Ile Asn Ile Leu Thr Asp Ile Ile Trp Arg Phe Thr Gly
                100                 105                 110

Asp Phe Met Ala Pro Asp Leu Val Cys Arg Val Val Arg Tyr Leu Gln
            115                 120                 125

Val Val Leu Leu Tyr Ala Ser Thr Tyr Val Leu Val Ser Leu Ser Ile
        130                 135                 140

Asp Arg Tyr His Ala Ile Val Tyr Pro Met Lys Phe Leu Gln Gly Ala
145                 150                 155                 160

Glu Lys Gln Ala Lys Val Leu Ile Gly Ile Ala Trp Ser Leu Ser Phe
                165                 170                 175

Leu Phe Ser Ile Pro Thr Leu Ile Ile Phe Gly Lys Arg Thr Leu Ser
            180                 185                 190

Asn Gly Glu Val Gln Cys Trp Ala Leu Trp Pro Asp Ser Tyr Trp
        195                 200                 205

Thr Pro Tyr Met Thr Ile Val Ala Phe Leu Val Tyr Phe Ile Pro Leu
    210                 215                 220

Ala Ile Ile Ser Val Ile Tyr Gly Leu Val Ile Arg Thr Ile Trp Met
225                 230                 235                 240

Lys Ser Lys Thr His Glu Thr Val Ile Ser Asn Cys Ser Asp Gly Lys
                245                 250                 255

Leu Cys Cys Ser Tyr Asn Arg Gly Leu Ile Ser Lys Ala Lys Ile Lys
            260                 265                 270

Ala Ile Lys Tyr Ser Ile Val Ile Ile Leu Ala Phe Ile Cys Cys Trp
        275                 280                 285

Ser Pro Tyr Phe Leu Phe Asp Ile Leu Asp Asn Phe Asn Val Leu Pro
    290                 295                 300

Asp Thr Lys Glu Arg Phe Tyr Ala Ser Val Ile Ile Gln Asn Leu Pro
305                 310                 315                 320

Ala Leu Asn Ser Ala Ile Asn Pro Leu Ile Tyr Cys Ile Phe Ser Ser
                325                 330                 335

Ser Ile Cys Ser Pro Cys Lys Met Gln Arg Ser Gln Asp Ser Arg Met
            340                 345                 350

Thr Tyr Arg Glu Arg Ser Glu Arg His Glu Met Gln Ile Leu Ser Lys
        355                 360                 365

Pro Glu Phe Ile
    370

<210> SEQ ID NO 84
<211> LENGTH: 1116
<212> TYPE: DNA
<213> ORGANISM: Mouse

<400> SEQUENCE: 84
atgccagcca acctcacaga gggcagcttt catgccaacc agactgtgcc gatgctagat      60
tcttccccag tagcttgcac tgaaattgtg acgttcactg aagcactggt ggctgaggag     120
tggggctcct tctactcctc ctttaagaca gaacagctga taaccctgtg gtcctgtttt     180
gtcgtcacta ttgtgggaaa ctctgttgtg ctgttctcca cgtgcagaag aaaaagaaag     240
tccagaatga ccttctttgt gacacaattg gccatcacag actccttcac gggcctgatc     300
aacatcttga cagacattat ttggcgattc acaggagact tcatgccccc tgacctggca     360
gtttgcagag tcgtccgcta cttgcaggtt gtcctgctgt atgcctctac ctacgtcctg     420
gtgtccctca gcatagacag ataccatgcc atcgtttacc ccatgaagtt tcttcaagga     480
```

-continued

```
gagaagcaag ccaaagtcct catcggaata gcgtggagcc tctcgttcct gttctccatt    540
cccacgctga tcatatttgg gaaaaggaca ctttccaatg gtgaggtgca gtgctgggca    600
ctgtggccgg atgactccta ctggaccccg tacatgacca tcgtcgcctt tctggtgtac    660
ttcattccct ggcaattat cagcgttatc tatggccttg tgatccgaac tatttggatg     720
aaaagcaaaa cccatgagac ggtgatttcc aactgctcag atggcaaact atgctgcagc    780
tacaaccgag ggctcatctc taaggcaaaa atcaaggcca tcaagtatag catcgtcata    840
atccttgctt tcatctgctg ctggagccca tacttcctct ttgacatatt agacaacttc    900
aacgtccttc cagacaccaa ggagcgtttc tatgcctctg tgattatcca gaacctgccc    960
gccttgaaca gtgccattaa ccccctcatc tactgcatct tcagcagctc catctgctcc   1020
ccctgcaaga tgcaaagatc acaggattcc agaatgacat accgagagag aagcgagaga   1080
cacgagatgc agattctctc caagccggaa ttcatc                             1116
```

<210> SEQ ID NO 85
<211> LENGTH: 371
<212> TYPE: PRT
<213> ORGANISM: Rat

<400> SEQUENCE: 85

```
Met Pro Ala Asn Leu Thr Glu Gly Ser Phe His Ala Asn Gln Thr Val
                5                  10                  15

Pro Met Leu Asp Ser Ser Pro Val Ala Cys Thr Glu Ile Val Thr Phe
            20                  25                  30

Thr Glu Ala Leu Glu Ala Glu Trp Gly Ser Phe Tyr Ser Ser Phe
        35                  40                  45

Lys Thr Glu Gln Leu Ile Thr Leu Trp Val Leu Phe Val Phe Thr Ile
    50                  55                  60

Val Gly Asn Ser Val Val Leu Phe Ser Thr Trp Arg Arg Lys Arg Lys
65                  70                  75                  80

Ser Arg Met Thr Phe Phe Val Thr Gln Leu Ala Ile Thr Asp Ser Phe
                85                  90                  95

Thr Gly Leu Ile Asn Ile Leu Thr Asp Ile Ile Trp Arg Phe Thr Gly
            100                 105                 110

Asp Phe Met Ala Pro Asp Leu Val Cys Arg Ile Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Glu
145                 150                 155                 160

Lys Gln Ala Lys Val Leu Ile Gly Ile Ala Trp Ser Leu Ser Phe Leu
                165                 170                 175

Phe Ser Ile Pro Thr Leu Ile Ile Phe Gly Lys Arg Thr Leu Ser Asn
            180                 185                 190

Gly Glu Val Gln Cys Trp Ala Leu Trp Pro Asp Asp Ser Tyr Trp Thr
        195                 200                 205

Pro Tyr Met Thr Ile Val Ala Phe Leu Val Tyr Phe Ile Pro Leu Thr
    210                 215                 220

Ile Ile Ser Val Ile Tyr Gly Leu Val Ile Arg Thr Ile Trp Ile Lys
225                 230                 235                 240

Ser Lys Ala His Glu Thr Val Ile Ser Asn Cys Ser Asp Gly Glu Leu
                245                 250                 255
```

-continued

```
Cys Cys Ser Tyr Asn Arg Gly Leu Ile Ser Lys Ala Lys Ile Lys Ala
            260                 265                 270
Ile Lys Tyr Ser Ile Val Ile Leu Ala Phe Ile Cys Cys Trp Ser
        275                 280                 285
Pro Tyr Phe Leu Phe Asp Met Leu Asp Asn Phe Asn Leu Leu Pro Asp
    290                 295                 300
Thr Lys Glu Arg Phe Tyr Ala Ser Val Ile Ile Gln Asn Leu Pro Ala
305                 310                 315                 320
Leu Asn Ser Ala Ile Asn Pro Leu Ile Tyr Cys Ile Phe Ser Gly Ser
                325                 330                 335
Leu Cys Ser Pro Cys Lys Val Arg Arg Ser Gln Asp Ser Arg Met Thr
            340                 345                 350
Tyr Arg Glu Arg Ser Glu Arg His Glu Met Gln Ile Leu Ser Lys Pro
        355                 360                 365
Glu Phe Ile
    370

<210> SEQ ID NO 86
<211> LENGTH: 1113
<212> TYPE: DNA
<213> ORGANISM: Rat

<400> SEQUENCE: 86
atgccggcca acctcacaga gggcagcttt catgccaacc agactgtgcc gatgctagat    60
tcttcccctg tagcttgcac tgaaattgtg actttcactg aagcgctgga ggctgaggag   120
tggggctcct tctactcgtc ctttaagaca gagcagctga taaccctgtg ggtcctgttt   180
gtcttcacta ttgtgggaaa ctcggtcgtg ctgttctcca catggagaag aaaaagaaag   240
tccagaatga ccttctttgt gactcaattg gccatcacag actccttcac aggcctgatc   300
aacatcctga cagacattat ttggcgattc acgggagact tcatggcccc tgacctggtc   360
tgcagaatcg tccgctactt acaggttgtc ctgctttatg cctctaccta tgtcctggtg   420
tccctcagca tagacagata ccatgccatc gtttacccca tgaaattcct tcaaggagag   480
aagcaagcca agtcctcat cggaatagca tggagcctct ccttcctgtt ctccatcccc   540
acactgatca tatttgggaa aaggacactt tccaatggtg aggtacagtg ctgggcactg   600
tggccagacg actcctactg gacccatat atgaccatcg ttgcctttct ggtgtacttc   660
atccccttga caattatcag cgtcatctat ggccttgtga tccgaactat ttggattaaa   720
agcaaagccc atgagacggt gatttccaac tgctcagatg agaactatg ctgcagctac   780 aaccgaggcc tcatctcaaa agcaaaaatc aaggccatca agtacagcat cgtcataatc   840
cttgctttca tctgctgctg gagtccatac ttcctctttg acatgttaga caacttcaac   900
ctccttccag acaccaagga gcgtttctat gcctctgtga ttatccagaa cctgcctgcc   960
ttgaacagtg ccattaaccc cctcatctac tgcatcttca gcggctccct ctgctccccc  1020
tgcaaggtgc gaagatccca ggattccaga atgacgtacc gagagagaag cgagaggcat  1080
gagatgcaga ttctctccaa gcctgaattc atc                               1113

<210> SEQ ID NO 87
<211> LENGTH: 371
<212> TYPE: PRT
<213> ORGANISM: Rat

<400> SEQUENCE: 87

Met Pro Ala Asn Leu Thr Glu Gly Ser Phe His Ala Asn Gln Thr Val
```

```
                  5                   10                  15
Pro Met Leu Asp Ser Ser Pro Val Ala Cys Thr Glu Ile Val Thr Phe
             20                  25                  30

Thr Glu Ala Leu Glu Ala Glu Trp Gly Ser Phe Tyr Ser Ser Phe
         35                  40                  45

Lys Thr Glu Gln Leu Ile Thr Leu Trp Val Leu Phe Val Phe Thr Ile
         50                  55                  60

Val Gly Asn Ser Val Val Leu Phe Ser Thr Trp Arg Arg Lys Arg Lys
65                   70                  75                  80

Ser Arg Met Thr Phe Phe Val Thr Gln Leu Ala Ile Thr Asp Ser Phe
                 85                  90                  95

Thr Gly Leu Ile Asn Ile Leu Thr Asp Ile Ile Trp Arg Phe Thr Gly
             100                 105                 110

Asp Phe Met Ala Pro Asp Leu Val Cys Arg Ile Val Arg Tyr Leu Gln
             115                 120                 125

Val Val Leu Leu Tyr Ala Ser Thr Tyr Val Leu Val Ser Leu Ser Ile
130                 135                 140

Asp Arg Tyr His Ala Ile Val Tyr Pro Met Lys Phe Leu Gln Gly Glu
145                 150                 155                 160

Lys Gln Ala Lys Val Leu Ile Gly Ile Ala Trp Ser Leu Ser Phe Leu
                 165                 170                 175

Phe Ser Ile Pro Thr Leu Ile Ile Phe Gly Lys Arg Thr Leu Ser Asn
             180                 185                 190

Gly Glu Val Gln Cys Trp Ala Leu Trp Pro Asp Asp Ser Tyr Trp Thr
             195                 200                 205

Pro Tyr Met Thr Ile Val Ala Phe Leu Val Tyr Phe Ile Pro Leu Thr
         210                 215                 220

Ile Ile Ser Val Ile Tyr Gly Leu Val Ile Arg Thr Ile Trp Ile Lys
225                 230                 235                 240

Ser Lys Ala His Glu Thr Val Ile Ser Asn Cys Ser Asp Gly Glu Leu
                 245                 250                 255

Cys Arg Ser Tyr Asn Arg Gly Leu Ile Ser Lys Ala Lys Ile Lys Ala
             260                 265                 270

Ile Lys Tyr Ser Ile Val Ile Ile Leu Ala Phe Ile Cys Cys Trp Ser
         275                 280                 285

Pro Tyr Phe Leu Phe Asp Met Leu Asp Asn Phe Asn Leu Leu Pro Asp
         290                 295                 300

Thr Lys Glu Arg Phe Tyr Ala Ser Val Ile Ile Gln Asn Leu Pro Ala
305                 310                 315                 320

Leu Asn Ser Ala Ile Asn Pro Leu Ile Tyr Cys Ile Phe Ser Gly Ser
                 325                 330                 335

Leu Cys Ser Pro Cys Lys Val Gln Arg Ser Gln Asp Ser Arg Met Thr
             340                 345                 350

Tyr Arg Glu Arg Ser Glu Arg His Glu Met Gln Ile Leu Ser Lys Pro
         355                 360                 365

Glu Phe Ile
     370

<210> SEQ ID NO 88
<211> LENGTH: 1113
<212> TYPE: DNA
<213> ORGANISM: Rat

<400> SEQUENCE: 88
```

```
atgccggcca acctcacaga gggcagcttt catgccaacc agactgtgcc gatgctagat    60
tcttcccctg tagcttgcac tgaaattgtg actttcactg aagcgctgga ggctgaggag   120
tgggctcct  tctactcgtc ctttaagaca gagcagctga taaccctgtg gtcctgttt    180
gtcttcacta ttgtgggaaa ctcggtcgtg ctgttctcca catggagaag aaaaagaaag   240
tccagaatga ccttctttgt gactcaattg ccatcacag  actccttcac aggcctgatc   300
aacatcctga cagacattat ttggcgattc acgggagact tcatggcccc tgacctggtc   360
tgcagaatcg tccgctactt acaggttgtc ctgctttatg cctctaccta tgtcctggtg   420
tccctcagca tagacagata ccatgccatc gtttaccca  tgaaattcct tcaaggagag   480
aagcaagcca agtcctcat  cggaatagca tggagcctct ccttcctgtt ctccatcccc   540
acactgatca tatttgggaa aaggacactt tccaatggtg aggtacagtg ctgggcactg   600
tggccagacg actcctactg gacccatat  atgaccatcg ttgcctttct ggtgtacttc   660
atccccttga caattatcag cgtcatctat ggccttgtga tccgaactat ttggattaaa   720
agcaaagccc atgagacggt gatttccaac tgctcagatg gagaactatg ccgcagctac   780
aaccgaggcc tcatctcaaa agcaaaaatc aaggccatca gtacagcat  cgtcataatc   840
cttgctttca tctgctgctg gagtccatac ttcctctttg acatgttaga caacttcaac   900
ctccttccag acaccaagga gcgtttctat gcctctgtga ttatccagaa cctgcctgcc   960
ttgaacagtg ccattaaccc cctcatctac tgcatcttca gcggctccct ctgctccccc  1020
tgcaaggtgc aaagatccca ggattccaga atgacgtacc gagagagaag cgagaggcat  1080
gagatgcaga ttctctccaa gcctgaattc atc                                1113
```

<210> SEQ ID NO 89
<211> LENGTH: 371
<212> TYPE: PRT
<213> ORGANISM: Rat

<400> SEQUENCE: 89

```
Met Pro Ala Asn Leu Thr Glu Gly Ser Phe His Ala Asn Gln Thr Val
              5                  10                  15

Pro Met Leu Asp Ser Ser Pro Val Ala Cys Thr Glu Ile Val Thr Phe
         20                  25                  30

Thr Glu Ala Leu Glu Ala Glu Glu Trp Gly Ser Phe Tyr Ser Ser Phe
     35                  40                  45

Lys Thr Glu Gln Leu Ile Thr Leu Trp Val Leu Phe Val Phe Thr Ile
 50                  55                  60

Val Gly Asn Ser Val Val Leu Phe Ser Thr Trp Arg Arg Lys Arg Lys
 65                  70                  75                  80

Ser Arg Met Thr Phe Phe Val Thr Gln Leu Ala Ile Thr Asp Ser Phe
                 85                  90                  95

Thr Gly Leu Ile Asn Ile Leu Thr Asp Ile Ile Trp Arg Phe Thr Gly
            100                 105                 110

Asp Phe Met Ala Pro Asp Leu Val Cys Arg Ile Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Glu
145                 150                 155                 160

Lys Gln Ala Lys Val Leu Ile Gly Ile Ala Trp Ser Leu Ser Phe Leu
                165                 170                 175
```

-continued

```
Phe Ser Ile Pro Thr Leu Ile Ile Phe Gly Lys Arg Thr Leu Ser Asn
            180                 185                 190
Gly Glu Val Gln Cys Trp Ala Leu Trp Pro Asp Ser Tyr Trp Thr
            195                 200                 205
Pro Tyr Met Thr Ile Val Ala Phe Leu Ala Tyr Phe Ile Pro Leu Thr
    210                 215                 220
Ile Ile Ser Val Ile Tyr Gly Leu Val Ile Arg Thr Ile Trp Ile Lys
225                 230                 235                 240
Ser Lys Ala His Glu Thr Val Ile Ser Asn Cys Ser Asp Gly Glu Leu
                245                 250                 255
Cys Cys Ser Tyr Asn Arg Gly Leu Ile Ser Lys Ala Lys Ile Lys Ala
            260                 265                 270
Ile Lys Tyr Ser Ile Val Ile Ile Leu Ala Phe Ile Cys Cys Trp Ser
            275                 280                 285
Pro Tyr Phe Leu Phe Asp Met Leu Asp Asn Phe Asn Leu Leu Pro Asp
    290                 295                 300
Thr Lys Glu Arg Phe Tyr Ala Ser Val Ile Ile Gln Asn Leu Pro Ala
305                 310                 315                 320
Leu Asn Ser Ala Ile Asn Pro Leu Ile Tyr Cys Ile Phe Ser Gly Ser
                325                 330                 335
Leu Cys Ser Pro Cys Lys Val Gln Arg Ser Gln Asp Ser Arg Met Thr
            340                 345                 350
Tyr Arg Glu Arg Ser Glu Arg His Glu Met Gln Ile Leu Ser Lys Pro
            355                 360                 365
Glu Phe Ile
    370

<210> SEQ ID NO 90
<211> LENGTH: 1113
<212> TYPE: DNA
<213> ORGANISM: Rat

<400> SEQUENCE: 90
atgccggcca acctcacaga gggcagcttt catgccaacc agactgtgcc gatgctagat      60
tcttcccctg tagcttgcac tgaaattgtg actttcactg aagcgctgga ggctgaggag     120
tggggctcct ctactcgtc ctttaagaca gagcagctga taaccctgtg gtcctgttt      180 gtcttcacta ttgtgggaaa ctcggtcgtg ctgttctcca catggagaag aaaaagaaag     240
tccagaatga ccttctttgt gactcaattg gccatcacag actccttcac aggcctgatc     300
aacatcctga cagacattat tggcgattc acgggagact tcatggcccc tgacctggtc     360
tgcagaatcg tccgctactt acaggttgtc ctgctttatg cctctaccta tgtcctggtg     420
tccctcagca tagacagata ccatgccatc gtttacccca tgaaattcct tcaaggagag     480
aagcaagcca agtcctcat cggaatagca tggagcctct ccttcctgtt ctccatcccc     540
acactgatca tatttgggaa aaggacactt ccaatggtg aggtacagtg ctgggcactg     600
tggccagacg actcctactg gaccccatat atgaccatcg ttgcctttct ggcgtacttc     660 atcccctga caattatcag cgtcatctat ggccttgtga tccgaactat ttggattaaa     720
agcaaagccc atgagacggt gatttccaac tgctcagatg gagaactatg ctgcagctac     780
aaccgaggcc tcatctcaaa agcaaaaatc aaggccatca gtacagcat cgtcataatc     840 cttgctttca tctgctgctg gagtccatac ttcctctttg acatgttaga caacttcaac     900
ctccttccag acaccaagga gcgtttctat gcctctgtga ttatccagaa cctgcctgcc     960
```

```
ttgaacagtg ccattaaccc cctcatctac tgcatcttca gcggctccct ctgctccccc    1020
tgcaaggtgc aaagatccca ggattccaga atgacgtacc gagagagaag cgagaggcat    1080
gagatgcaga ttctctccaa gcctgaattc atc                                 1113
```

<210> SEQ ID NO 91
<211> LENGTH: 372
<212> TYPE: PRT
<213> ORGANISM: Rat

<400> SEQUENCE: 91

Met Pro Ala Asn Leu Thr Glu Gly Ser Phe His Ala Asn Gln Thr Val
              5                  10                  15

Pro Met Leu Asp Ser Ser Pro Val Ala Cys Thr Glu Ile Val Thr Phe
         20                  25                  30

Thr Glu Ala Leu Glu Ala Glu Trp Gly Ser Phe Tyr Ser Ser Phe
     35                  40                  45

Lys Thr Glu Gln Leu Ile Thr Leu Trp Val Leu Phe Val Phe Thr Ile
 50                  55                  60

Val Gly Asn Ser Val Val Leu Phe Ser Thr Trp Arg Arg Lys Arg Lys
 65                  70                  75                  80

Ser Arg Met Thr Phe Phe Val Thr Gln Leu Ala Ile Thr Asp Ser Phe
                 85                  90                  95

Thr Gly Leu Ile Asn Ile Leu Thr Asp Ile Ile Trp Arg Phe Thr Gly
            100                 105                 110

Asp Phe Met Ala Pro Asp Leu Val Cys Arg Ile Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Ala
145                 150                 155                 160

Glu Lys Gln Ala Lys Val Leu Ile Gly Ile Ala Trp Ser Leu Ser Phe
                165                 170                 175

Leu Phe Ser Ile Pro Thr Leu Ile Ile Phe Gly Lys Arg Thr Leu Ser
            180                 185                 190

Asn Gly Glu Val Gln Cys Trp Ala Leu Trp Pro Asp Asp Ser Tyr Trp
        195                 200                 205

Thr Pro Tyr Met Thr Ile Val Ala Phe Leu Val Tyr Phe Ile Pro Leu
    210                 215                 220

Thr Ile Ile Ser Val Ile Tyr Gly Leu Val Ile Arg Thr Ile Trp Ile
225                 230                 235                 240

Lys Ser Lys Ala His Glu Thr Val Ile Ser Asn Cys Ser Asp Gly Glu
                245                 250                 255

Leu Cys Cys Ser Tyr Asn Arg Gly Leu Ile Ser Lys Ala Lys Ile Lys
            260                 265                 270

Ala Ile Lys Tyr Ser Ile Val Ile Leu Ala Phe Ile Cys Cys Trp
        275                 280                 285

Ser Pro Tyr Phe Leu Phe Asp Met Leu Asp Asn Phe Asn Leu Leu Pro
    290                 295                 300

Asp Thr Lys Glu Arg Phe Tyr Ala Ser Val Ile Ile Gln Asn Leu Pro
305                 310                 315                 320

Ala Leu Asn Ser Ala Ile Asn Pro Leu Ile Tyr Cys Ile Phe Ser Gly
                325                 330                 335

Ser Leu Cys Ser Pro Cys Lys Val Gln Arg Ser Gln Asp Ser Arg Met
            340                 345                 350

-continued

```
Thr Tyr Arg Glu Arg Ser Glu Arg His Glu Met Gln Ile Leu Ser Lys
        355                 360                 365
Pro Glu Phe Ile
    370
```

<210> SEQ ID NO 92
<211> LENGTH: 1116
<212> TYPE: DNA
<213> ORGANISM: Rat

<400> SEQUENCE: 92

```
atgccggcca acctcacaga gggcagcttt catgccaacc agactgtgcc gatgctagat      60
tcttcccctg tagcttgcac tgaaattgtg actttcactg aagcgctgga ggctgaggag     120
tggggctcct tctactcgtc ctttaagaca gagcagctga taccctgtg ggtcctgttt      180
gtcttcacta ttgtgggaaa ctcggtcgtg ctgttctcca catggagaag aaaaagaaag     240
tccagaatga ccttctttgt gactcaattg ccatacag actccttcac aggcctgatc       300
aacatcctga cagacattat ttggcgattc acgggagact tcatggcccc tgacctggtc     360
tgcagaatcg tccgctactt acaggttgtc ctgctttatg cctctaccta tgtcctggtg     420
tccctcagca tagacagata ccatgccatc gtttacccca tgaaattcct tcaaggagca     480
gagaagcaag ccaaagtcct catcggaata gcatggagcc tctccttcct gttctccatc     540
cccacactga tcatatttgg gaaaaggaca ctttccaatg tgaggtaca gtgctgggca      600
ctgtggccag acgactccta ctggaccca tatatgacca tcgttgcctt tctggtgtac      660
ttcatcccct tgacaattat cagcgtcatc tatgccttg tgatccgaac tatttggatt      720
aaaagcaaag cccatgagac ggtgatttcc aactgctcag atggagaact atgctgcagc     780
tacaaccgag gcctcatctc aaaagcaaaa atcaaggcca tcaagtacag catcgtcata     840
atccttgctt tcatctgctg ctggagtcca tacttcctct tgacatgtt agacaacttc     900
aacctccttc cagacaccaa ggagcgtttc tatgcctctg tgattatcca gaacctgcct     960
gccttgaaca gtgccattaa ccccctcatc tactgcatct tcagcggctc cctctgctcc    1020
ccctgcaagg tgcaaagatc ccaggattcc agaatgacgt accgagagag aagcgagagg    1080
catgagatgc agattctctc caagcctgaa ttcatc                               1116
```

<210> SEQ ID NO 93
<211> LENGTH: 372
<212> TYPE: PRT
<213> ORGANISM: Rat

<400> SEQUENCE: 93

```
Met Pro Ala Asn Leu Thr Glu Gly Ser Phe His Ala Asn Gln Thr Val
              5                   10                  15
Pro Met Leu Asp Ser Ser Pro Val Ala Cys Thr Glu Ile Val Thr Phe
         20                  25                  30
Thr Glu Ala Leu Glu Ala Glu Glu Trp Gly Ser Phe Tyr Ser Ser Phe
     35                  40                  45
Lys Thr Glu Gln Leu Ile Thr Leu Trp Val Leu Phe Val Phe Thr Ile
 50                  55                  60
Val Gly Asn Ser Val Val Leu Phe Ser Thr Trp Arg Arg Lys Arg Lys
 65                  70                  75                  80
Ser Arg Met Thr Phe Phe Val Thr Gln Leu Ala Ile Thr Asp Ser Phe
                 85                  90                  95
```

-continued

Thr Gly Leu Ile Asn Ile Leu Thr Asp Ile Ile Trp Arg Phe Thr Gly
            100                 105                 110

Asp Phe Met Ala Pro Asp Leu Val Cys Arg Ile Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Ala
145                 150                 155                 160

Glu Lys Gln Ala Lys Val Leu Ile Gly Ile Ala Trp Ser Leu Ser Phe
                165                 170                 175

Leu Phe Ser Ile Pro Thr Leu Ile Ile Phe Gly Lys Arg Thr Leu Ser
            180                 185                 190

Asn Gly Glu Val Gln Cys Trp Ala Leu Trp Pro Asp Asp Ser Tyr Trp
        195                 200                 205

Thr Pro Tyr Met Thr Ile Val Ala Phe Leu Val Tyr Phe Ile Pro Leu
    210                 215                 220

Thr Ile Ile Ser Val Ile Tyr Gly Leu Val Ile Arg Thr Ile Trp Ile
225                 230                 235                 240

Lys Ser Lys Ala His Glu Thr Val Ile Ser Asn Cys Ser Asp Gly Glu
                245                 250                 255

Leu Cys Cys Ser Tyr Asn Arg Gly Leu Ile Ser Lys Ala Lys Ile Lys
            260                 265                 270

Ala Ile Lys Tyr Ser Ile Val Ile Ile Leu Ala Phe Ile Cys Cys Trp
        275                 280                 285

Ser Pro Tyr Phe Leu Phe Asp Met Leu Asp Asn Phe Asn Leu Leu Pro
    290                 295                 300

Asp Thr Lys Glu Arg Phe Tyr Ala Ser Val Ile Ile Gln Asn Leu Pro
305                 310                 315                 320

Ala Leu Asn Ser Ala Ile Asn Pro Leu Ile Tyr Cys Ile Phe Ser Gly
                325                 330                 335

Ser Leu Cys Ser Pro Cys Lys Val Arg Arg Ser Gln Asp Ser Arg Met
            340                 345                 350

Thr Tyr Arg Glu Arg Ser Glu Arg His Glu Met Gln Ile Leu Ser Lys
        355                 360                 365

Pro Glu Phe Ile
    370

<210> SEQ ID NO 94
<211> LENGTH: 1116
<212> TYPE: DNA
<213> ORGANISM: Rat

<400> SEQUENCE: 94
atgccggcca acctcacaga gggcagcttt catgccaacc agactgtgcc gatgctagat      60
tcttcccctg tagcttgcac tgaaattgtg actttcactg aagcgctgga ggctgaggag     120 tgggctcct tctactcgtc ctttaagaca gagcagctga taaccctgtg ggtcctgttt      180
gtcttcacta ttgtgggaaa ctcggtcgtg ctgttctcca catggagaag aaaaagaaag     240
tccagaatga ccttctttgt gactcaattg ccatcacag actccttcac aggcctgatc      300
aacatcctga cagacattat ttggcgattc acgggagact tcatggcccc tgacctggtc     360
tgcagaatcg tccgctactt acaggttgtc ctgctttatg cctctaccta tgtcctggtg     420
tccctcagca tagacagata ccatgccatc gtttacccca tgaaattcct tcaaggagca     480
gagaagcaag ccaaagtcct catcggaata gcatggagcc tctccttcct gttctccatc     540

-continued

```
cccacactga tcatatttgg gaaaaggaca ctttccaatg gtgaggtaca gtgctgggca      600
ctgtggccag acgactccta ctggacccca tatatgacca tcgttgcctt tctggtgtac      660
ttcatcccct tgacaattat cagcgtcatc tatggccttg tgatccgaac tatttggatt      720
aaaagcaaag cccatgagac ggtgatttcc aactgctcag atggagaact atgctgcagc      780
tacaaccgag gcctcatctc aaaagcaaaa atcaaggcca tcaagtacag catcgtcata      840
atccttgctt tcatctgctg ctggagtcca tacttcctct ttgacatgtt agacaacttc      900
aacctccttc cagacaccaa ggagcgtttc tatgcctctg tgattatcca gaacctgcct      960
gccttgaaca gtgccattaa ccccctcatc tactgcatct tcagcggctc cctctgctcc     1020
ccctgcaagg tgcgaagatc ccaggattcc agaatgacgt accgagagag aagcgagagg     1080
catgagatgc agattctctc caagcctgaa ttcatc                                1116
```

<210> SEQ ID NO 95
<211> LENGTH: 371
<212> TYPE: PRT
<213> ORGANISM: Human

<400> SEQUENCE: 95

```
Met Pro Ala Asn Phe Thr Glu Gly Ser Phe Asp Ser Ser Gly Thr Gly
                 5                  10                  15

Gln Thr Leu Asp Ser Ser Pro Val Ala Cys Thr Glu Thr Val Thr Phe
            20                  25                  30

Thr Glu Val Val Glu Gly Lys Glu Trp Gly Ser Phe Tyr Tyr Ser Phe
        35                  40                  45

Lys Thr Glu Gln Leu Ile Thr Leu Trp Val Leu Phe Val Phe Thr Ile
    50                  55                  60

Val Gly Asn Ser Val Val Leu Phe Ser Thr Trp Arg Arg Lys Lys Lys
65                  70                  75                  80

Ser Arg Met Thr Phe Phe Val Thr Gln Leu Ala Ile Thr Asp Ser Phe
                85                  90                  95

Thr Gly Leu Val Asn Ile Leu Thr Asp Ile Ile Trp Arg Phe Thr Gly
            100                 105                 110

Asp Phe Thr Ala Pro Asp Leu Val Cys Arg Val Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Glu
145                 150                 155                 160

Lys Gln Ala Arg Val Leu Ile Val Ile Ala Trp Ser Leu Ser Phe Leu
                165                 170                 175

Phe Ser Ile Pro Thr Leu Ile Ile Phe Gly Lys Arg Thr Leu Ser Asn
            180                 185                 190

Gly Glu Val Gln Cys Trp Ala Leu Trp Pro Asp Asp Ser Tyr Trp Thr
        195                 200                 205

Pro Tyr Met Thr Ile Val Ala Phe Leu Val Tyr Phe Ile Pro Leu Thr
    210                 215                 220

Ile Ile Ser Ile Met Tyr Gly Ile Val Ile Arg Thr Ile Trp Ile Lys
225                 230                 235                 240

Ser Lys Thr Tyr Glu Thr Val Ile Ser Asn Cys Ser Asp Gly Lys Leu
                245                 250                 255

Cys Ser Ser Tyr Asn Arg Gly Leu Ile Ser Lys Ala Lys Ile Lys Ala
            260                 265                 270
```

```
Ile Lys Tyr Ser Ile Ile Ile Leu Ala Phe Ile Cys Cys Trp Ser
            275                 280                 285

Pro Tyr Phe Leu Phe Asp Ile Leu Asp Asn Phe Asn Leu Leu Pro Asp
        290                 295                 300

Thr Gln Glu Arg Phe Tyr Ala Ser Val Ile Ile Gln Asn Leu Pro Ala
305                 310                 315                 320

Leu Asn Ser Ala Ile Asn Pro Leu Ile Tyr Cys Val Phe Ser Ser Ser
                325                 330                 335

Ile Ser Phe Pro Cys Arg Glu Gln Arg Ser Gln Asp Ser Arg Met Thr
            340                 345                 350

Phe Arg Glu Arg Thr Glu Arg His Glu Met Gln Ile Leu Ser Lys Pro
            355                 360                 365

Glu Phe Ile
        370

<210> SEQ ID NO 96
<211> LENGTH: 1116
<212> TYPE: DNA
<213> ORGANISM: Human

<400> SEQUENCE: 96
atgccagcca acttcacaga gggcagcttc gattccagtg ggaccgggca gacgctggat      60
tcttccccag tggcttgcac tgaaacagtg acttttactg aagtggtgga aggaaaggaa     120
tggggttcct tctactactc ctttaagact gagcaattga taactctgtg ggtcctcttt     180
gttttaccca ttgttggaaa ctccgttgtg ctttttttcca catggaggag aaagaagaag     240
tcaagaatga ccttctttgt gactcagctg ccatcacag attctttcac aggactggtc      300
aacatcttga cagatattat ttggcgattc actggagact tcacggcacc tgacctggtt     360
tgccgagtgg tccgctattt gcaggttgtg ctgctctacg cctctaccta cgtcctggtg     420
tccctcagca tagacagata ccatgccatc gtctacccca tgaagttcct tcaaggagaa     480
aagcaagcca gggtcctcat tgtgatcgcc tggagcctgt cttttctgtt ctccattccc     540
accctgatca tatttgggaa gaggacactg tccaacggtg aagtgcagtg ctgggccctg     600
tggcctgacg actcctactg gacccccatac atgaccatcg tggccttcct ggtgtacttc     660
atccctctga caatcatcag catcatgtat ggcattgtga tccgaactat ttggattaaa     720 agcaaaaccct acgaaacagt gatttccaac tgctcagatg ggaaactgtg cagcagctat     780
aaccgaggac tcatctcaaa ggcaaaaatc aaggctatca gtatagcat catcatcatt     840 cttgccttca tctgctgttg gagtccatac ttcctgtttg acatttttgga caatttcaac     900 ctccttccag acacccagga gcgtttctat gcctctgtga tcattcagaa cctgccagca     960
ttgaatagtg ccatcaaccc cctcatctac tgtgtcttca gcagctccat ctctttcccc    1020
tgcagggagc aaagatcaca ggattccaga atgacgttcc gggagagaac tgagaggcat    1080
gagatgcaga ttctgtccaa gccagaattc atctag                              1116

<210> SEQ ID NO 97
<211> LENGTH: 371
<212> TYPE: PRT
<213> ORGANISM: Human

<400> SEQUENCE: 97

Met Pro Ala Asn Phe Thr Glu Gly Ser Phe Asp Ser Ser Gly Thr Gly
                5                  10                  15
```

-continued

```
Gln Thr Leu Asp Ser Ser Pro Val Ala Cys Thr Glu Thr Val Thr Phe
             20                  25                  30
Thr Glu Val Val Glu Gly Lys Glu Trp Gly Ser Phe Tyr Tyr Ser Phe
         35                  40                  45
Lys Thr Glu Gln Leu Ile Thr Leu Trp Val Leu Phe Val Phe Thr Ile
     50                  55                  60
Val Gly Asn Ser Val Val Leu Phe Ser Thr Trp Arg Lys Lys Lys
 65                  70                  75                  80
Ser Arg Met Thr Phe Phe Val Thr Gln Leu Ala Ile Thr Asp Ser Phe
                 85                  90                  95
Thr Gly Leu Val Asn Ile Leu Thr Asp Ile Asn Trp Arg Phe Thr Gly
             100                 105                 110
Asp Phe Thr Ala Pro Asp Leu Val Cys Arg Val Val Arg Tyr Leu Gln
         115                 120                 125
Val Val Leu Leu Tyr Ala Ser Thr Tyr Val Leu Val Ser Leu Ser Ile
     130                 135                 140
Asp Arg Tyr His Ala Ile Val Tyr Pro Met Lys Phe Leu Gln Gly Glu
145                 150                 155                 160
Lys Gln Ala Arg Val Leu Ile Val Ile Ala Trp Ser Leu Ser Phe Leu
                 165                 170                 175
Phe Ser Ile Pro Thr Leu Ile Ile Phe Gly Lys Arg Thr Leu Ser Asn
             180                 185                 190
Gly Glu Val Gln Cys Trp Ala Leu Trp Pro Asp Asp Ser Tyr Trp Thr
         195                 200                 205
Pro Tyr Met Thr Ile Val Ala Phe Leu Val Tyr Phe Ile Pro Leu Thr
     210                 215                 220
Ile Ile Ser Ile Met Tyr Gly Ile Val Ile Arg Thr Ile Trp Ile Lys
225                 230                 235                 240
Ser Lys Thr Tyr Glu Thr Val Ile Ser Asn Cys Ser Asp Gly Lys Leu
                 245                 250                 255
Cys Ser Ser Tyr Asn Arg Gly Leu Ile Ser Lys Ala Lys Ile Lys Ala
             260                 265                 270
Ile Lys Tyr Ser Ile Ile Ile Leu Ala Phe Ile Cys Cys Trp Ser
         275                 280                 285
Pro Tyr Phe Leu Phe Asp Ile Leu Asp Asn Phe Asn Leu Leu Pro Asp
     290                 295                 300
Thr Gln Glu Arg Phe Tyr Ala Ser Val Ile Ile Gln Asn Leu Pro Ala
305                 310                 315                 320
Leu Asn Ser Ala Ile Asn Pro Leu Ile Tyr Cys Val Phe Ser Ser Ser
                 325                 330                 335
Ile Ser Phe Pro Cys Arg Glu Arg Arg Ser Gln Asp Ser Arg Met Thr
             340                 345                 350
Phe Arg Glu Arg Thr Glu Arg His Glu Met Gln Ile Leu Ser Lys Pro
         355                 360                 365
Glu Phe Ile
     370
```

<210> SEQ ID NO 98
<211> LENGTH: 1116
<212> TYPE: DNA
<213> ORGANISM: Human

<400> SEQUENCE: 98
atgccagcca acttcacaga gggcagcttc gattccagtg ggaccgggca gacgctggat         60

| | |
|---|---|
| tcttccccag tggcttgcac tgaaacagtg acttttactg aagtggtgga aggaaaggaa | 120 |
| tggggttcct tctactactc ctttaagact gagcaattga taactctgtg ggtcctcttt | 180 |
| gttttttacca ttgttggaaa ctccgttgtg ctttttttcca catggaggag aaagaagaag | 240 |
| tcaagaatga ccttctttgt gactcagctg ccatcacag attctttcac aggactggtc | 300 |
| aacatcttga cagatattaa ttggcgattc actggagact tcacggcacc tgacctggtt | 360 |
| tgccgagtgg tccgctattt gcaggttgtg ctgctctacg cctctaccta cgtcctggtg | 420 |
| tccctcagca tagacagata ccatgccatc gtctacccca tgaagttcct tcaaggagaa | 480 |
| aagcaagcca gggtcctcat tgtgatcgcc tggagcctgt cttttctgtt ctccattccc | 540 |
| accctgatca tatttgggaa gaggacactg tccaacggtg aagtgcagtg ctgggccctg | 600 |
| tggcctgacg actcctactg gaccccatac atgaccatcg tggccttcct ggtgtacttc | 660 |
| atccctctga caatcatcag catcatgtat ggcattgtga tccgaactat tggattaaaa | 720 |
| agcaaaacct acgaaacagt gatttccaac tgctcagatg gaaactgtg cagcagctat | 780 |
| aaccgaggac tcatctcaaa ggcaaaaatc aaggctatca agtatagcat catcatcatt | 840 |
| cttgccttca tctgctgttg gagtccatac ttcctgtttg acattttgga caatttcaac | 900 |
| ctccttccag acacccagga gcgtttctat gcctctgtga tcattcagaa cctgccagca | 960 |
| ttgaatagtg ccatcaaccc cctcatctac tgtgtcttca gcagctccat ctcttttccc | 1020 |
| tgcagggagc gaagatcaca ggattccaga atgacgttcc gggagagaac cgagaggcat | 1080 |
| gagatgcaga ttctgtccaa gccagaattc atctag | 1116 |

<210> SEQ ID NO 99
<211> LENGTH: 1116
<212> TYPE: DNA
<213> ORGANISM: Human

<400> SEQUENCE: 99

| | |
|---|---|
| atgccagcca acttcacaga gggcagcttc gattccagtg ggaccgggca gacgctggat | 60 |
| tcttccccag tggcttgcac tgaaacagtg acttttactg aagtggtgga aggaaaggaa | 120 |
| tggggttcct tctactactc ctttaagact gagcaattga taactctgtg ggtcctcttt | 180 |
| gttttttacca ttgttggaaa ctccgttgtg ctttttttcca catggaggag aaagaagaag | 240 |
| tcaagaatga ccttctttgt gactcagctg ccatcacag attctttcac aggactggtc | 300 |
| aacatcttga cagatattat ttggcgattc actggagact tcacggcacc tgacctggtt | 360 |
| tgccgagtgg tccgctattt gcaggttgtg ctgctctacg cctctaccta cgtcctggtg | 420 |
| tccctcagca tagacagata ccatgccatc gtctacccca tgaagttcct tcaaggagaa | 480 |
| aagcaagcca gggtcctcat tgtgatcgcc tggagcctgt cttttctgtt ctccattccc | 540 |
| accctgatca tatttgggaa gaggacactg tccaacggtg aagtgcagtg ctgggccctg | 600 |
| tggcctgacg actcctactg gaccccatac atgaccatcg tggcctttct ggtgtacttc | 660 |
| atccctctga caatcatcag catcatgtat ggcattgtga tccgaactat tggattaaaa | 720 |
| agcaaaacct acgaaacagt gatttccaac tgctcagatg gaaactgtg cagcagctat | 780 |
| aaccgaggac tcatctcaaa ggcaaaaatc aaggctatca agtatagcat catcatcatt | 840 |
| cttgccttca tctgctgttg gagtccatac ttcctgtttg acattttgga caatttcaac | 900 |
| ctccttccag acacccagga gcgtttctat gcctctgtga tcattcagaa cctgccagca | 960 |
| ttgaatagtg ccatcaaccc cctcatctac tgtgtcttca gcagctccat ctcttttccc | 1020 |
| tgcagggagc aaagatcaca ggattccaga atgacgttcc gggagagaac tgagaggcat | 1080 |

-continued

```
gagatgcaga ttctgtccaa gccagaattc atctag                               1116

<210> SEQ ID NO 100
<211> LENGTH: 1113
<212> TYPE: DNA
<213> ORGANISM: Human

<400> SEQUENCE: 100
atgccagcca acttcacaga gggcagcttc gattccagtg ggaccgggca gacgctggat      60
tcttccccag tggcttgcac tgaaacagtg acttttactg aagtggtgga aggaaaggaa     120
tggggttcct tctactactc ctttaagact gagcaattga taactctgtg ggtcctcttt     180
gtttttacca ttgttggaaa ctccgttgtg cttttttcca catggaggag aaagaagaag     240
tcaagaatga ccttctttgt gactcagctg ccatcacag attctttcac aggactggtc      300
aacatcttga cagatattat ttggcgattc actggagact tcacggcacc tgacctggtt     360
tgccgagtgg tccgctattt gcaggttgtg ctgctgtacg cctctaccta cgtcctggtg     420
tccctcagca tagacagata ccatgccatc gtctacccca tgaagttcct tcaaggagaa     480
aagcaagcca gggtcctcat tgtgatcgcc tggagcctgt cttttctgtt ctccattccc     540
accctgatca tatttgggaa gaggacactg tccaacggtg aagtgcagtg ctgggcccctg    600 tggcctgacg actcctactg gacccatac atgaccatcg tggccttcct ggtgtacttc     660
atccctctga caatcatcag catcatgtat ggcattgtga tccgaactat ttggattaaa    720
agcaaaacct acgaaacagt gatttccaac tgctcagatg ggaaactgtg cagcagctat     780
aaccgaggac tcatctcaaa ggcaaaaatc aaggctatca agtatagcat catcatcatt    840
cttgccttca tctgctgttg gagtccatac ttcctgtttt gacattttgga caatttcaac    900 ctccttccag acacccagga gcgtttctat gcctctgtga tcattcagaa cctgccagca    960
ttgaatagtg ccatcaaccc cctcatctac tgtgtcttca gcagctccat ctctttcccc    1020
tgcagggagc aaagatcaca ggattccaga atgacgttcc gggagagaac tgagaggcat    1080
gagatgcaga ttctgtccaa gccagaattc atc                                 1113

<210> SEQ ID NO 101
<211> LENGTH: 1113
<212> TYPE: DNA
<213> ORGANISM: Human

<400> SEQUENCE: 101
atgccagcca acttcacaga gggcagcttc gattccagtg ggaccgggca gacgctggat      60
tcttccccag tggcttgcac tgaaacagtg acttttactg aagtggtgga aggaaaggaa     120
tggggttcct tctactactc ctttaagact gagcaattga taactctgtg ggtcctcttt     180
gtttttacca ttgttggaaa ctccgttgtg cttttttcca catggaggag aaagaagaag     240
tcaagaatga ccttctttgt gactcagctg ccatcacag attctttcac aggactggtc      300
aacatcttga cagatattat ttggcgattc actggagact tcacggcacc tgacctggtt     360
tgccgagtgg tccgctattt gcaggttgtg ctgctctacg cctctaccta cgtcctggtg     420
tccctcagca tagacagata ccatgccatc gtctacccca tgaagttcct tcaaggagaa     480
aagcaagcca gggtcctcat tgtgatcgcc tggagcctgt cttttctgtt ctccattccc     540
accctgatca tatttgggaa gaggacactg tccaacggtg aagtgcagtg ctgggcccctg    600 tggcctgacg actcctactg gacccatac atgaccatcg tggccttcct ggtgtacttc     660
```

```
atccctctga caatcatcag catcatgtat ggcattgtga tccgaactat ttggattaaa        720
agcaaaacct acgaaacagt gatttccaac tgctcagatg ggaaactgtg cagcagctat        780
aaccgaggac tcatctcaaa ggcaaaaatc aaggctatca agtatagcat catcatcatt        840
cttgccttca tctgctgttg gagtccatac ttcctgtttg acattttgga caatttcaac        900
ctccttccag acacccagga gcgtttctat gcctctgtga tcattcagaa cctgccagca        960
ttgaatagtg ccatcaaccc cctcatctac tgtgtcttca gcagctccat ctctttcccc       1020
tgcagggagc gaagatcaca ggattccaga atgacgttcc gggagagaac cgagaggcat       1080
gagatgcaga ttctgtccaa gccagaattc atc                                    1113
```

<210> SEQ ID NO 102
<211> LENGTH: 371
<212> TYPE: PRT
<213> ORGANISM: Human

<400> SEQUENCE: 102

```
Met Pro Ala Asn Phe Thr Glu Gly Ser Phe Asp Ser Ser Gly Thr Gly
                 5                  10                  15

Gln Thr Leu Asp Ser Ser Pro Val Ala Cys Thr Glu Thr Val Thr Phe
             20                  25                  30

Thr Glu Val Val Glu Gly Lys Glu Trp Gly Ser Phe Tyr Tyr Ser Phe
         35                  40                  45

Lys Thr Glu Gln Leu Ile Thr Leu Trp Val Leu Phe Val Phe Thr Ile
     50                  55                  60

Val Gly Asn Ser Val Val Leu Phe Ser Thr Trp Arg Arg Lys Lys Lys
 65                  70                  75                  80

Ser Arg Met Thr Phe Phe Val Thr Gln Leu Ala Ile Thr Asp Ser Phe
                 85                  90                  95

Thr Gly Leu Val Asn Ile Leu Thr Asp Ile Asn Trp Arg Phe Thr Gly
            100                 105                 110

Asp Phe Thr Ala Pro Asp Leu Val Cys Arg Val Val Arg Tyr Leu Gln
        115                 120                 125

Val Val Leu Leu Tyr Ala Ser Thr Tyr Val Leu Val Ser Leu Ser Ile
    130                 135                 140

Asp Arg Tyr His Ala Ile Val Tyr Pro Met Lys Phe Leu Gln Gly Glu
145                 150                 155                 160

Lys Gln Ala Arg Val Leu Ile Val Ile Ala Trp Ser Leu Ser Phe Leu
                165                 170                 175

Phe Ser Ile Pro Thr Leu Ile Ile Phe Gly Lys Arg Thr Leu Ser Asn
            180                 185                 190

Gly Glu Val Gln Cys Trp Ala Leu Trp Pro Asp Asp Ser Tyr Trp Thr
        195                 200                 205

Pro Tyr Met Thr Ile Val Ala Phe Leu Val Tyr Phe Ile Pro Leu Thr
    210                 215                 220

Ile Ile Ser Ile Met Tyr Gly Ile Val Ile Arg Thr Ile Trp Ile Lys
225                 230                 235                 240

Arg Lys Thr Tyr Glu Thr Val Ile Ser Asn Cys Ser Asp Gly Lys Leu
                245                 250                 255

Cys Ser Ser Tyr Asn Arg Gly Leu Ile Ser Lys Ala Lys Ile Lys Ala
            260                 265                 270

Ile Lys Tyr Ser Ile Ile Ile Leu Ala Phe Ile Cys Cys Trp Ser
        275                 280                 285

Pro Tyr Phe Leu Phe Asp Ile Leu Asp Asn Phe Asn Leu Leu Pro Asp
```

```
                    290                 295                 300
Thr Gln Glu Arg Phe Tyr Ala Ser Val Ile Ile Gln Asn Leu Pro Ala
305                 310                 315                 320

Leu Asn Ser Ala Ile Asn Pro Leu Ile Tyr Cys Val Phe Ser Ser Ser
                325                 330                 335

Ile Ser Phe Pro Cys Arg Glu Arg Ser Gln Asp Ser Arg Met Thr
            340                 345                 350

Phe Arg Glu Arg Thr Glu Arg His Glu Met Gln Ile Leu Ser Lys Pro
        355                 360                 365

Glu Phe Ile
    370

<210> SEQ ID NO 103
<211> LENGTH: 1113
<212> TYPE: DNA
<213> ORGANISM: Human

<400> SEQUENCE: 103
atgccagcca acttcacaga gggcagcttc gattccagtg ggaccgggca gacgctggat    60
tcttccccag tggcttgcac tgaaacagtg acttttactg aagtggtgga aggaaaggaa   120
tggggttcct tctactactc ctttaagact gagcaattga taactctgtg ggtcctcttt   180
gtttttacca ttgttggaaa ctccgttgtg cttttttcca catggaggag aaagaagaag   240
tcaagaatga ccttctttgt gactcagctg ccatcacag attctttcac aggactggtc    300
aacatcttga cagatattaa ttggcgattc actggagact tcacggcacc tgacctggtt   360
tgccgagtgg tccgctattt gcaggttgtg ctgctctacg cctctaccta cgtcctggtg   420
tccctcagca tagacagata ccatgccatc gtctacccca tgaagttcct tcaaggagaa   480
aagcaagcca gggtcctcat tgtgatcgcc tggagcctgt cttttctgtt ctccattccc   540
accctgatca tatttgggaa gaggacactg tccaacggtg aagtgcagtg ctgggccctg   600
tggcctgacg actcctactg gacccatac atgaccatcg tggccttt ct ggtgtacttc   660 atccctctga caatcatcag catcatgtat ggcattgtga tccgaactat ttggattaaa   720
aggaaaacct acgaaacagt gatttccaac tgctcagatg gaaactgtg cagcagctat   780 aaccgaggac tcatctcaaa ggcaaaaatc aaggctatca gtatagcat catcatcatt   840 cttgccttca tctgctgttg gagtccatac ttcctgtttg acatttggga caatttcaac   900
ctccttccag acacccagga gcgtttctat gcctctgtga tcattcagaa cctgccagca   960
ttgaatagtg ccatcaaccc cctcatctac tgtgtcttca gcagctccat ctctttcccc  1020
tgcagggagc gaagatcaca ggattccaga atgacgttcc gggagagaac cgagaggcat  1080
gagatgcaga ttctgtccaa gccagaattc atc                               1113

<210> SEQ ID NO 104
<211> LENGTH: 371
<212> TYPE: PRT
<213> ORGANISM: Human

<400> SEQUENCE: 104

Met Pro Ala Asn Phe Thr Glu Gly Ser Phe Asp Ser Ser Gly Thr Gly
                5                   10                  15

Gln Thr Leu Asp Ser Ser Pro Val Ala Cys Thr Glu Thr Val Thr Phe
            20                  25                  30

Thr Glu Val Val Glu Gly Lys Glu Trp Gly Ser Phe Tyr Tyr Ser Phe
        35                  40                  45
```

| Lys | Thr | Glu | Gln | Leu | Ile | Thr | Leu | Trp | Val | Leu | Phe | Val | Phe | Thr | Ile |
|---|---|---|---|---|---|---|---|---|---|---|---|---|---|---|---|
| | 50 | | | | 55 | | | | 60 | | | | | | |

Val Gly Asn Ser Val Val Leu Phe Ser Thr Trp Arg Lys Lys Lys
 65              70                  75                  80

Ser Arg Met Thr Phe Phe Val Thr Gln Leu Ala Ile Thr Asp Ser Phe
                 85                  90                  95

Thr Gly Leu Val Asn Ile Leu Thr Asp Ile Ile Trp Arg Phe Thr Gly
             100                 105                 110

Asp Phe Thr Ala Pro Asp Leu Val Cys Arg Val Val Arg Tyr Leu Gln
             115                 120                 125

Val Val Leu Leu Tyr Ala Ser Thr Tyr Val Leu Val Ser Leu Ser Ile
 130                 135                 140

Asp Arg Tyr His Ala Ile Val Tyr Pro Met Lys Phe Leu Gln Gly Glu
 145                 150                 155                 160

Lys Gln Ala Arg Val Leu Ile Val Ile Ala Trp Ser Leu Ser Phe Leu
                 165                 170                 175

Phe Ser Ile Pro Thr Leu Ile Ile Phe Gly Lys Arg Thr Leu Ser Asn
             180                 185                 190

Gly Glu Val Gln Cys Trp Ala Leu Trp Pro Asp Asp Ser Tyr Trp Thr
             195                 200                 205

Pro Tyr Met Thr Ile Val Ala Phe Leu Val Tyr Phe Ile Pro Leu Thr
 210                 215                 220

Ile Ile Ser Ile Met Tyr Gly Ile Val Ile Arg Thr Ile Trp Ile Lys
225                 230                 235                 240

Arg Lys Thr Tyr Glu Thr Val Ile Ser Asn Cys Ser Asp Gly Lys Leu
                 245                 250                 255

Cys Ser Ser Tyr Asn Arg Gly Leu Ile Ser Lys Ala Lys Ile Lys Ala
             260                 265                 270

Ile Lys Tyr Ser Ile Ile Ile Leu Ala Phe Ile Cys Cys Trp Ser
             275                 280                 285

Pro Tyr Phe Leu Phe Asp Ile Leu Asp Asn Phe Asn Leu Leu Pro Asp
 290                 295                 300

Thr Gln Glu Arg Phe Tyr Ala Ser Val Ile Ile Gln Asn Leu Pro Ala
305                 310                 315                 320

Leu Asn Ser Ala Ile Asn Pro Leu Ile Tyr Cys Val Phe Ser Ser Ser
             325                 330                 335

Ile Ser Phe Pro Cys Arg Glu Arg Arg Ser Gln Asp Ser Arg Met Thr
             340                 345                 350

Phe Arg Glu Arg Thr Glu Arg His Glu Met Gln Ile Leu Ser Lys Pro
             355                 360                 365

Glu Phe Ile
     370

<210> SEQ ID NO 105
<211> LENGTH: 1113
<212> TYPE: DNA
<213> ORGANISM: Human

<400> SEQUENCE: 105

| atgccagcca | acttcacaga | gggcagcttc | gattccagtg | ggaccgggca | gacgctggat | 60 |
|---|---|---|---|---|---|---|
| tcttccccag | tggcttgcac | tgaaacagtg | acttttactg | aagtggtgga | aggaaaggaa | 120 |
| tggggttcct | tctactactc | ctttaagact | gagcaattga | taactctgtg | ggtcctcttt | 180 |
| gtttttacca | ttgttggaaa | ctccgttgtg | cttttttcca | catggaggag | aaagaagaag | 240 |

```
tcaagaatga ccttctttgt gactcagctg gccatcacag attctttcac aggactggtc    300
aacatcttga cagatattat ttggcgattc actggagact tcacggcacc tgacctggtt    360
tgccgagtgg tccgctattt gcaggttgtg ctgctctacg cctctaccta cgtcctggtg    420
tccctcagca tagacagata ccatgccatc gtctacccca tgaagttcct tcaaggagaa    480
aagcaagcca gggtcctcat tgtgatcgcc tggagcctgt cttttctgtt ctccattccc    540
accctgatca tatttgggaa gaggacactg tccaacggtg aagtgcagtg ctgggccctg    600
tggcctgacg actcctactg gaccccatac atgaccatcg tggcctttct ggtgtacttc    660
atccctctga caatcatcag catcatgtat ggcattgtga tccgaactat ttggattaaa    720
aggaaaacct acgaaacagt gatttccaac tgctcagatg ggaaactgtg cagcagctat    780
aaccgaggac tcatctcaaa ggcaaaaatc aaggctatca agtatagcat catcatcatt    840
cttgccttca tctgctgttg gagtccatac ttcctgtttg acattttgga caatttcaac    900
ctccttccag cacccagga gcgtttctat gcctctgtga tcattcagaa cctgccagca    960
ttgaatagtg ccatcaaccc cctcatctac tgtgtcttca gcagctccat ctctttcccc   1020
tgcagggagc gaagatcaca ggattccaga atgacgttcc gggagagaac cgagaggcat   1080
gagatgcaga ttctgtccaa gccagaattc atc                                1113
```

<210> SEQ ID NO 106
<211> LENGTH: 33
<212> TYPE: DNA
<213> ORGANISM: Artificial Sequence
<220> FEATURE:
<223> OTHER INFORMATION: Designed oligonucleotide primer to amplify DNA
      encoding human TGR23-1A

<400> SEQUENCE: 106
ctatttggat taaaaggaaa acctacgaaa cag                                  33

<210> SEQ ID NO 107
<211> LENGTH: 33
<212> TYPE: DNA
<213> ORGANISM: Artificial Sequence
<220> FEATURE:
<223> OTHER INFORMATION: Designed oligonucleotide primer to amplify DNA
      encoding human TGR23-1A

<400> SEQUENCE: 107
ctgtttcgta ggttttcctt ttaatccaaa tag                                  33

<210> SEQ ID NO 108
<211> LENGTH: 30
<212> TYPE: DNA
<213> ORGANISM: Artificial Sequence
<220> FEATURE:
<223> OTHER INFORMATION: Designed oligonucleotide primer to amplify DNA
      encoding human TGR23-1C

<400> SEQUENCE: 108
cttgacagat attatttggc gattcactgg                                      30

<210> SEQ ID NO 109
<211> LENGTH: 30
<212> TYPE: DNA
<213> ORGANISM: Artificial Sequence
<220> FEATURE:
<223> OTHER INFORMATION: Designed oligonucleotide primer to amplify DNA
      encoding human TGR23-1C

```
<400> SEQUENCE: 109
ccagtgaatc gccaaataat atctgtcaag                                      30

<210> SEQ ID NO 110
<211> LENGTH: 31
<212> TYPE: DNA
<213> ORGANISM: Artificial Sequence
<220> FEATURE:
<223> OTHER INFORMATION: Designed oligonucleotide primer to amplify DNA
      encoding human TGR23-1D

<400> SEQUENCE: 110
cccctgcagg gagcgaagat cacaggattc c                                    31

<210> SEQ ID NO 111
<211> LENGTH: 31
<212> TYPE: DNA
<213> ORGANISM: Artificial Sequence
<220> FEATURE:
<223> OTHER INFORMATION: Designed oligonucleotide primer to amplify DNA
      encoding human TGR23-1D

<400> SEQUENCE: 111
ggaatcctgt gatcttcgct ccctgcaggg g                                    31

<210> SEQ ID NO 112
<211> LENGTH: 33
<212> TYPE: DNA
<213> ORGANISM: Artificial Sequence
<220> FEATURE:
<223> OTHER INFORMATION: Designed oligonucleotide primer to amplify DNA
      encoding human TGR23-1B

<400> SEQUENCE: 112
ctatttggat taaaaggaaa acctacgaaa cag                                  33

<210> SEQ ID NO 113
<211> LENGTH: 33
<212> TYPE: DNA
<213> ORGANISM: Artificial Sequence
<220> FEATURE:
<223> OTHER INFORMATION: Designed oligonucleotide primer to amplify DNA
      encoding human TGR23-1B

<400> SEQUENCE: 113
ctgtttcgta ggttttcctt ttaatccaaa tag                                  33

<210> SEQ ID NO 114
<211> LENGTH: 18
<212> TYPE: DNA
<213> ORGANISM: Artificial Sequence
<220> FEATURE:
<223> OTHER INFORMATION: Designed oligonucleotide primer to amplify
      partial DNA encoding human TGR23-2

<400> SEQUENCE: 114
atgccagcca acttcaca                                                   18

<210> SEQ ID NO 115
<211> LENGTH: 21
<212> TYPE: DNA
<213> ORGANISM: Artificial Sequence
<220> FEATURE:
<223> OTHER INFORMATION: Designed oligonucleotide primer to amplify
      partial DNA encoding human TGR23-2

<400> SEQUENCE: 115
```
ttcactggag acttcacggc a                                     21

<210> SEQ ID NO 116
<211> LENGTH: 31
<212> TYPE: DNA
<213> ORGANISM: Artificial Sequence
<220> FEATURE:
<223> OTHER INFORMATION: Designed oligonucleotide primer to amplify
      DNA encoding rat TGR23-5

<400> SEQUENCE: 116
ttccttcaag gagcagagaa gcaagccaaa g                          31

<210> SEQ ID NO 117
<211> LENGTH: 31
<212> TYPE: DNA
<213> ORGANISM: Artificial Sequence
<220> FEATURE:
<223> OTHER INFORMATION: Designed oligonucleotide primer to amplify
      DNA encoding rat TGR23-5

<400> SEQUENCE: 117
ctttggcttg cttctctgct ccttgaagga a                          31

<210> SEQ ID NO 118
<211> LENGTH: 36
<212> TYPE: DNA
<213> ORGANISM: Artificial Sequence
<220> FEATURE:
<223> OTHER INFORMATION: Designed oligonucleotide primer to amplify
      partial DNA encoding rat TGR23-1

<400> SEQUENCE: 118
gtcgacatgc cggccaacct cacagagggc agcttt                     36

<210> SEQ ID NO 119
<211> LENGTH: 36
<212> TYPE: DNA
<213> ORGANISM: Artificial Sequence
<220> FEATURE:
<223> OTHER INFORMATION: Designed oligonucleotide primer to
      amplify partial DNA encoding rat TGR23-1

<400> SEQUENCE: 119
actagtttag atgaattcag gcttggagag aatctg                     36

<210> SEQ ID NO 120
<211> LENGTH: 22
<212> TYPE: DNA
<213> ORGANISM: Artificial Sequence
<220> FEATURE:
<223> OTHER INFORMATION: Primer

<400> SEQUENCE: 120
gacattattt ggcgattcac gg                                    22

<210> SEQ ID NO 121
<211> LENGTH: 22
<212> TYPE: DNA
<213> ORGANISM: Artificial Sequence
<220> FEATURE:
<223> OTHER INFORMATION: Primer

<400> SEQUENCE: 121
tgtaagtagc ggacgattct gc                                    22

```
<210> SEQ ID NO 122
<211> LENGTH: 28
<212> TYPE: DNA
<213> ORGANISM: Artificial Sequence
<220> FEATURE:
<223> OTHER INFORMATION: Probe

<400> SEQUENCE: 122
ttggagttat ccggtcctct cttccaag                                          28

<210> SEQ ID NO 123
<211> LENGTH: 20
<212> TYPE: DNA
<213> ORGANISM: Artificial Sequence
<220> FEATURE:
<223> OTHER INFORMATION: Designed oligonucleotide

<400> SEQUENCE: 123
gacccacaga gttatcaatt                                                   20

<210> SEQ ID NO 124
<211> LENGTH: 20
<212> TYPE: DNA
<213> ORGANISM: Artificial Sequence
<220> FEATURE:
<223> OTHER INFORMATION: Designed oligonucleotide

<400> SEQUENCE: 124
ttaactattg agacacccag                                                   20
```